US009169502B2

(12) United States Patent

Wittmann et al.

(10) Patent No.: US 9,169,502 B2
(45) Date of Patent: Oct. 27, 2015

(54) **METHOD OF PRODUCING L-LYSINE USING A *CORYNEBACTERIUM GLUTAMICUM* MICROORGANISM**

(75) Inventors: Christoph Wittmann, Wolfenbuttel (DE); Judith Becker, Braunschweig (DE)

(73) Assignee: Paik Kwang Industrial Co., Ltd., Gunsan-si (KR)

( * ) Notice: Subject to any disclaimer, the term of this patent is extended or adjusted under 35 U.S.C. 154(b) by 277 days.

(21) Appl. No.: 13/704,565

(22) PCT Filed: Jun. 15, 2010

(86) PCT No.: PCT/KR2010/003820

§ 371 (c)(1), (2), (4) Date: Apr. 12, 2013

(87) PCT Pub. No.: WO2011/158975

PCT Pub. Date: Dec. 22, 2011

(65) Prior Publication Data

US 2013/0203130 A1 Aug. 8, 2013

(51) Int. Cl.

| | |
|---|---|
| ***C12P 13/08*** | (2006.01) |
| ***C12N 1/20*** | (2006.01) |
| ***C12N 9/04*** | (2006.01) |
| ***C12N 9/12*** | (2006.01) |
| ***C12N 9/16*** | (2006.01) |
| ***C12N 15/52*** | (2006.01) |
| ***C12P 13/20*** | (2006.01) |

(52) U.S. Cl.

CPC ............... *C12P 13/08* (2013.01); *C12N 9/0006* (2013.01); *C12N 9/1217* (2013.01); *C12N 9/16* (2013.01); *C12N 15/52* (2013.01); *C12P 13/20* (2013.01)

(58) Field of Classification Search

None

See application file for complete search history.

(56) References Cited

U.S. PATENT DOCUMENTS

2008/0176296 A1 7/2008 Zelder et al.

FOREIGN PATENT DOCUMENTS

WO WO 2007017710 A1 * 2/2007
WO WO 2008049781 A1 * 5/2008
WO WO 2009133114 A1 * 11/2009

OTHER PUBLICATIONS

Becker et al., Appl. Environ. Microbiol. 75:7866-7869, Oct. 2009.*
Becker et al., J. Biotechnol. 132:99-109, 2007.*
Judith Becker et al., "Amplified Expression of Fructose 1,6-Bisphosphatase in *Corynebacterium glutamicum* Increases in Vivo Flux through the Pentose Phosphate Pathway and Lysine Production on Different Carbon Sources", Applied and Environmental Microbiology, Dec. 2005, vol. 71, No. 12, pp. 8587 8596.
Masato Ikeda et al., "Hyperproduction of Tryptophan by *Corynebacterium glutamicum* with the Modified Pentose Phosphate Pathway", Applied Environmental Microbiology, Jun. 1999, vol. 65, No. 6, pp. 2497-2502.
Patrick Kiefer et al., "Comparative Metabolic Flux Analysis of Lysine-Producing *Corynebacterium glutamicum* Cultured on Glucose", Applied Environmental Microbiology, Jan. 2004, vol. 70, No. 1, pp. 229-239.
Jens O. Kromer et al., "Physiological response of *Corynebacterium glutamicum* to Oxidative Stress Induced by Deletion of the Transcriptional Repressor McbR", Microbiology, (2008), vol. 154, pp. 3917-3930.
Bernd Moritz et al., "Kinetic Properties of the Glucose-6-phosphate and 6-phosphogluconate Dehydrogenases from *Corynebacterium glutamicum* and their Application for Predicting Pentose Phosphate Pathway Flux in Vivo", Eur J. Biochem, (2000) vol. 267, pp. 3442-3452.
Bernd Moritz et al., "Changes of Pentose Phosphate Pathway Flux in Vivo in *Corynebacterium glutamicum* during Leucine-Limited Batch Cultivation as Determined from Intracellular Metabolite Concentration Measurements", Metabolic Engineering, (2002), vol. 4, pp. 295-305.
J. Ohnishi et al., "A Novel Methodology Employing *Corynebacterium glutamicum* Genome Information to Generate a New L-lysine-producing mutant", Applied Microbiology Biotechnology, (2002), vol. 58, pp. 217-223.
Soren Petersen et al., "Metabolic Consequences of Altered Phosphoenolpyruvate Carboxykinase Activity in *Corynebacterium glutamicum* Reveal Anaplerotic Regulation Mechanisms in Vivo", Metabolic Engineering, (2001), vol. 3, pp. 344-361.
Petra G. Peters-Wendisch et al., "Pyruvate Carboxylase is a Major Bottleneck for Glutamate and Lysine Production by *Corynebacterium glutamicum*", J Mol Microbiol Biotechnol, vol. 3, No. 2, pp. 295-300, 2001.
Christoph Wittmann et al., "The L-Lysine Story: From Metabolic Pathways to Industrial Production", Microbiology Monogr., Feb. 24, 2007, Springer-Verlag Berlin Heidelberg 2007, pp. 39-70.
Christoph Wittmann et al., "Genealogy Profiling through Strain Improvement by Using Metabolic Network Analysis: Metabolic Flux Genealogy of Several Generations of Lysine-Producing Corynebacteria", Appl Environ Microbiol, (2002), vol. 68, No. 12, pp. 5843-5859.

* cited by examiner

*Primary Examiner* — David J Steadman

(74) *Attorney, Agent, or Firm* — Baker & Hostetler LLP

(57) ABSTRACT

The present invention is directed to a method utilizing a recombinant microorganism for the production of aspartate derived amino acids and precursors thereof, in particular for the production of L-lysine. Furthermore, the present invention relates to a recombinant microorganism having improved aspartate-derived amino acid synthesis activity in comparison to the initial microorganism and the use of such microorganisms in producing said amino acids and precursors and derivatives, in particular in the synthesis of L-lysine.

3 Claims, 16 Drawing Sheets

Fig. 23
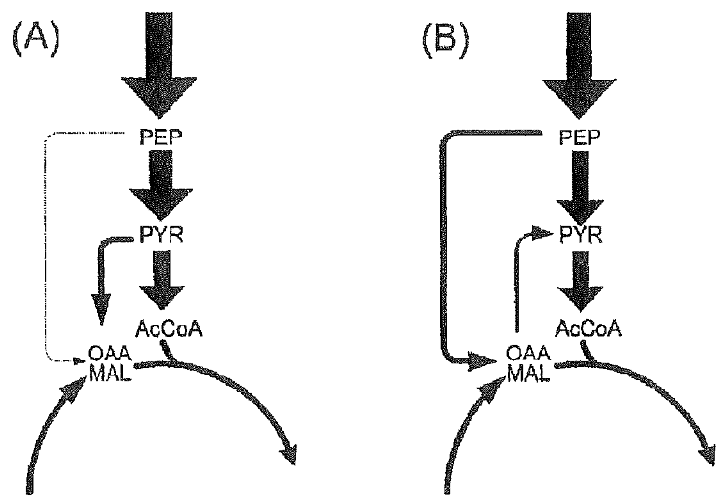
Fig. 24
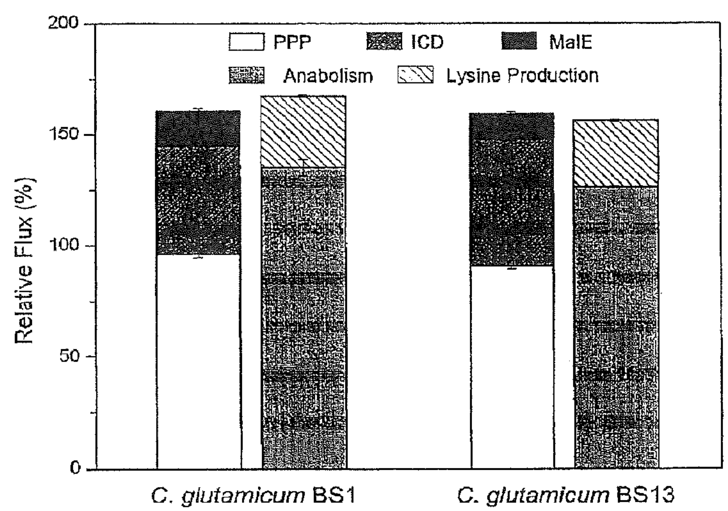
Fig. 25
| | | | | |
|---|---|---|---|---|
| pClik int sacB PDH | GGAGGTGTGGAA | G | TGGCCGATCAAGCAA | SEQ ID NO: 97 |
| Clone 2 | GGAGGTGTGGAA | G | TGGCCGATCAAGCAA | SEQ ID NO: 98 |
| Clone 4 | GGAGGTGTGGAA | G | TGGCCGATCAAGCAA | SEQ ID NO: 99 |
| BS87 | GGAGGTGTGGAA | A | TGGCCGATCAAGCAA | SEQ ID NO: 100 |

Fig. 26
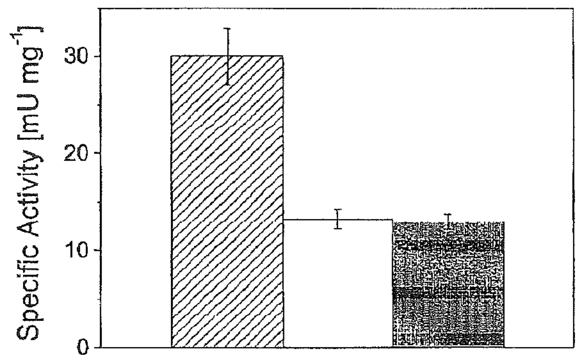
Fig. 27
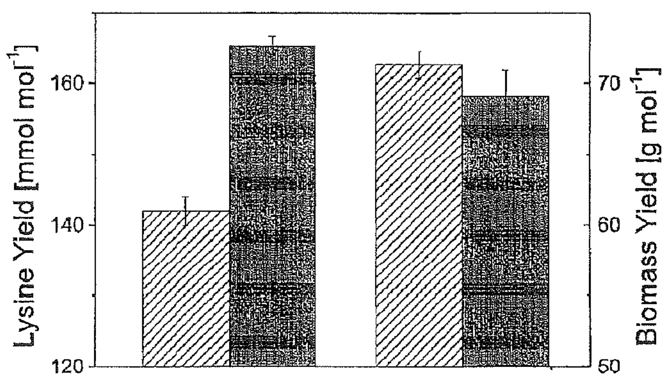
Fig. 28
| | | | | |
|---|---|---|---|---|
| pClik int sacB ICD | ATCAACCAAGGAGACTC | G | TGGCTAAGATCATCT | SEQ ID NO: 101 |
| Clone 1 | ATCAACCAAGGAGACTC | G | TGGCTAAGATCATCT | SEQ ID NO: 102 |
| Clone 2 | ATCAACCAAGGAGACTC | G | TGGCTAAGATCATCT | SEQ ID NO: 103 |
| Clone 3 | ATCAACCAAGGAGACTC | G | TGGCTAAGATCATCT | SEQ ID NO: 104 |
| Clone 5 | ATCAACCAAGGAGACTC | G | TGGCTAAGATCATCT | SEQ ID NO: 105 |
| BS87 | ATCAACCAAGGAGACTC | A | TGGCTAAGATCATCT | SEQ ID NO: 106 |

[Fig. 29]
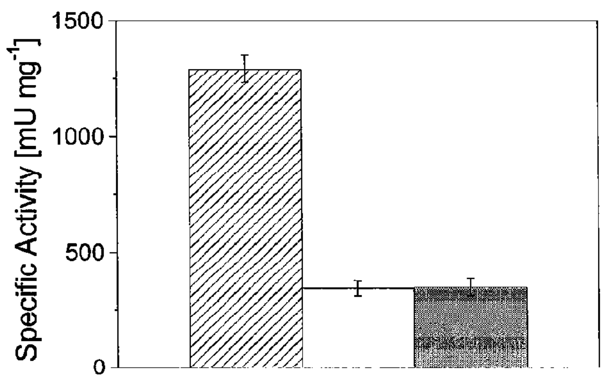
[Fig. 30]
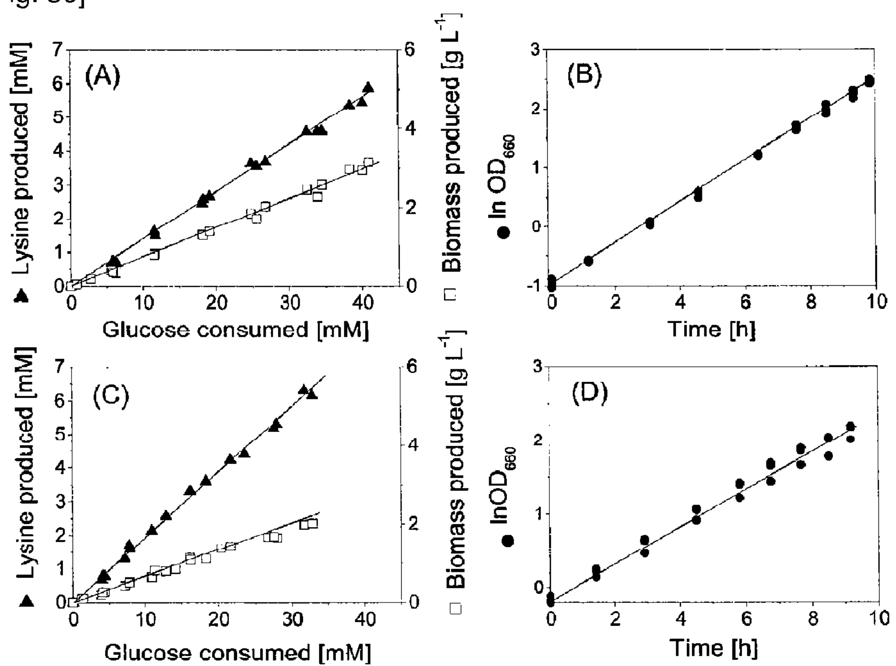
[Fig. 31]
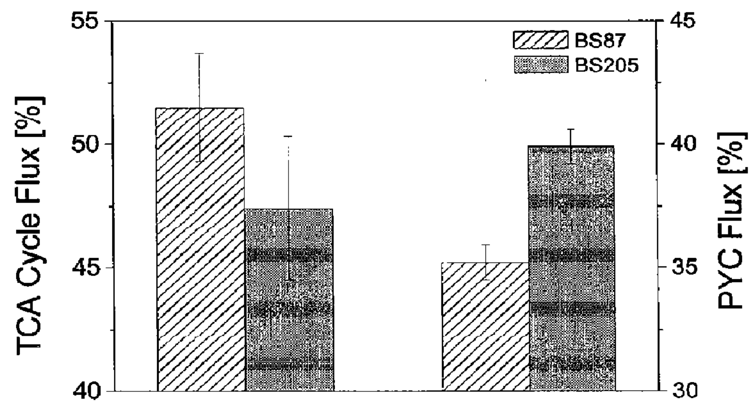

[Fig. 32]
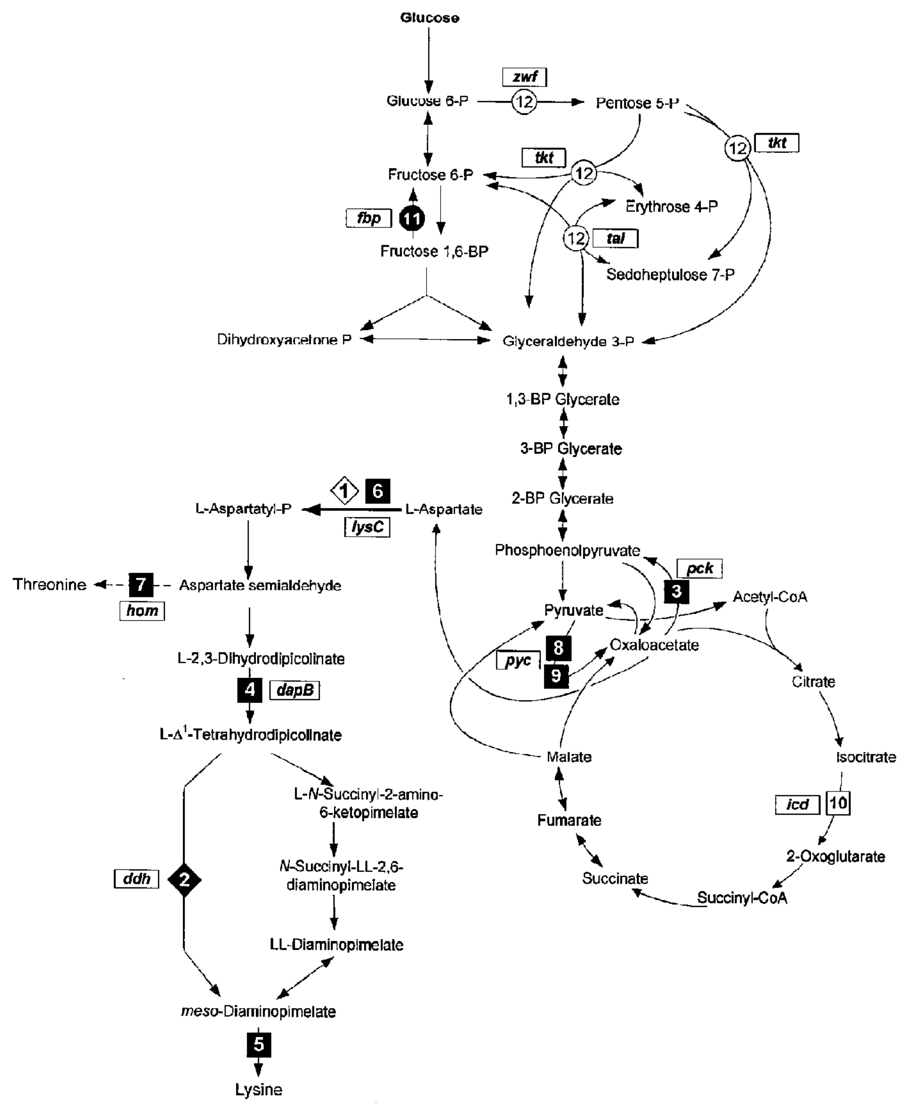
[Fig. 33]
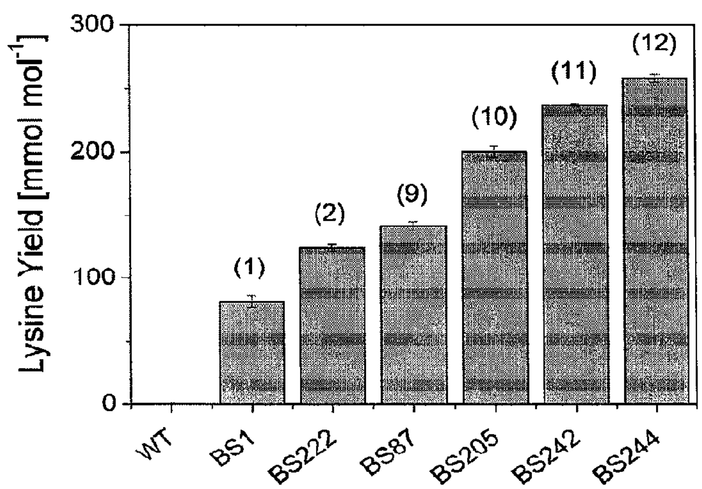

[Fig. 34]
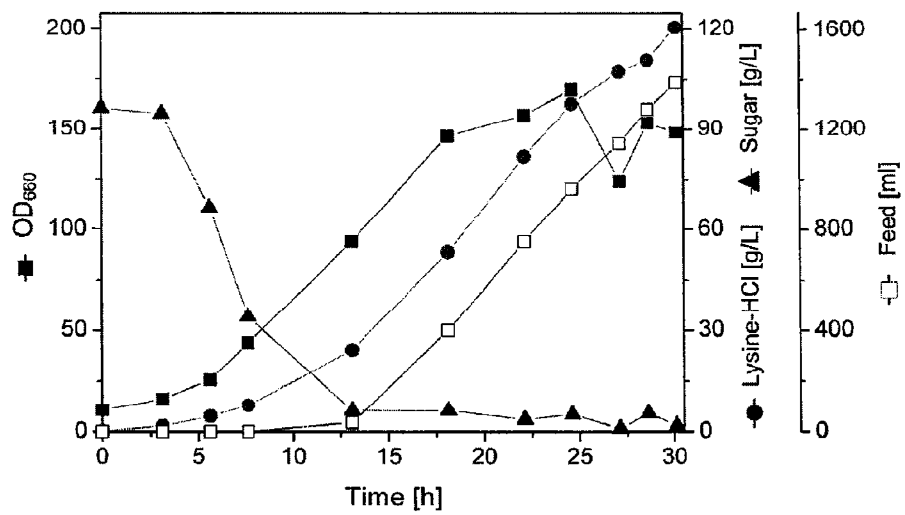
[Fig. 35]
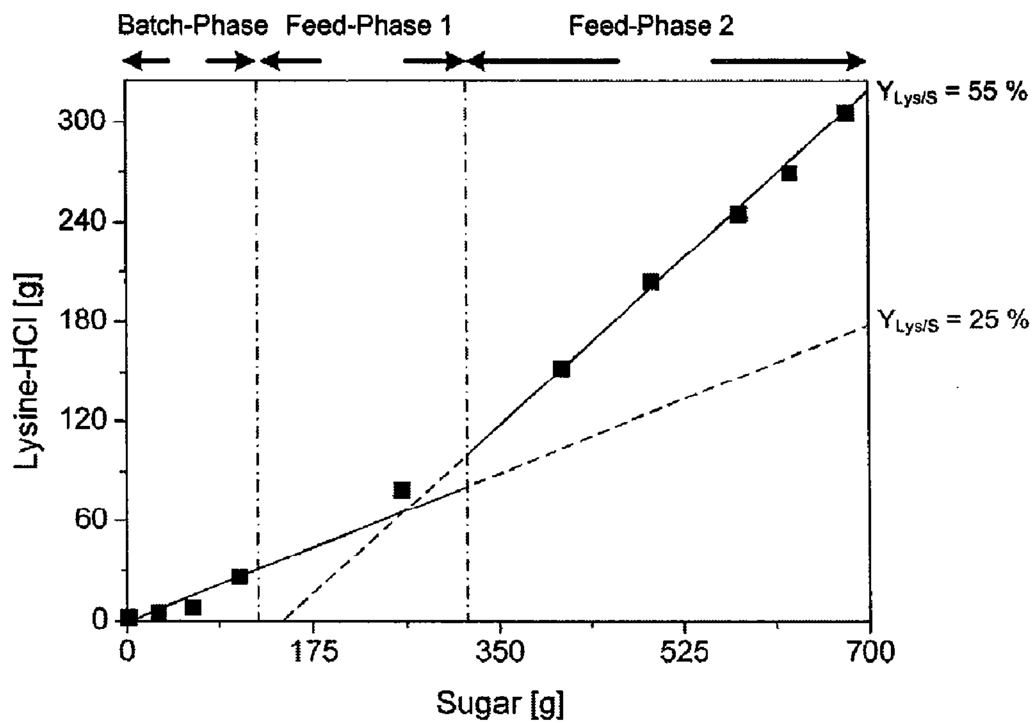

METHOD OF PRODUCING L-LYSINE USING A *CORYNEBACTERIUM GLUTAMICUM* MICROORGANISM

CROSS-REFERENCE TO RELATED APPLICATIONS

This application is a National Stage of International Patent Application No. PCT/KR2010/003820, filed Jun. 15, 2010, the content of which is incorporated herein by reference in its entirety.

TECHNICAL FIELD

The present invention is directed to a method for the production of amino acids of the aspartate family, in particular L-lysine, and precursors thereof, utilizing a recombinant microorganism. Furthermore, the present invention relates also to a recombinant microorganism having modified pathways involved in the synthesis of amino acids of the aspartate family in comparison to the initial microorganism and the use of such microorganism in producing amino acids of the aspartate family, particularly L-lysine, and precursors.

BACKGROUND ART

Amino acids and their derivatives are important precursors in the pharmaceutical industry and added to a wide variety of food and feed as supplements. Several amino acids, such as glutamate, lysine and threonine are produced using their natural biosynthetic pathways. In natural amino acid biosynthesis the amino acid aspartate serves as the precursor for the production of other amino acids, such as lysine, threonine, isoleucine and methionine.

With a world-market of 900,000 t/a, the essential amino acid L-lysine is one of the most important biotechnological fermentation products (Kohl and Tauch, 2009). It is mainly applied as supplement to animal feed (Anastassiadis, 2007). Supplementation of such feed materials with a lysine rich source leads to optimized growth of e.g. pigs or chicken. The continuing increase in consumption of white meat has led to an increased demand for lysine during the past decades.

Lysine can be produced by e.g. fermentation methods. For this purpose, certain microorganisms such as *C. glutamicum* have been proven to be particularly suited. Fermentation as technique for the industrial production of amino acids emerged with the discovery of the glutamate secreting bacterium *Corynebacterium glutamicum*. Within a few years from its discovery, the first lysine excreting mutants of *C. glutamicum* were applied for large scale production (Kinoshita, et al., 1961). Research continues to be directed towards new technologies to establish high-efficient fermentation including optimization of the fermentation procedure, down-stream processing as well as strain engineering.

Classically strains were engineered by an iterative approach of random mutagenesis with UV light or chemical mutagens and subsequent strain selection. The key to success in these days was the use of toxic lysine analogues, such as S-(2-aminoethyl) cysteine, to select for feedback resistant strains (Nakayama and Araki, 1973). These classical strains typically shared point mutations in the aspartokinase gene, which release the encoded enzyme from feedback inhibition by lysine and threonine (Kalinowski, et al., 1991; Thierbach, et al., 1990). Remarkable production properties such as a conversion yield up to 50% and a lysine•Cl titre of 100 g $L^{-1}$ are achieved with such classically derived strains (Leuchtenberger, et al., 2005). This was, however, typically linked to extensive fermentation times of 2-3 days, limiting productivity. Additionally, auxotrophy and the weak stress tolerance, resulting from undesired mutations which accumulated during strain development (Ohnishi, et al., 2002), further display severe disadvantages of conventional production strains. In recent years, recombinant DNA technology and molecular biology initiated a new era of strain engineering-rational optimization by metabolic engineering (Ikeda, et al., 2006). Many of these studies have focused on optimization of the flux through the lysine biosynthesis by directly modifying enzymes of this pathway. The release of aspartate kinase from feedback control is today regarded as one of the most important features of industrial production strains. Beside modifications concerning pathway regulation, the intracellular activity of rate determining enzymes of the biosynthetic pathway is a key point for strain engineering. Strategies for increasing enzyme activity within the cell involve overexpression by the use of stronger promoters, mutating the promoter sequences or regulatory regions upstream of the gene, or increasing the copy number of the coding gene. Plasmid-related overexpression in this context is appropriate to achieve higher enzyme activities and better lysine yields (Eggeling, et al., 1998) but can hardly be applied in an industrial process.

Identification of beneficial targets apart from the biosynthetic pathway itself became soon necessary to abolish bottlenecks within the precursor and co-factor supply towards creation of competitive production strains. This is, however, more challenging and difficult as it requires understanding of the organism on a systems level. In this regard, the availability of the genome sequence of *Corynebacterium glutamicum* has been a mile stone for metabolic engineering (Haberhauer, et al., 2001; Kalinowski, et al., 2003; Ohnishi, et al., 2002; Pompejus, et al., 2002). It provided the basis for (i) genome breeding by comparative sequence analysis between classically derived production strains and the wild type (Ohnishi, et al., 2002), (ii) a detailed in silico reconstruction of the metabolic network of *C. glutamicum* (Kjeldsen and Nielsen, 2009) including stoichiometric modelling approaches to analyze the theoretical production capacity as well as metabolic pathways involved (Kromer, et al., 2006; Wittmann and Becker, 2007), and (iii) the discovery of transcriptional regulatory networks by means of specific sequence motives within the genome (Kohl and Tauch, 2009). These models, however, are not applicable to predict the activity of the metabolic pathways in vivo, i.e. the fluxome, as key characteristic for systems understanding and guidance of strain engineering. Flux analysis is a central element of metabolic engineering (Stephanopoulos, 1999), as indicated by the impressive progress to estimate metabolic fluxes in vivo (Christensen and Nielsen, 2000; Christensen, et al., 2000; Frick and Wittmann, 2005; Van Dien, et al., 2006; Wittmann, 2007; Wittmann and Heinzle, 2002). Beyond the insight into the biological system, 13C metabolic flux analysis has proven useful for strain characterization and identification of beneficial targets for lysine production (Kiefer, et al., 2004; Wittmann and Heinzle, 2002). Together with complementary findings from determination of the active set of genes (transcriptome) (Hayashi, et al., 2006) and proteins (proteome) (Bendt, et al., 2003) and from quantification of intracellular metabolite levels (metabolome) (Borner, et al., 2007) an extensive data set is provided to gain a deep insight into cell physiology on a global level. This systems-oriented approach displays an excellent platform for metabolic engineering (Lee, et al., 2005).

The major lysine-producing microorganism *Corynebacterium glutamicum* was discovered in the 1950s in a large screening program in Japan. Strains were successively optimized for lysine production using an iterative process of random mutagenesis and screening for improved production characteristics. This resulted in efficient production strains but also led to an accumulation of side-mutations causing impaired growth, weak stress tolerance or increased nutrition demands. Accordingly, the production performance currently obtained is significantly below the theoretical capacity predicted for *C. glutamicum*. The progress in molecular biology and systems-oriented tools for the analysis of the metabolism and regulatory state of the cell nowadays shifts strain engineering to a more precise and targeted optimization systems metabolic engineering. This aims at superior hyper-producing strains with exclusive sets of beneficial modifications exhibiting increased production yield, titre and productivity.

In the past, various attempts have been made to increase the production of L-lysine using microorganisms. General attempts to increase production of e.g. methionine or lysine by up- and/or downregulating the expression of genes being involved in the biosynthesis of methionine or lysine are e.g. described in WO 02/10209, WO 2006/008097, and WO 2005/059093.

The central catabolic network, previously identified in *C. glutamicum*, comprises the pathways of glycolysis, pentose phosphate pathway (PPP), tricarboxylic acid (TCA) cycle and glyoxylate shunt.

WO 03/042389 relates to a genetically modified microorganism into which a G6PD gene (zwf) has been introduced or in which a G6PD gene has been modified, and the use of such microorganism in preparing a compound of interest, such as an amino acid, particularly preferably lysine.

WO 0220542 relates to a process for the fermentative preparation of L-amino acids, in particular L-lysine, in which the metabolic pathways which reduce the formation of the desired L-amino acid are at least partly eliminated are employed, e.g. using an enhanced gap2 gene. A long list of additional genes that may be modified is mentioned as well.

EP 0435132 discloses microorganisms of the genus *Corynebacterium* or *Brevibacterium* which contain a recombinant DNA and are suitable for obtaining amino acids, especially L-lysine. The DNA sequences are derived, in particular, from L-lysine-producing strains of the genus *Corynebacterium* or *Brevibacterium*, preferably from a mutant obtained by mutagenesis of *Corynebacterium glutamicum* ATCC 13032 with reduced feedback inhibition of aspartate kinase.

EP1067193 discloses an L-lysine producing coryneform bacterium (A) with an amplified pyc (pyruvate carboxylase) gene in which at least one of the additional genes dapA (dihydropicolinate synthase), lysC (aspartate kinase), lysE (lysine exportercarrier) and/or dapB (dihydropicolinate reductase) is amplified, preferably over-expressed.

EP0854189 discloses a coryneform bacterium harboring an aspartokinase in which feedback inhibition by L-lysine and L-threonine is substantially desensitized, and comprising an enhanced DNA sequence coding for a dihydrodipicolinate reductase, an enhanced DNA sequence coding for dihydropicolinate reductase, an enhanced DNA sequence coding for dihydropicolinate synthase, an enhanced DNA sequence coding for diaminopimelate decarboxylase and an enhanced DNA sequence coding for aspartate aminotransferase.

EP0857784 relates to a DNA comprising aspartokinase gene free from feed back inhibition by L-lysine, etc., and containing diaminopimelic acid decarboxylase gene and improved in L-lysine-producing ability of a coryneform bacterium.

WO/2007/017526 discloses a process for the preparation of a aspartate and derived amino acids like lysine, threonine, isoleucine, methionine, or homoserine employing microorganism with enhanced isocitrate lyase and/or malate synthase expression.

DISCLOSURE OF INVENTION

Technical Problem

The main objective of the invention was the optimization of lysine production by rational strain engineering. As a model microorganism, *Corynebacterium glutamicum* was used in a systems-oriented approach. As the raw material costs account for the major production costs in industrial lysine production, strain optimization aimed at an increasing lysine yield, titre and productivity. The central strategy aimed at state-of-art technologies to unravel the metabolic and regulatory state of *C. glutamicum* on a systems oriented level and use the obtained knowledge to identify genetic targets towards optimal production performance. In *C. glutamicum* lysine biosynthesis is closely connected to the central metabolism via the requirement of the carbon precursors and NADPH as reducing power. Due to this, the study included the reactions of the central metabolic pathways as promising targets for strain optimization. The strategies focussed mainly on the NADPH metabolism, TCA cycle, engineering of oxaloacetate supply as well as lysine biosynthesis. First, the value of several engineering strategies towards improved lysine production was investigated by target evaluation in lysine producing strains. The inventive strains have been investigated in detail by comparative cultivation experiments as well as on the level of transcriptome, metabolome, and fluxome to (i) gain a deep insight into the cellular physiology, (ii) to estimate the benefit of the applied strategy with regard to industrial application and (iii) to provide valuable information for the rational design of a production strain.

Furthermore, modifications of the biosynthesis pathways, particularly the NADPH metabolism, the TCA cycle, the engineering of oxaloacetate supply in microorganisms according to the present invention are of importance not only for the production of L-lysine, but are relevant also for the production of other amino acids of the aspartate family and precursors thereof. Further members of the family of apartate-derived amino acids, such as methionine, threonine or isoleucine may therefore also be produced taking into account the information provided herein.

These and other objectives as they will become apparent from the ensuing description of the invention are solved by the present invention as described in the independent claims. The dependent claims relate to preferred embodiments.

Solution to Problem

The invention relates particularly to the creation of aspartate derived amino acid hyper-producing microorganism, preferably lysine hyper-producing microorganism strains based on the wild type of *C. glutamicum* and to methods using the same. Such strains have been obtained by beneficial modifications identified in this work. The tailor-made cell factory has a high carbon conversion yield as well as a high space-time yield, a high final lysine titre, good growth behaviour and preferably also a reduction in formed by-products. These production characteristics ensure a fast and efficient conversion of the supplied substrates and thus a cost-effective production of lysine.

Furthermore, the production of aspartate derived amino acids, preferably L-lysine, is improved using genetically modified microorganisms, preferably *Corynebacterium*, more preferably *C. glutamicum.*

In a preferred method for the production of aspartate derived amino acids, more preferably in the production of L-lysine, a microorganism with e.g. modified lysine biosynthesis and modified lysine precursor supply is used. Preferably, the microorganism is a recombinant microorganism. In a particularly preferred embodiment, the microorganism may have a modified, e.g. increased glucose 6-phosphate dehydrogenase gene and enzyme activity. More preferably, the modified glucose 6-phosphate-dehydrogenase gene (zwf) comprises a modified promoter, preferably a replacement of the wild-type promoter of the zwf-gene by a heterologous, i.e. non-natural promoter, more preferably the promoter of superoxide dismutase (sod). The non-natural promoter may be derived from the same organism, but from another gene or from a different species. Still more preferably, the microorganism comprises also the point mutation A243T in the zwf gene. In a further preferred embodiment, the microorganism comprises a modified tkt-operon, wherein the wild-type promoter of the tkt-operon has been replaced by a heterologous promoter, preferably by the sod promoter, resulting also in an increased activity of the glucose 6-phosphate dehydrogenase gene and enzyme, respectively. Using the strong sod-promoter, the zwf-gene may also be over-expressed by overexpression of the tkt-operon that comprises, inter alia, the transketolase-gene (tkt), the gene encoding transaldolase (tal) and zwf.

In yet another preferred embodiment, the microorganism further has also an increased activity of fructose 1,6-bisphosphatase gene and enzyme (fbp). This objective is fulfilled by a microorganism that, in addition to the above modifications, comprises a strong heterologous promoter, e.g. the sod-promoter or, preferably, the eftu-promoter, replacing the original promoter.

It is also preferred that the microorganism further comprises an attenuated isocitrate dehydrogenase gene (icd) and a correspondingly decreased enzyme activity, preferably through substitution of the original ATG start codon by a GTG start codon.

In a still more preferred embodiment, the microorganism further has an increased diamionopimelate dehydrogenase gene and enzyme activity. This can be achieved, e.g. by overexpression of the corresponding gene encoding diaminopimelate dehydrogenase (ddh). More preferably, diaminopimelate dehydrogenase is overexpressed by a microorganism that comprises at least one additional copy of the ddh-gene.

Moreover, it is particularly preferred that the microorganism in addition to the above modifications comprises a modified aspartate kinase (lysC) with increased gene and enzyme activity, preferably through the amino acid exchange T311I.

Preferred embodiments relate to micrororganisms comprising in addition to the above described modifications at least one of the following modifications: (i) overexpression of dihydropicolinate reductase (dapB), diaminopimelate decarboxylase (lysA), (ii) modification of homoserine dehydrogenase by introduction of a mutant variant comprising the amino acid exchange V59A, (iii) overexpression and modification of pyruvate carboxylase, and (iv) deletion of PEP carboxykinase.

The microorganism, which is preferably used in the methods according to the invention is *Corynebacterium glutamicum*, preferably a derivative of *C. glutamicum* ATCC13032, more preferably a microorganism deposited according to the Budapest Treaty at the Deutsche Sammlung von Mikroorganismen and Zellkulturen GmbH (DSMZ), Germany, 11 May 2010 and which has the deposit number DSM 23586.

Advantageous Effects of Invention

In accordance with the present invention, the inventive microorganisms are suitable for the use in a method of producing asparatate-derived amino acids, preferably L-lysine. Further preferred aspects of the invention can be derived from the following detailed description and the examples.

The cells used in the production method may be prokaryotes, lower eukaryotes, isolated plant cells, yeast cells, isolated insect cells or isolated mammalian cells, in particular cells in cell culture systems. In the context of present invention, the term "microorganism" is used for said kinds of cells. A preferred kind of microorganism for performing the present invention is a *Corynebacterium* and particularly preferably a *C. glutamicum.*

Figure 8:
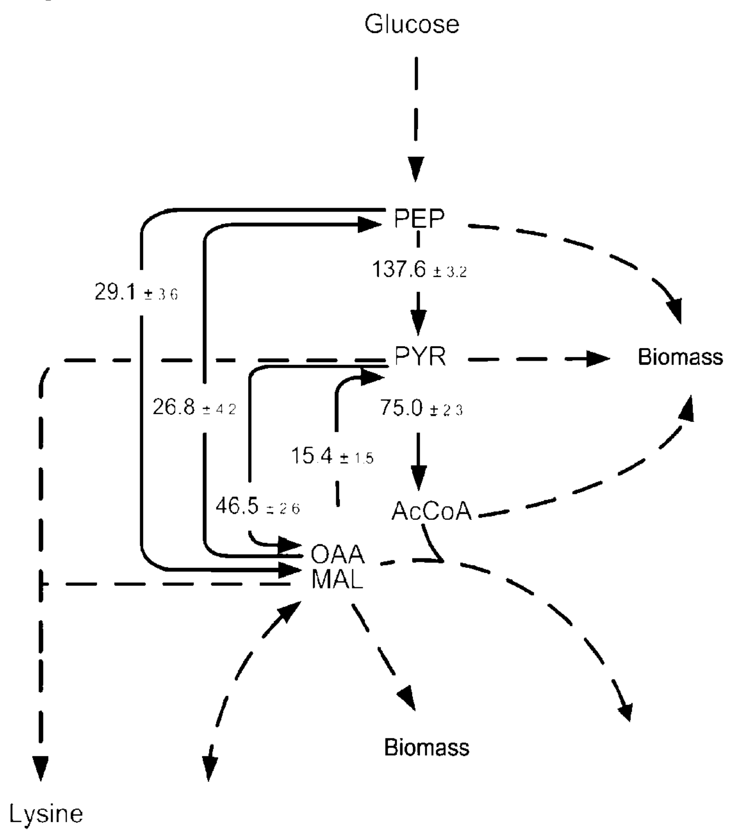

FIG. 8: Carbon flux distribution at the pyruvate node of lysine-producing *C. glutamicum* BS 1 during growth on glucose. All fluxes are given as a molar percentage of the specific glucose uptake rate of qGlc=4.6 mmol $g^{-1}$ $h^{-1}$, which is set to 100%. The errors reflect the corresponding 90% confidence intervals for the different fluxes, obtained by a Monte-Carlo analysis.

Figure 9:
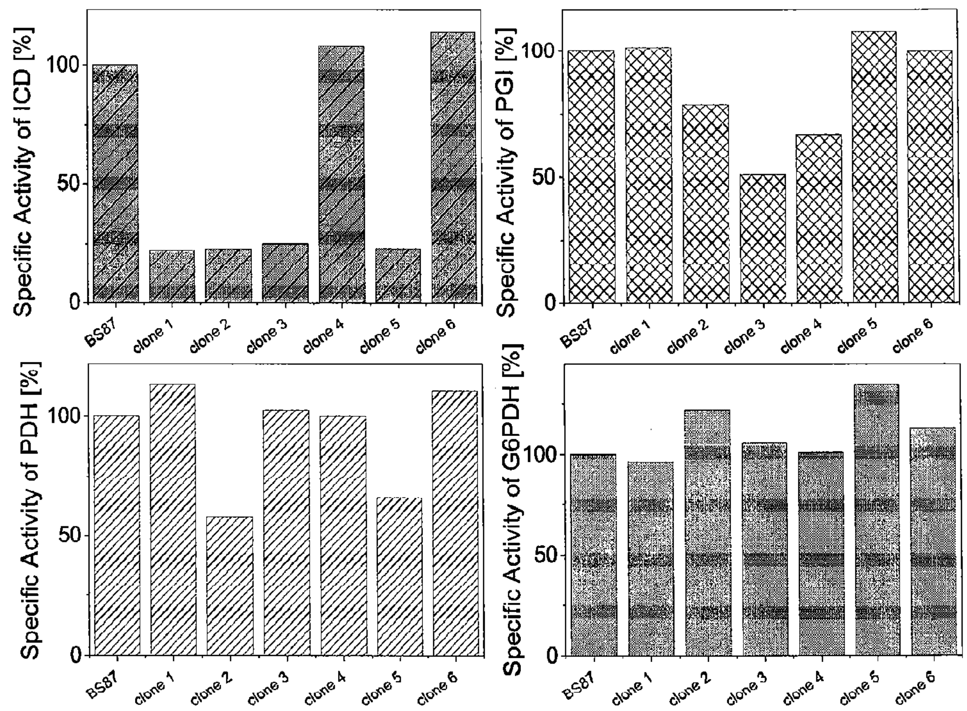

FIG. 9: Specific activity of isocitrate dehydrogenase (ICD), phosphoglucoisomerase (PGI) pyruvate dehydrogenase (PDH) and glucose 6-phosphate dehydrogenase (G6PDH) in crude cell extracts of *C. glutamicum* BS87 and 6 mutants from the second recombination event as possible candidates for nucleotide exchange. Data represent single measurement of cells grown in complex medium.

Figure 10:
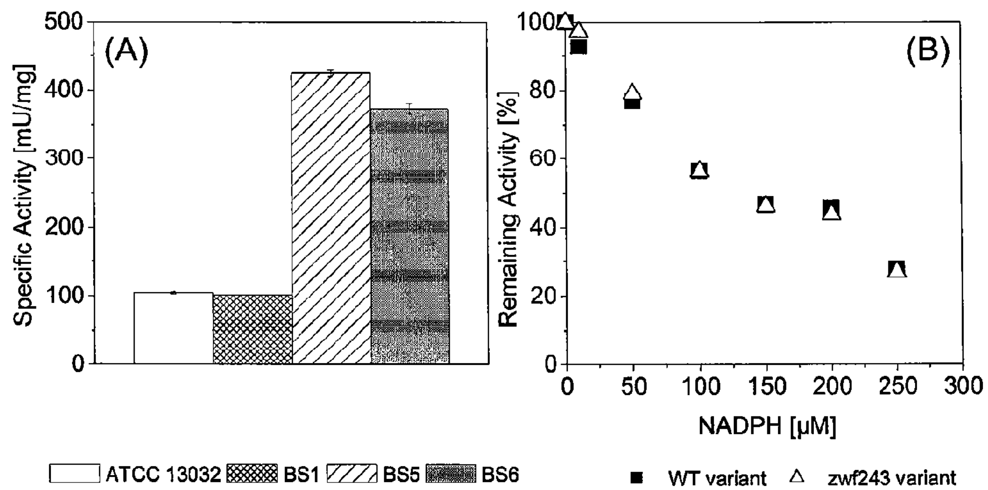

FIG. 10: Specific in vitro activity of G6P dehydrogenase in the strains *C. glutamicum* ATCC 13032, BS1 (lysCT311I), BS5 (Psodzwf) and BS6 (PsodzwfA243T) (A); specific in vitro activity [%] of the wild type and the A243T variant by addition of NADPH as inhibitor (B). The data represent mean values from three different measurements of cell extracts from cells grown in minimal medium with glucose as carbon source and corresponding deviations.

Figure 11:
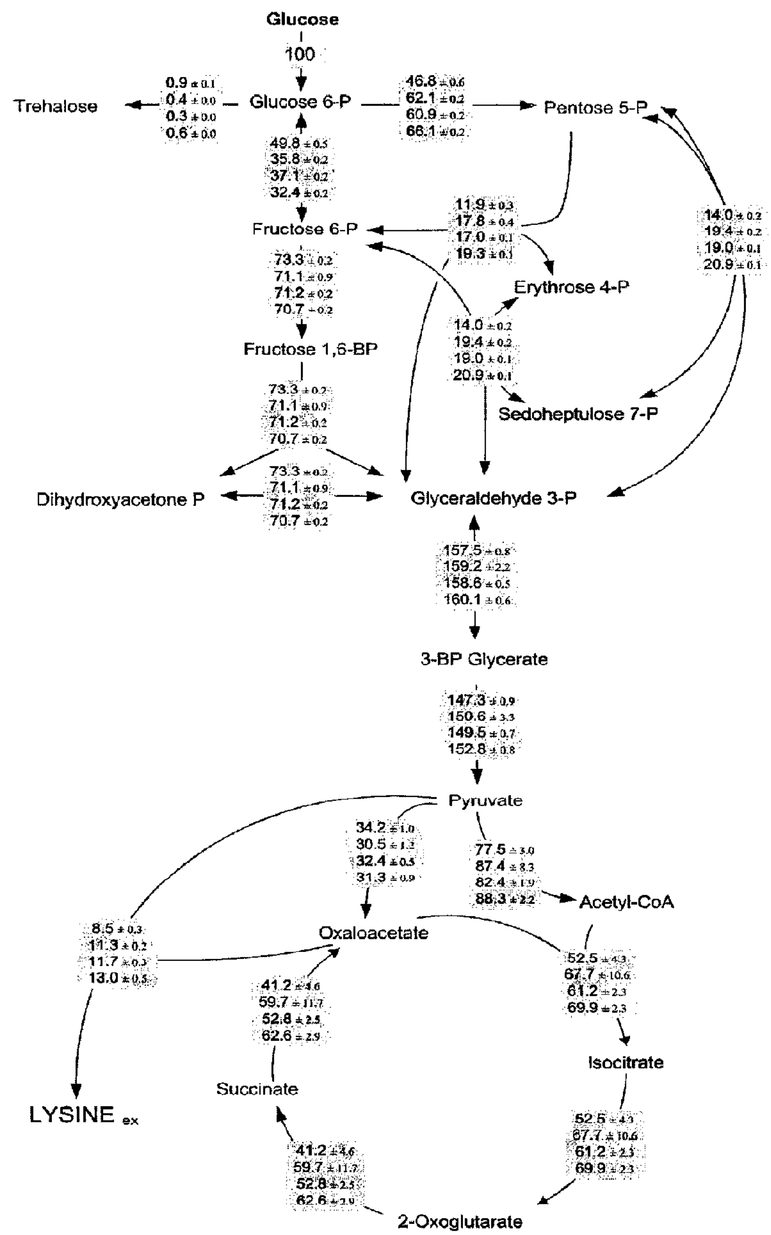

FIG. 11: Intracellular fluxes and corresponding 90% confidence intervals for *C. glutamicum* BS1, *C. glutamicum* BS5, *C. glutamicum* BS6 and *C. glutamicum* BS7 (from top to bottom) cultivated on [1-$^{13}$C] glucose. The data are given as relative values (in %) normalized to the glucose uptake rate (Table 15). The flux data for the reference strain *C. glutamicum* BS1 are taken from (Becker, et al., 2005).

Figure 12:
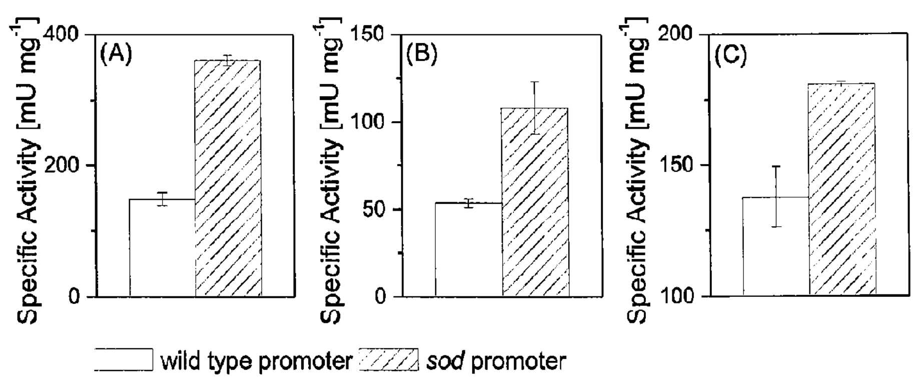

FIG. 12: Specific activity of glucose 6-phosphate dehydrogenase (A), transaldolase (B) and transketolase (C) in response to overexpression of the tkt-operon by the promoter of superoxide dismutase (sod).

Figure 13:
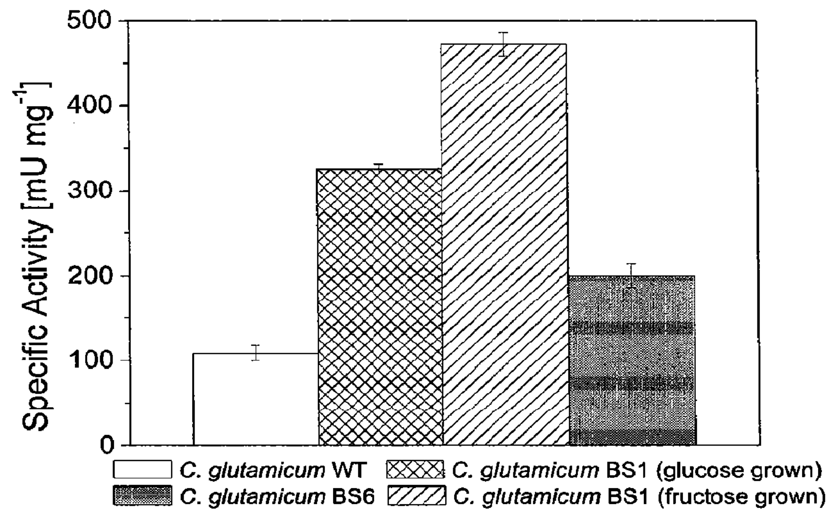

FIG. 13: Specific activity of malic enzyme in crude cell extracts of *C. glutamicum* WT, *C. glutamicum* BS1 (lysCT311I) and *C. glutamicum* BS6 (PsodzwfA243T) grown on glucose or fructose, respectively. Determination was performed in triplicate and corresponding deviations are given.

Figure 14:
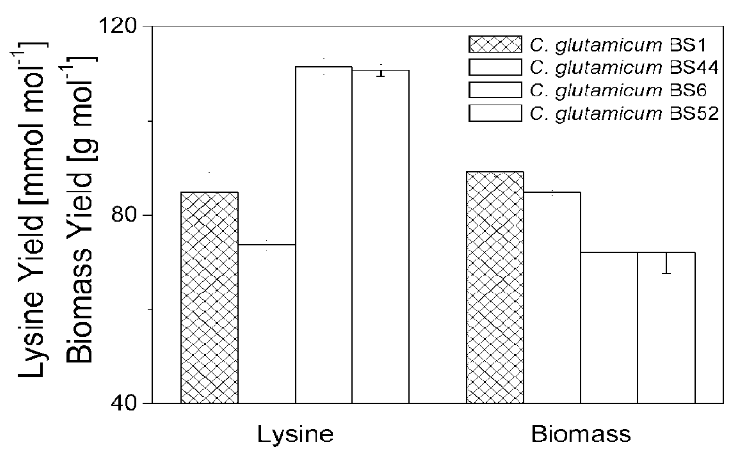

FIG. 14: Production characteristics of different lysine-producing strains of *C. glutamicum* during batch cultivation on glucose. Yields were determined as slope of the linear best fit between biomass or lysine formation, respectively, and substrate consumption over the whole cultivation time. Yields were determined from three biological replicates.

Figure 15:
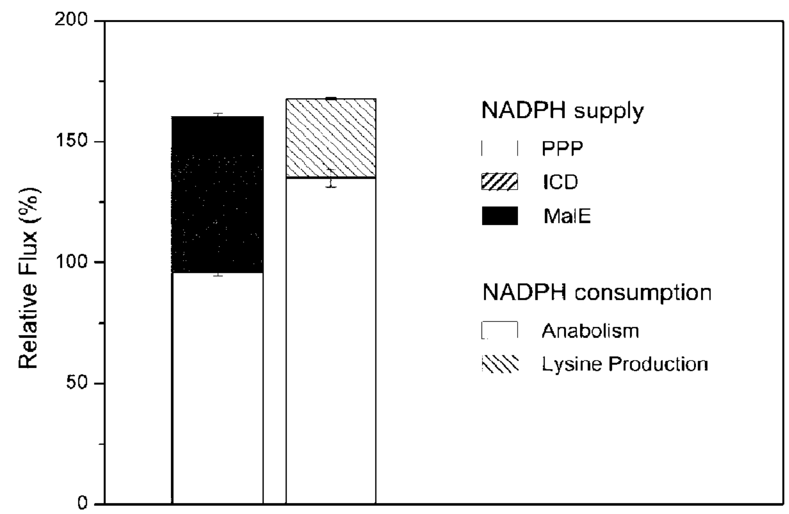

FIG. 15: NADPH balance of *C. glutamicum* BS1 (lysC$^{T311I}$) calculated from the in vivo fluxes considering PPP, isocitrate dehydrogenase and malic enzyme as NADPH providing reaction and biomass formation an lysine secretion as NADPH consuming reactions.

Figure 16:
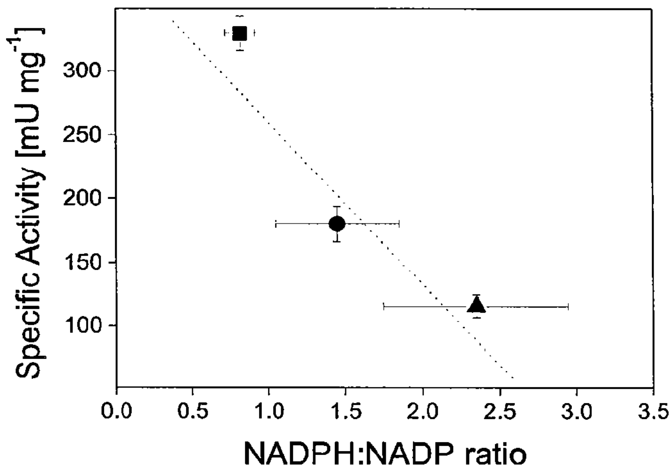

FIG. 16: Correlation between NADPH/NADP ratio and specific malic enzyme activity in *C. glutamicum* ATCC 13032 (triangle), *C. glutamicum* BS1 (lysC$^{T311I}$) (square) and *C. glutamicum* BS6 ($P_{sod}$zwf$^{A243T}$) (circle).

Figure 17:
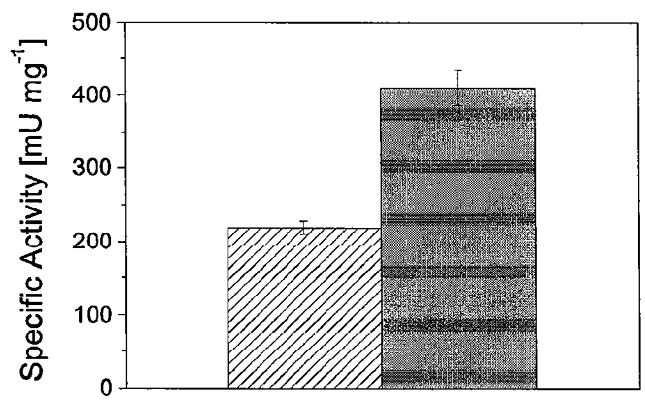

FIG. 17: Specific activity of diaminopimelate dehydrogenase in crude cell extracts of *C. glutamicum* BS1 (striped column) and *C. glutamicum* BS222 (grey column) grown in standard minimal medium using glucose as sole carbon source.

Figure 18:
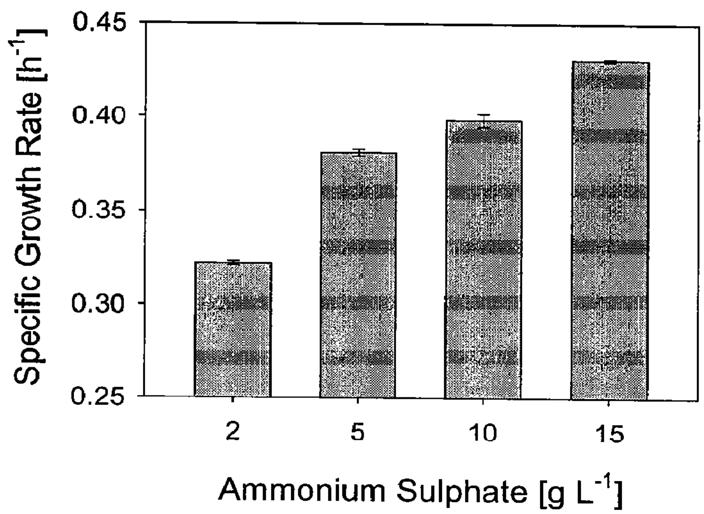

FIG. 18: Specific growth rate of *C. glutamicum* BS1 (lysC$^{T311I}$) at different ammonium sulphate concentrations.

Figure 19:
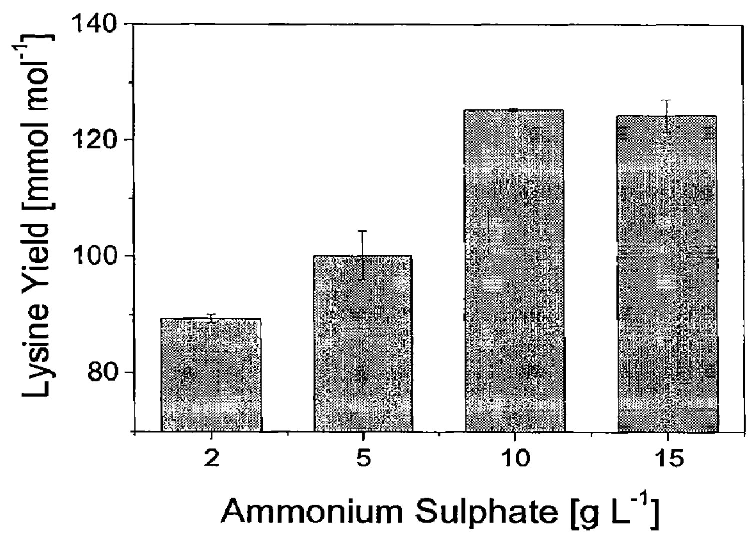

FIG. 19: Lysine yield of *C. glutamicum* BS222 grown in minimal medium at varied ammonium sulphate concentrations.

Figure 20:
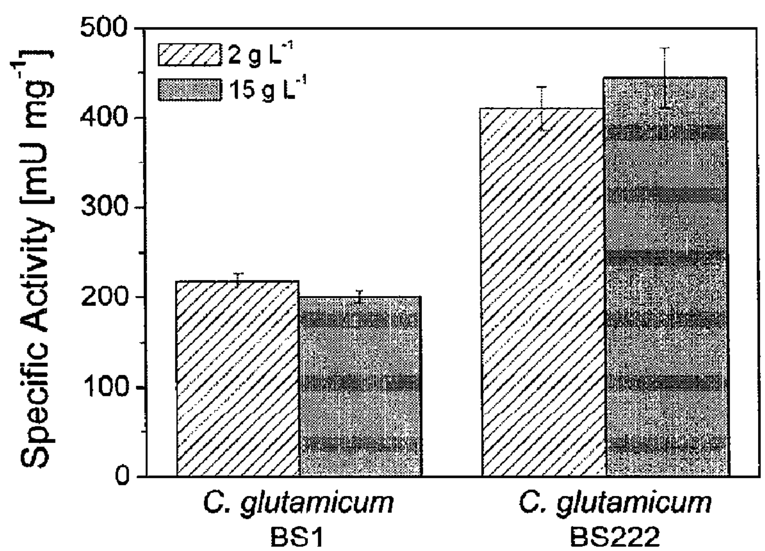

FIG. 20: Specific activity of diaminopimelate dehydrogenase of *C. glutamicum BS*1 and *C. glutamicum* BS222 at 2 g $L^{-1}$ and 15 g $L^{-1}$ ammonium sulphate, respectively.

Figure 21:
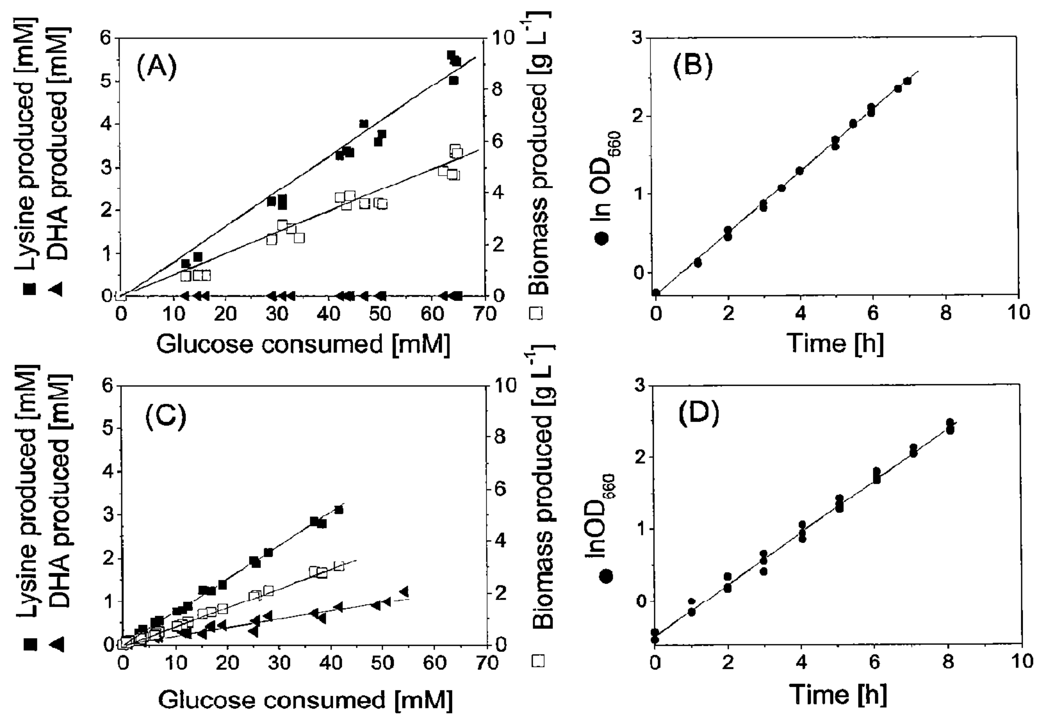

FIG. 21: Quantitative physiological characteristics of lysine-producing *C. glutamicum* BS1 (A, B) and its pyk deletion derivative BS13 (C, D) in batch culture on glucose. The linear correlation between growth, production of lysine and dihydroxyacetone (DHA) and consumption of glucose indicates metabolic steady-state during the cultivation.

Figure 22:
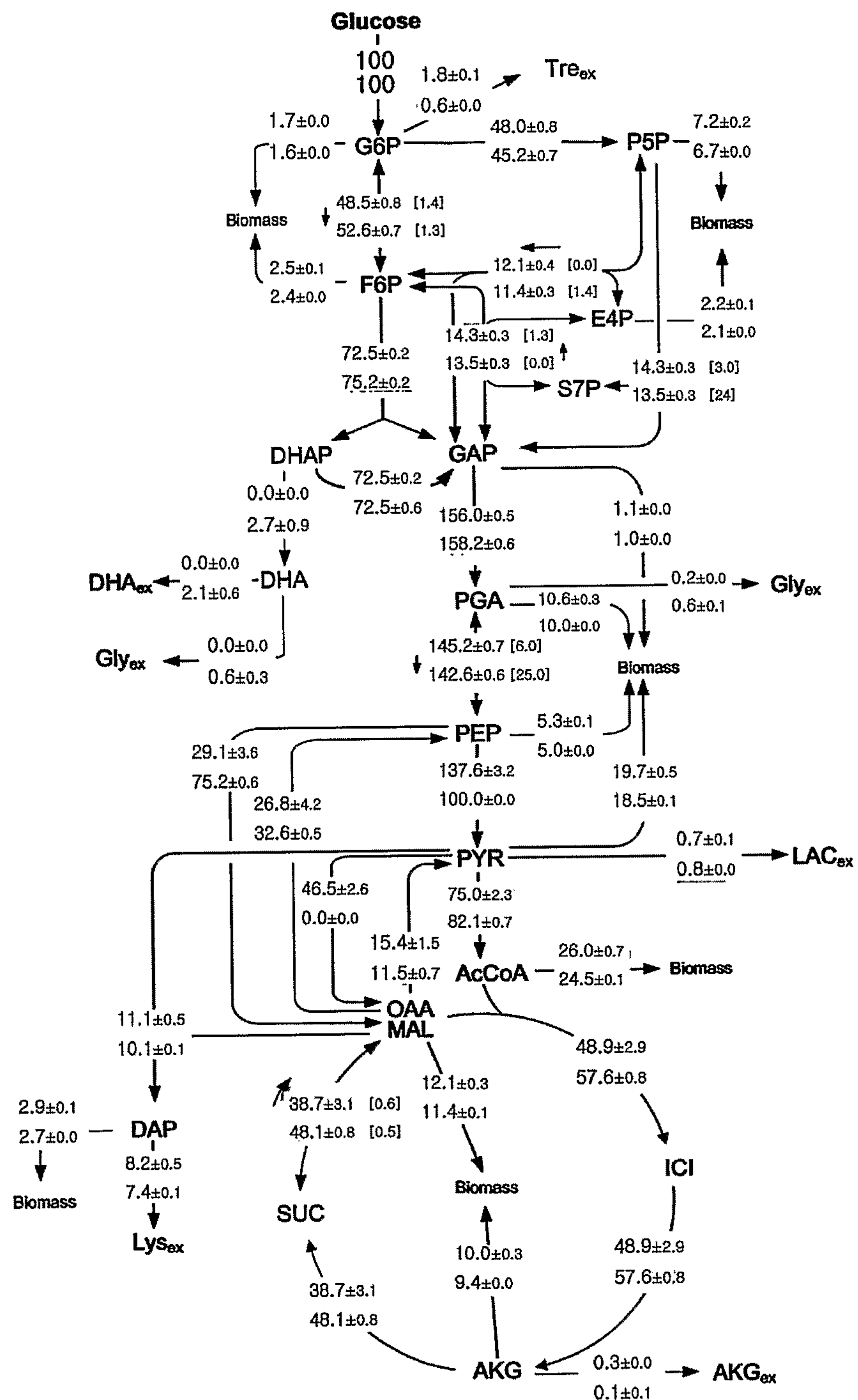

FIG. 22: In vivo carbon flux distribution in the central metabolism of lysine-producing *C. glutamicum* BS1 (top) and its pyruvate kinase deficient derivative *C. glutamicum* BS13 (bottom) during growth on glucose. All fluxes are given as a molar percentage of the mean specific glucose uptake rate of qGlc=4.6 mmol $g^{-1}$ $h^{-1}$ (for BS1) and 4.5 mmol $g^{-1}h^{-1}$ (for BS13), which is set to 100%. For reversible metabolic reactions, the flux reversibility is additionally given in brackets and the direction of the net flux is indicated by an arrow.

FIG. 23: Carbon net flux distribution at the pyruvate node of lysine producing *C. glutamicum* BS1 (A) and its pyruvate kinase deficient derivative *C. glutamicum* BS13 (B) cultivated on glucose. The actual flux values are represented by the thickness of the corresponding arrows.

FIG. 24: NADPH balance for *C. glutamicum* BS 1 (left) and its pyruvate kinase deficient derivative *C. glutamicum* BS13 (right).

FIG. 25: Extract of the start codon region from the sequence alignment of the parent strain *C. glutamicum* BS87, two mutants from the second recombination event with reduced specific PDH activity and the transformation vector used for strain construction.

FIG. 26: Specific enzyme activity of pyruvate dehydrogenase in glucose-grown *C. glutamicum* BS87 (striped column) and its aceEatt derivative *C. glutamicum* BS238 (white column). The grey column denotes specific enzyme activity of the start codon mutant after 50 generations of permanent growth in serial batches. Values were determined as triplicate and corresponding deviations are reflected by the error bars.

FIG. 27: Lysine and biomass yield of *C. glutamicum* BS87 (striped column) and *C. glutamicum* BS238 (grey column) determined in minimal medium from three biological replicates. Corresponding deviations are given. Yields were determined as slope of the linear best fit between product formation and substrate consumption.

FIG. 28: Alignment of the start codon region of the icd gene of *C. glutamicum* BS87, the transformation vector for start codon exchange for the icd gene and 4 clones from the second recombination event.

FIG. 29: Specific activity of isocitrate dehydrogenase in crude cell extracts of *C. glutamicum* BS87 (striped column) and *C. glutamicum* BS205 (icdatt) (white column), grown in minimal medium with glucose as sole carbon source. The grey column denotes specific ICD activity of the start codon mutant icd$^{att}$ after growth for 50 generations in serial batches. Data represent mean values from three parallels and corresponding deviations.

FIG. 30: Growth and production characteristics of lysine-producing *C. glutamicum BS*87 (A, B) and *C. glutamicum* BS205 (icd$^{att}$) (C, D) during batch cultivation on glucose. The linear correlation between biomass and lysine production and consumption of glucose, respectively, indicates metabolic steady-state during cultivation. The given data represent values from three biological replicates.

FIG. 31: In vivo fluxes through TCA cycle[a] and pyruvate carboxylase[b] of glucose-grown *C. glutamicum* BS87 and *C. glutamicum* BS205 (icd$^{att}$). The errors reflect the 90% confidence interval, obtained by a Monte-Carlo analysis.

[a] Given as entry flux through citrate synthase.

[b] Given as lumped net flux through anabolic carboxylation.

FIG. 32: Design and construction of a tailor-made lysine hyper-producing strain by pathway engineering. Modifications comprise lysC$^{T311I}$ (1), 2×ddh (2), Dpck (3), P$_{sod}$ dapB (4), 2 lysA (5), P$_{sod}$lysC$^{T311I}$ (6), hom$^{V59A}$ (7), pyc$^{P458S}$ (8), P$_{sod}$pyc$^{P458S}$ (9), icd$^{att}$ (10), P$_{eftu}$fbP (11) and P$_{sod}$tkt (12) which were implemented successively to construct the strains *C. glutamicum* BS1 (open diamond), *C. glutamicum* BS222 (closed diamond), *C. glutamicum* BS87 (closed square), *C. glutamicum* 205 (open square), *C. glutamicum* BS242 (closed circle) and *C. glutamicum* 244 (open circle).

FIG. 33: Lysine yield of a genealogy of wild type based lysine producers tested in shake flasks in minimal medium at 15 g L$^{-1}$ ammonium sulphate and glucose as sole carbon source. Data represent mean values from three biological replicates with corresponding deviations. Strains displayed are *C. glutamicum* WT (ATCC 13032), *C. glutamicum* BS1 (lysC$^{T311I}$) (1), *C. glutamicum* BS222 (ddh) (2), *C. glutamicum* BS87 (9), *C. glutamicum* BS205 (icd$^{att}$) (10), *C. glutamicum* BS242 (P$_{eftu}$fbp) (11) and *C. glutamicum* BS244 (P$_{sod}$tkt) (12).

FIG. 34: Cultivation profile of lysine producing *C. glutamicum* BS244 during fed-batch fermentation on a molasses based complex medium. Sugar concentration is given as lumped concentration of glucose, fructose and sucrose, respectively.

FIG. 35: Two-phase lysine production characteristics of *C. glutamicum* BS244 during fed-batch fermentation. Total lysine production is plotted against total sugar consumption.

BEST MODE FOR CARRYING OUT THE INVENTION

Enzymes and Genes of *C. glutamicum*

The enzymes and genes of *C. glutamicum* with relevance for the present work are listed in Table 1 with corresponding EC number and systematic gene name according to the KEGG database.

TABLE 1

Table 1: Systematic characterization of enzymes and genes of *C. glutamicum* according to the enzyme commission codes and gene nomenclature of the KEGG database.

| Enzyme | EC number | Gene | Locus tag |
|---|---|---|---|
| Pentose Phosphate Pathway | | | |
| Glucose 6-phosphate dehydrogenase | 1.1.1.49 | zwf | NCgl1514 |
| Transaldolase | 2.2.1.2 | lal | NCgl1513 |
| Transketolase | 2.2.1.1 | tkt | NCgl1512 |
| Glycolysis/Gluconeogenesis | | | |
| Fructose 1,6-bisphosphatase | 3.1.3.11 | fbp | NCgl0976 |
| Phosphoglucoisomerase | 5.3.1.9 | pgi | NCgl0851 |
| Pyruvate dehydrogenase (subunit 1) | 1.2.4.1 | aceE | NCgl2167 |
| Pyruvate kinase | 2.7.1.40 | pyk | NCgl2008 |
| TCA cycle/Anaplerosis | | | |
| Isocitrate dehydrogenase | 1.1.1.42 | icd | NCgl0634 |
| Malic enzyme | 1.1.1.40 | malE (mez) | NCgl2904 |
| PEP carboxykinase | 4.1.1.32 | pck | NCgl2765 |
| Pyruvate carboxylase | 6.4.1.1 | pyc | NCgl0659 |

TABLE 1-continued

Table 1: Systematic characterization of enzymes and genes of *C. glutamicum* according to the enzyme commission codes and gene nomenclature of the KEGG database.

| Enzyme | EC number | Gene | Locus tag |
|---|---|---|---|
| Amino acid synthesis | | | |
| Aspartokinase | 2.7.2.4 | lysC | NCgl0247 |
| Diaminopimelate dehydrogenase | 1.4.1.16 | ddh | NCgl2528 |
| Dihydrodipicolinate reductase | 1.3.1.26 | dapB | NCgl1898 |
| Homoserine dehydrogenase | 1.1.1.3 | hom | NCgl1136 |

As used in the context of present invention, the singular forms of "a" and "an" also include the respective plurals unless the context clearly dictates otherwise. Thus, the term "microorganism" can include more than one microorganism, namely two, three, four, five etc. microorganisms of a kind.

The term "about" in context with a numerical value or parameter range denotes an interval of accuracy that the person skilled in the art will understand to still ensure the technical effect of the feature in question. The term typically indicates deviation from the indicated numerical value of +/−10%, preferably +/−5%.

The term "host cell" for the purposes of the present invention refers to any isolated cell that is commonly used for expression of nucleotide sequences for production of e.g. polypeptides or fine chemicals. In particular the term "host cell" relates to prokaryotes, lower eukaryotes, plant cells, yeast cells, insect cells or mammalian cell culture systems.

The term "microorganism" relates to prokaryotes, lower eukaryotes, isolated plant cells, yeast cells, isolated insect cells or isolated mammalian cells, in particular cells in cell culture systems. The microorganisms suitable for performing the present invention comprise yeasts such as *S. pombe* or *S. cerevisiae* and *Pichia pastoris*. Mammalian cell culture systems may be selected from the group comprising e.g. NIH T3 cells, CHO cells, COS cells, 293 cells, Jurkat cells and HeLa cells. In the context of present invention, a microorganism is preferably a prokaryote or a yeast cell. Preferred microorganisms in the context of present invention are indicated below in the "detailed description" section. Particularly preferred are *Corynebacteria* such as *C. glutamicum* and derivatives thereof.

The term "native" is a synonym for "wild type" and "naturally occurring" A "wild type" microorganism is, unless indicated otherwise, the common naturally occurring form of the indicated microorganism. Generally, a wild-type microorganism is a non-recombinant microorganism.

"Initial" is a synonym to "starting." An "initial" nucleotide sequence or enzyme activity is the starting point for its modification, e.g. by mutation or addition of inhibitors. Any "initial" sequence, enzyme or microorganism lacks a distinctive feature which its "final" or "modified" counterpart possesses and which is indicated in the specific context. The term "initial" in the context of present invention encompasses the meaning of the term "native" and in a preferred aspect is a synonym for "native."

Any wild-type or mutant (non-recombinant or recombinant mutant) microorganism may be further modified by non-recombinant (e.g. addition of specific enzyme inhibitors) or recombinant methods resulting in a microorganism which differs for the initial microorganism in at least one physical or chemical property.

In the context of present invention, the initial, non-modified microorganism is designated as "initial microorganism" or "initial (microorganism) strain."

Any modification of activity of a selected gene or enzyme in a microorganism (for example the quantity of nucleic acids or proteins found in modified cells, or the quantity of product generated, e.g. the amount of L-lysine) in comparison to the initial strain with a given activity level is determined by comparison of activity in both microorganisms under comparable conditions using standard methods in molecular biology found in standard textbooks, or methods specifically disclosed in the examples section.

Typically, microorganisms in accordance with the invention are obtained by introducing genetic alterations in an initial microorganism which does not carry said genetic alteration.

A "derivative" of a microorganism strain is a strain that is derived from its parent strain by e.g. classical mutagenesis and selection or by directed mutagenesis.

The term "nucleotide sequence" or "nucleic acid sequence" for the purposes of the present invention relates to any nucleic acid molecule that encodes for polypeptides such as peptides, proteins etc. These nucleic acid molecules may be made of DNA, RNA or analogues thereof. However, nucleic acid molecules made of DNA are preferred.

"Recombinant" in the context of present invention means "being prepared by or the result of genetic engineering" Thus, a "recombinant microorganism" comprises at least one "recombinant nucleic acid or recombinant protein." A recombinant microorganism preferably comprises an expression vector or cloning vector, or it has been genetically engineered to contain the cloned nucleic acid sequence(s) in the endogenous genome of the host cell.

"Heterologous" is any nucleic acid or polypeptide/protein introduced into a cell or organism by genetic engineering with respect to said cell or organism, and irrespectively of its organism of origin. Thus, a DNA isolated from a microorganism and introduced into another microorganism of the same species is a heterologous DNA with respect to the latter, genetically modified microorganism in the context of present invention, even though the term "homologous" is sometimes used in the art for this kind of genetically engineered modifications. However, the term "heterologous" is preferably addressing a non-homologous nucleic acid or polypeptide/protein in the context of present invention. "Heterologous protein/nucleic acid" is synonymous to "recombinant protein/nucleic acid."

The terms "express", "expressing", "expressed" and "expression" refer to expression of a gene product (e.g., a biosynthetic enzyme of a gene of a pathway) in a host organism. The expression can be done by genetic alteration of the microorganism that is used as a starting organism. In some embodiments, a microorganism can be genetically altered (e.g., genetically engineered) to express a gene product at an increased level relative to that produced by the starting microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

A "conservative amino acid exchange" means that one or more amino acids in an initial amino acid sequence are substituted by amino acids with similar chemical properties, e.g. Val by Ala. The ratio of substituted amino acids in comparison to the initial polypeptide sequence is preferably from 0 to 30% of the total amino acids of the initial amino acid sequence, more preferably from 0 to 15%, most preferably from 0 to 5%.

Conservative amino acid exchanges are preferably between the members of one of the following amino acid groups:

- acidic amino acids (aspartic and glutamic acid);
- basic amino acids (lysine, arginine, histidine);
- hydrophobic amino acids (leucine, isoleucine, methionine, valine, alanine);
- hydrophilic amino acids (serine, glycine, alanine, threonine);
- amino acids having aliphatic side chains (glycine, alanine, valine, leucine, isoleucine);
- amino acids having aliphatic-hydroxyl side chains (serine, threonine);
- amino acids having amide-containing side chains (asparagine, glutamine);
- amino acids having aromatic side chains (phenylalanine, tyrosine, tryptophan);
- amino acids having sulfur-containing side chains (cysteine, methionine).

Specifically preferred conservative amino acid exchanges are as follows:

| Native residue | Substituting residue |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term "isolated" means "separate or purified from its organism of origin." More specifically, an isolated cell of a multicellular organism is separate or has been purified from its organism of origin. This encompasses biochemically purified and recombinantly produced cells.

In the context of the present invention, the term "aspartate-derived amino acid" designates the amino acids lysine, methionine, isoleucine and threonine, preferably these amino acids are in L-configuration.

As used herein, a "precursor" or "biochemical precursor" of an amino acid is a compound preceding ("upstream") the amino acid in the biochemical pathway leading to the formation of said amino acid in the microorganism of present invention, especially a compound formed in the last few steps of said biochemical pathway. In the context of present invention, a "precursor" of the amino acid lysine is any intermediate formed during biochemical conversion of aspartate to lysine in a wild-type organism in vivo.

An "intermediate" or "intermediate product" is understood as a compound which is transiently or continuously formed during a chemical or biochemical process, in a not necessarily analytically directly detectable concentration. Said intermediate may be removed from said biochemical process by a second, chemical or biochemical reaction, in particular by a subsequent enzymatic conversion as defined below in the detailed description section. Said subsequent enzymatic conversion preferably takes place in the microorganism according to present invention. In the method according to this preferred aspect, the microorganism comprises at least one heterologous enzyme catalyzing a reaction step in the subsequent conversion of the endogenous intermediate to the final product of the method.

"Carbon yield" is the carbon amount found (of the product) per carbon amount consumed (of the carbon source used in the fermentation, usually a sugar), i.e. the carbon ratio of product to source.

"Modification" or "modified" used within the context of the present invention means that the genome of the microorganisms of the present invention has been altered using methods known in the art such as mutations, deletions, insertions, substitutions, additions of nucleic acid residues via homologous recombination, exchange of promoter sequences, duplication of genes and so forth; respective exemplary textbooks are mentioned supra. As a result of such modification, the nucleic acid information of microorganisms of the present invention is different when compared to e.g. a wild-type microorganism or an already modified microorganism used for further modification. The result of modification techniques can be verified using techniques known in the art, e.g. PCR-based methods, Southern Blot, Northern Blot, Western Blot, restriction enzyme digests and visualization of the amplified and/or digested nucleic acid fragments, measurement of enzymatic activities compared with the initial microorganism that was used for further modification and so forth.

As an example for a modification within the context of the present invention "modified glucose-6-phosphate-dehydrogenase" means that the nucleic acid encoding said gene (zwf) or the operon comprising said gene has been altered, i.e. the nucleic acid sequence is different from the wild-type or initially found nucleic acid sequence encoding said enzyme. As a consequence of such modification, the enzymatic activity is generally also different from the initial enzyme when compared under similar conditions and may be expressed as units per milligram of enzyme (specific activity) or as molecules of substrate transformed per minute per molecule of enzyme. Preferably, the nucleic acid encoding the above enzyme has been altered so that the initial promoter has been replaced by a strong heterologous promoter such as the promoter of superoxide dismutase (sod). Alternatively, or in addition to the use of a strong promoter, the nucleic acid sequence encoding the above enzyme may be mutated. A preferred modification is a mutation resulting in an amino acid sequence wherein the alanine residue (A) at position 243 is substituted by a threonine residue (T). In a further preferred embodiment, the promoter of the tkt-operon has been replaced by a heterologous promoter such as the above-mentioned sod-promoter.

"G6PDH activity" in the context of present invention means any enzymatic activity of ICD, especially any catalytic effect exerted by G6PDH. Specifically, the conversion of isocitrate into alpha-ketoglutarate is meant by "G6PDH activity." G6PDH activity may be expressed as units per milligram of enzyme (specific activity) or as molecules of substrate transformed per minute per molecule of enzyme.

In the context of the present invention, whenever the activity of a modified gene or enzyme is described as "improved", "increased", "attenuated", "decreased", "lowered", "reduced", "decreased" or "inhibited" etc. this means that the gene in question is transcribed and translated either to a higher or lower extent (i.e. in higher or lower quantities per time unit, e.g. per day, hour, minute etc.) when compared with the original non-modified gene. Accordingly, the enzymatic activity of the modified gene product will also be higher or lower, respectively.

Activities of genes or enzymes that may be modified in microorganisms according the invention may be determined in generally similar ways as described above with respect to the zwf-gene and the encoded enzyme. Specific methods for the determination of respective activities are disclosed in the Examples section.

DETAILED DESCRIPTION OF THE INVENTION

The present invention pertains to the production of a modified microorganism and its use in the production of L-lysine. In the following, preferred modifications of the nucleic acids of the inventive microorganisms are described in more detail.

The inventive microorganism strains have been generated on the basis of detailed knowledge of the metabolism of *C. glutamicum*. In this regard, $^{13}C$ metabolic flux analysis provided valuable information on the in vivo activity of pathways and (i) predicted targets to overcome bottlenecks i.e. in the pentose phosphate pathway as major NADPH source as well as in lysine biosynthesis itself, and (ii) identified reactions such as the TCA cycle, which directly compete with lysine biosynthesis. To enlarge the number of measurable fluxes in *C. glutamicum* an existing model for flux determination was significantly extended within the context of the invention. This focussed on the reaction network connecting $C^3$ metabolites of glycolysis and $C^4$ metabolites of the TCA cycle. In the modelling part, this included separation of the metabolite pools of pyruvate and phosphoenolpyruvate and the implementation of additional mass isotopomer fractions for flux estimation. For the experimental set-up, a combinatory approach of tracer experiments with $[1^{-13}C]$ glucose and an equimolar mixture of naturally labelled and $[U^{-13}C]$ glucose was applied. Using this approach, each reaction involved in anaplerotic carboxylation or decarboxylation could be precisely resolved. This extended model was subsequently applied to unravel the metabolic consequences of pyruvate kinase deletion in lysine-producing *C. glutamicum*. Said modification, assumed to increase lysine production by a flux shift from pyruvate kinase towards anaplerotic carboxylation and thus increased supply of the lysine precursor oxaloacetate, was in vivo compensated by a metabolic by-pass created by PEP carboxylase and malic enzyme, demonstrating the high flexibility of *C. glutamicum* towards genetic disturbances.

Genetic engineering towards strain optimization according to the present invention comprises modification of lysine-relevant key pathways by a variety of methods, including for example gene deletion, overexpression by promoter exchange or codon adaptation. The benefit of the performed changes may be validated by cultivation experiments, enzyme assays as well as metabolome and fluxome analysis.

For start codon substitution, it was observed that usage of the rare start codon GTG always resulted in a lowered specific enzyme activity in the cell when compared to gene expression under control of the common ATG start codon. This method can thus be applied to alter the specific enzyme activity thereby complementing the experimental toolbox nowadays applied for genetic engineering. Alternatively, the rare start codon TTG may be used to replace more frequent start codons.

In one embodiment of the present invention, improvement of precursor supply was achieved by down-regulation of pyruvate dehydrogenase (PDH), which directly competes with pyruvate carboxylase, the major enzyme supplying the lysine precursor oxaloacetate. Attenuation of PDH in the wild type based lysine producer *C. glutamicum* BS87 was achieved by replacement of the ATG start codon by GTG. This resulted in a 60% decreased specific activity of PDH and an increased lysine yield by 17%. Estimation of the metabolic fluxes revealed that the improvement was due to an efficient flux redirection from pyruvate dehydrogenase towards pyruvate carboxylase, leading to a more effective supply of oxaloacetate.

Engineering of the TCA cycle turned out to be an efficient alternative to improve precursor supply in *C. glutamicum*. Start codon exchange (ATG→GTG) in the icd gene, encoding isocitrate dehydrogenase (ICD), improved lysine production by more than 40% due to a 70% decreased specific ICD activity. In the present invention *C. glutamicum* responded to this intentionally induced bottleneck by a flux rerouting towards anaplerotic carboxylation.

Direct engineering of the lysine biosynthetic pathway by overexpression of the ddh gene, encoding diaminopimelate dehydrogenase, clearly showed that the benefit of an implemented modification can be even enhanced by appropriate cultivation conditions. In this case, the improvement is particularly pronounced when the ammonium concentration in the culture medium ranging from about 2 g $L^{-1}$ to 10 g $L^{-1}$ ammonium sulphate leading to an about 10% to about 50% improvement in lysine yield, respectively. In a preferred embodiment of the method of the present invention, the cultivation conditions are adapted accordingly, i.e. the ammonium concentration in the culture medium ranges preferably form about 10 to 100 g $L^{-1}$, more preferably to a range of about 20 to 100 g $L^{-1}$, 30 to 100 g $L^{-1}$, 40 to 100 g $L^{-1}$, 50 to 100 g $L^{-1}$, 30 to 90 g $L^{-1}$, 30 to 80 g $L^{-1}$, 30 to 70 g $L^{-1}$, 30 to 60 g $L^{-1}$, 30 to 50 g $L^{-1}$, more preferably 40 to 90 g $L^{-1}$, 40 to 80 g $L^{-1}$, 40 to 70 g $L^{-1}$, 40 to 60 g $L^{-1}$, or 40 to 50 g $L^{-1}$.

The successful studies on metabolic engineering of the lysine biosynthetic pathway itself and the supply of the central precursor oxaloacetate was then complemented by targeted optimization of the intracellular supply of NADPH, required as cofactor in high amounts for lysine biosynthesis.

An improved NADPH supply to support lysine production in *C. glutamicum* may be achieved by increasing the flux through the PPP, using overexpression of the rate controlling enzyme glucose 6-phosphate dehydrogenase (G6PDH), which is encoded by the zwf-gene. Moreover, the enzyme could be improved by implementation of the amino acid exchange A243T which decreased its sensitivity against negative regulation by metabolites stemming from the intermediary metabolism. Alternatively, in a preferred method of the invention the transketolase-operon (tkt) may be overexpressed such as to increase the expression of the zwf-gene.

In the background of *C. glutamicum* lysCT311I having a modified, improved aspartate kinase that is no longer subject to feed-back inhibition, these modifications resulted in a 15% increased PPP flux which significantly improved lysine production up to 40%.

Genetic localization of the zwf gene encoding glucose 6-phosphate dehydrogenase (G6PDH) within the transketolase operon alternatively allows overexpression of G6PDH in combination with transketolase and transaldolase, forming the non-oxidative part of the PPP. Using the sod-promoter for expression control resulted in a significantly increased activity of G6PDH, transketolase and transaldolase thereby abolishing potentially upcoming bottlenecks in the PPP.

In addition to direct modification of PPP enzymes, the NADPH supply was further improved by overexpression of fructose 1,6-bisphosphatase (fbp). In combination with overexpression and modification of G6PDH these changes boosted the lysine yield on glucose by 70%. A significant improvement was also achieved for the other industrially relevant sugars, fructose and sucrose. Preferably, strains having improved NADPH supply on one or more of the above relevant sugars have a modified lysC-gene, e.g. lysC$^{T311I}$.

As an additional benefit from the PPP engineering according to the present invention, formation of the by-product trehalose was reduced as consequence of a decreased intracellular G6P level. Detailed metabolic investigations could further provide new insights in the NADPH metabolism. So far, mainly PPP and ICD were regarded as NADPH source in lysine producing *C. glutamicum*. When compared to the wild type, lysine producing strains of *C. glutamicum* exhibited an increased specific activity of the NADPH-dependent malic enzyme (MalE). Deletion of the encoding malE gene in the background of the parent *C. glutamicum* lysC$^{T311I}$ indeed reduced the formation of the NADPH demanding products biomass and lysine. The overall reduced NADPH consumption hereby perfectly matched with the in vivo flux of 15% through malic enzyme, determined by $^{13}$C flux analysis. This suggests that *C. glutamicum* activates malic enzyme under NADPH limited conditions to meet the changed physiological requirements.

Based on the extensive knowledge on the metabolism of *C. glutamicum* and the different key targets identified in the present invention, a superior lysine producer has been created in a preferred embodiment of the present invention. For this purpose, an exclusive set of beneficial modifications was integrated into the genome of the non-producing wild type *C. glutamicum* ATCC 13032.

Comparison of the production performance of the created strain genealogy showed that a subset of only 5 modifications according to the present invention was especially preferred to increase the production of aspartate-derived amino acids, in particular of lysine production. These modifications comprised deregulation of aspartate kinase (lysC) from feedback inhibition, overexpression of diaminopimelate dehydrogenase, attenuation of icd, and engineering of the NADPH metabolism by overexpression of fructose 1,6-bisphosphatase and of the transketolase operon. The rationally designed strain exhibited remarkable production properties such as a final lysine HCl titre of 120 g $L^{-1}$ which was achieved within 30 h and a conversion yield up to 55%. With this production performance the lysine hyper-producer created within the context of the present invention is the best wild-type based production strain to our knowledge. The achieved final lysine titre and the carbon conversion yield even lie at the maximum limit achieved by industrially applied production stains, which have been optimized for more than 40 years. With regard to the space-time yield, the wild type based producer is even superior to classical strains due to the fast growth and thus reduced fermentation time. With these production properties this strain is highly attractive for industrial production.

A particularly preferred strain comprised 12 genetic modifications. Hereby, modification of the lysine biosynthesis (feedback deregulation and overexpression of aspartate kinase, overexpression of diaminopimelate dehydrogenase, dihydrodipicolinate reductase and diaminopimelate decarboxylase) and of the precursor supply (overexpression and mutation of pyruvate carboxylase, deletion of PEP carboxykinase and mutation of homoserine dehydrogenase) was complemented with further key targets of the precursor supply (attenuation of isocitrate dehydrogenase) and of the NADPH metabolism (overexpression of fructose 1,6-bisphosphatase and of the transketolase operon).

In a preferred aspect of present invention, the production method is a fermentative method. However, other methods of biotechnological production of chemical compounds are also contemplated, including in vivo production in plants and non-human animals.

The method for the fermentative production according to the present invention may comprise the cultivation of at least one preferably recombinant—microorganism comprising the above described modifications.

In a further preferred aspect of the invention, the microorganism used in the production method is a recombinant microorganism. In so far as other methods of biotechnological production of chemical compounds are also considered, including in vivo production in plants and non-human animals, the organism of choice is also preferably a recombinant organism.

In preferred embodiments of present invention, the glucose 6-phosphate dehydrogenase (zwf) activity in the microorganism used is modified, i.e. the gene is overexpressed. In the context of the present invention “overexpression” or “increased activity” mean that the initial activity of the non-modified microorganism of the same species and genetic background is lower, preferably at least 10%, 20%, 30%, 40%, 50%, 60% 70%, 80%, 90%, 95% lower or even more. Inversely, the activity of the gene or enzyme in the modified microorganism is increased preferably at least at about 10%, 20%, 30%, 40%, 50%, 60%, 70%, 80%, 90%, 95% or even more. Similar considerations made with respect to the activity of glucose-6-phosphate dehydrogenase apply also to further genes or enzymes that may be overexpressed in the context of the present invention, i.e. diaminopimelate dehydrogenase (ddh), transketolase (tkt), transaldolase (tal), fructose 1,6-bisphosphatase (fbp), aspartate kinase (lysC), dihydropicolinate reductase (dapB), diaminopimelate decarboxylase (lysA), or pyruvate carboxylase (pyc).

It is understood that it is not always desirable to increase the activity of the above-mentioned genes or enzymes as much as possible. In certain cases an incomplete reduction of any of the levels indicated above, but also of intermediate levels like, e.g., 25%, 40%, 50% etc., may be sufficient and desirable.

Furthermore, microorganisms according to the present invention having reduced enzymatic activity, for example those that have lost their initial ICD activity partially or completely when compared with an initial microorganism of the same species and genetical background are preferred. Preferably, about at least 1%, at least 2%, at least 4%, at least 6%, at least 8%, at least 10%, more preferably at least 20%, at least 40%, at least 60%, at least 80%, at least 90%, at least 95% or all of the initial activity of ICD is lost. The extent of reduction of activity is determined in comparison to the level of activity of the endogenous ICD activity in an initial microorganism under comparable conditions.

Similarly to the reduced activity of isocitrate dehydrogenase, other genes or enzymes that are expressed at a lower level within the context of the present invention are e.g. phosphoenolpyruvate carboxykinase (pck) and, optionally, also pyruvate dehydrogenase may be modified, although this is not the most preferred embodiment of the invention. It is understood that it is not always desirable to reduce the activity of these genes or enzymes as much as possible. In certain cases an incomplete reduction of any of the levels indicated above, but also of intermediate levels like, e.g., 25%, 40%, 50% etc., may be sufficient and desirable.

In embodiments wherein a complete or near complete (i.e. 90% or greater) loss of a particular enzymatic activity characterizes the microorganism, the cultivation media for the microorganism, especially the media used in the methods according to the present invention may be supplemented by one or more essential compounds lacking in the microorganism due to the suppression of the enzymatic activity. For example, when the activity of ICD is suppressed, glutamate may be supplemented to the media as it is an inexpensive, easily accessible compound.

A further example of an enzyme with decreased activity used in the context of the present invention is the hom-gene. The modification of this gene is described in more detail below. The point mutation of e.g. V59A results in decreased activity and a reduced flow towards threonine synthesis.

The increase or reduction of enzymatic activity, respectively, necessary for present invention may be either an endogenous trait of the microorganism used in the method according to the present invention, e.g. a trait due to spontaneous mutations, or due to any method known in the art for enhancing, suppressing or inhibiting an enzymatic activity in part or completely, especially an enzymatic activity in vivo. The increase or reduction of enzymatic activity, respectively, may occur at any stage of enzyme synthesis and enzyme reactions, at the genetic, transcription, translation or reaction level.

The increase or decrease of enzymatic activity, respectively, is preferably the result of genetic engineering. To increase or reduce the amount of expression of one or more endogenous gene(s) in a host cell and to thereby decrease the amount and/or activity of the enzyme in the host cell in which the target gene(s) is/are enhanced or suppressed, respectively, any method known in the art may be applied.

For down-regulating expression of a gene within a microorganism such as *E. coli* or *C. glutamicum* or other host cells such as *P. pastoris* and *A. niger*, a multitude of technologies such as gene knockout approaches, antisense technology, RNAi technology etc. are available. One may delete the initial copy of the respective gene and/or replace it with a mutant version showing decreased activity, particularly decreased specific activity, or express it from a weak promoter. Or one may exchange the start codon of a gene, the promoter of a gene, introduce mutations by random or target mutagenesis, disrupt or knock-out a gene. Furtheron, one may introduce destabilizing elements into the mRNA or introduce genetic modifications leading to deterioration of ribosomal binding sites (RBS) of the RNA. Finally, one may add specific ICD inhibitors to the reaction mixture.

For up-regulating (e.g. overexpressing) or enhancing the expression of a gene within a microorganism such as *E. coli* or *C. glutamicum* or other host cells such as *P. pastoris* and *A.*

*niger*, a multitude of technologies exist, for example the use of stronger promoters, amplification of genes etc. may be used.

In one preferred aspect, "reduction of expression" means the situation that if one replaces an endogenous nucleotide sequence coding for a polypeptide with a modified nucleotide sequence that encodes for a polypeptide of substantially the same amino acid sequence and/or function, a reduced amount of the encoded polypeptide will be expressed within the modified cells.

In a further preferred aspect, "reduction of expression" means the down-regulation of expression by antisense technology or RNA interference (where applicable, e.g. in eucaryotic cell cultures) to interfere with gene expression. These techniques may affect mRNA levels and/or translational efficiency.

In yet a further preferred aspect, "reduction of expression" means the deletion or disruption of the gene combined with the introduction of a "weak" gene, i.e. a gene encoding a protein whose enzymatic activity is lower than the initial activity, or by integration of the gene at a weakly expressed site resulting in less enzymatic activity inside the cell. This may be done by integrating the gene at a chromosomal locus from which genes are less well transcribed, or by introducing a mutant or heterologous gene with lower specific activity or which is less efficiently transcribed, less efficiently translated or less stable in the cell. The introduction of this mutant gene can be performed by using a replicating plasmid or by integration into the genome.

In yet a further preferred aspect, "reduction of expression" means that the reduced activity is the result of lowering the mRNA levels by lowering transcription from the chromosomally encoded gene, preferably by mutation of the initial promoter or replacement of the initial promoter by a weakened version of said promoter or by a weaker heterologous promoter.

In yet a further preferred aspect, "reduction of expression" means that the reduced enzymatic activity is the result of RBS mutation leading to a decreased binding of ribosomes to the translation initiation site and thus to a decreased translation of mRNA. The mutation can either be a simple nucleotide change and/or also affect the spacing of the RBS in relation to the start codon. To achieve these mutations, a mutant library containing a set of mutated RBSs may be generated. A suitable RBS may be selected, e.g. by selecting for lower enzyme activity. The initial RBS may then be replaced by the selected RBS.

In yet a further preferred aspect, "reduction of expression" is achieved by lowering mRNA levels by decreasing the stability of the mRNA, e.g. by changing the secondary structure.

In yet a further preferred aspect, "reduction of expression" is achieved by regulators, e.g. transcriptional regulators.

In case of modified nucleotide sequences that are to be expressed in *Corynebacterium* and particularly preferably in *C. glutamicum* for reducing the amount of the gene or enzyme encoded by said nucleotide sequence, at least one, at least two, at least three, at least four, at least five, at least six, at least seven, at least eight, at least nine, at least ten, preferably at least 1%, at least 2%, at least 4%, at least 6%, at least 8%, at least 10%, more preferably at least 20%, at least 40%, at least 60%, at least 80%, even more preferably at least 90% or least 95% and most preferably all of the codons of the non-modified nucleotide sequences may be replaced in the modified nucleotide sequence by less frequently used codons for the respective amino acid. In an even more preferred embodiment the afore-mentioned number of codons to be replaced refers to frequent, very frequent, and extremely frequent or the most frequent codons. In another particularly preferred embodiment, the above numbers of codons are replaced by the least frequently used codons. In all these cases will the reference codon usage be based on the codon usage of the *Corynebacterium* and preferably *C. glutamicum* and preferably on the codon usage of abundant proteins of *Corynebacterium* and preferably *C. glutamicum*. See also PCT/EP2007/061151 for detailed explanation.

As indicated above, the present invention pertains not only to a method for the production of lysine, but also to microorganisms and to the use of microorganisms in lysine production. The term "microorganism" for the purposes of the present invention refers to any non-human organism that is commonly used for expression of nucleotide sequences for production of L-lysine, in particular microorganisms as defined above, plants including algae and mosses, yeasts, and non-human animals. Organisms besides microorganisms which are particularly suitable for L-lysine production may be plants and plant parts. Such plants may be monocots or dicots such as monocotyledonous or dicotyledonous crop plants, food plants or forage plants. Examples for monocotyledonous plants are plants belonging to the genera of *avena* (oats), *triticum* (wheat), *secale* (rye), *hordeum* (barley), *oryza* (rice), *panicum, pennisetum, setaria*, sorghum (millet), zea (maize) and the like.

Dicotyledonous crop plants comprise inter alia cotton, leguminoses like pulse and in particular alfalfa, soybean, rapeseed, tomato, sugar beet, potato, ornamental plants as well as trees. Further crop plants can comprise fruits (in particular apples, pears, cherries, grapes, citrus, pineapple and bananas), oil palms, tea bushes, cacao trees and coffee trees, tobacco, sisal as well as, concerning medicinal plants, rauwolfia and digitalis. Particularly preferred are the grains wheat, rye, oats, barley, rice, maize and millet, sugar beet, rapeseed, soy, tomato, potato and tobacco. Further crop plants can be taken from U.S. Pat. No. 6,137,030.

The person skilled in the art is well aware that different organisms and cells such as microorganisms, plants and plant cells, animals and animal cells etc. will differ with respect to the number and kind of genes and proteins in a cell used in the context of the present invention. Even within the same organism, different strains may show a somewhat heterogeneous expression profile on the protein level.

In case an organism different from a microorganism is used in performing the present invention, a non-fermentative production method may be applied.

In the present invention, any microorganism as defined above may be used. Preferably, the microorganism is a prokaryote. Particularly preferred for performing the present invention are microorganisms being selected from the genus of *Corynebacterium* and *Brevibacterium*, preferably *Corynebacterium*, with a particular focus on *Corynebacterium glutamicum*, the genus of *Escherichia* with a particular focus on *Escherichia coli*, the genus of *Bacillus*, particularly *Bacillus subtilis*, the genus of *Streptomyces* and the genus of *Aspergillus*.

A preferred embodiment of the invention relates to the use of microorganisms which are selected from coryneform bacteria such as bacteria of the genus *Corynebacterium*. Particularly preferred are the species *Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola* and *Corynebacterium effiziens*. Other preferred embodiments of the invention relate to the use of Brevibacteria and particularly the species *Brevibacterium flavum, Brevibacterium lactofermentum* and *Brevibacterium divarecatum.*

In preferred embodiments of the invention the microorganism may be selected from the group consisting of *Corynebacterium glutamicum* ATCC13032, *C. acetoglutamicum* ATCC15806, *C. acetoacidophilum* ATCC13870, *Corynebacterium thermoaminogenes* FERMBP-1539, *Corynebacterium melassecola* ATCC17965, *Corynebacterium effiziens* DSM 44547, *Corynebacterium effiziens* DSM 44549, *Brevibacterium flavum* ATCC14067, *Brevibacterium lactoformentum* ATCC13869, *Brevibacterium divarecatum* ATCC 14020, *Corynebacterium glutamicum* KFCC10065 and *Corynebacterium glutamicum* ATCC21608 as well as strains that are derived thereof by e.g. classical mutagenesis and selection or by directed mutagenesis.

Other preferred strains of *C. glutamicum* may be selected from the group consisting of ATCC13058, ATCC13059, ATCC13060, ATCC21492, ATCC21513, ATCC21526, ATCC21543, ATCC13287, ATCC21851, ATCC21253, ATCC21514, ATCC21516, ATCC21299, ATCC21300, ATCC39684, ATCC21488, ATCC21649, ATCC21650, ATCC19223, ATCC13869, ATCC21157, ATCC21158, ATCC21159, ATCC21355, ATCC31808, ATCC21674, ATCC21562, ATCC21563, ATCC21564, ATCC21565, ATCC21566, ATCC21567, ATCC21568, ATCC21569, ATCC21570, ATCC21571, ATCC21572, ATCC21573, ATCC21579, ATCC19049, ATCC19050, ATCC19051, ATCC19052, ATCC19053, ATCC19054, ATCC19055, ATCC19056, ATCC19057, ATCC19058, ATCC19059, ATCC19060, ATCC19185, ATCC13286, ATCC21515, ATCC21527, ATCC21544, ATCC21492, NRRL B8183, NRRL W8182, B12NRRLB12416, NRRLB12417, NRRLB12418 and NRRLB11476.

The abbreviation KFCC stands for Korean Federation of Culture Collection, ATCC stands for American-Type Strain Culture Collection and the abbreviation DSM stands for Deutsche Sammlung von Mikroorganismen and Zellkulturen. The abbreviation NRRL stands for ARS cultures collection Northern Regional Research Laboratory, Peorea, Ill., USA.

Such a strain is e.g. *Corynebacterium glutamicum* ATCC13032, and especially derivatives thereof. The strains ATCC 13286, ATCC 13287, ATCC 21086, ATCC 21127, ATCC 21128, ATCC 21129, ATCC 21253, ATCC 21299, ATCC 21300, ATCC 21474, ATCC 21475, ATCC 21488, ATCC 21492, ATCC 21513, ATCC 21514, ATCC 21515, ATCC 21516, ATCC 21517, ATCC 21518, ATCC 21528, ATCC 21543, ATCC 21544, ATCC 21649, ATCC 21650, ATCC 21792, ATCC 21793, ATCC 21798, ATCC 21799, ATCC 21800, ATCC 21801, ATCC 700239, ATCC 21529, ATCC 21527, ATCC 31269 and ATCC 21526 which are known to produce lysine can also preferably be used. Particularly preferred are *Corynebacterium glutamicum* strains that are already capable of producing L-lysine. Therefore strains derived from *Corynebacterium glutamicum* having a feedback-resistant aspartokinase and derivatives thereof are particularly preferred. This preference encompasses strains derived from *Corynebacterium glutamicum* ATCC 13032 having a feedback-resistant aspartokinase, and particularly concerns the strains ATCC13032lysC$^{fbr}$ and ATCC13286.

*C. glutamicum* ATCC13032lysC$^{fbr}$, ATCC13032 or ATCC13286 and derivatives thereof having a feedback-resistant aspartokinase are specifically preferred microorganisms in the context of present invention. Also preferred is ATCC13032lysC$^{fbr}$ or ATCC13286.

ATCC13032 lysC$^{fbr}$ may be produced starting from ATCC13032. In order to generate such a lysine producing strain, an allelic exchange of the lysC wild type gene is performed in *C. glutamicum* ATCC 13032. To this end a nucleotide exchange is introduced into the lysC gene such that the resulting protein carries an isoleucine at position 311 instead of threonine. The detailed construction of this strain is described in patent application WO 2005/059093. The accession no. of the lysC gene is P26512.

Derivatives of ATCC13032 lysC$^{fbr}$ may be used, wherein the ICD activity is reduced by replacement of ATG as start codon of the isocitrate dehydrogenase encoding nucleotide sequence, preferably by replacement of ATG with GTG. The strain described in the examples section wherein the icd start codon was changed is especially preferred in the context of present invention (i.e. the strain ICD ATG→GTG).

For techniques that may be used for the modification of the microorganisms described herein, see, for example, Ausubel et al., (eds.), CURRENT PROTOCOLS IN MOLECULAR BIOLOGY, pages 8.2.8 to 8.2.13 (1990), Wosnick et al., Gene 60:115 (1987); Ausubel et al. (eds.), SHORT PROTOCOLS IN MOLECULAR BIOLOGY, 3rd Edition, pages 8-8 to 8-9, John Wiley & Sons, Inc. (1995), which are hereby incorporated by reference.

DNA molecules of genes encoding the clostridial enzymes utilized herein, which have been discussed above, can be obtained by screening cDNA or genomic libraries with polynucleotide probes having nucleotide sequences reverse-translated from the respective amino acid sequences or with polynucleotide probes having the respective nucleotide sequences. For example, a suitable library can be prepared by obtaining genomic DNA from *Clostridium subterminale* strain SB4 (ATCC No. 29748) and constructing a library according to standard methods. See, for example, Ausubel et al. (eds.), SHORT PROTOCOLS IN MOLECULAR BIOLOGY, 3rd Edition, pages 2-1 to 2-13 and 5-1 to 5-6 (John Wiley & Sons, Inc. 1995).

Alternatively, the genes can be obtained by synthesizing DNA molecules using mutually priming long oligonucleotides or PCR. See, for example, Ausubel et al., (eds.), CURRENT PROTOCOLS IN MOLECULAR BIOLOGY, pages 8.2.8 to 8.2.13 (1990), Wosnick et al., Gene 60:115 (1987); Ausubel et al. (eds.), SHORT PROTOCOLS IN MOLECULAR BIOLOGY, 3rd Edition, pages 8-8 to 8-9, John Wiley & Sons, Inc. (1995) in connection with DNA synthesis, which are hereby incorporated by reference.

The enzymes referred to within the context of the present invention may be encoded by a nucleic acid sequence, which is adapted to the codon usage of said parent microorganism having the ability to produce lysine.

The method according to the present invention may further include a step of recovering the target compound (L-lysine) or a precursor thereof. The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example the target compound can be recovered from culture media by first removing the microorganisms. The remaining broth is then passed through or over a cation exchange resin to remove unwanted cations and then through or over an anion exchange resin to remove unwanted inorganic anions and organic acids.

A person skilled in the art is familiar with how to replace e.g. a gene or endogenous nucleotide sequence that encodes for a certain polypeptide with a modified nucleotide sequence. This may e.g. be achieved by introduction of a suitable construct (plasmid without origin of replication, linear DNA fragment without origin of replication) by electroporation, chemical transformation, conjugation or other suitable transformation methods. This is followed by e.g. homologous recombination using selectable markers which ensure that only such cells are identified that carry the modified nucleotide sequence instead of the endogenous naturally occurring sequence. Other methods include gene disruption of the endogenous chromosomal locus and expression of the modified sequences from e.g. plasmids. Yet other methods include e.g. transposition. Further information as to vectors and host cells that may be used will be given below.

In general, the person skilled in the art is familiar with designing constructs such as vectors for driving expression of a polypeptide in microorganisms such as *E. coli* and *C. glutamicum*. The person skilled in the art is also well acquainted with culture conditions of microorganisms such as *C. glutamicum* and *E. coli* as well as with procedures for harvesting and purifying amino acids and particularly lysine from the aforementioned microorganisms. Some of these aspects will be set out in further detail below.

The person skilled in the art is also well familiar with techniques that allow to change the original non-modified nucleotide sequence into a modified nucleotide sequence encoding for polypeptides of identical amino acid but with different nucleic acid sequence. This may e.g. be achieved by polymerase chain reaction based mutagenesis techniques, by commonly known cloning procedures, by chemical synthesis etc. Standard techniques of recombinant DNA technology and molecular biology are described in various publications, e.g. Sambrook et al. (2001), Molecular Cloning: A Laboratory Manual, 3rd edition, Cold Spring Harbor Laboratory Press, or Ausubel et al. (Eds.) Current protocols in molecular biology (John Wiley & Sons, Inc. 2007). Ausubel et al., Current Protocols in Protein Science, (John Wiley & Sons, Inc. 2002). Ausubel et al. (eds.), SHORT PROTOCOLS 1N MOLECULAR BIOLOGY, 3rd Edition (John Wiley & Sons, Inc. 1995). Methods specifically for *C. glutamicum* are described in Eggeling and Bott (eds.) Handbook of *Corynebacterium* (Taylor and Francis Group, 2005). Some of these procedures are set out below and in the "examples" section.

In the following, it will be described and set out in detail how genetic manipulations in microorganisms such as *Corynebacterium glutamicum* can be performed.

Vectors and Host Cells

As used herein, the term "vector" refers to a nucleic acid molecule capable of transporting another nucleic acid to which it has been linked.

One type of vector is a "plasmid", which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A recombinant expression vector suitable for preparation of the recombinant microorganism of the invention may comprise a heterologous nucleic acid as defined above in a form suitable for expression of the respective nucleic acid in a host cell, which means that the recombinant expression vectors include one or more regulatory sequences, selected on the basis of the host cells to be used for expression, which is operatively linked to the nucleic acid sequence to be expressed.

Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). Such regulatory sequences are described, for example, in Goeddel; Gene Expression Technology Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-, tet-, lpp-, lac-, lpp-lac-, lacIq-, T7-, T5-, T3-, gal-, trc-, ara-, SP6-, arny, SP02, e-Pp-ore PL, SOD, EFTu, EFTs, GroEL, MetZ (last five from *C. glutamicum*), which are used preferably in bacteria. Additional regulatory sequences are, for example, promoters from yeasts and fungi, such as ADC1, MFa, AC, P-60, CYC1, GAPDH, TEF, rp28, ADH, promoters from plants such as CaMV/355, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors can be introduced into host cells to thereby produce proteins or peptides, including fusion proteins or peptides.

Any vector that is suitable to drive expression of a modified nucleotide sequence in a host cell, preferably in *Corynebacterium* and particularly preferably in *C. glutamicum* may be used. Such vector may e.g. be a plasmid vector which is autonomously replicable in coryneform bacteria. Examples are pZ1 (Menkel et al. (1989), Applied and Environmental Microbiology 64:549-554), pEKEx1 (Eikmanns et al. (1991), Gene 102:93-98), pHS2-1 (Sonnen et al. (1991), Gene 107: 69-74). These vectors are based on the cryptic plasmids pHM1519, pBL1 oder pGA1. Other suitable vectors are pClik5MCS (WO 2005/059093), or vectors based on pCG4 (U.S. Pat. No. 4,489,160) or pNG2 (Serwold-Davis et al. (1990), FEMS Microbiology Letters 66:119-124) or pAG1 (U.S. Pat. No. 5,158,891). Examples for other suitable vectors can be found in the Handbook of *Corynebacterium*, Chapter 23 (edited by Eggeling and Bott, ISBN 0-8493-1821-1, 2005).

Recombinant expression vectors can be designed for expression of specific nucleotide sequences in prokaryotic or eukaryotic cells. For example, the nucleotide sequences can be expressed in bacterial cells such as *C. glutamicum* and *E. coli*, insect cells (using baculovirus expression vectors), yeast and other fungal cells (see Romanos, M. A. et al. (1992), Yeast 8:423-488; van den Hondel, C. A. M. J. J. et al. (1991) in: More Gene Manipulations in Fungi, J. W. Bennet & L. L. Lasure, eds., p. 396-428, Academic Press: San Diego; and van den Hondel, C. A. M. J. J. & Punt, P. J. (1991) in: Applied Molecular Genetics of Fungi, Peberdy, J. F. et al., eds., p. 1-28, Cambridge University Press: Cambridge), algae and multicellular plant cells (see Schmidt, R. and Willmitzer, L. (1988) Plant Cell Rep.:583-586). Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins.

Fusion vectors add a number of amino acids to a protein encoded therein, usually to the amino terminus of the recombinant protein but also to the C-terminus or fused within suitable regions in the proteins. Such fusion vectors typically serve four purposes: 1) to increase expression of recombinant protein; 2) to increase the solubility of the recombinant protein; 3) to aid in the purification of the recombinant protein by acting as a ligand in affinity purification; and 4) to provide a "tag" for later detection of the protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively.

Examples of suitable inducible non-fusion *E. coli* expression vectors include pTrc (Amann et al., (1988) Gene 69: 301-315), pLG338, pACYC184, pBR322, pUC18, pUC19, pKC30, pRep4, pHS1, pHS2, pPLc236, pMBL24, pLG200, pUR290, pIN-III113-B1, egt11, pBdC1, and pET 11d (Studier et al., Gene Expression Technology:Methods in Enzymology 185, Academic Press, San Diego, Calif. (1990) 60-89; and Pouwels et al., eds. (1985) Cloning Vectors. Elsevier: New York, ISBN 0 444 904018). Target gene expression from the pTrc vector relies on host RNA polymerase transcription from a hybrid trp-lac fusion promoter. Target gene expression from the pET 11d vector relies on transcription from a T7 gnlO-lac fusion promoter mediated by a coexpressed viral RNA polymerase (T7gnl). This viral polymerase is supplied by host strains BL21 (DE3) or HMS 174 (DE3) from a resident X prophage harboring a T7gnl gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming *Streptomyces*, while plasmids pUB110, pC194 or pBD214 are suited for transformation of *Bacillus* species. Several plasmids of use in the transfer of genetic information into *Corynebacterium* include pHM1519, pBL1, pSA77 or pAJ667 (Pouwels et al., eds. (1985) Cloning Vectors. Elsevier: New York ISBN 0 444 904018).

Examples of suitable *C. glutamicum* and *E. coli* shuttle vectors are e.g. pClik5aMCS (WO 2005/059093) or can be found in Eikmanns et al. ((1991) Gene 102:93-8).

Examples for suitable vectors to manipulate *Corynebacteria* can be found in the Handbook of *Corynebacterium* (edited by Eggeling and Bott, ISBN 0-8493-1821-1, 2005). One can find a list of *E. coli-C. glutamicum* shuttle vectors (table 23.1), a list of *E. coli-C. glutamicum* shuttle expression vectors (table 23.2), a list of vectors which can be used for the integration of DNA into the *C. glutamicum* chromosome (table 23.3), a list of expression vectors for integration into the *C. glutamicum* chromosome (table 23.4.), as well as a list of vectors for site-specific integration into the *C. glutamicum* chromosome (table 23.6).

In another embodiment, the expression vector is a yeast expression vector. Examples of vectors for expression in yeast *S. cerevisiae* include pYepSec1 (Baldari, et al., (1987) Embo J. 6:229-234), 2i, pAG-1, Yep6, Yep13, pEMBLYe23, pMFa (Kurjan and Herskowitz, (1982) Cell 30:933-943), pJRY88 (Schultz et al., (1987) Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) in: Applied Molecular Genetics of Fungi, J. F. Peberdy et al., eds., p. 1-28, Cambridge University Press: Cambridge, and Pouwels et al., eds. (1985) Cloning Vectors. Elsevier: New York (ISBN 0 444 904018).

For the purposes of the present invention, an operative link is understood to be the sequential arrangement of promoter (including the ribosomal binding site (RBS)), coding sequence, terminator and, optionally, further regulatory elements in such a way that each of the regulatory elements can fulfill its function, according to its determination, when expressing the coding sequence.

In another embodiment, heterologous nucleotide sequences may be expressed in unicellular plant cells (such as algae) or in plant cells from higher plants (e.g., the spermatophytes, such as crop plants). Examples of plant expression vectors include those detailed in: Becker, D., Kemper, E., Schell, J. and Masterson, R. (1992) Plant Mol. Biol. 20:1195-1197; and Bevan, M. W. (1984) Nucl. Acid. Res. 12:8711-8721, and include pLGV23, pGHlac+, pBIN19, pAK2004, and pDH51 (Pouwels et al., eds. (1985) Cloning Vectors. Elsevier: New York ISBN 0 444 904018).

For other suitable expression systems for both prokaryotic and eukaryotic cells see chapters 16 and 17 of Sambrook, J. et al. Molecular Cloning: A Laboratory Manual. 3rd ed., Cold Spring Harbor Laboratory, Cold Spring Harbor Laboratory Press, Cold Spring Harbor, N.Y., 2003.

In another embodiment, a recombinant expression vector is capable of directing expression of a nucleic acid preferentially in a particular cell type, e.g. in plant cells (e.g., tissue-specific regulatory elements are used to express the nucleic acid). Tissue-specific regulatory elements are known in the art.

Another aspect of the invention pertains to organisms or host cells into which a recombinant expression vector or nucleic acid has been introduced. The resulting cell or organism is a recombinant cell or organism, respectively. It is understood that such terms refer not only to the particular subject cell but also to the progeny or potential progeny of such a cell when the progeny is comprising the recombinant nucleic acid. Because certain modifications may occur in succeeding generations due to either mutation or environmental influences, such progeny may not, in fact, be identical to the parent cell, but are still included within the scope of the term as used herein, inasfar as the progeny still expresses or is able to express the recombinant protein.

Vector DNA can be introduced into prokaryotic or eukaryotic cells via conventional transformation or transfection techniques. As used herein, the terms “transformation” and “transfection”, “conjugation” and “transduction” are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA)) into a host cell, including calcium phosphate or calcium chloride coprecipitation, DEAE-dextran-mediated transfection, lipofection, natural competence, conjugation chemical-mediated transfer, or electroporation. Suitable methods for transforming or transfecting host cells can be found in Sambrook, et al. (Molecular Cloning: A Laboratory Manual. 3rd ed., Cold Spring Harbor Laboratory, Cold Spring Harbor Laboratory Press, Cold Spring Harbor, N.Y., 2003), and other laboratory manuals.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycine, tetracycline, ampicillin and methotrexate. Nucleic acid encoding a selectable marker can be introduced into a host cell on the same vector as that encoding the above-mentioned modified nucleotide sequences or can be introduced on a separate vector. Cells stably transfected with the introduced nucleic acid can be identified by drug selection (e.g., cells that have incorporated the selectable marker gene will survive, while the other cells die).

When plasmids without an origin of replication and two different marker genes are used (e.g. pClik int sacB), it is also possible to generate marker-free strains which have part of the insert inserted into the genome. This is achieved by two consecutive events of homologous recombination (see also Becker et al., APPLIED AND ENVIRONMENTAL MICROBIOLOGY, 71 (12), p. 8587-8596; Eggeling and Bott (eds) Handbook of *Corynebacterium* (Taylor and Francis Group, 2005)). The sequence of plasmid pClik int sacB can be found in WO 2005/059093 as SEQ ID NO:24; therein, the plasmid is called pCIS.

In another embodiment, recombinant microorganisms can be produced which contain selected systems which allow for regulated expression of the introduced gene. For example, inclusion of a nucleotide sequence on a vector placing it under control of the lac operon permits expression of the gene only in the presence of IPTG. Such regulatory systems are well known in the art.

Growth of *Escherichia coli* and *Corynebacterium glutamicum*-Media and Culture Conditions In one embodiment, the method comprises culturing the microorganism in a suitable medium for lysine production. In another embodiment, the method further comprises isolating lysine from the medium or the host cell.

The person skilled in the art is familiar with the cultivation of common microorganisms such as *C. glutamicum* and *E. coli*. Thus, a general teaching will be given below as to the cultivation of *E. coli* and *C. glutamicum*. Additional information may be retrieved from standard textbooks for cultivation of *E. coli* and *C. glutamicum*.

*E. coli* strains are routinely grown in MB and LB broth, respectively (Follettie et al. (1993) J. Bacteriol. 175:4096-4103). Minimal media for *E. coli* is M9 and modified MCGC (Yoshihama et al. (1985) J. Bacteriol. 162:591-597), respectively. Glucose may be added at a final concentration of 1%. Antibiotics may be added in the following amounts (micrograms per milliliter): ampicillin, 50; kanamycin, 25; nalidixic acid, 25. Amino acids, vitamins, and other supplements may be added in the following amounts: methionine, 9.3 mM; arginine, 9.3 mM; histidine, 9.3 mM; thiamine, 0.05 mM. *E. coli* cells are routinely grown at 37° C., respectively.

Genetically modified *Corynebacteria* are typically cultured in synthetic or natural growth media. A number of different growth media for *Corynebacteria* are both well-known and readily available (Liebl et al. (1989) Appl. Microbiol. Biotechnol., 32:205-210; von der Osten et al. (1998) Biotechnology Letters, 11:11-16; U.S. Pat. No. DE 4,120,867; Liebl (1992) “The Genus *Corynebacterium*”, in: The Procaryotes, Volume II, Balows, A. et al., eds. Springer-Verlag). Instructions can also be found in the Handbook of *Corynebacterium* (edited by Eggeling and Bott, ISBN 0-8493-1821-1, 2005).

These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, lactose, maltose, sucrose, glycerol, raffinose, starch or cellulose serve as carbon sources.

It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamine, folic acid, nicotinic acid, pantothenate and pyridoxine. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook “Applied Microbiol. Physiology, A Practical Approach” (Eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

Examples for preferred media in the context of present invention are described in the Examples section below.

All medium components should be sterilized, either by heat (20 min at 1.5 bar and 121° C.) or by sterile filtration. The components can either be sterilized together or, if necessary, separately.

All media components may be present at the beginning of growth, or they can optionally be added continuously or batchwise. Culture conditions are defined separately for each experiment.

The temperature depends on the microorganism used and usually should be in a range between 15° C. and 45° C. The temperature can be kept constant or can be altered during the experiment. The pH of the medium may be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed. Examples for preferred culture conditions are described in the Examples section below.

If genetically modified clones are tested, an unmodified control clone (e.g. the parent strain) or a control clone containing the basic plasmid without any insert should also be tested. The medium is inoculated to an OD600 of 0.5-1.5 using cells grown on agar plates, such as CM plates (10 g/l glucose, 2.5 g/l NaCl, 2 g/l urea, 10 g/l polypeptone, 5 g/l yeast extract, 5 g/l meat extract, 22 g/l agar, pH 6.8 with 2M NaOH) that had been incubated at 30° C. Inoculation of the media is accomplished by either introduction of a saline suspension of *C. glutamicum* cells from CM plates or addition of a liquid preculture of this bacterium.

Quantification of Amino Acids and their Intermediates

Quantification of amino acids and their intermediates may be performed by any textbook method known to a person skilled in the art. In the following, said quantification is exemplified by the quantification of methionine. Further exemplifications of quantification are presented in the Examples section. The latter are preferred in the context of present invention.

The analysis is done by HPLC (Agilent 1100, Agilent, Waldbronn, Germany) with a guard cartridge and a Synergi 4 μm column (MAX-RP 80 Å 150*4.6 mm) (Phenomenex, Aschaffenburg, Germany). Prior to injection the analytes are derivatized using o-phthaldialdehyde (OPA) and mercaptoethanol as reducing agent (2-MCE). Additionally sulfhydryl groups are blocked with iodoacetic acid. Separation is carried out at a flow rate of 1 ml/min using 40 mM $NaH_2PO_4$ (eluent A, pH=7.8, adjusted with NaOH) as polar and a methanol water mixture (100/1) as non-polar phase (eluent B). The following gradient is applied: Start 0% B; 39 min 39% B; 70 min 64% B; 100% B for 3.5 min; 2 min 0% B for equilibration. Derivatization at room temperature is automated as described below. Initially 0.5 μl of 0.5% 2-MCE in bicine (0.5M, pH 8.5) are mixed with 0.5 μl cell extract. Subsequently 1.5 μl of 50 mg/ml iodoacetic acid in bicine (0.5M, pH 8.5) are added, followed by addition of 2.5 μl bicine buffer (0.5M, pH 8.5). Derivatization is done by adding 0.5 μl of 10 mg/ml OPA reagent dissolved in 1/45/54 v/v/v of 2-MCE/MeOH/bicine (0.5M, pH 8.5). Finally the mixture is diluted with 32 μl $H_2O$. Between each of the above pipetting steps there is a waiting time of 1 min. A total volume of 37.5 μl is then injected onto the column. The analytical results can be significantly improved, if the auto sampler needle is periodically purified during (e.g. within waiting time) and after sample preparation. Detection is performed by a fluorescence detector (340 nm excitation, emission 450 nm, Agilent, Waldbronn, Germany). For quantification α-amino butyric acid (ABA) is used as internal standard.

Recombination protocol for *C. glutamicum*

In the following it will be described how a strain of *C. glutamicum* with increased efficiency of fine chemical production can be constructed using a specific recombination protocol.

"Campbell in," as used herein, refers to a transformant of an original host cell in which an entire circular double stranded DNA molecule (for example a plasmid being based on pClik int sacB) has integrated into a chromosome by a single homologous recombination event (a cross-in event), which effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point. The name comes from Professor Alan Campbell, who first proposed this kind of recombination.

"Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell or strain is usually, but not necessarily, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that lead to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

For practicality, in *C. glutamicum*, typical first and second homologous DNA sequences are at least about 200 base pairs in length, and can be up to several thousand base pairs in length, however, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs. The "Campbell In and -Out-method" is described in WO 2007/012078 and Eggeling and Bott (eds) Handbook of *Corynebacterium* (Taylor and Francis Group, 2005), Chapter 23. Preferred recombination protocols for *C. glutamicum* are described in the Examples section.

The present invention is described in more detail by reference to the following examples. It should be understood that these examples are for illustrative purposes only and are not to be construed as limiting the invention.

Examples

In the following examples, standard techniques of recombinant DNA technology and molecular biology were used that were described in various publications, e.g. Sambrook et al. (2001), Molecular Cloning: A Laboratory Manual, 3rd edition, Cold Spring Harbor Laboratory Press, or Ausubel et al. (2007), Current Protocols in Molecular Biology, Current Protocols in Protein Science, edition as of 2002, Wiley Interscience. Unless otherwise indicated, all cells, reagents, devices and kits were used according to the manufacturer's instructions.

Material and Methods

Bacterial Strains

All strains of *C. glutamicum* were derived from the wild type ATCC 13032 (American Type Culture Collection, Manassas, Va., USA) by stable genetic modification. *Escherichia coli* DH5α and NM522, purchased from Invitrogen (Karlsruhe, Germany) were used for vector amplification and DNA methylation, respectively. All strains are listed in Table 2.

TABLE 2

Table 2: Bacterial strains used in the present work for metabolic and genetic engineering

| Strain | Genotype |
|---|---|
| *C. glutamicum* ATCC 13032 | Wild type |
| BS1 (lysC$^{T311I}$) | Wild type + nucleotide exchange in the lysC gene, encoding aspartokinase resulting in the amino acid exchange T311I |
| BS3 (zwf$^{A243T}$) | BS1 + nucleotide exchange in the zwf gene, encoding glucose 6-phosphate dehydrogenase resulting in the amino acid exchange A243T |
| BS5 ($P_{sod}$zwf) | BS1 + overexpression of zwf by replacement of the natural promoter by the promoter of sod, encoding superoxide dismutase |
| BS6 ($P_{sod}$zwf$^{A243T}$) | BS3 + overexpression of the mutant zwf gene by the sod-promoter |
| BS7 ($P_{sod}$fbp__zwf$^{A243T}$) | BS6 + overexpression of fbp, encoding fructose 1,6-bisphosphatase by the sod-promoter |
| BS13 (lysC$^{T311I}$Δpyk) | BS1 + deletion of pyruvate kinase (pyk) |
| BS44 (lysC$^{T311I}$ ΔmalE) | BS1 + deletion of malic enzyme (malE) |
| BS52 | BS6 + deletion of malic enzyme (malE) |
| BS222 (ddh) | BS1 + additional copy of the ddh gene, encoding di-aminopimelate dehydrogenase |
| BS87 | BS222 + deletion of pck, encoding PEP-carboxykinase, + overexpression of dapB, encoding dihydrodipicolinate reductase, by the promoter of sod + additional copy of lysA (and argS, both of which are found in the same gene cluster), encoding diaminopimelate decarboxylase + overexpression of lysC by the promoter of sod + mutation V59A in homoserine dehydrogenase (hom) + mutation P458S in pyruvate carboxylase (pyc) and overexpression of pyc by the sod promoter |
| BS205 (icd$^{att}$) | BS87 + replacement of the start codon ATG by the rare GTG in the gene of icd, encoding isocitrate dehydrogenase |

TABLE 2-continued

| Table 2: Bacterial strains used in the present work for metabolic and genetic engineering | |
|---|---|
| Strain | Genotype |
| BS242 ($P_{eftu}$fbp) | BS205 + replacement of the natural promoter of fbp by the promoter of eftu, encoding elongation factor tu. |
| BS244 ($P_{sod}$tkt) | BS242 + replacement of the natural promoter of the tkt-operon, comprising the genes zwf, tal, encoding transaldolase, tkt, encoding transketolase, opcA, encoding a putative subunit of glucose 6-phosphate dehydrogenase and pgl, encoding 6-phosphogluconolactonase by the sod promoter |
| BS238 (aceE$^{att}$) | BS87 + replacement of the start codon ATG by GTG in the gene of aceE, encoding subunit one of pyruvate dehydrogenase complex (PDH) |
| BS240 (pgi$^{att}$) | BS87 + replacement of the start codon ATG by GTG in the gene of pgi, encoding phosphoglucoisomerase |
| BS293 (zwf$^{up}$) | BS87 + replacement of the start codon GTG by ATG in the gene of zwf |
| *E. coli* DH5α | Heat shock competent cells for amplification of the transformation vector |
| NM522 | Heat shock competent cells carrying the pTC plasmid (Table 2). Used for amplification and DNA methylation of the transformation vector |

Wild type *C. glutamicum* ATCC 13032 was obtained by the American Type Culture Collection (Manassas, USA).

Primers and Plasmids

Figure 1:
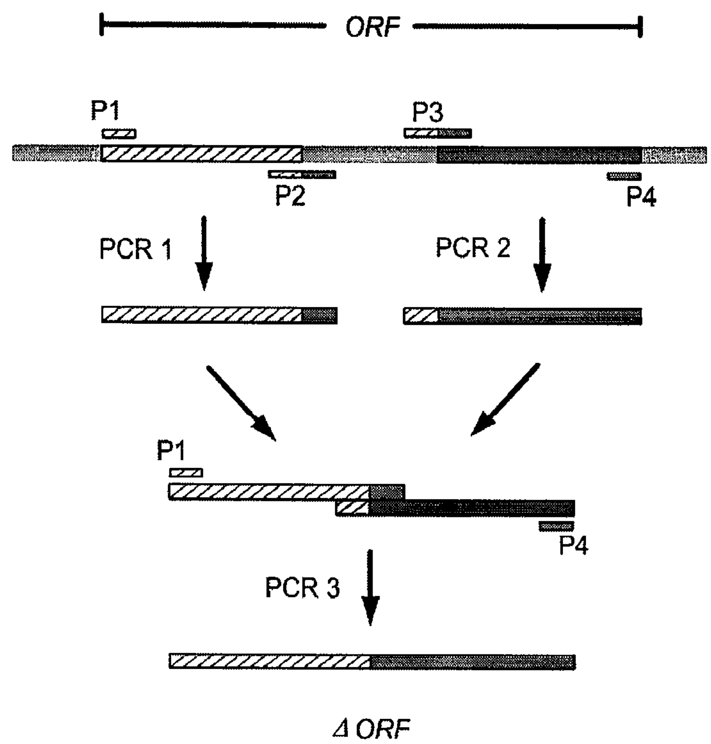
FIG. 1: PCR strategy for insert-construction exemplified for gene deletion by partly deleting the sequence of the open reading frame (ORF). Two separate DNA fragments were fused in three PCR steps using site-specific primers (for example those referred to as P1, P2, P3 and P4).
Figure 2:
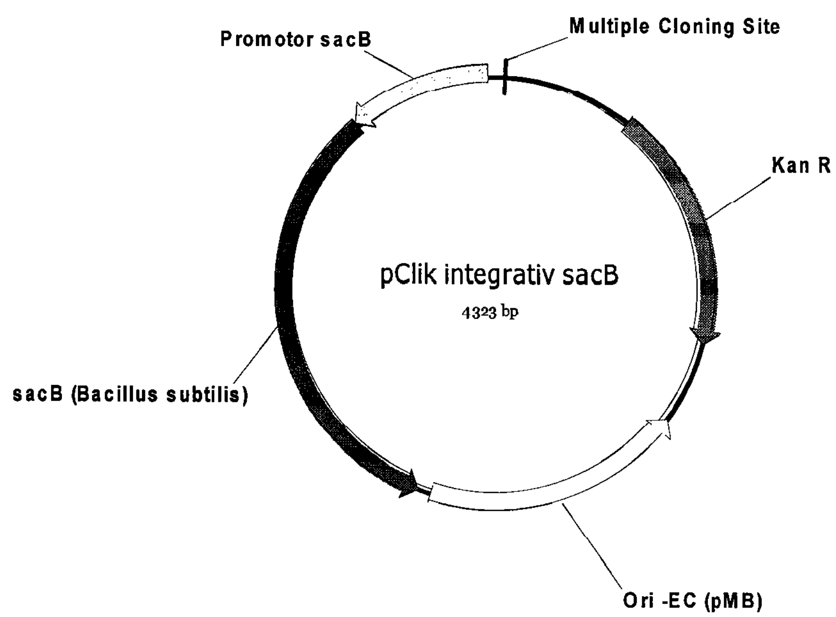
FIG. 2: Integrative transformation vector pClik with selection markers KanR and sacB, an ORI for *E. coli* and a multiple cloning site.

Transformation of *C. glutamicum* was performed with the integrative vectors pK19 or pClik (FIG. 2) (Becker, et al., 2005), respectively. The original vectors have a size of 4 kbp and contain an origin of replication (ORI) for *E. coli*, a multiple cloning site (MCS), a kanamycin resistance marker (Kan$^R$) and the open reading frame of the sacB gene, encoding levansucrase of *B. subtilis*. Kan$^R$ and sacB are used as positive selection markers for the two recombination events (Jager, et al., 1995; Jager, et al., 1992).

The respective DNA-fragment for genetic modification of *C. glutamicum* was obtained by PCR and subsequently inserted into the MCS of the basic vector via recognition sites of selected restriction enzymes. The plasmids and primer sequences used for strain construction are listed in Table 3 and 4, respectively. The software Vector NTI 10.0 (Invitrogen GmbH, Karlsruhe, Germany) was applied for primer design and development of the cloning strategy.

TABLE 3

| Table 3: Plasmids used in the present work | | |
|---|---|---|
| No | Plasmid | Description |
| 1 | pTC | Expression vector for DNA-methyltransferase of *C. glutamicum*, ORI for *E. coli* and tetracycline resitance as selection marker. Used in *E. coli* NM522 to add the *C. glutamicum*-specific DNA-methylation pattern to the integrative transformation vector. |
| 2 | pClik | Integrative transformation vector for *C. glutamicum* with MCS, ORI for *E. coli*, and Kan$^R$ and sacB as selection markers. |
| 3 | pK19 | Integrative transformation vector for *C. glutamicum* with MCS, ORI for *E. coli*, and Kan$^R$ and sacB as selection markers. |
| 4 | pClik_lysC$^{T311I}$ | Integrative transformation vector for implementation of the mutation T311I into aspartate kinase (lysC) |
| 5 | K19_2×ddh | Integrative transformation vector for implementation of an additional gene copy of ddh |
| 6 | pClik_Δpck | Integrative transformation vector for deletion of the pck gene, encoding PEP carboxykinase |
| 7 | pK19_$P_{sod}$dapB | Integrative transformation vector for replacement of the natural promoter of the dapB gene, encoding dihydrodipicolinate reductase by the promoter of sod, encoding superoxide dismutase |
| 8 | pK19_2×lysA | Integrative transformation vector for implementation of an additional copy of lysA and argS, encoding diaminopimelate de-carboxylase and arginyl-tRNA-synthetase |
| 9 | pClik_$P_{sod}$lysC | Integrative transformation vector for replacement of the natural promoter of the lysC gene, encoding aspartokinase by the sod promoter |
| 10 | pClik_hom$^{V59A}$ | Integrative transformation vector for implementation of the mutation V59A into the hom gene, encoding homoserine dehydrogenase |
| 11 | pClik_pyc$^{P458S}$ | Integrative transformation vector for implementation of the mutation P458S into the pyc gene, encoding pyruvate carboxylase |
| 12 | pClik_$P_{sod}$pyc | Integrative transformation vector for replacement of the natural promoter of the pyc gene by the sod promoter |

TABLE 3-continued

Table 3: Plasmids used in the present work

| No | Plasmid | Description |
|---|---|---|
| 13 | pClik_icd$^{A1G}$ | Integrative transformation vector for replacement of the natural start codon ATG of the icd gene, encoding isocitrate dehydrogenase by the start codon GTG |
| 14 | pClik_P$_{eftu}$fbp | Integrative transformation vector for replacement of the natural promoter of the fbp gene, encoding fructose 1,6-bisphosphatase by the promoter of eftu, encoding elongation factor tu |
| 15 | pClik_P$_{sod}$tkt | Integrative transformation vector for replacement of the natural promoter of the transketolase operon tkt by the promoter of sod |
| 16 | pClik_ΔmalE | Integrative transformation vector for deletion of the malE gene |
| 17 | pClik_aceE$^{A1G}$ | Integrative transformation vector for replacement of the natural start codon ATG of the aceE gene by the start codon GTG |
| 18 | pClik_pgi$^{A1G}$ | Integrative transformation vector for replacement of the natural start codon ATG of the pgi gene by the start codon GTG |
| 19 | pClik_zwf$^{G1A}$ | Integrative transformation vector for replacement of the natural start codon GTG of the zwf gene by the start codon ATG |

The plasmids used for strain construction of *C. glutamicum* BS87 are listed in the table below.

TABLE 4

Table 4: Plasmids used for construction of the strain C. glutamicum BS87.

| Plasmid | Description |
|---|---|
| pClik_Δpck | Integrative transformation vector for deletion of the pck gene, encoding PEP carboxykinase |
| pK19_P$_{sod}$dapB | Integrative transformation vector for replacement of the natural promoter of the dapB gene, encoding dihydrodipicolinate reductase by the promoter of sod, encoding superoxide dismutase |
| pK19_2×ysA | Integrative transformation vector for implementation of an additional copy of lysA, encoding diaminopimelate decarboxylase |
| pClik_P$_{sod}$lysC | Integrative transformation vector for replacement of the natural promoter of the lysC gene, encoding aspartokinase by the sod promoter |
| pClik_hom$^{V59A}$ | Integrative transformation vector for implementation of the mutation V59A into the hom gene, encoding homoserine dehydrogenase |
| pClik_pyc$^{P458S}$ | Integrative transformation vector for implementation of the mutation P458S into the pyc gene, encoding pyruvate carboxylase |
| pK19_2×ddh | Integrative transformation vector for implementation of an additional gene copy of ddh |

The nucleotide sequences of the genes referred to herein are also accessible via public databases, including the National Center for Biotechnology Information database.

The complete genome of *Corynebacterium glutamicum* has been sequenced and is available under the GenBank accession number BA000036.3.

Chemicals

Yeast extract, beef extract, tryptone, peptone and agar were purchased from Difco Laboratories (Detroit, USA). All other chemicals were of analytical grade and obtained from Sigma, Fluka or Merck. Labelled glucose was purchased from Campro Scientific (Veenendaal, The Netherlands). Restriction enzymes were obtained from Fermentas (St. Leon-Roth, Germany).

Medium Composition

Complex Media

LB Medium

Cultivation of *E. coli* on agar plates or in liquid culture was performed in LB (Luria-Bertani) medium. This contained per liter: 5 g yeast extract, 10 g tryptone and 5 g NaCl. Agar plates were prepared by addition of 18 g $L^{-1}$ agar. Sterilization was performed by autoclaving for 20 minutes at 121° C. If appropriate, kanamycin and tetracycline was added to a final concentration of 50 $\mu mL^{-1}$ or 12.5 $\mu g\ mL^{-1}$, respectively.

SOC Medium

Regeneration of *E. coli* DH5α and NM522 after heat shock transformation was performed in enriched SOB medium (Super Optimized Broth), consisting of three solutions. Solution 1 contained 20 g tryptone, 5 g yeast extract, 0.5 g NaCl and 10 mL KCl (250 mM) in a total volume of 975 mL and was sterilized by autoclaving. After cooling down to room temperature, 5 mL sterile $MgCl_2$ (2 M) and 20 mL sterile glucose (1 M) were added.

CM Medium

First pre-culture of *Corynebacterium glutamicum* was grown in CM medium. For preparation, 10 g peptone, 5 g beef extract, 5 g yeast extract and 2.5 g NaCl were dissolved in 925 mL water and autoclaved for 20 minutes at 121° C. Subsequently, 25 mL glucose (400 g $L^{-1}$, sterilized by filtration, 0.2 μm Ultrafree-MC, Millipore) and 50 mL urea (40 g $L^{-1}$, sterilized by filtration, 0.2 μm Ultrafree-MC, Millipore) were added. Agar plates were prepared by addition of 18 g $L^{-1}$ agar. For selection purposes during strain construction $CM^{Kan}$ agar plates were prepared by addition of 100 g sucrose before autoclaving. $CM^{Kan}$ agar contained kanamycin with a final concentration of 50 μg $mL^{-1}$. Kanamycin was added from a 50 mg $mL^{-1}$ stock solution after the autoclaved agar had cooled down to 50-60° C.

BHI++ Medium

BHI++ medium, used to grow cells for electroporation, was prepared by dissolving 37 g BHI (Brain-Heart-Infusion) in 850 mL water. After autoclaving (20 min, 121° C.), 50 mL of sterile 2 M $(NH_4)_2SO_4$ and 100 mL sterile 40% glucose were added.

BHIS Medium

For cell regeneration after electroporation, *C. glutamicum* was grown for 90 min without selection pressure in BHIS medium. One liter BHIS contained 37 g BHI and 250 mL 2 M sorbitol, which was sterilized by filtration and added after autoclaving.

Minimal Media

For physiological studies including metabolic flux analysis, minimal medium was used (Table 5. This consisted of different solutions which were combined freshly before use.

TABLE 5

Table 5: Composition of the synthetic media used for cultivation of *C. glutamicum.*

| | Standard Medium | | | Modified Medium | | |
|---|---|---|---|---|---|---|
| Solution A | 559 | mL | | 500 | mL | |
| | 1.0 | g | NaCl | 1.0 | g | NaCl |
| | 55 | mg | $CaCl_2$ | 55 | mg | $CaCl_2$ |
| | 0.2 | g | $MgSO_4*H_2O$ | 0.2 | g | $MgSO_4*H_2O$ |
| Solution B | 200 | mL | | 100 | mL | |
| | 5.0 | g | $(NH_4)_2SO_4$ | 15.0 | g | $(NH_4)_2SO_4$ pH 7.0 |
| Solution C | 100 | mL | | 100 | mL | |
| | 16.0 | g | $K_2HPO_4$ | 31.6 | g | $K_2HPO_4$ |
| | 2.0 | g | $KH_2PO_4$ | 2.5 | g | $KH_2PO_4$ |
| Solution D | 100 | mL | | 100 | mL | |
| | 15.0 | g | glucose, fructose or sucrose, respectively pH 5.0 | 10 | g | Glucose |
| Solution E | 10 | mL | | 10 | mL | |
| | 20 | mg | $FeSO_4 * 7 H_2O$ pH 1.0-1.1 | 20 | mg | $FeSO_4 * 7 H_2O$ pH 1.0-1.1 |
| Solution F | 20 | mL | | 20 | mL | |
| Solution G | 10 | mL | | 10 | mL | |
| Solution H | 1 | mL | | 1 | mL | |
| Water | | | | 159 | mL | |

| | | | |
|---|---|---|---|
| Solution F | 100 | mL | |
| | 2.5 | mg | Biotin |
| | 5.0 | mg | Thiamin*HCl |
| | 5.0 | mg | Pantothenic acid Ca-salt |
| Solution G | 1000 | mL | |
| | 200 | mg | $FeCl_3 * 6 H_2O$ |
| | 200 | mg | $MnSO_4 * H_2O$ |
| | 50 | mg | $ZnSO_4 * H_2O$ |
| | 20 | mg | $CuCl_2 *2 H_2O$ |
| | 20 | mg | $Na_2B_4O_7 * 10 H_2O$ |
| | 10 | mg | $(NH_4)_6Mo_7O_{24} * 4 H_2O$ |
| | | ad | pH 1.0 with HCl (1M) |
| Solution H | 10 | mL | |
| | 300 | mg | Dihydroxybenzoic acid |
| | 500 | μL | NaOH (6M) |

Solutions A-D and water were sterilized by autoclaving for 20 min at 121° C. Solutions F—H were sterilized by filtration (0.2 μm Ultrafree-MC, Millipore). The minimal medium was modified in selected experiments by elevating the ammonium concentration and buffer capacity and reducing the substrate concentration.

Industrial Production Medium

Fed-batch fermentation in a 5 L Sartorius fermenter was performed in a molasses based complex medium which was supplemented with vitamins and trace elements. The composition of the batch medium is displayed in Table 6. For preparation of the feeding solution, 200 g molasses and 800 g glucose*$H_2O$ were dissolved in 1.8 L water and sterilized by autoclaving for 20 min at 121° C. Subsequently, sterile 200 mL $(NH_4)_2SO_4$ solution (400 g $L^{-1}$), 0.8 mL Solution E and 2 ml antifoam (Tego antifoam KS911, Goldschmidt GmbH, Essen, Germany) were added.

TABLE 6

Table 6: Composition of the molasses based batch medium used for fermentation.
Batch Medium

| | | | |
|---|---|---|---|
| Solution A | 500 | mL | |
| | 72.44 | g | Molasses |
| | 35.00 | mL | Corn steep liquor |
| | 0.55 | mL | $FeSO_4$-Citrate solution |
| | 5.00 | mL | Tego antifoam KS911 |
| Solution B | 90 | mL | |
| | 36 | g | $(NH_4)_2SO_4$ |
| | 0.27 | g | $MgSO_4$ |
| | 225 | μL | $H_3PO_4$ (85%) |
| Solution C | 10 | mL | |
| | 0.25 | g | $KH_2PO_4$ |
| Solution D | 140 | mL | |
| | 70 | g | Glucose*$H_2O$ |
| Solution E | 7 | mL | |
| Water | 203 | mL | |

Solution E contained 300 mg $L^{-1}$ biotin, 500 mg $L^{-1}$ thiamin*HCl, 2 g $L^{-1}$ pantothenic acid Ca-salt and 600 mg $L^{-1}$ nicotinamide. $FeSO_4$-Citrate solution consisted of 20 g $L^{-1}$ $FeSO_4$*7 $H_2O$ and 18.14 g $L^{-1}$ citrate. Solutions A-D and water were sterilized by autoclaving for 20 min at 121° C. Solution E was sterilized by filtration (0.2 μm Ultrafree-MC, Millipore).

Strain Conservation

One mL of exponentially growing cells from complex liquid culture (LB for *E. coli* and CM for *C. glutamicum*) was mixed with 1 mL sterile 60% glycerol and stored at −80° C.

Strain Construction

Isolation of Nucleic Acids

Isolation of DNA from *C. glutamicum*

For isolation of purified genomic DNA, cells from agar plates incubated for 2 days at 30° C. were harvested with a sterile inoculation loop and resolved in 500 μl of sterile water. Cell disruption was performed for 1 minute at 30 Hz in a ribolyzer (MM301, Retsch, Haan, Germany) after addition of two spatula tips of glass beads (0.45-0.5 mm) and 700 μl of a mixture of phenol-chlorophorm-isoamyl-alcohol (Carl-Roth GmbH, Karlsruhe, Germany). After separation of aqueous and organic phase (5 min, 13.000 rpm, Centrifuge 5415R, Eppendorf, Hamburg, Germany), DNA from the aqueous phase was precipitated by addition of 65 μl sodium acetate (3 M, pH 5.5) and 1.3 mL ethanol (100%) and a centrifugation step (10 min, 13.000 rpm, Centrifuge 5415R). Subsequently, the supernatant was removed and genomic DNA was dissolved in 100 μl sterile water. DNA concentration was determined with the NanoDrop Spectrophotometer ND-1000 (Thermo Fisher Scientific, Waltham, USA) and genomic DNA was stored at 4° C. For fast isolation of DNA for screening purposes during strain construction, single colonies were picked with a sterile tooth pick and dissolved in 500 μl of sterile water and cell disruption was performed as described above. Cell debris was removed by centrifugation and 10 μl of the supernatant were used for PCR analysis.

Plasmid Isolation from *E. coli*

Isolation of plasmid DNA from *Escherichia coli* NM522 and DH5α was performed using the DNA isolation kits HiSpeed Plasmid Midi Prep Kit (Qiagen, Hilden, Germany) and GFX Micro Plasmid Prep Kit (GE Healthcare, Munich, Germany), respectively. Plasmid isolation with GFX Micro Plasmid Prep Kit was performed with 3 mL of an overnight culture of DH5α grown in $LB^{Kan}$ medium as described in the manual. For plasmid isolation from NM522, a 10 mL preculture ($LB^{Tet+Kan}$) was inoculated with a single colony from agar plate and grown for 8 h. Cells from the preculture were used to inoculate the main culture, which was performed in 50 mL $LB^{Tet+Kan}$ and grown overnight. Cell harvest and plasmid isolation was performed according to the HiSpeed Plasmid Midi Prep manual. DNA concentration was determined with a NanoDrop and isolated plasmids were controlled by digestion with two different restriction enzymes and stored at −20° C. All cultivations were performed in baffled shake flasks on a rotary shaker (Multitron, Infors AG, Bottmingen, Switzerland) at 37° C. and 230 rpm with a shaking diameter of 5 cm.

Polymerase Chain Reaction

Insert construction and strain verification was performed by PCR using the mastercycler EP gradient (Eppendorf, Hamburg, Germany). For insert construction and PCR products designed for sequencing, a PWO master (Roche Applied Science, Mannheim, Germany) with proof reading function was used, whereas strain verification was performed with the PCR master (Roche Applied Science, Mannheim, Germany) containing Taq polymerase. Obtaining desired DNA fragments for vector construction, induction of gene deletions, introduction of point mutations, artificial addition of recognition sites for restriction enzymes for directed ligation with transformation vectors was performed according to conventionally used methods. After each reaction, PCR products were purified using the GFX™ PCR DNA and Gel Band purification kit (GE Healthcare, Munich, Germany). Amplification was carried out with a standard temperature profile starting with an initial denaturation step (5 min at 95° C.). This was followed by 30 cycles of 0.5 min denaturation at 95° C., 0.5 min annealing and 1 min of elongation at 72° C. After a final elongation step of 5 min at 72° C., the cycler was cooled down to 15° C. The annealing temperature was adjusted individually to the primers and calculated in dependence of their GC content according to the following equation:

$$T = 64 + \frac{(G + C - 16.4)}{(G + C + T + A)} \tag{2}$$

Reactions were typically performed in a total volume of 50 μl. Primers were added to a final concentration of 400 nM. One μl of purified genomic DNA or plasmid DNA was added as template. For colony PCR, template DNA from the fast isolation was used and the volume was increased to 10 μl. Negative control was performed without template DNA.

Gel Electrophoresis

Products from polymerase chain reaction or enzymatic digestion were separated electrophoretically in a 1% agarose gel. Electrophoresis was performed in 1×TAE buffer at 100-120 V for 1-1.5 h (B1A easy cast mini gel or D2 wide gel system, Thermo Scientific, Rochester, USA with Power Pack P25T, Biometra, Gottingen, Germany). Band size was determined by a 1 kb DNA ladder (O'GeneRuler™ 1 kb DNA Ladder ready-to-use, Fermentas, St. Leon-Roth, Germany). Before gel loading, samples were mixed with 1/10 volume OrangeG loading buffer. Composition of TAE buffer and OrangeG are displayed in Table 7.

TABLE 7

Table 7: Composition of gel loading buffer OrangeG and TAE buffer used for gel electrophoresis.

| Orange G | |
|---|---|
| 25 mL | Glycerol (99.9%) |
| 75 mg | OrangeG |
| 1 mL | EDTA (1M, pH 8.0) |
| Ad 50 mL | $H_2O$ |
| **50 × TAE-Buffer** | |
| 242.28 g | Tris |
| 100 mL | Acetic acid (100%) |
| 100 mL | EDTA (0.5M, pH 8.0) |
| Ad 1000 mL | $H_2O$ |

Gels were stained in an ethidium bromide dye bath (0.5 μg $mL^{-1}$ ethidium bromide). DNA detection was performed under UV light in the Gel Ix Imager (Intas, Gottingen, Germany).

Enzymatic Digestion

For construction of the transformation vector, the empty vector pClik and the insert, obtained by fusion PCR were digested with two distinct restriction enzymes. The reaction for vector digestion was performed in a total volume of 25 μl and contained 1 μl of each enzyme, 2.5 μl reaction buffer (10×), 5 μl plasmid DNA and 15.5 μl water. Digestion was performed overnight at 37° C. or for 20 minutes when FastDigest enzymes (Fermentas, St. Leon-Roth, Germany) were used. Subsequently, the phosphate residue from the linearized vector was removed by alkaline phosphatase treatment (Shrimp alkaline phosphatase (SAP), Fermentas) for 1 h at room temperature to avoid religation of the vector. Digestion after plasmid isolation from NM522 was performed without SAP treatment. The insert digestion was carried out with 25 μl of the PCR product from fusion PCR, 2 μl of each enzyme, 5 μl of 10× reaction buffer and 16 μl of water.

DNA Ligation

For ligation two mixes with different vector-insert-ratios were prepared. The reaction was carried out with the Rapid-DNA ligation Kit (Roche Applied Science, Mannheim, Germany) and contained 0.5 μl or 1 μl linearized vector, 2 μl insert DNA, 2 μl dilution buffer, 10 μl ligation buffer, 1 μl T4 ligase and 4 μl or 4.5 μl water. The mixes were incubated for 30 min at room temperature and subsequently applied for heat shock transformation of *E. coli* DH5α.

Transformation

Preparation of Heat Shock Competent *E. Coli* (Inoue, et al., 1990)

Cells were grown in one pre-culture and one main culture at 23° C. and 230 rpm on a rotary shaker (Multitron, Infors). The pre-culture (5 mL LB medium containing 20 mM $MgCl_2$) was inoculated with a single colony from agar plate and grown overnight. For *E. coli* NM522 carrying the pTC plasmid, 12.5 μg $mL^{-1}$ tetracycline was added. Two ml of the overnight culture was used to inoculate the main culture which was performed in a 2 L baffled shake flask with 250 mL medium. At an $OD_{600}$ of 0.4-0.6, cells were placed for 10 min on ice, subsequently transferred into pre-cooled sterile 50 mL falcon tubes and centrifuged for 10 min (5000 rpm. 4° C., Centrifuge 5804R, Eppendorf, Hamburg, Germany). After a washing step with 40 mL of ice cold TB buffer (Table 8), cells were resolved in 20 mL of the same buffer and 1.5 mL DMSO, placed for 10 min on ice and finally split in 220 μl aliquots in pre-cooled 1.5 mL Eppendorf tubes which were then shock frozen in an ethanol-dry-ice-bath. Competent cells were stored at −80° C.

TABLE 8

Table 8: Composition of the TB buffer used for preparation of heat shock competent *E. coli*

| | | | |
|---|---|---|---|
| TB buffer | 2 | mL | Pipes-NaOH (0.5M, pH 6.7) |
| | 3 | mL | $CaCl_2$ (0.5M) |
| | 12.5 | mL | KCl (2M) |
| | 5.5 | mL | $MnCl_2$ (1M) |
| | Ad 100 | mL | $H_2O$ |

Sterilized by filtration (0.2 μm Ultrafree-MC, Millipore)

Heat Shock Transformation

After thawing on ice, 50 μl of competent *E. coli* cells were mixed with 3 μl plasmid DNA and incubated for 30 min on ice. Heat shock was performed for 45 sec at 45° C. in a thermo block (Thermomixer comfort, Eppendorf, Hamburg, Germany). Cells were immediately placed on ice afterwards for 2 minutes. Subsequently, 900 μl SOC medium was added and cell regeneration was performed without selection pressure for 60 min at 37° C. in a thermo mixer at 500 rpm (Thermomixer comfort, Eppendorf). For selection purpose, cells were then plated on $LB^{Kan}$ or $LB^{Tet+Kan}$ plates and incubated for 1 day at 37° C. Single colonies were picked. Plasmid isolation and vector digestion was performed as described above. Strains containing the desired vector were stored at −80° C.

Preparation of Electro-Competent *C. glutamicum*

Cells from glycerol stocks were spread on agar plates and incubated for 48 h at 30° C. First pre-culture (5 mL $BHI^{++}$ medium) was inoculated with a single colony, grown overnight at 30° C. and 230 rpm a rotary shaker (shaking diameter 5 cm, Multitron, Infors AG, Bottmingen, Switzerland) and used as seed for the main culture. This was performed in 50 mL $BHI^{++}$ medium and inoculated with an $OD_{660}$ of 0.3. At an $OD_{660}$ of 1.2-1.5 cells were harvested (7500×g, 3 min, 4° C.) in sterile pre-cooled 50 mL falcon tubes, washed 4 times with ice cold 10% glycerol and subsequently resolved in 4 mL glycerol per gram cell wet weight (CWW). Cell suspension was used to test the electroporation time ($t_E$). If appropriate ($t_E$<8 ms) cell suspension was further diluted with 10% glycerol.

Transformation by Electroporation

Electroporation of *C. glutamicum* was performed with 200 μl cell suspension and 2.5 μg and 5 μg plasmid DNA, respectively at 2.5 kV, 25 μF and 400Ω in 2 mm electroporation cuvettes with the BioRad gene pulser Xcell™ (Biorad, Hercules, US). A reaction without DNA was used as negative control. Immediately after the electro pulse, 1 mL BHIS medium was added and the cell suspension was transferred in eppendorf tubes and incubated without selection pressure for 90 min (30° C., 500 rpm, Thermo mixer comfort, Eppendorf, Hamburg, Germany). Since pClik and pK19 cannot replicate in *C. glutamicum*, heredity transmission of the vector requires integration of the plasmid DNA into the genome via homologous recombination. Selection of transformants having past the first recombination event was performed on $CM^{Kan}$ agar plates for 2 days at 30° C. Single colonies from $CM^{Kan}$ were used for the second recombination.

Second Recombination

For marker free modification of *C. glutamicum*, the vector introduced by electroporation was removed by a second recombination event and selection on sucrose (Jager, et al., 1992). For this purpose, single colonies from the first recombination event were grown overnight in 5 mL $BHI^{++}$ medium (30° C., 230 rpm) and 1000 and 200 μl, respectively, of a 1:1000-dilution were plated on $CM^{Sac}$. Due to lethality of sacB expression during growth of *C. glutamicum* on sucrose only recombinant strains can grow in which the plasmid including sacB was removed by the second homologous recombination event. Single colonies grown on $CM^{Sac}$ were picked with a tooth pick and patched on $CM^{Sac}$ and $CM^{Kan}$ raster plates. Ten to fifteen randomly chosen kanamycin sensitive and sucrose tolerant clones were further investigated with regard to the desired modification.

Screening and Strain Validation

Depending on the modification, screening and strain validation comprised PCR analysis, determination of enzyme activity or sequencing. Promoter exchange and gene deletion was generally screened by PCR and validated by determination of specific enzyme activity. Screening for substitution of the start codon, however, was performed by enzyme activity tests and promising clones with a changed specific enzyme activity were investigated in more detail by sequence analysis.

Strain Characterization

Batch Cultivation in Minimal Medium

Cultivation in shake flasks was carried out at 30° C. and 230 rpm on a rotary shaker (shaking diameter 5 cm, Multitron, Infors AG, Bottmingen, Switzerland). First precultures (50 mL medium in 500 mL baffled flask) were inoculated with single colonies from 2 days old agar plates and incubated for 8 h. Cells were harvested by centrifugation (8800×g, 2 min, 4° C.), washed with sterile 0.9% NaCl, and used as inoculum for the second pre-cultivation. This was then carried out in 50 mL minimal medium in 500 mL baffled flasks, containing the carbon source of the subsequent main culture. Main cultures were performed in triplicate (25 mL in 250 mL baffled flasks or 200 mL in 2 L baffled flasks) using cells from the second pre-culture as inoculum. Dissolved oxygen in the flasks was monitored via immobilized sensor spots containing a fluorophore with an $O_2$-dependent luminescent decay time (Wittmann, et al., 2003). The dissolved oxygen level was above 20% of saturation during each cultivation so that sufficient oxygen supply of the cells was ensured. The pH was in the range of 7.0±0.2 during the whole cultivation. For tracer experiments, naturally labelled glucose was replaced by either 99% [1-$^{13}$C] glucose, 99% [6-$^{13}$C] glucose or an equimolar mixture of naturally labelled and 99% [U-$^{13}$C] glucose. Biorector fermentation in minimal medium was performed in a 250 mL bioreactor (Meredos, Bovenden, Germany) with 100 mL working volume at 30±0.1° C., pH 7.0±0.1 and 800 rpm. The dissolved oxygen level was above 20% of saturation during the whole cultivation. The aeration rate was maintained at 100 mL $min^{-1}$ by a mass flow controller (Brooks Instruments, Veenendaal, The Netherlands). The composition of aeration and exhaust gas was measured online by a quadrupole mass spectrometer (Omnistar, Balzers, Vaduz, Liechtenstein) with 2 min intervals.

Fed-Batch Fermentation

Fed-batch fermentation in the molasses based production medium was carried out in a Sartorius bioreactor with a Biostat B plus control unit in a 5 L vessel. The aeration rate was set to 2.5 L $min^{-1}$ by the integrated gas flow controller. A pH electrode (Mettler Toledo, Giessen, Germany) was used for pH monitoring. To keep pH constant at 6.9, 25% $NH_4OH$ was added with a peristaltic pump system of the Biostat control unit. The added volume was determined gravimetrically (Lab Balance Cupis, Sartorius, Gottingen, Germany). Dissolved oxygen was determined using a $pO_2$ electrode (Mettler Toledo, Giessen, Germany) and maintained at a saturation of 20% by variation of the stirrer velocity. This was controlled by the process control software BaseLab (BASF SE, Ludwigshafen, Germany). For calibration of the $pO_2$ electrode, the medium was in turn aerated with synthetic air and nitrogen, respectively. Temperature was adjusted to 30°

C. using a jacket cooling. $CO_2$ and $O_2$ in the exhaust gas were analyzed by a mass spectrometer. All process data were monitored online and recorded in a 5 min interval by the process control software BaseLab. Feeding was initiated by a $pO_2$ signal. Variation of the dissolved oxygen with a rate higher than 10% $min^{-1}$ activated the peristaltic feed pump of the Biostat control unit. Dosage was controlled by the process control software via the gravimetrically determined feed amount added.

Fermentation was started in a volume of 1 L. This was inoculated with cells grown for 6 h at 30° C. and 230 rpm on a rotary shaker (shaking diameter 5 cm, Multitron, Infors AG, Bottmingen, Switzerland) in CM medium. Cells from 600 mL pre-culture were harvested by centrifugation (8800×g, 2 min, RT), resolved in 50 mL sterile NaCl (0.9%) and used for inoculation. Batch fermentation was started with an optical density of 10. The feeding phase was initiated after 9 h and fermentation was carried out for a total of 30 h.

General Outline of the Stepwise Construction of Vectors and Transformation into Bacteria Construction of Transformation Vector No 4 (pClik_lysC$^{T311I}$) Carrying a Modified Aspartate Kinase Gene Vector No 4 (pClik_lysC$^{T311I}$) Referred To In Table 3 (Supra) Is Constructed Using primers P1 to P4 (SEQ ID Nos: 35 to 38) to introduce a point mutation in the background of, e.g. wild type *C. glutamicum* ATCC 13032 by allelic replacement.

For the preparation of a *C. glutamicum* strain carrying a point mutation resulting in an amino acid substitution from threonine to isoleucine at position 311 of the wildtype LysC-polypeptide (SEQ ID NO: 2), the ORF encoding aspartate kinase gene (lysC, SEQ ID NO: 1) was amplified.

To this end, isolated genomic DNA of *C. glutamicum* ATCC 13032 is subjected to PCR-amplification using appropriate primers introducing a nucleic acid modification at position 932 of the wildtype lysC-gene.

The amino acid sequence and the nucleotide sequence sequence of modified lysC/LysC are respresented in SEQ ID NO: 3 and 4, respectively.

In more detail, two separate DNA fragments are first PCR-amplified using primer pairs P1/P2 (PCR1) and P3/P4 (PCR2), respectively. PCR1 and PCR2 are used to implement the point mutation at position 932 in the nucleotide sequence of the lysC gene via P2 and P3, respectively. Primers P1 and P4 are used to add the recognition sites for restriction enzymes, e.g. for XhoI and SpeI.

In PCR1 a DNA fragment of 1467 bp is obtained that contains about 500 bp of the sequence upstream of lysC and about 946 bp of the lysC gene, including the point mutation at position 932, and the recognition site of XhoI.

In PCR2 a DNA fragment of 449 bp is obtained that contains a part of the lysC gene, including the nucleotide exchange at position 932 of the lysC gene, about 150 bp of the sequence downstream of the lysC gene with the artificially added recognition site of SpeI.

In the next step, these two DNA fragments are fused in PCR3 using the primer combination P1 and P4 as well as purified DNA produced in PCR1 and PCR2, respectively, as templates. The resulting DNA fragment has a size of 1916 bp and contains about 500 bp of the upstream sequence of lysC, the complete ORF of lysC including the point mutation at position 932 and about 150 bp of the downstream sequence of lysC as well as the artificially added recognition sites for XhoI and SpeI.

In an alternative method, the desired vector construct is obtained using primers P1 and P4 and a DNA template that already contains the desired nucleotide exchange within the lysC gene.

Subsequent to the amplification steps, the PCR-product is digested using restriction enzymes XhoI and SpeI and inserted into the vector pClik, which is subsequently used to transform *E. coli* DH5α. Following cultivation of transformed *E. coli* DH5α, the vector is isolated and used to transform *E. coli* NM522. This strain already harbors the pTC plasmid (Table 3, supra), an expression vector of the DNA-methyltransferase of *C. glutamicum*. Co-existence of both plasmids in *E. coli* NM522 results in an amplification of a correctly methylated transformation vector.

Plasmid pClik_lysC$^{T311I}$ containing the correctly methylated lysC$^{T311I}$ gene is used to transform wild type strains ATCC 13032 using electroporation. First and second recombination procedures are performed as described above. Randomly chosen strains are investigated by sequence analysis. Positively identified recombinants, in the following referred to as Strain 1, are used for subsequent genetic modifications.

Construction of Transformation Vector No 5 (pK19__2×ddh) Harbouring Two Copies of the ddh-Gene Encoding Diaminopimelate Dehydrogenase Vector No. 5 (cf. Table 3) is constructed using primers designated as P5 to P8 (SEQ ID Nos: 39 to 42) to introduce a second gene copy of ddh in the background of the above-described Strain 1 by allelic replacement.

To amplify the wild-type ddh gene (SEQ ID NO: 5), encoding diaminopimelate dehydrogenase (SEQ ID NO: 6), isolated genomic DNA of, e.g. *C. glutamicum* ATCC 13032 is subjected to PCR-amplification using primers P5, P6, P7, and P8.

In PCR1 the complete ddh sequence as well as 245 bp of the sequence upstream of the ddh gene and 84 bp downstream of the dhh gene are amplified using P5 and P6. The resulting PCR product had a size of 1305 bp and contains a recognition site for EcoRI that is introduced by P5.

In PCR2 the complete sequence of ddh is amplified together with 245 bp upstream of the ddh gene and 84 bp downstream of the ddh gene using primers P7 and P8. The resulting DNA fragment has a size of 1305 bp and contains a recognition site of SalI that is added by P8.

In the next step, two purified DNA products obtained in PCR1 and PCR2, respectively, are used as templates and fused in PCR3 using the primer combination P5 and P8.

The resulting DNA fragment has a size of 2530 bp and contains two complete ddh genes each flanked by a 245 bp sized upstream part and a 84 bp sized downstream part as well as recognition sites for EcoRI and SalI (cf. SEQ ID NO: 7)

Subsequent to the amplification steps, the PCR-product was digested using restriction enzymes EcoRI and SalI and inserted into the vector pK19 which was used to transform *E. coli* DH5α. Following a cultivation step, the vector was isolated and used to transform *E. coli* NM522 carrying the pTC plasmid allowing for an amplification of a correctly methylated transformation vector.

Plasmid pK19__2×ddh harbouring correctly methylated ddh genes is used to transform the above described Strain 1 using electroporation. First and second recombination procedures are performed as described above. Randomly chosen strains are investigated by PCR analysis and by determination of enzyme activity. Positively identified recombinants, in the following referred to as Strain 2, are used for subsequent genetic modifications.

Construction of transformation vector No 6 (pClik_Δpck) Harbouring a Partially Deleted PEP Carboxykinase For the construction of transformation vector No 6 (pClik_Δpck; Table 3, supra) primers P9-P12 (SEQ ID NO: 43 to 46) were used to introduce a disrupted form of the gene pck (SEQ ID NO: 10) encoding a truncated PEP-carboxykinase (SEQ ID NO: 11) in the background of the above-described Strain 2 via allelic replacement.

For the partial deletion introduced into the wildtype pck gene (SEQ ID NO: 8), encoding PEP carboxykinase (SEQ ID NO: 9) genomic DNA of *C. glutamicum* ATCC 13032 is subjected to PCR-amplification using primers P9, P10, P11, and P12.

Using primers P9 and P10, a DNA fragment of 420 bp is amplified containing the nucleotides 111-509 of the pck gene in PCR1. P10 is also used to artificially add 21 bp that are complementary to 21 bp of primer P11. The obtained sequence contains a natural recognition site for BamHI.

In PCR2 a DNA fragment of 417 bp that comprises nucleotides 1437-1833 of the pck gene using primer pair P11 and P12 is amplified. P11 is used to artificially add 21 bp that are complementary to 21 bp of P10. To artificially add the recognition site of BamHI P12 is used.

In the next step, two purified DNA fragments obtained in PCR1 and PCR2, respectively, are fused in PCR3 using the primer combination P9 and P12. The resulting DNA fragment has a size of 807 bp and contains nucleotides 111-509 and 1437-1833 of the pck gene, 21 additional base pairs added by primers P11 and P12 as well as two recognition sites for BamHI.

Subsequent to the amplification steps, the PCR-product is digested using restriction enzyme BamHI and inserted into the vector pClik which is used to transform *E. coli* DH5α. The vector is subsequently isolated from the transformed *E. coli* DH5a and used for the transformation of *E. coli* NM522 as described above. leading to an amplification of the correctly methylated transformation vector. Correctly methylated DNA harboured by the plasmid pClik_Δpck transformed into the above mentioned Strain 2 using electroporation. First and second recombination procedures are performed as described above. Randomly chosen strains are investigated by PCR analysis and Southern Blotting. Positively identified recombinants, in the following referred to as Strain 3, are used for subsequent genetic modifications.

Construction of Transformation Vector No 7 (pK19_$P_{sod}$dapB) Harbouring a Modified Dihydrodipicolinate Reductase Transformation vector No 7 (pK19_$P_{sod}$dapB; cf. Table 3, supra) is prepared using primers that specifically bind in the sod promoter, within the dapB gene (SEQ ID NO: 12) encoding dihydrodipicolinate reductase (SEQ ID NO: 13) and upstream of the dapB gene to introduce a promoter modification in the background of the above described Strain 3 via allelic replacement.

In more detail, for promoter exchange of the dapB gene, genomic DNA of *C. glutamicum* ATCC 13032 is subjected to PCR-amplification using primers that specifically bind within the sequence of the sod promoter, the dapB gene, and upstream of the dapB gene respectively. Appropriate primer sequences designated as P13, P14, P15, P16, P17 and P18 are depicted in SEQ ID NOs: 47 to 52.

In PCR1 a DNA-fragment of about 200 bp is amplified that contains the sequence of the sod-promoter. This is achieved with P13 and P14, whereby a sequence overlapping with the dapB gene is artificially added at the 3'-end.

In PCR2 a part of the dapB gene, including the start codon and the 5'-part of the gene is amplified. This is effected with primers P15 and P16, artificially adding an overlapping sequence with the sod promoter at the 5'-end of the start codon.

In the next step, the two purified DNA fragments obtained in PCR1 and PCR2, respectively, are fused in PCR3 with sod and dapB specific primer sequences.

In PCR4 a portion of the upstream sequence of the dapB gene is amplified. This is achieved using primers P17 and P18, which artificially add a sequence overlapping with the sod promoter at the 3'-end.

In the next step purified DNA-fragments obtained in PCR3 and PCR4, respectively, are fused using primers P17 and P16. These primers flank the final DNA-fragment and artificially add recognition sites for restriction enzymes that are suitable for vector-insert-ligation.

For the vector-insert-ligation, the PCR-product and the vector are cut with the chosen restriction enzymes, subsequently ligated and used to transform *E. coli* DH5α. After a cultivation step, the vector was isolated and used to transform *E. coli* NM522 carrying the pTC plasmid allowing for an amplification of a correctly methylated transformation vector.

Correctly methylated plasmid pK19_$P_{sod}$dapB is used to transform the above described Strain 3 using electroporation. First and second recombination procedures are performed as described above. Randomly chosen strains are investigated by PCR analysis. Positively identified recombinants, in the following referred to as Strain 4, are used for subsequent genetic modifications.

Construction of Transformation Vector No 8 (pK19_2×lysA and of argS) Harbouring Two Copies of Diaminopimelate Decarboxylase The transformation vector No 8 (pK19_2×argSlysA; Table 3, supra) is prepared with the aid of primers that specifically bind upstream and within the argS gene encoding arginyl-tRNA synthetase as well as within and downstream of the lysA gene to obtain a second gene copy of lysA together with the sequence of argS that are introduced into Strain 4 by allelic replacement. The argSlysA gene cluster is shown in SEQ ID NO: 15. The amino acid of LysA is depicted in SEQ ID NO: 17.

For implementation of a second gene copy of lysA and argS, genomic DNA, e.g. of *C. glutamicum* ATCC 13032 is subjected to PCR-amplification. To this end, each copy of the argSlysA cluster is constructed from 3 separately amplified DNA-fragments covering the entire cluster. These fragments are obtained in separate PCRs. Primer sequences used for this purpose are P19, P20, P21, P22, P23, P24, P25 and P26 (SEQ ID NOs: 53 to 60).

In PCR1, using primers P19 and P20, the 5' part of the argS gene is amplified together with about 500 bp upstream of the argS gene. The 5' part includes the promoter sequence of argS. Primer P19 is also used to artificially add the recognition site of BamHI. Primer P20 is located at a naturally occurring recognition site for EcoR I. The obtained DNA fragment has a size of 1410 bp.

Using primers P21 and P22 the 3' part of the argS gene together with the 5' part of the lysA gene is amplified in PCR2. Primer P21 is located at a naturally occurring recognition site for EcoRI. Primer P22 is localized at a naturally occurring recognition site of SalI. The obtained DNA fragment has a size of about 935 bp.

In PCR3 the 3' part of the lysA gene is amplified together with about 80 bp of the downstream sequence of lysA using primers P23 and P24. Primer P23 is located at a naturally occurring recognition site for SalI. Primer P24 is used to add a recognition site for XbaI. The obtained DNA fragment has a size of about 1290 bp. The DNA fragments were subsequently linked via the recognition sites of EcoRI and SalI. The linked DNA fragments from PCR1, PCR2 and PCR3 represent a first copy of the cluster argSlysA. In the next step, the second argSlysA cluster is constructed.

In PCR4, using P25 and P20, the 5' part of the argS gene is amplified together with about 500 bp upstream of the argS gene. This upstream part includes the promoter sequence of argS. P25 is used to artificially add the recognition site of XbaI. P20 is located at a naturally occurring recognition site for EcoRI. The obtained DNA fragment has a size of around 1374 bp.

In PCR5, using primers P21 and P22, the 3' part of the argS gene is amplified together with the 5' part of the lysA gene. P21 is located at a naturally occurring recognition site for EcoRI, P22 at a naturally occurring recognition site of SalI. The obtained DNA fragment has a size of about 935 bp.

In PCR6, using primers P23 and P26, the 3' part of the lysA gene is amplified together with about 70 bp of the downstream sequence of lysA. P23 is located at a naturally occurring recognition site for SalI. P26 is used to add a recognition site for HindIII. The obtained DNA fragment has a size of about 1256 bp.

The DNA fragments are subsequently linked via the recognition sites of EcoRI and SalI. The linked DNA fragments from PCR4, PCR5 and PCR6 represent the second copy of the cluster argSlysA.

Copy 1 and copy 2 of argSlysA, respectively, are linked via the recognition site of XbaI, which was added by primers P24 and P25. The linked copies (SEQ ID NO: 16) are inserted in the transformation vector pK19 via recognition sites of BamHI and Hind III that are added via primers P19 and P26, respectively. The obtained vector is used to transform *E. coli* DH5α. After a cultivation step, the vector is isolated and used to transform *E. coli* NM522 carrying the pTC plasmid allowing for an amplification of a correctly methylated transformation vector. The correctly methylated construct harboured by the plasmid pK19__2×argSlysA is used to transform Strain 4 using electroporation. First and second recombination procedures are performed as described above. Randomly chosen strains are investigated by PCR analysis. Positively identified recombinants, in the following referred to as Strain 5, were used for subsequent genetic modifications.

Construction of Transformation Vector No 9 (pClik_$P_{sod}$LysC) Harbousing an Aspartate Kinase Gene with sod-Promoter Construction of transformation vector No 9 (pClik_$P_{sod}$lysC; Table 3, supra) using primers that specifically bind in the sod promoter, within the lysC gene and upstream of the lysC gene and introduction of a promoter modification and concomitant exchange of the start codon from GTG to ATG in the background of Strain 5 by allelic replacement. The DNA sequence of lysC carrying the start codon modification, the sod promoter and the substitution T311I is shown in SEQ ID NO: 3.

For promoter exchange of the lysC gene, genomic DNA of e.g. *C. glutamicum* ATCC 13032 is subjected to PCR-amplification using primers that specifically bind within the sequence of the sod promoter, the lysC gene and upstream of the lysC gene, respectively. Appropriate primers designated as P27, P28, P29, P30, P31 and P32 (SEQ ID NO: 61 to 66).

In PCR1, a DNA-fragment of about 200 bp is amplified that contains the sequence of the sod-promoter. This is realized using primers P27 and P28, whereby a sequence overlapping with the lysC gene is artificially added at the 3'-end. P28 carries the desired nucleotide exchange at the position of the start codon of lysC so that the exchange from the start codon GTG to ATG is achieved.

In PCR2 a part of the lysC gene, including the start codon and the 5'-part of the gene is amplified. This is realized using primers P29 and P30, whereby a sequence overlapping with the sod promoter is added at the 5'-end adherent at the start codon. P29 additionally contains the desired nucleotide exchange for the start codon substitution. In the next step, the two obtained and purified DNA fragments produced in PCR1 and PCR2 are fused in PCR3 with the aid of sod and lysC specific primer sequences previously utilized in PCR1 and PCR2, respectively.

In PCR4 a part of the upstream sequence of the lysC gene is amplified with the aid of P31 and P32, whereby a sequence overlapping with the sod promoter is artificially added at the 3'-end.

In the next step the DNA-fragments from PCR3 and PCR4 are fused using purified DNA from PCR3 and PCR4 as template as well as primers P31 and P30.

The end primers (P31 and P30) are used to artificially add recognition sites for restriction enzymes that are suitable for vector-insert-ligation. To this end, the PCR-product and the vector are cut with the chosen restriction enzymes, subsequently ligated and thereafter used to transform *E. coli* DH5α. After a cultivation step, the vector is isolated and used to transform *E. coli* NM522 carrying the pTC plasmid allowing for an amplification of a correctly methylated transformation vector. The correctly methylated construct harboured by pClik_$P_{50d}$lysC is used to transform Strain 5 using electroporation. First and second recombination procedures are performed as described above. Randomly chosen strains are investigated by PCR analysis. Positively identified recombinants, in the following referred to as Strain 6, are used for subsequent genetic modifications.

Construction of Transformation Vector No 10 (pClik_hom$^{V59A}$) Harbouring a Mutated Homoserine Dehydrogenase Transformation vector No 10 (pClik_hom$^{V59A}$, Table 3, supra) is constructed using primers P33-P36 (SEQ ID NOs: 67 to 70) to introduce a point mutation in the hom gene (SEQ ID NO: 18) in the background of Strain 6 by allelic replacement.

For the preparation of a *C. glutamicum* strain carrying a point mutation resulting in an amino acid substitution from valine to alanine at position 59 of the Hom-polypeptide (SEQ ID NO: 19), the ORF encoding homoserine dehydrogenase is amplified.

To this end, genomic DNA of e.g. *C. glutamicum* ATCC 13032 is subjected to PCR-amplification using appropriate primers resulting in a nucleic acid modification at position 176 of the wildtype horn-gene. This is achieved using P33, P34, P35, and P36. The nucleotide sequence and the polypeptide sequence of modified hom/Hom are respresented in SEQ ID NO: 20 and 21, respectively.

In more detail, two separate DNA fragments are first amplified using for primers P33/P34 (PCR1) and P35/P36 (PCR2), respectively.

PCR1 and PCR2, respectively, are used to implement the point mutation at position 176 in the nucleotide sequence of the horn gene with the aid of primers 34 and 35.

When this primer combination is used, a DNA fragment of 686 bp is obtained in PCR1 which contains about 500 bp of the upstream sequence of the horn gene and about 186 bp of the horn gene, including the point mutation at position 176.

In PCR2, a DNA fragment of 1054 bp is obtained containing a part of the horn gene, which comprises a nucleotide exchange at position 176 of the horn gene.

In the next step, these two DNA fragments are fused in PCR3 using the primer combination P33 and P36 and purified DNA obtained in PCR1 and PCR2 as templates, respectively. The resulting DNA fragment has a size of 1718 bp and contains about 500 bp of the upstream sequence of horn and an incomplete horn gene of about 1218 bp including the point mutation at position 176.

Alternatively, the desired construct is obtained using primers P33 and P36 and a DNA template that already contains the desired nucleotide exchange within the horn gene. When primers P33-P36 are used the amplified DNA fragment naturally contains recognition site for XmaI and NheI.

Subsequent to the amplification steps, the PCR-product is digested using restriction enzymes XmaI and NheI and the resulting fragment is inserted into the vector pClik which was previously digested with XmaI and SpeI. SpeI and NheI form compatible sticky ends during DNA digestion. The vectors is then used to transform *E. coli* DH5α. After a cultivation step, the vector is isolated and used to transform *E. coli* NM522 carrying the pTC plasmid allowing for an amplification of a correctly methylated transformation vector. The correctly methylated hom$^{V59A}$ gene harboured by plasmid pClik_hom$^{V59A}$ is used to transform Strain 6 using electroporation. First and second recombination procedures were performed as described above. Randomly chosen strains were investigated by sequence analysis. Positively identified recombinants, in the following referred to as Strain 7, were used for subsequent genetic modifications.

Construction of Transformation Vector No 11 (pClik_pyc$^{P458S}$) Harbouring a Mutant Pyruvate Carboxylase Transformation vector No 11 (pClik_pyc$^{P458S}$, Table 3, supra) is constructed with primers P37 to P40 that are suitable for introduction of a point mutation in the pyc gene (SEQ ID NO: 22) in the background of Strain 7 by allelic replacement.

For the preparation of a *C. glutamicum* strain carrying a point mutation resulting in an amino acid substitution from proline to serine at position 458 of the Pyc-polypeptide (SEQ ID NO: 23), the ORF encoding pyruvate carboxylase was amplified.

To this end, isolated genomic DNA of, e.g. *C. glutamicum* ATCC 13032 is subjected to PCR-amplification using appropriate primers which result in a nucleic acid modification at position 1372 of the wildtype pyc-gene. These is achieved with primers designated P37, P38, P39, and P40 (SEQ ID NOs: 71 to 74). The nucleotide sequence and the polypeptide sequence of modified pyc/Pyc are respresented in SEQ ID NO: 24 and 25, respectively.

In more detail, two separate DNA fragments are first produced using primers P37/P38 (PCR1) and P39/P40 (PCR2), respectively. In this case, PCR1 and PCR2 are used to introduce a point mutation at position 1372 in the nucleotide sequence of the pyc gene with the aid of P38 and P39, respectively.

In PCR1 a DNA fragment of 745 bp is obtained which contains an incomplete pyc gene including the point mutation at position 1372 of the gene.

In PCR2 a DNA fragment of 744 bp is obtained containing a part of the pyc gene, including the nucleotide exchange at position 1372 of the pyc gene.

In the next step, these two DNA fragments obtained in PCR1 and PCR2, respectively, are fused in PCR3 using primer combination P37 and P40. The resulting DNA fragment has a size of 1461 bp and contains an incomplete sequence of the pyc gene comprising the desired point mutation at position 1372 of the gene.

Alternatively, the desired construct is obtained using the primers P37 and P40 and a DNA template that already contains the desired nucleotide exchange in the pyc gene. The amplified DNA fragment can be inserted into the vector pClik via appropriate recognition sites for restriction enzymes such as MluI and SalI.

The vector harbouring the mutant pyruvate carboxylase is subsequently used to transform *E. coli* DH5α. After a cultivation step, the vector is isolated and used to transform *E. coli* NM522 carrying the pTC plasmid allowing for an amplification of a correctly methylated transformation vector. The correctly methylated pyC$^{P458S}$ gene harboured by the plasmid pClik_pycP$^{458S}$ is used to transform Strain 7 by electroporation. First and second recombination procedures are performed as described above. Randomly chosen strains are investigated by sequence analysis. Positively identified recombinants, in the following referred to as Strain 8, are used for subsequent genetic modifications.

Construction of Transformation Vector No 12 (pClik_P$_{sod}$-pyc) Harbouring a Pyruvate Carboxylase with an Sod-Promoter Transformation vector No 12 (pClik_P$_{sod}$pyc) is constructed with the aid of primers that specifically bind in the sod promoter, within the pyc gene and upstream of the pyc gene to introduce a promoter exchange in the background of Strain 8 via allelic replacement. The pyc sequence with an sod-promoter is shown in SEQ ID NO: 24. This sequence also contains the amino acid substitution at position 458 described above.

For a promoter exchange of the pyc gene genomic DNA of, e.g. *C. glutamicum ATCC* 13032 was subjected to PCR-amplification using primers that specifically bind within the sequence of the sod promoter and the pyc gene, as well as upstream of the pyc gene respectively. Appropriate primer sequences are shown in the sequences encoding primers designated as P41, P42, P43, P44, P45 and P46 (SEQ ID Nos 75 to 80).

In PCR1, a DNA-fragment of about 200 bp is amplified that contains the sequence of the sod-promoter. This is achieved using P41 and P42, whereby a sequence overlapping with the pyc gene is artificially added at the 3'-end.

In PCR2, a part of the pyc gene, including the start codon and the 5'-part of the gene is amplified. This is realized using P43 and P44, whereby a sequence overlapping with the sod promoter is artificially added at the 5'-end adherent at the start codon.

In the next step, the two obtained DNA fragments are fused in PCR3 with the sod and pyc specific primer sequences used in PCR1 and PCR2, respectively and purified DNA from PCR1 and PCR2.

In PCR4 a part of the upstream sequence of the pyc gene is amplified. This might be realized with primers P45 and P46, whereby a sequence overlapping with the sod promoter is artificially added at the 3'-end.

Thereafter, the DNA-fragments resulting from PCR3 and PCR4 are fused using purified DNA from PCR3 and PCR4 as templates and primers P45 and P44. The primers P45 and P44 are used to artificially add recognition sites for restriction enzymes that assist in vector-insert-ligation. To this end, the PCR-product and the vector are cut with the chosen restriction enzymes, subsequently ligated and used to transform *E. coli* DH5α. After a cultivation step, the vector is isolated and used to transform *E. coli* NM522 carrying the pTC plasmid allowing for an amplification of a correctly methylated transformation vector. The correctly methylated construct harboured by the plasmid pClik_$P_{sod}$pyc is used to transform Strain 8 by electroporation. First and second recombination procedures are performed as described above. Randomly chosen strains are investigated by PCR analysis. Positively identified recombinants, in the following referred to as Strain 9, are used for subsequent genetic modifications.

Construction of transformation vector No 13 (pClik_icd$^{A1G}$) Harbouring a Modified Isocitrate Dehydrogenase Gene Transformation vector No 13 (pClik_icd$^{A1G}$; Table 3, supra) is constructed with the aid of primers P47-P50 to introduce a start codon exchange in the background of Strain 9 via allelic replacement.

For the preparation of a *C. glutamicum* strain carrying the start codon exchange ATG→GTG in the icd gene, encoding isocitrate dehydrogenase (SEQ ID NO: 27), the ORF encoding isocitrate dehydrogenase (icd, SEQ ID NO: 26) is amplified.

To this end, previously isolated genomic DNA of *C. glutamicum* ATCC 13032 was subjected to PCR-amplification using appropriate primers which introduce a nucleic acid modification at the start codon position of the icd-gene. Primers P47, P48, P49 and P50 are used (SEQ ID NO: 81 to 84). The nucleotide sequence of modified icd gene is represented in SEQ ID NO: 28.

In more detail, two separate DNA fragments are first amplified using PCR-primers P47/P48 (PCR1) and P49/P50 (PCR2), respectively. PCR1 and PCR2 are used to implement the point mutation at the start codon position in the nucleotide sequence of the icd gene using P48 and P49. P47 was used to add the recognition site of XhoI and P50 was used to add the recognition site of MluI.

In PCR1 a DNA fragment of about 520 bp was obtained which contained about 502 bp of the upstream sequence of icd and about 18 bp of the icd gene, including the point mutation at the start codon position, and the recognition site of XhoI.

In PCR2 a DNA fragment of 520 bp containing a part of the icd gene, including the nucleotide exchange at the start codon position of the icd gene about 7 bp of the sequence upstream the icd gene and the recognition site of MluI is obtained.

In the next step, the two obtained DNA fragments are fused in PCR3 using the primer combination P47 and P50 and purified DNA from PCR1 and PCR2, respectively, as templates. The resulting DNA fragment has a size of 1014 bp and contains about 500 bp of the upstream sequence of icd, the start codon substitution and about 500 bp of the icd gene as well as the recognition sites for XhoI and MluI. Subsequent to the amplification steps, the PCR-product is digested using restriction enzymes XhoI and MluI and inserted into the vector pClik which is subsequently used to transform *E. coli* DH5α. After a cultivation step, the vector is isolated and used to transform *E. coli* NM522 carrying the pTC plasmid allowing for an amplification of a correctly methylated transformation vector.

The correctly methylated icd$^{A1G}$ gene harboured by the plasmid pClik_icd$^{A1G}$ is used to transform Strain 9 using electroporation. First and second recombination procedures are performed as described above. Randomly chosen strains are investigated by enzyme activity and sequence analysis. Positively identified recombinants, in the following referred to as Strain 10, are used for subsequent genetic modifications.

Construction of Transformation Vector No 14 (pClik_$P_{eftu}$fbp) Harbouring Fructose 1,6-bisphosphatase with eftu-Promoter Vector No 14 (pClik_$P_{eftu}$fbp); Table 3, supra) is constructed using primers specifically binding in the eftu promoter, in the fbp gene and upstream of the fbp gene. The vector is used for an introduction of a promoter exchange in the background of the above-described Strain 10 by allelic replacement.

For promoter exchange of the wildtype fbp gene (SEQ ID NO: 29 showing the sequence of the fbp gene and the native promoter) encoding fructose 1,6-bisphosphatase (SEQ ID NO: 30), genomic DNA of *C. glutamicum* ATCC 13032 was subjected to PCR-amplification. Primers that specifically bind within the sequence of the eftu promoter and the fbp gene (the fbp nucleotide sequence recombined with eftu-promoter is shown SEQ ID NO: 31), as well as upstream of the fbp gene respectively, are used. Appropriate primer sequences are depicted in SEQ ID NO: 85 to 90 encoding primers designated as P51, P52, P53, P54, P55 and P56.

In PCR1, using P51 and P52, a DNA-fragment of about 200 bp is amplified that contains the sequence of the eftu-promoter. In PCR2 a part of the fbp gene, including the start codon and the 5'-part of the gene is amplified. This is achieved using P53 and P54, whereby a sequence overlapping with the eftu promoter is artificially added at the 5'-end adherent at the start codon.

In the next step, two purified DNA fragments obtained in PCR1 and PCR2, respectively, are fused in PCR3 with the eftu and fbp specific primers used in PCR1 and PCR2, respectively.

In PCR4 a part of the upstream sequence of the fbp gene is amplified. This is achieved with the primers P55 and P56, whereby a sequence overlapping with the eftu promoter is artificially added at the 3'-end.

In the next step the DNA-fragments from PCR3 and PCR4 are fused using primers P55 and P54 as well as purified DNA from PCR3 and PCR4 as templates. The primers P55 and P54 are also suitable to add artificial recognition sites for restriction enzymes such as MluI and SalI that can be used for vector-insert-ligation. To this end, the PCR-product and the vector are digested with the chosen restriction enzymes, subsequently ligated and used to transform *E. coli* DH5α. After a cultivation step, the vector is isolated and used to transform *E. coli* NM522 carrying the pTC plasmid allowing for an amplification of a correctly methylated transformation vector. The correctly methylated construct harboured by the plasmid pClik_$P_{eftu}$fbp is then used to transform Strain 10 using electroporation. First and second recombination procedures are performed as described above. Randomly chosen strains are investigated by PCR analysis. Positively identified recombinants, in the following referred to as Strain 11, are used for subsequent genetic modifications.

Construction of Transformation Vector No 15 (pClik_$P_{sod}$tkt) Harbouring the Tkt Operon and an sod-Promoter Transformation vector No 15 (pClik_$P_{sod}$tkt) is constructed using primers that specifically bind in the sod promoter, within the tkt gene and upstream of the tkt gene resulting in a promoter exchange in the background of Strain 11 via allelic replacement.

In detail, to implement a promoter exchange of the tkt-operon (SEQ ID NO: 32, which shows the sequence of the tkt-promoter and the tkt-gene, which is the first gene in the tkt-operon), genomic DNA of e.g. *C. glutamicum* ATCC 13032 is subjected to PCR-amplification using primers that specifically bind within the sequence of the sod promoter and the tkt gene, which is the first gene of the tkt-operon and encodes the transketolase (SEQ ID NO: 33) as well as upstream of the tkt gene respectively. Appropriate primer sequences are represented in primer sequences designated as P57, P58, P59, P60, P61 and P62 (SEQ ID NO: 91 to 96).

In PCR1 a DNA-fragment of about 200 bp is amplified that contains the sequence of the sod-promoter. This is realized using P57 and P58. A recombination of the sod promoter sequence and the tkt-gene is shown in SEQ ID NO: 34.

In PCR2 a part of the tkt gene, including the start codon and the 5'-part of the gene, is amplified. This is realized using P58 and P59, whereby an sequence overlapping with the sod promoter is artificially added at the 5'-end adherent at the start codon.

In the next step, the two DNA fragments obtained in PCR1 and PCR2, were purified and used as templates in PCR3 to fuse both fragments with the sod and tkt specific primer sequences used in PCR1 and PCR2.

In PCR4 a part of the upstream sequence of the tkt gene is amplified. This is realized with the primers P61 and P62, whereby an overlapping sequence with the sod promoter is artificially added at the 3'-end.

In the next step the DNA-fragments from PCR3 and PCR4 are fused using purified DNA obtained in PCR3 and PCR4 as templates and P61 and P60 as primers. P61 and P60 are used to artificially add recognition sites for restriction enzymes such as MluI and SalI that are suitable for vector-insert-ligation. To this end, the PCR-product and the vector are cut with the chosen restriction enzymes, subsequently ligated and used to transform *E. coli* DH5α. After a cultivation step, the vector is isolated and used to transform *E. coli* NM522 carrying the pTC plasmid allowing for an amplification of a correctly methylated transformation vector.

The correctly methylated construct harboured by the plasmid pClik_$P_{sod}$tkt is then used to transform Strain 11 using electroporation. First and second recombination procedures are performed as described above. Randomly chosen strains are investigated by PCR analysis. Positively identified recombinants are in the following referred to as Strain 12.

Construction of a Tailor-Made Lysine Hyper-Producer

In a preferred embodiment of the present invention different strategies were successfully employed to rationally optimize lysine production by *C. glutamicum.*

Exemplified for the parent strains *C. glutamicum* BS1 and *C. glutamicum* BS87, the benefit of several targets from the key pathways of lysine biosynthesis, NADPH metabolism, precursor supply and $CO_2$ formation were investigated. With the objective of creating a wild type based hyper-producer, the identified modifications were combined in a single strain.

Based on the wild type *C. glutamicum* ATCC 13032 only beneficial modifications were implemented to minimize any detrimental side effect appearing in industrial production strains.

Strain Construction and Production Performance

The first step towards creation of the hyper-producer was release of aspartate kinase from feedback inhibition by lysine and threonine, introducing the amino acid exchange T311I (Becker, et al., 2005). This was complemented by the above described overexpression of ddh. Sole implementation of these two modifications and additional medium optimization created a lysine producer which already produced 125 mmol lysine (mol glucose)$^{-1}$.

To avoid further bottlenecks within the biosynthetic pathway of lysine, dihydrodipicolinate reductase (dapB), aspartate kinase (lysC) and diaminopimelate decarboxylase (lysA) were over expressed in addition to ddh. These enzymes are all part of the common route for lysine biosynthesis. The effect on lysine production should thus be independent of the flux partitioning between the succinylase and the dehydrogenase branch.

Further strain optimization was carried out by implementation of several additional genetic modifications. This comprised replacement of the natural homoserine dehydrogenase by a mutant variant exhibiting the amino acid exchange V59A. This mutation improves lysine production by reducing the carbon flux towards the threonine pathway, which directly competes with lysine biosynthesis (Ohnishi, et al., 2002). To ensure sufficient supply of oxaloacetate for lysine formation, additional modifications focussed on the precursor supply. These implied overexpression and modification of the major anaplerotic enzyme pyruvate carboxylase (Ohnishi, et al., 2002; Peters-Wendisch, et al., 2001) and deletion of the OAA-consuming reaction PEP carboxykinase (Petersen, et al., 2001). The resulting strain *C. glutamicum* BS87 thus comprised 9 modifications within the lysine biosynthesis and the precursor supply (FIG. 32).

From the comparison with its early ancestor strain *C. glutamicum* BS222, only exhibiting the regulatory point mutation in the lysC gene and a second copy of the ddh gene, it becomes obvious, that the additional modifications in *C. glutamicum* BS87 only provide a minor improvement of lysine production (FIG. 18). An engineering strategy that is solely focussed on a specific part of the metabolism is consequently not suitable to create an efficient production strain. The history of strain optimization towards improved lysine production by metabolic engineering, however, is clearly marked by this strategy. The key pathways TCA cycle and NADPH metabolism as major reactions in the concept of an optimized lysine producer were so far almost neglected. In this regard, the present work exposed genetic targets that perfectly complemented with previous strategies to overcome these limitations thereby advancing to the construction of a superior production strain. The next step towards creation of the intended hyper-producer was therefore focussed on the TCA cycle. As described above, attenuation of isocitrate dehydrogenase (icd$^{att}$) in the background of *C. glutamicum* BS87 significantly improved lysine production by efficient flux redirection from TCA cycle towards anaplerotic carboxylation. With regard to lysine production this engineering strategy benefits from an increased supply of oxaloacetate as well as a reduced carbon loss via $CO_2$-formation. Subsequent engineering of the NADPH metabolism was performed via two different strategies. Initially, the gluco-neogenetic enzyme fructose 1,6-bisphosphatase was over expressed, which was previously shown to significantly contribute to an improved NADPH supply (Becker, et al., 2005). As demonstrated above, this approach nicely complements with amplified expression of glucose 6-phosphate dehydrogenase. To circumvent further limitations in the PPP by a limited capacity of transketolase and transaldolase right from the beginning, overexpression of G6PDH was realized concomitantly with overexpression of transketolase and transaldolase by up-regulation of the complete tkt-operon via the sod promoter as described above. In response to the promoter exchange, the specific activity of G6PDH, transketolase and transaldolase was significantly increased. The concept of the engineering strategy is illustrated in FIG. 32. The benefit of the modifications becomes obvious from the comparison of the carbon conversion yield of the obtained genealogy (FIG. 18).

Starting with wild type *C. glutamicum* ATCC 13032, subsequent implementation of the beneficial modifications resulted in a wild type based lysine hyper-producer. The present work is the first report of such a complete rational strain in which all relevant pathways were considered. Of importance was the initially introduced modification within aspartate kinase to overcome the feedback inhibition of this key regulatory enzyme. The significant benefit of almost 50% improvement resulting from ddh overexpression clearly revealed, that the overall capacity of the lysine biosynthetic pathway in the genetic background of *C. glutamicum* BS1 (lysC$^{T311I}$) strongly limited lysine production. Further modification of the lysine pathway, however, as well as engineering of the precursor supply, which was described as beneficial in previous studies (Ohnishi, et al., 2002; Peters-Wendisch, et al., 2001; Petersen, et al., 2001), was here only of moderate success. This explicitly indicates that other bottlenecks arose within the central metabolism of *C. glutamicum* that impair lysine production. In the present study, the interest towards further engineering of lysine production was thus shifted to other parts of the intermediary metabolism. The success of this concept was immediately reflected by the response to attenuation of isocitrate dehydrogenase ($icd^{att}$). Implementation of a single nucleotide exchange in the start codon of icd increased the lysine yield from 141 mmol $mol^{-1}$ in *C. glutamicum* BS87 up to 200 mmol $mol^{-1}$ in the corresponding icd mutant representing an increase of 40%. Subsequent overexpression of fructose 1,6-bisphosphatase, previously shown to result in efficient flux redirection towards the NADPH providing PPP (Becker, et al., 2005), further enhanced lysine production by 18% (FIG. 18). The finally introduced modification in the here described genealogy comprised promoter exchange of the tkt-operon. This significantly increased the activity of the enzymes G6PDH, TKT and TAL encoded by this operon which in turn resulted in a 13% improved lysine yield. The benefit from overexpression of fbp and the tkt-operon clearly shows that insufficient supply of NADPH strongly limits lysine production in *C. glutamicum* and that engineering strategies aiming at an increased PPP flux are essential with the aim to create an efficient lysine hyper-producing strain. An additional benefit of amplified expression of the pentose phosphate pathway genes was observed concerning the growth behaviour. As compared to its ancestor *C. glutamicum* BS242 ($P_{eftu}$fbp), exhibiting a specific growth rate of 0.23 $h^{-1}$, the tkt-mutant grew with a rate of 0.32 $h^{-1}$. The higher carbon conversion yield ($Y_{Lys/S}$=26%) in combination with the improved growth behaviour of *C. glutamicum* BS244 increased the overall production performance of this strain, as it allows efficient lysine production in shortened fermentation times. By implementation of the last three modifications, an overall improvement of lysine production of almost 90% was achieved. This is a remarkable and also surprising profit resulting from only three genetic changes. It can thus be assumed, that these engineering strategies partly benefit from previously implemented mutations, e.g. removal of bottlenecks within lysine biosynthesis.

The production characteristics of the investigated strains were so far tested in shake flask cultivations for exponentially growing cells in minimal medium. Under these conditions the best producer *C. glutamicum* BS244 already exhibited a remarkable lysine yield of 26%, although the experimental set-up, comprising shake flask cultivation in minimal medium at low substrate concentrations, certainly limits its productivity. It was thus relevant to investigate the production performance of the lysine hyper-producer in a fed-batch fermentation process on an industrially relevant production medium as this cultivation strategy is most close to industrial production. Moreover, it allows a more realistic evaluation of the potential of the novel hyper-producer, especially in comparison with classically derived production strains. The best producer *C. glutamicum* BS244($P_{sod}$tkt) was investigated under industrial conditions comprising fed-batch fermentation on a molasses based complex medium.

Production Performance under Industrial Fermentation Conditions

The cultivation profile of the fed-batch fermentation of *C. glutamicum* BS244 is displayed in FIG. 19. Lysine production started early on and the lysine concentration in the culture supernatant continuously increased within 30 h up to a surprisingly high final titre of 120 g $L^{-1}$. The major increase was mainly achieved during the feeding phase, which was initiated after the initial sugar supplied in the batch medium (100 g $L^{-1}$) was consumed. As signal for automated feeding, a dissolved oxygen ($pO_2$) based signal was used during the process. The $O_2$ saturation in the fermenter was controlled via the stirrer velocity and kept constant at 20%. Carbon limitation in the medium resulted in an immediate and fast increase of the $pO_2$ which activated the feeding pump when the $pO_2$ increase exceeded 10% $min^{-1}$. The feeding solution, based on molasses and glucose, was additionally enriched with ammonium sulphate to ensure sufficient ammonium supply for lysine production. By this strategy the sugar concentration in the feeding phase was maintained at a concentration below 10 g $L^{-1}$.

The time course of biomass concentration, reflected by the optical density, was clearly different from lysine concentration (FIG. 34). During the batch phase, the optical density increased by a factor of five, whereas in the feeding phase only a threefold enhancement was observed. Moreover, biomass concentration did not increase until the end of the cultivation period but reached a maximum after 24 h.

A closer inspection of the production characteristics of the strain *C. glutamicum BS*244 revealed that the fermentation process can be further divided. As displayed in FIG. 35, the different phases can be distinguished on basis of the achieved lysine yield. In the best production phase, here designated as feed-phase 2, the lysine hyper-producer exhibited a lysine yield of 55%. A further characteristic of this phase is the almost stagnating biomass concentration. The consumed sugar is thus, efficiently channeled towards the lysine biosynthetic pathway. In the beginning of the fermentation process, the lysine yield was lower. This interval comprising batch phase and feed-phase 1 can clearly be described as major growth phase, characterized by extensive biomass formation (FIG. 34). Interestingly, in this phase a lysine yield of 25% was achieved which corresponds very well with the lysine yield achieved in shake flask cultivation experiments during the exponential growth phase.

The lysine hyper-producer created in this work is the best wild type based production strain so far described. Considering the final lysine titre as well as carbon and space-time yield it is clearly superior to previously described rationally created strains (Ikeda, et al., 2006). With a final lysine titre of 120 g $L^{-1}$ and a carbon conversion yield of up to 55% this strain even exhibits production characteristics that lie at the maximum limit of classically derived strains with reported carbon yields of 40-50% (Leuchtenberger, et al., 2005) and lysine titers of 80-120 g $L^{-1}$ (Anastassiadis, 2007). This production performance of the classical producers is, however, typically linked to long fermentation times up to 100 h (Anastassiadis, 2007), which significantly impairs the space-time yield. This is in general related to poor growth caused by numerous detrimental secondary mutations that accumulated during strain development due to the unspecific mutagenesis. By sole implementation of an exclusive set of only 12 beneficial modifications, these undesired side effects could be avoided in the wild type based production strain. The fast growth and thus shortened fermentation time of only 30 h results in a remarkable high space-time yield of 4 g $L^{-1}$ $h^{-1}$ which is considerably higher than the space-time yield of 2.1 g $L^{-1}$ $h^{-1}$ achieved during fed-batch fermentation by classical producers (Hirao, et al., 1989). The productivity obtained here, could be even increased by further genetic engineering or improvement of the process operations. In this regard, especially an optimized feeding strategy could significantly improve the productivity (Hirao, et al., 1989; Ikeda, 2003).

The wild type based lysine hyper-producer of the present invention demonstrates the potential of systems metabolic engineering as method for strain optimization. The strain *C. glutamicum* BS244 is an excellent proof of concept and proof of value of a complete rational production strain which is highly attractive for industrial application.

Analytical Methods

Cell Concentration

Sampling

For determination of the optical density from shake flasks, 1 mL samples were taken under sterile conditions with a pipette and transferred in an eppendorf tube. For gravimetrical determination of cell concentration, 10-15 mL sample were taken with a sterile one-way research pipette (Sarstedt, Numbrecht, Germany) and transferred into pre-dried 15 mL falcon tubes. The exact culture volume was determined on an analytical balance (CP225D, Sartorius, Gottingen, Germany). Foreshots and samples from bioreactor cultivation were taken with a syringe via a threeway cock and subsequently transferred into a falcon tube.

Quantification

Figure 3:
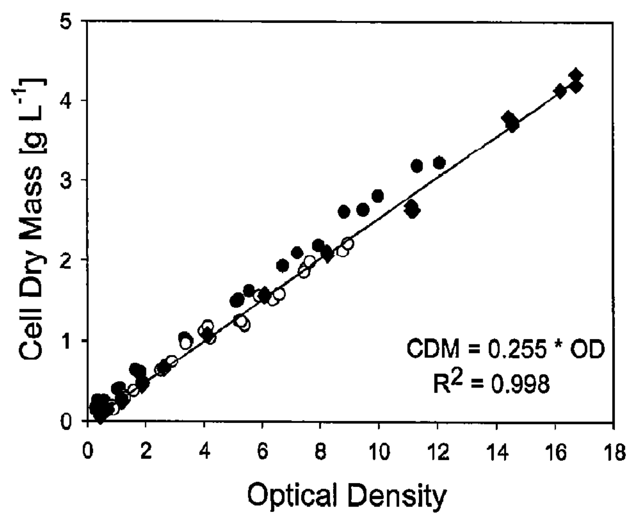
FIG. 3: Correlation between optical density (OD660, Libra S11) and cell dry mass for *C. glutamicum* BS1 (closed diamonds), *C. glutamicum* BS 87 (closed circles) and *C. glutamicum* BS 205 (open circles) from three biological replicates each.

Cell concentration was determined photometrically (Libra S11, Biochrome, Cambridge, UK and NovaspecII, Pharmacia Biotech, Little Chalfont, UK) at 660 nm in 1.5 mL polystyrene cuvettes (Plastibrand, Wertheim, Germany) using water as reference. If appropriate, cell suspension was diluted on an analytical balance (CP225D, Sartorius, Gottingen, Germany) to obtain an optical density between 0.05 and 0.3. All measurements were performed in duplicates. To obtain a correlation between optical density and cell dry mass (CDM), cell concentration was additionally determined gravimetrically (CP225D, Sartorius, Gottingen, Germany). For the latter, 15 mL falcon tubes were dried until constant weight at 80° C. and used to harvest cells from 15 mL culture broth by centrifugation (10 min, 9800×g, Biofuge stratos, Heraeus, Hanau, Germany). The supernatant was carefully discarded to avoid loss of cell material. Cells were washed three times with water and subsequently dried at 80° C. until constant weight. The correlation was determined for three strains with three biological replicates, each. The resulting correlation between $OD_{660}$ (Libra S11, Biochrome, Cambridge, UK) and CDM is displayed in FIG. 3. The corresponding correlation factor was determined by linear regression to CDM=0.255× OD (given in gram per liter).

Amino Acids

Sampling

Supernatant used for quantification of amino acids was obtained by separation of biomass in a centrifugation step (13000×g, 5 min, 4° C. for eppendorf tubes, 8500×g, 5 min, 4° C. for falcon tubes). Samples from fed-batch fermentation were additionally sterile filtered (0.2 μm Minisart filter, Sartorius, Gottingen, Germany) to ensure complete removal of biomass as fermentation broth exhibited a very high biomass concentration which was not properly removed by centrifugation.

Quantification

For determination of amino acids from cultivation in minimal medium, the culture supernatant was diluted 1:10 with α-amino butyric acid (237.18 μm) as internal standard. Analysis was performed by HPLC (Agilent Series 1100, Agilent Technology, Waldbronn, Germany). The protocol included pre-column derivatization with ophtaldialdehyde (OPA) and separation on a C18 column (Gemini5u, Phenomenex, Aschaffenburg, Germany) with a gradient of eluent A (40 mM $NaH_2PO_4$, pH 7.8) and eluent B (45% methanol, 45% acetonitrile, 10% water) at 40° C. (Kromer, et al., 2005). Separation of all proteinogenic amino acids was achieved by the time profile of the standard method displayed above. In cases the supernatant only contained lysine as well as small amounts of glutamate and glycine, the gradient was modified to reduce measurement time (Table 9).

TABLE 9

Table 9: Gradient profile of eluent A and eluent B for separation and quantification of amino acids by HPLC on a Gemini5u column (Phenomenex, Aschaffenburg, Germany).

| Standard Method | | | Modified Method | | |
|---|---|---|---|---|---|
| Time [min] | A [%] | B [%] | Time [min] | A [%] | B [%] |
| 0.0 | 100 | 0 | 0.0 | 100 | 0 |
| 41.0 | 59 | 41 | 16.0 | 64 | 36 |
| 46.0 | 19 | 81 | 17.0 | 0 | 100 |
| 46.5 | 0 | 100 | 20.0 | 0 | 100 |
| 49.0 | 0 | 100 | 20.5 | 100 | 0 |
| 49.5 | 100 | 0 | 22.0 | 100 | 0 |
| 52.0 | 100 | 0 | | | |

Lysine concentration of samples from fed-batch fermentation was determined in the 1:20 diluted supernatant as lysine-HCl by HPLC (Agilent Series 1100, Agilent Technology, Waldbronn, Germany) using a RI detector. Separation was carried out on an Ionospher 5C column (100×3.0 mm; Chrompack, Engstingen, Germany) at 40° C. and a flow rate of 1.5 mL $min^{-1}$. The mobile phase consisted of 1.80 mM citrate, 4.88 mM ethylenediamine and 20 mM 2,3-dihydroxysuccinate in 5% methanol and 95% water.

Sugars and Organic Acids

Sampling

Supernatant used for quantification of sugars and organic acids was obtained as described above by a centrifugation step and filtration.

Quantification

Supernatant from cultivation in minimal medium was diluted 1:10 and used for determination of the substrates glucose and fructose and the by-products trehalose, glycerol, DHA as well as organic acids by HPLC (Kontron Instruments, Neufahrn, Germany). Separation was carried out on an Aminex HPX-87H column (300×7.8 mm; Bio-Rad, Hercules, USA) at 45° C. with 5 mM $H_2SO_4$ as mobile phase and a flow rate of 0.5 mL $min^{-1}$. Refraction index (sugars, glycerol) and UV absorption at 210 nm (organic acids, DHA) was used for detection. For quantification of sucrose, the column temperature was reduced to 15° C. The eluent concentration was increased to 10 mM $H_2SO_4$. Glucose was alternatively quantified with a biochemical analyzer (YSI 2700 Select, Kreienbaum, Langenfeld, Germany).

Concentration of sugar and organic acids from fed-batch fermentation was determined in undiluted supernatant samples by HPLC (Agilent Series 1100, Agilent Technology, Waldbronn, Germany). An Aminex HPX-87H column (300× 7.8 mm; Bio-Rad, Hercules, USA) with a Cation H pre-column was used at 30° C. with 5 mM $H_2SO_4$ as mobile phase at a flow rate of 0.5 mL $min^{-1}$. Sugar concentration of the feed solution was determined in 1:10 dilution. Refraction index was used for detection.

Mass Isotopomers by GC-MS

Sampling

Cells were harvested in the exponential growth phase (13.000 rpm, Biofuge fresco, Heraeus, Hanau, Germany), washed two times with water and stored at −20° C. Supernatant was obtained by cell separation in the centrifugation step and stored separately at −20° C.

Quantification

Cells equal of about 1 mg CDM were resolved in 500HCl (6 M) and cell protein was hydrolyzed for 24 h at 105° C. Hydrolysates were neutralized with 6 M NaOH and cell debris was removed by filtration (Ultrafree-MC centrifugal Filter Devices, Amicon, Bioseparations, Bedford, USA). The labelling pattern was then determined by GC-MS as previously described (Wittmann, et al., 2002). The GC-MS consisted of a HP 6890 gas chromatograph (Hewlett Packard, Paolo Alto, Calif.) with a HP-5-MS column (5% phenyl-methyl-siloxan-diphenylpolysiloxan; 60 m×0.251 mm×0.25 μm, Agilent, Waldbronn, Germany) and helium as carrier gas. Detection was carried out by a quadrupol MS 5973 detector (Agilent). Sample preparation included lyophilisation and derivatization. The lyophilized hydrolysates were dissolved in 500 dimethylformamide (DMF+0.1% pyridine) and 50 μl N-methyl-N-t-butyl-dimethylsilyl-trifluoracetamid (MBDSTFA, Macherey-Nagel, Duren, Germany) and then incubated for 30 min at 80° C. If appropriate, salts were removed by centrifugation before measurement. Amino acid identification was performed via retention time and fragmentation pattern using an amino acid standard. Amino acids, derivatized with MBDSTFA show a typical fragmentation pattern comprising the mass fragments [M-57], [M-85] and [M-159], whereby the [M-57] contains the complete carbon backbone of the amino acid. Separation of the amino acid residue results in the formation of a fragment with the mass 302, containing the carbon atoms $C_1$ and $C_2$ of the respective amino acid. The mass fragments used for flux determination are listed and specified in Table 10.

Mass isotopomer distribution of trehalose was determined in 50 μl lyophilized cultivation supernatant. Derivatization was carried out with 50 μl methoxylamine (25 mg $mL^{-1}$ methoxylamin in pyridine) and 50 μl BSTFA (Macherey-Nagel) for 30 min at 80° C. (Kiefer, et al., 2004).

TABLE 10

Table 10: Mass fragments of proteinogenic amino acids as TBDMS derivates used for flux estimation. The mass given refers to the fragment $M_0$ comprising solely non-labelled mass isotopomers of C, O, H, N, S and Si.

| Analyte | $M_0$ [m/z] | Fragment | Carbon Atoms |
|---|---|---|---|
| Alanine | 260 | M-57 | $C_1$-$C_3$ |
| | 232 | M-85 | $C_2$, $C_3$ |
| Glycine | 246 | M-57 | $C_1$, $C_2$ |
| | 218 | M-85 | $C_2$ |
| Valine | 288 | M-57 | $C_1$-$C_5$ |
| | 260 | M-85 | $C_2$-$C_5$ |
| | 218 | M-159 | $C_2$-$C_5$ |
| Threonine | 404 | M-57 | $C_1$-$C_4$ |
| | 376 | M-85 | $C_2$-$C_4$ |
| Aspartate | 418 | M-57 | $C_1$-$C_4$ |
| | 390 | M-85 | $C_2$-$C_4$ |
| | 316 | M-159 | $C_2$-$C_4$ |
| Glutamate | 432 | M-57 | $C_1$-$C_5$ |
| | 330 | M-85 | $C_2$-$C_5$ |
| Serine | 390 | M-57 | $C_1$-$C_3$ |
| | 362 | M-85 | $C_2$, $C_3$ |
| | 288 | M-159 | $C_2$, $C_3$ |
| Phenylalanine | 336 | M-57 | $C_1$-$C_9$ |
| | 234 | M-159 | $C_2$-$C_9$ |
| | 302 | M-residue | $C_1$, $C_2$ |
| Tyrosin | 446 | M-57 | $C_1$-$C_9$ |
| | 302 | M-residue | $C_1$, $C_2$ |
| Arginine | 442 | M-57 | $C_1$-$C_6$ |

Positional Isotopomers by NMR

Sampling

Cells were grown as described above in two pre and one main culture. The naturally labelled glucose was replaced by [6-$^{13}$C] glucose. Supernatant was obtained by centrifugation (13.000 rpm, Biofuge fresco, Heraeus, Hanau, Germany) and dried under nitrogen flux.

Quantification

Labile protons were exchanged with deuterium by lyophilizing twice in 3 mL 99.9% $D_2O$ (Eurisotop, Saint-Aubain Cedex, France), and the final sample was suspended in 600 μl of 100 mM DC1 (Eurisotop). All 1D and 2D NMR spectra were obtained on an Avance 500 MHz spectrometer (Bruker, Wissembourg, Cedex, France) equipped with a 5 mm z-gradient BBI probe. The data were acquired and processed using TOPSPIN 1.3 software. The temperature was 298 K. The 1D proton spectra were recorded using quantitative conditions. To have full signal recovery, the relaxation delay between scans was 30 s and the pulse angle was 30°. The sweep width was 5000 Hz and the acquisition time was 1.6 s. A total of 16 scans was accumulated. Selective excitations were performed with shaped pulses. The excitation range was 60 Hz except for the protons, for which it was 100 Hz because of the larger multiplet width. The 1D $^{13}$C-decoupled DANTE-Z sequence consisted of eight consecutive scans of on-resonance Inversion BURP (I-BURP) pulses followed by eight consecutive scans of off-resonance I-BURP pulses (Geen and Freeman, 1991). This cycle was repeated four times. A 0.7 G $mm^{-1}$ purge gradient was applied after the selective excitation. The 1D $^{13}$C-decoupled DPFGSE sequence consisted of two REfocusing BURP (RE-BURP) pulses. The gradient powers were set at 0.7 and 0.3 G $mm^{-1}$, respectively. The decoupling of $^{13}$C nuclei during the selective pulses was performed using a GARP4 sequence at a power of 3.8 kHz. A $^{13}$C-decoupled DANTE-Z, Zero-Quantum Filtered TOCSY (DANTE-Z ZQF-TOCSY) sequence was generated by inserting a $^{13}$C-decoupled DANTE-Z pulse module into the previously described ZQFTOCSY sequence (Massou, et al., 2007). The $^{13}$C-decoupled DANTE-Z pulse was applied with the same parameters as above. The TOCSY transfer was carried out using a DIPSI-2 mixing sequence applied during 20 ms with 10 kHz field width. At the end of the mixing period, in-plane magnetization was suppressed by a square 2.6 G $mm^{-1}$ purge gradient. A Zero-Quantum Filter (Thrippleton and Keeler, 2003) consisting of a 180° CHIRP adiabatic pulse with 10% smoothing, 20 kHz sweep width, and 30 ms duration at 330 Hz maximal RF power, was applied before acquisition. A square 0.2 G $mm^{-1}$ gradient pulse was applied during the adiabatic pulse. All NMR measurements were performed at the institute Ingenierie des systemes biologiques et des procedes (INSA, Toulouse, France).

Intracellular Metabolites

Sampling

For methanol quenching 12 mL cell suspension ($OD_{660}$=5) was sucked into a plastic syringe and directly injected into a pre-cooled falcon tube filled with 24 mL of 60% methanol (−58° C., 10 mM HEPES, pH 7), immediately mixed vigorously and centrifuged for 5 min (10.000×g, −19° C., Biofuge Stratos, Kendro Laboratory Products, Langenselbold, Germany). Sampling was carried out fourfold in parallel for acid as well as alkaline extraction.

Whole culture quenching was performed transferring 10 mL culture with cells from the exponential growth phase into glass vials, incubated in liquid nitrogen. In parallel, supernatant samples were taken, involving cell separation by filtration (0.2 μm pore size, Sartorius, Gottingen, Germany) to account for metabolites occurring in the supernatant (Bolten, et al., 2007). Methanol quenching was carried out for sampling of nucleotides, whereas samples from whole culture quenching were used for determination of glucose 6-phosphate and fructose 6-phosphate, respectively.

Extraction

Oxidized nucleotides from methanol quenching were extracted by addition of 900 μl $HClO_4$ (pH 1) to the cell pellet, incubation for 7 min at 55° C. in a water bath and afterwards immediately placed on ice to eliminate metabolite instability. The perchloric acid samples were centrifuged for 5 min at 10.000×g and 4° C. to separate cell debris. Neutralization of the supernatant was achieved by careful addition of 5 M $K_2CO_3$ until a pH of 7.0 was achieved. The resulting precipitate ($KClO_4$) was removed by centrifugation (5 min at 13000×g). Alkaline extraction of the reduced nucleotides was performed by addition of 900 μl ethanolic KOH solution (200 mL 1M $K_2HPO_4$+50 mL EtOH+20 mL 5 M KOH, pH 12.4) to the cell pellet and incubation for 2 min at 55° C. in a water bath followed by incubation in ice-water and a final centrifugation step to remove the cell debris (5 min at 10.000×g and 4° C.). Metabolites from whole culture quenching were extracted by addition of 10 M HCl to a final pH of 1.2. Subsequently, cells were thawed and extraction was carried out for 8 min at 50° C. in a water bath which was followed by neutralizing with 10 M KOH and removal of cell debris by centrifugation (15 min, 10.000×g at 4° C.).

Quantification

The phosphorylated nucleotides NADP and NADPH were quantified in a 96-well plate at 540 nm (iEMS Reader MF, Thermo Fisher Scientific, Waltham, Mass., USA) by an enzymatic cycling assay (Bernofsky and Swan, 1973). For measurement a master mix for 110 reactions was prepared containing 50 mM Tris-HCl (pH 7.8), 250 mM glucose 6-phosphate, 0.5 mM thiazolyl blue, 2 mM phenazine ethosulfate and 100 mU $mL^{-1}$ glucose 6-phosphate dehydrogenase. 25 μm sample or standard solution (NADP or NADPH, respectively) were provided in the well plate and subsequently, the reaction was started by addition of 175 μl master mix. Change in absorbance was monitored for 10 minutes. Quantification was performed using a calibration curve with a nucleotide standard.

Glucose 6-phosphate (G6P) and fructose 6-phosphate (F6P) were determined enzymatically in a multi-step reaction (Bergmeyer and Hohorst, 1970). For measurement, a reaction mix with a total volume of 1 mL containing 200 mM Tris-HCl (pH 7.6), 0.2 mM NADP, 5 mM $MgCl_2$ and 500 μl sample was incubated for 5 min and the basic absorbance at 340 nm was determined (E0). Subsequently 5 μl glucose 6-phosphate dehydrogenase (34 U $mL^{-1}$) was added and E1 was determined after 5 min. Conversion of F6P was initiated by addition of 10 μl PGI (35 U mL) and the final absorbance at 340 nm was measured after another 5 min (E2). Positive control was carried out with a standard solution containing a mixture of G6P and F6P, negative control with water. Considering an extinction coefficient of NADPH of $\epsilon_{340}$=6.22 L $mmol^{-1}$ $cm^{-1}$ and the dilution factor DF of the sample, concentrations of G6P and F6P can be calculated by the following equations:

$$G6P\ [mM] = \left(\frac{E1 - E0}{6.22}\right) \times DF \tag{3}$$

$$F6P\ [mM] = \left(\frac{E2 - E1}{6.22}\right) \times DF \tag{4}$$

Enzyme Activities

Sampling

In the exponential growth phase, cells were harvested by centrifugation (5 min, 9800×g, Biofuge stratos, Heraeus, Hanau, Germany), washed once with disruption buffer and finally suspended to 0.25 g CWW per mL. Disruption was performed by sonication (MSE soniprep 150, Sanyo Europe, Munich, Germany) in a ice-water-bath with five 15 sec pulses at 20 microns, or mechanically. To this end, cell suspension was aliquoted in 750 μl amounts in 2 mL Eppendorf tubes containing glass beads. Disruption was performed in a ribolyser (MM301, Retsch, Haan, Germany) at 30 Hz (2×5 min; 5 minutes break in between). Crude cell extracts were obtained by centrifugation for 10 minutes at 13000 rpm (Biofuge fresco, Heraeus, Hanau, Germany) for ribolyser disruption or 2×30 min at 8500 rpm (Biofuge stratos, Heraeus, Hanau, Germany) for disruption by sonication. Protein content was determined by the method of Bradford (Bradford, 1976) with a reagent solution from BioRad (Quick Start Bradford Dye, BioRad, Hercules, USA) and a BSA protein standard.

Quantification

All measurements were performed as triplicates in a total volume of 1 mL by online monitoring of the change in absorbance in a photospectrometer (Specord 40, Analytik Jena, Jena, Germany or Helios alpha, Thermo Scientific, Waltham, USA). Negative controls were carried out without substrate or cell extract, respectively. Activities are given as specific enzyme activity [U $mg^{-1}$] with 1 U=1 μmol $min^{-1}$ at 30° C. and calculated from the change in absorbance [A $min^{-1}$] and a specific extinction coefficient of $\epsilon_{340}$=6.22 L $mmol^{-1}$ $cm^{-1}$ for NAD(P)H. As a general procedure, a master mix without substrate and cell extract was prepared from the stock solutions for the reaction buffer, $MgCl_2$, Co-factors (NADP, NAD, NADH, ADP, TPP, CoA) and coupling enzymes (LDH, G6PDH, PGI, ribose 5-phosphate isomerase (RPI), ribulose 5-phosphate epimerase (RPE), TPI/GDH) and incubated for 10 min at 30° C. Substrate solution and cell extract were provided in 1.5 mL polystyrene cuvettes (Plastibrand, Wertheim, Germany). The reaction was started by quick addition of the master mix.

Glucose 6-phosphate Dehydrogenase (G6PDH) (Moritz, et al. 2000)

Cell disruption was performed in a buffer containing 100 mM Tris/HCl (pH 7.5), 10 mM $MgCl_2$ and 0.75 mM DTT. DTT was prepared freshly as 100 mM stock solution and added to the cell suspension before disruption. Due to instability of the enzyme, the activity was measured immediately after cell disruption. The reaction mix for quantification of the G6P dehydrogenase activity contained 100 mM Tris/HCl (pH 7.8), 200 mM KCl, 1 mM NADP, 10 mM $MgCl_2$, 5 mM G6P and 50 μl cell extract. Michaelis-Menten affinity constants were determined by varying the concentrations of the substrates, G6P or NADP, respectively. To test the influence of effectors on activity, the reaction mix was additionally supplemented with ATP, PEP, FBP or NADPH in varied concentrations.

Pyruvate Kinase (PYK) (Netzer, et al., 2004)

For determination of pyruvate kinase activity, cells were disrupted in 100 mM Tris/HCl (pH 7.5) containing 10 mM $MgCl_2$. Activity was determined using lactate dehydrogenase (LDH) as coupling enzyme and online monitoring of $A_{340}$. The assay was performed at pH 7.0 with 100 mM Tris/HCl, 15 mM $MgCl_2$, 1 mM ADP, 0.25 mM NADH, 5.5 U LDH, 10 mM phosphoenolpyruvate (PEP) and 10 μl crude cell extract. The stock solution of the substrate (1 M PEP) was adjusted to pH 7.0 before use.

Malic Enzyme (MalE) (Gourdon, et al. 2000)

Disruption buffer for determination of malic enzyme activity contained 100 mM Tris/HCl (pH 7.8) and 200 mM KCl. MalE activity was measured in the same buffer additionally containing 2 mM $MgCl_2$, 1 mM NADP, 40 mM malate and 50

μl cell extract. Malate was prepared as stock solution in a concentration of 1 mol $L^{-1}$ and a pH of 7.8.

Isocitrate Dehydrogenase (ICD)

Cell disruption and activity measurement were carried out in 100 mM Tris/HCl (pH 7.8) containing 10 mM $MgCl_2$. The reaction mix for determination of enzyme activity additionally contained 1 mM isocitrate, 0.5 mM NADP and 250 of crude cell extract.

Pyruvate Dehydrogenase (PDH)

Disruption was performed in 100 mM Tris/HCl (pH 7.4), 10 mM $MgCl_2$ and 3 mM cysteine (Blombach, et al., 2007). The reaction mix for quantification of pyruvate dehydrogenase activity contained 50 mM Tris/HCl, 0.01 mM $CaCl_2$, 0.3 mM TPP, 0.12 mM CoA, 2 mM NAD, 3 mM cysteine, 5 mM pyruvate and 50 μl cell extract and was performed at pH 7.4 (Guest and Creaghan, 1974).

Phosphoglucoisomerase (PGD (Dominguez, et al., 1998)

For determination of PGI, cells were disrupted in 100 mM Tris/HCl (pH 7.8) containing 10 mM $MgCl_2$. Activity was quantified using glucose 6-phosphate dehydrogenase (G6PDH) as coupling enzyme and online monitoring of NADPH formation at 340 nm. The assay was performed at pH 7.8 with 100 mM Tris/HCl, 10 mM $MgCl_2$, 0.5 mM NADP, 1.25 U G6PDH, 4 mM fructose 6-phosphate and 10 μl crude cell extract.

Diaminopimelate dehydrogenase (DDH) (Cremer, et al. 1988)

Disruption buffer for determination of DDH activity consisted of 100 mM Tris/HCl and 10 mM $MgCl_2$ and was adjusted to pH 7.8. DDH activity was measured in the direction of meso-diaminopimelate oxidation and concomitant NADPH formation. To support this direction the reaction was performed at an alkaline pH of 10.5. The reaction was carried out with 200 mM glycine/NaOH (pH 10.5), 10 mM $MgCl_2$, 2 mM NADP, 4 mM meso-diaminopimelate and 50 μl cell extract.

Fructose 1,6-bisphosphatase (FBPase)

Determination of the in vitro activity of FBPase was based on the protocol of Sugimoto and Shiio (Sugimoto and Shiio, 1989) with slight modifications. The reaction mix contained 100 mM Tris/HCl, 10 mM $MgCl_2$, 0.5 mM NADP, 1 mM fructose 1,6 bisphosphate, 2 U of phosphoglucoisomerase, 1 U of glucose 6-phosphate dehydrogenase and 50 μl cell extract. Cell disruption was performed in 100 mM Tris/HCl buffer at pH 7.8.

Transketolase (TKT)

Crude cell extracts were prepared in 100 mM Tris/HCl at pH 7.8. Determination of TKT activity required application of several coupling enzymes. RPI and RPE served as coupling enzymes to provide the substrates ribulose 5-phosphate and xylulose 5-phosphate from ribose 5-phosphate (R5P) supplied in the assay. Online monitoring at 340 nm was enabled by further conversion of glyceraldehyde 3-phosphate as product of the TKT reaction by triosephosphate isomerase and glycerophosphate dehydrogenase (TPI/GDH). In contrast to the above mentioned procedure, two distinct mastermixes were prepared. Mix A contained buffer, TPI, RPI, RPE and NADH in a total volume of 650 μl, mix B contained buffer, TPP, $MgCl_2$ and cell extract in a total volume of 300 μl. Both were pre-warmed for 10 min at 30° C. Ribose 5-phosphate was provided in the cuvette and the reaction was started by subsequent addition of mix B and mix A. The final reaction mix contained 50 mM Tris/HCl (pH 7.8), 0.5 mM NADH, 1 U RPI, 0.5 U RPE, 1 U TPI/GDH, 10 mM $MgCl_2$, 0.2 mM TPP, 20 mM R5P and 50 μl of crude cell extract.

Transaldolase (TAL)

Cell disruption was performed in Tris/HCl buffer (100 mM, pH 7.8). The reaction for determination of transaldolase was performed in 50 mM Tris/HCl buffer (pH 7.8) additionally containing 1 mM fructose 6-phosphate, 0.5 mM NADH, 4 mM erythrose 4-phosphate, 6 U TPI/GDH and 50 μl of crude cell extract. TPI/GDH served as coupling enzymes to allow online monitoring at 340 nm.

Metabolic Flux Analysis

Systems-Wide [13C] Metabolic Flux Analysis

The metabolic network for growth of and lysine production by *C. glutamicum* grown on glucose comprised all central metabolic pathways, i.e., glycolysis, PPP, tricarboxylic acid cycle, and anaplerotic carboxylation and decarboxylation. Additionally, the pathways for the biosynthesis of lysine and different by-products as well as anabolic pathways from intermediary precursors to biomass were implemented. For glycine synthesis, two possible routes were considered, i.e., via serine and via threonine aldolase (Simic, et al., 2002). Based on previous results, the glyoxylate pathway was assumed to be inactive (Wittmann and Heinzle, 2002). In *C. glutamicum*, pyruvate carboxylase, PEP carboxylase, malic enzyme and phosphoenolpyruvate carboxykinase link glycolysis and TCA cycle through inter conversion of $C_3$ and $C_4$ metabolites (Wittmann and Becker, 2007). In the basic model, carboxylation and decarboxylation, respectively, were regarded as lumped fluxes. In an extended approach, however, all single enzymes were considered as separate reactions. For this purpose, PEP and pyruvate were divided into separate metabolic pools. Calculation of the anabolic demand for the different precursors was based on data for the biomass composition of *C. glutamicum* which considered the specific anabolic demand for cell wall synthesis based on the diaminopimelate content of the cell (Wittmann and de Graaf, 2005). Labelling data of proteinogenic amino acids and of trehalose and the mean values of the stoichiometric data from three parallel cultivations were combined for calculation of metabolic fluxes. The set of fluxes that gave minimum deviation between experimental (Mi,exp) and simulated (Mi,calc) mass isotopomer fractions was taken as the best estimate for the intracellular flux distribution. The network was over determined so that a least-squares approach was possible. A weighted sum of least squares was used as the error criterion (Wittmann and Heinzle, 2002). Statistical analysis of the obtained fluxes was carried out by a Monte Carlo approach (Wittmann and Heinzle, 2002). From the data obtained, 90% confidence limits for the single parameters were calculated. All metabolic simulations were carried out on a personal computer using Matlab 7.0 or Matlab 9.0 (Mathworks Inc.) (Wittmann and Heinzle, 2001a; Wittmann and Heinzle, 2001b; Wittmann and Heinzle, 2002). Flux partitioning ratio (Φ) and flux reversibility (ζ) were defined as relative flux into one of the two branches, and as ratio of backward or exchange flux to the net flux in the forward direction, respectively (Wittmann and Heinzle, 2002). For the pyruvate node with the reactions catalyzed by phosphoenolpyruvate carboxylase (PEPC), pyruvate carboxylase (PC), phosphoenolpyruvate carboxykinase (PEPCK), and malic enzyme (MAE) the definitions were as follows:

$$\Phi_{PEPC} = \frac{v_{PEPC}}{v_{PEPC} + v_{PC}} \tag{5}$$

$$\xi_{PEPC/PEPCK} = \frac{v_{PEPCK}}{v_{PEPC} - v_{PEPCK}} \tag{6}$$

$$\xi_{PC/MAE} = \frac{v_{MAE}}{v_{PC} - v_{MAE}} \tag{7}$$

Additionally, the split ratio of the lysine biosynthetic pathway was determined from the specific $^{13}C$ enrichment of the carbon atoms $C_?$ and $C_?$ from lysine and $C_?$ from acetate from the culture supernatant of *C. glutamicum* cultivated on [6-$^{13}$C] glucose by the following equation:

$$\upsilon_{DDH} = \frac{C_{\delta,Lysine} - C_{\beta,Lysine}}{2 \times C_{\beta,Acetate} - C_{\delta,Lysine} - C_{\beta,Lysine}} \quad (8)$$

Stoichiometry Based Flux Estimation

The close correlation of the relative citrate synthase flux ($\nu_{CIS}$) and the relative pyruvate dehydrogenase flux ($\nu_{PDH}$) with the lysine yield ($Y_{Lys/S}$) and the biomass yield ($Y_{X/S}$) provided a solid basis for flux estimation based on stoichiometric data.

The required stoichiometric correlation was achieved by a paraboloid fitting of a rich data set from 18 independent flux estimates and allowed the calculation of $\nu_{CIS}$ and $\nu_{PDH}$ as follows:

$$\upsilon_{CIS}=105.1-1.27\times Y_{Lys_S}+0.35\times Y_{X_S}-9.35\times10^{-3}\times {Y_{Lys_S}}^2-11.16\times10^{-3}\times {Y_{X_S}}^2 \quad (9)$$

$$\upsilon_{PDH}=101.8-1.92\times Y_{Lys_S}+0.72\times Y_{X_S}+1.97\times10^{-2}\times {Y_{Lys_S}}^2-1.02\times10^{-2}\times {Y_{X_S}}^2 \quad (10)$$

Similarly, the net flux through anaplerosis ($\nu_{PYC}$) is closely correlated to stoichiometric characteristics (Wittmann and Heinzle, 2002). The lack of any by-product formation from the TCA cycle, as observed here, allowed the calculation of $\nu_{py0}$ via the withdrawal of carbon from the TCA cycle for anabolism and lysine synthesis:

$$\upsilon_{PYC}\upsilon_{OAA,Analbolism}+\upsilon_{AKG,Analbolism}+\upsilon_{OAA,Ly\ sin\ e} \quad (11)$$

The anabolic demand for oxaloacetate ($\nu_{OAA,Anabolism}$) and a-ketoglutarate ($\nu_{AKG}$, Anabolism) was determined from the biomass yield and the cellular composition of *C. glutamicum* given in Table A.4 (Wittmann and de Graaf, 2005). Mean values and confidence intervals for these flux parameters were calculated from 100 statistically varied values for biomass yield, lysine yield and anabolic fluxes using a Monte-Carlo approach. The flux values were statistically evaluated by a t-test, using the software Origin (Microcal Origin 6.0).

Redox Balancing

To obtain a closer insight into the cofactor metabolism a complete redox balance (Equation 12) was set up on basis of the flux data and the metabolic network of *C. glutamicum*. For calculation, all possible redox reactions during the oxidative phosphorylation were considering (Yang, et al., 2006a).

$$\nu_{O2}-(\tfrac{1}{2}{}_{XADH}-\tfrac{1}{2}\nu_{NADPH})=0 \quad (12)$$

Here $\nu_{O2}$ denotes the oxygen consumption flux and $\nu_{XADH}$ and $\nu_{NADPH}$ are the net production of NADH, FADH and NADPH, respectively. Taking all relevant reactions into account $\nu_{XADH}$ and $\nu_{NADPH}$ can be calculated from the fluxes of the metabolic network of *C. glutamicum:*

$$\nu_{XADH}-\nu_{13}+\nu_{21}+\nu_{25}+\nu_{27}+\nu_{29}+Y_{NADH/X}Y_{X/S} \quad (13)$$

$$\nu_{NADPH}=\nu_2+\nu_3+\nu_{24}-Y_{NADPH/X}Y_{X/S}-4\nu_{33} \quad (14)$$

with an anabolic NADPH consumption of $Y_{NADPH/X}$=16.4 mmol $g^{-1}$ (Wittmann and de Graaf, 2005) and an anabolic NADH production of $Y_{NADH/X}$=3.2 mmol $g^{-1}$ (Yang, et al., 2006a). G6P dehydrogenase ($\nu_2$), 6-phosphogluconate dehydrogenase ($\nu_3$) and isocitrate dehydrogenase ($\nu_{24}$) are considered as major NADPH supplying enzymes (Wittmann and de Graaf, 2005). The oxygen consumption flux was calculated via the experimentally determined respiratory quotient (RQ) and the carbon dioxide production flux ($\nu_{CO2}$):

$$\nu_{02}=\nu_{C02}\times RQ \quad (15)$$

For calculation of $\nu_{CO2}$ all $CO_2$ producing and consuming reactions from central carbon metabolism and from anabolism were considered, whereby $$\nu_{anaplcrosis}=\nu_{18}+\nu_{20}-\nu_{17}-\nu_{19}-\nu_{30} \quad (16)$$

displays the anaplerotic net flux and the anabolic $CO_2$ production for *C. glutamicum* is $Y_{CO2/X}$=1025 μmol $g^{-1}$ (Yang, et al., 2006a).

$$\nu_{CO2}=\nu_3+\nu_{21}+\nu_{21}+\nu_{25}+\nu_{32}-\nu_{anaplcrosis}+Y_{CO2/X}Y_{X/S} \quad (17)$$

Metabolic Flux Analysis of Lysine-Producing *C. glutamicum*

Resolution of the in vivo fluxes provides crucial information on the metabolic response of the investigated organism to genetic or environmental disturbances. This is especially important for rational strain optimization, as the complexity of living cells impedes an exact prediction of the impact of genetic modifications.

Prerequisites

Figure 4:
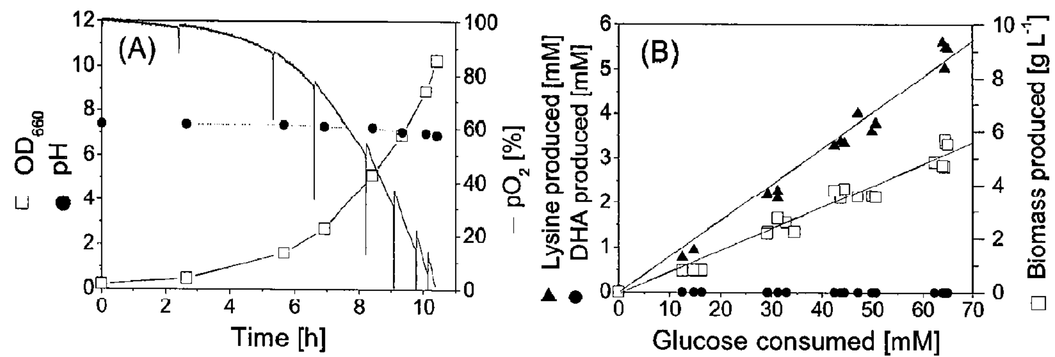
FIG. 4: Cultivation profile of *C. glutamicum* BS1 (lysCT311I) during growth in standard minimal medium with glucose as sole carbon source (A) and growth and production characteristics (B). The linear correlation between formation of biomass and lysine and consumption of glucose, respectively, indicates metabolic steady-state.

Metabolic flux analysis in this work was performed as stationary flux analysis using labelling information obtained from hydrolyzed cell protein by GC-MS. This approach requires a metabolic and isotopic steady-state of the investigated culture, whereby constant batch parameter, i.e. pH and $pO_2$ are indispensable. As exemplified in FIG. 4A for the strain *C. glutamicum* BS1 (lysC$^{T311I}$), the chosen cultivation conditions supported exponential growth of *C. glutamicum* and maintenance of pH as well as sufficient oxygen supply in the applied baffled shake flasks up to an optical density of 10 (Novaspec III). The presence of metabolic steady-state was additionally ensured from the constant growth and production behaviour of the investigated strains (FIG. 4B).

Figure 5:
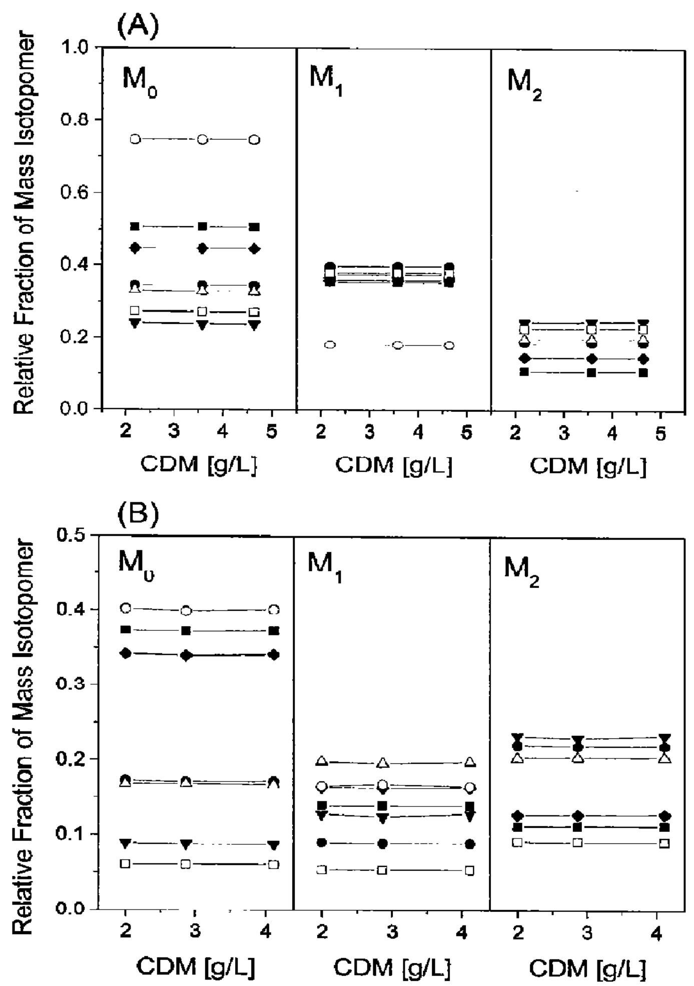
FIG. 5: Verification of isotopic steady-state of *C. glutamicum* BS 13 grown on [$1^{-13}$C] glucose (A) and an equimolar mixture of [$U^{-13}$C] glucose and naturally labelled glucose (B). The labelling patterns of the amino acids were determined at different cell dry mass (CDM) concentrations during the cultivation. The amino acids shown here exemplarily stem from different parts of the metabolic network and comprise alanine (solid square), phenylalanine (open square), valine (closed circle), glycine (open circle), glutamate (closed triangle), threonine (open triangle) and serine (closed diamond). M0 (non labelled), M1 (single labelled) and M2 (double labelled) denote the relative fractions of the corresponding mass isotopomers.

As exemplified for different proteinogenic amino acids from the two parallel tracer studies sampled at different time points of the cultivation, also the $^{13}$C labelling patterns of the metabolites remained constant over time (FIG. 5). This indicated isotopic steady-state during the cultivation, so that the flux distributions obtained can be taken as representative for the whole cultivation period.

The calculation of the metabolic fluxes was based on minimizing the deviation between the experimentally measured and the simulated mass isotopomer fractions. The approach comprised metabolic balancing during each step considering stoichiometric data on growth and product formation from three parallel cultivations and an anabolic demand for biomass precursors (Wittmann and de Graaf, 2005).

Metabolic Fluxes of *C. glutamicum* lysC$^{T311I}$

Metabolic pathway activities of *C. glutamicum* BS1 (lysC$^{T311I}$) were determined from labelling experiments using [1-$^{13}$C] glucose as tracer substrate. The flux model comprised all relevant metabolic pathways of *C. glutamicum* i.e. pentose phosphate pathway, glycolysis, TCA cycle, anaplerotic carboxylation and decarboxylation as well as lysine biosynthesis. Based on previous findings, the glyoxylic acid shunt was assumed to be inactive during growth on glucose (Wittmann and Heinzle, 2002). Pyruvate and PEP and oxaloacetate and malate, respectively, were considered as lumped pools. The interconnecting reactions, i.e. pyruvate carboxylase, PEP carboxylase, malic enzyme and PEP carboxykinase were thus determined as lumped fluxes through carboxylation and decarboxylation, respectively. Concerning the obtained fit, excellent agreement between experimentally determined and calculated mass isotopomer fractions was achieved (Table 11).

TABLE 11

Table 11: Relative mass isotopomer fractions of amino acids from the cell protein and of secreted trehalose of lysine-producing *C. glutamicum* BS1 (lysC$^{T311I}$) cultivated on 99% [1-$^{13}$C] glucose. Data comprise experimental GC-MS data (Exp) and values predicted by the solution of the mathematical model corresponding to the optimized set of fluxes (Calc).

| | | *C. glutamicum* lysC$^{T311I}$ | | |
|---|---|---|---|---|
| Analyte | | $M_0$ | $M_1$ | $M_2$ |
| Alanine (m/z 260) | Calc | 0.509 | 0.354 | 0.106 |
| | Exp | 0.509 | 0.353 | 0.106 |
| Valine (m/z 288) | Calc | 0.348 | 0.398 | 0.184 |
| | Exp | 0.346 | 0.398 | 0.185 |
| Threonine (m/z 404) | Calc | 0.334 | 0.376 | 0.196 |
| | Exp | 0.333 | 0.376 | 0.196 |
| Aspartate (m/z 418) | Calc | 0.333 | 0.375 | 0.196 |
| | Exp | 0.334 | 0.375 | 0.196 |
| Glutamate (m/z 432) | Calc | 0.250 | 0.366 | 0.239 |
| | Exp | 0.247 | 0.365 | 0.240 |
| Serine (m/z 390) | Calc | 0.449 | 0.358 | 0.143 |
| | Exp | 0.450 | 0.358 | 0.143 |
| Phenylalanine (m/z 336) | Calc | 0.274 | 0.381 | 0.228 |
| | Exp | 0.271 | 0.382 | 0.228 |
| Glycine (m/z 246) | Calc | 0.742 | 0.185 | |
| | Exp | 0.741 | 0.185 | |
| Tyrosine (m/z 466) | Calc | 0.236 | 0.356 | 0.742 |
| | Exp | 0.234 | 0.353 | 0.741 |
| Trehalose (m/z 361) | Calc | 0.062 | 0.607 | 0.207 |
| | Exp | 0.061 | 0.601 | 0.207 |

From the resulting flux map it becomes obvious, that the central pathway activities, especially flux through the pentose phosphate pathway and the glycolytic flux were determined with very high precision.

As compared with the wild type (Kim, et al., 2006; Kromer, et al., 2008), release of aspartate kinase from feedback inhibition by lysine and threonine in *C. glutamicum* resulted in significant flux changes. The most obvious difference is certainly the 8% increased lysine flux which is a direct consequence of the deregulated lysine production. The net flux through anaplerotic carboxylation was significantly increased to supply sufficient oxaloacetate required for lysine production. Moreover, the deregulation mutant exhibited changed fluxes through the pentose phosphate pathway and the TCA cycle. Due to the reduced biomass formation, in *C. glutamicum* BS1, less carbon is withdrawn from the intermediary metabolism to meet the anabolic demand. The here applied approach for flux determination is perfectly suitable to resolve these global flux changes with comparably low effort. The experimental set-up as well as the flux model comprising labelling information from 29 mass isotopomer fractions could thus be effectively applied for routine $^{13}$C MFA to survey the effect of genetic changes or environmental conditions.

Extended Flux Analysis

In selected cases, the above applied approach for flux determination was, however, not sufficient. Resolution of the complete metabolic network around the pyruvate node comprising pyruvate carboxylase, PEP carboxylase, malic enzyme and PEP carboxykinase is significantly more elaborate. With regard to lysine production in *C. glutamicum*, these reactions have considerable importance. The flux model was therefore extended to resolve all the fluxes through PEP carboxylase (PEPC), pyruvate carboxylase (PC) and malic enzyme (MalE) as well as PEP carboxykinase (PEPCK).

Network Design and Experimental Set-Up

Figure 6:
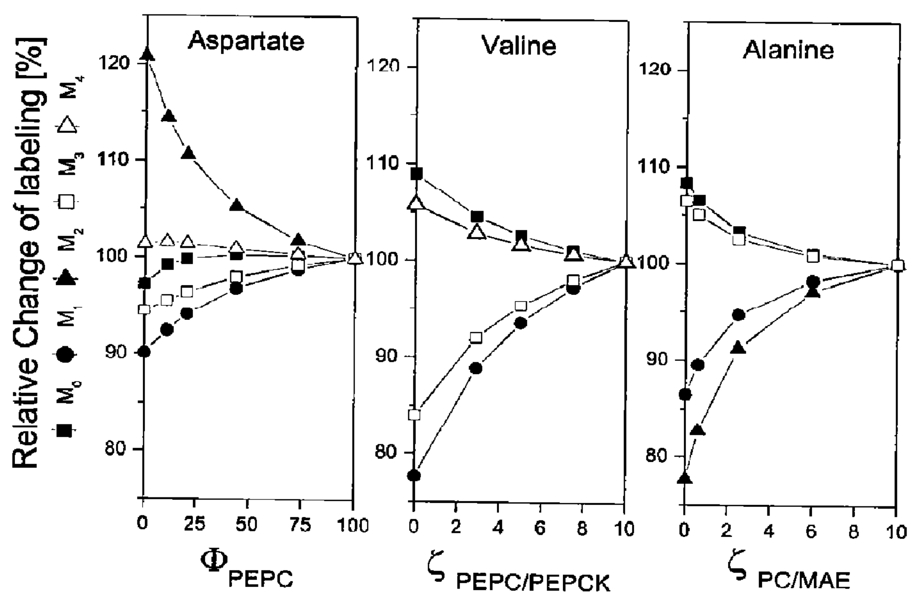
FIG. 6: Experimental design for quantification of flux parameters at the pyruvate node of *Corynebacterium glutamicum* with an equimolar mixture of [$U^{-13}$C] glucose and naturally labelled glucose. Relative change of the mass isotopomer distribution of aspartate (m/z 418) with varied ΦPEPC, relative change of the mass isotopomer distribution of valine (m/z 288) with varied ζEPC/PEPCK, relative change of the mass isotopomer distribution of alanine (m/z 260) with varied ζPC/MalE.

A first step for model adaptation was an extension of the metabolic network by considering PEP and pyruvate as separate pools and PC, PEPC, PEPCK and malic enzyme as separate enzymatic reactions. For this scenario, the above described approach utilizing labelling data from a single tracer study with [1-$^{13}$C] glucose was significantly extended, since this was not capable to completely resolve all these fluxes, but only lumped carboxylation and decarboxylation fluxes (Kim, et al., 2006). Concerning the central metabolic pathways, [1-$^{13}$C] glucose is valuable for resolving the upper part of metabolism, in particular the oxidative PP pathway, glycolysis and, if present, the Entner-Doudoroff pathway, whereas the use of a mixture of [U-$^{13}$C] glucose and unlabeled glucose is particularly useful to resolve fluxes downstream of PEP, especially at the pyruvate node (Fischer, et al., 2004; Wittmann and Heinzle, 2001b). Due to this the experimental strategy was based on two parallel tracer studies with (i) [1-$^{13}$C] glucose and (ii) a mixture of [U-$^{13}$C] glucose and naturally labelled glucose to combine the information content available from the GC-MS labelling analysis of metabolites from the different tracer substrates for flux calculation. Since it is known, that more detailed information for flux calculation can be obtained with GC-MS via additional analysis of fragment ions which contain only specific parts of the carbon skeleton of the analyte, a number of fragment ions from the proteinogenic amino acids were additionally considered which have previously proven useful for flux analysis in complex metabolic networks of prokaryotes (Klapa, et al., 2003) and eukaryotes (Frick and Wittmann, 2005). Overall, 197 different mass isotopomer fractions were considered here for each strain, whereas the original simplified approach with only one single tracer experiment and less fragments measured considered 29 mass isotopomer fractions. The extended approach was tested by computer based simulation studies to see, weather the additionally considered labelling information can be utilized to determine the additionally introduced free fluxes around the pyruvate node. For this purpose, sensitivities for the available mass isotopomer fractions and the flux parameters of interest were derived from partial derivatives as previously described (Wittmann and Heinzle, 2001b). The labelling patterns of a number of newly considered fragment ions were affected by variation of the free fluxes around the pyruvate node and thus contain sensitive information to determine these flux parameters of interest. This is exemplified for the study with [U-$^{13}$C] glucose and unlabelled glucose as tracer substrate and variation of the free flux parameters ΦPEPC (flux partitioning between PEPC and PC), ζPEPC/PEPCK (exchange flux by PEPC and PEPCK) and ζPC/MalE (exchange flux by PC and malic enzyme) which strongly influence the labelling pattern of analyzed metabolites (FIG. 6).

The labelling patterns at sole contribution of PEPC (ΦPEPC=100%), and highly reversible fluxes at the pyruvate node (ζPEPC/PEPCK=ζPC/MalE=10) are taken as reference point and set to 100%. Using synthetic labelling data sets, a unique solution for the free fluxes was obtained in multiple parameter estimations with randomized varied starting values, demonstrating the observability and identifiability of all free fluxes in the network and the suitability of the developed extended approach. Applicability for a biological system was validated with the strains *C. glutamicum* BS 1 (lysC$^{T311I}$) and *C. glutamicum* BS 13 (lysC$^{T311I}$ Dpyk).

Tracer Studies and Parameter Estimation

Figure 7:
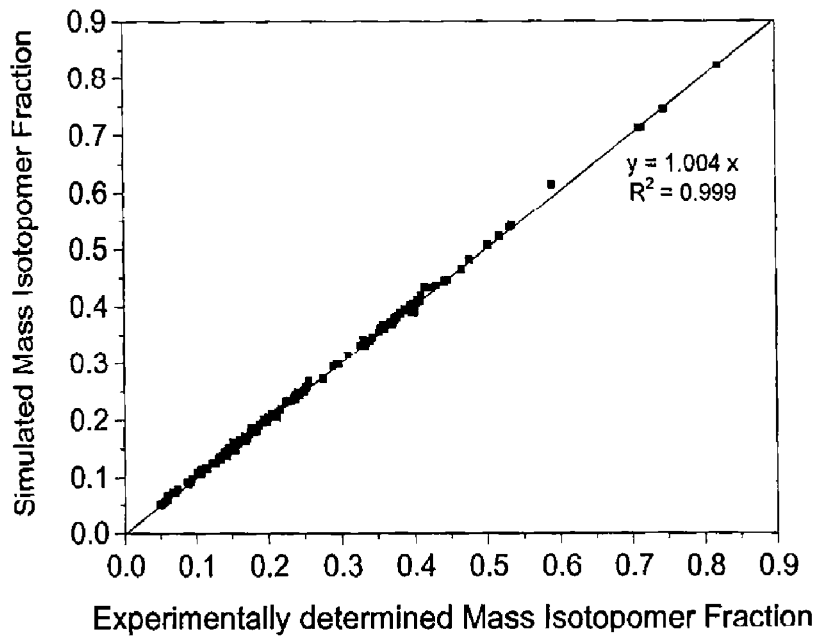
FIG. 7: Correlation of experimentally determined and simulated mass isotopomer fractions of amino acids from the cell protein and of secreted trehalose during cultivation of *C.* glutamicum BS 1 on 99% [$1^{-13}$C] glucose and 50% [$U^{-13}$C] glucose. The data comprise experimental GC-MS data and values predicted by the solution of the mathematical model corresponding to the optimized set of fluxes.

The constant growth and production characteristics as well as the isotopic steady-state demonstrated above allowed flux determination from the $^{13}$C enrichment of the proteinogenic amino acids from cell protein. Metabolic flux distribution was obtained by minimizing the deviation between the experimentally determined and the calculated mass isotopomer fractions. Obviously, an excellent fit was achieved as illustrated for matching of the labelling pattern of *C. glutamicum* BS 1 (FIG. 7).

The metabolic network model applied here considers malate and oxaloacetate as a single pool, i.e. fully equilibrated labelling exchange between the two pools. The excellent fit of the labelling data supports the presence of a reversible inter conversion between malate and oxaloacetate. Further evidence comes from in vitro studies in *C. glutamicum* demonstrating the reversible inter conversion of malate and oxaloacetate by concerted action of the cytoplasmatic (MDH) and the membrane bound malate dehydrogenase (MQO) (Molenaar, et al., 2000). The set of intracellular fluxes that gave minimum deviation between experimental and simulated labelling patterns was taken as best estimate for the intracellular flux distribution. FIG. 8 displays a close-up of the complex network around the pyruvate node and the in vivo fluxes determined for *C. glutamicum* BS 1.

Using the extended model, the in vivo fluxes through PEPC, PC, PEPCK and malic enzyme were determined very precisely which is reflected in the narrow confidence intervals obtained by statistical evaluation. Whereas PC is the major anaplerotic enzyme in *C. glutamicum* BS 1, PEPC only contributes to a minor extend to anaplerotic carboxylation. This very well fits previous findings that lysine production in *C. glutamicum* significantly depends on the expression level of pyruvate carboxylase (Peters-Wendisch, et al., 2001) whereas PEP carboxylase activity is dispensable for lysine production (Peters-Wendisch, et al., 1993). Moreover, the extended approach revealed a significant flux through malic enzyme. This provided a first hint that malic enzyme serves as NADPH source during growth on glucose, a physiological role so far only postulated for fructose-grown *C. glutamicum* (Dominguez, et al., 1998; Kiefer, et al., 2004). The net fluxes through carboxylation and decarboxylation, respectively, determined by the extended model, agree very well with the lumped fluxes obtained by the simple model. The additional effort required for complete resolution of this complex network is thus only worthwhile in selected cases that demand exact determination of one of the involved fluxes.

Codon Adaptation as Tool for Metabolic Engineering

In the recent years, metabolic and genetic engineering has emerged as powerful approach in lysine production with *Corynebacterium glutamicum* to create superior strains. This approach requires a sophisticated toolbox for strain characterization such as the above described methodology for unravelling of central metabolic pathway activities. The intended modifications for strain optimization, however, also have to be realized by genetic tools. In this regard, targeted modulation of enzyme activities within the cell is crucial to increase or reduce carbon conversion by selected metabolic pathways. The genetic changes applied for this purpose are typically strong, i.e. cause a complete pathway block through gene deletion or a manifold amplification through plasmid based gene overexpression. In many cases, these extreme changes result in disadvantageous side effects. Deletion of the central glycolytic enzymes phosphoglucoisomerase for instance, caused a severe growth deficiency in *C. glutamicum* (Marx, et al., 2003). Pyruvate dehydrogenase deletion mutants of *C. glutamicum* cannot grow on sugar based production media and further show extensive by-product formation (Blombach, et al., 2007). In the present work, the above mentioned toolbox, nowadays used for metabolic engineering, was complemented by a more gentle approach utilizing start codon exchange to alter specific enzyme activity in *C. glutamicum*.

Start Codon Usage in *Corynebacterium glutamicum*

In *C. glutamicum* the translational start position is indicated by one of the start codons ATG, GTG or TTG. For determination of the exact start codon distribution, all the entire genome sequence was downloaded from NCBI database as FASTA-file and searched for the exact number of A, G and T as initial nucleotide at the start codon position using Excel (MS Office, 2003). The exact number of A, G and T was determined to 2215, 627 and 215, respectively, which corresponds to a relative frequency of 72%, 21% and 7%. The frequency of these start codons is slightly different in the central metabolism of *C. glutamicum* with 81% ATG, 15% GTG and 4% TTG.

From the genes of the central metabolic pathways, three genes were selected for replacement of ATG by GTG and one for replacement of the natural GTG by ATG. The chosen enzymes PGI, PDH, ICD and G6PDH are located at key branch points. Flux redirection at these nodes, e.g. pentose phosphate pathway (PPP), anaplerotic carboxylation and TCA cycle, is of generally high importance for targeted over production of lysine (Wittmann and Becker, 2007; Wittmann and Heinzle, 2002).

Modulation of Enzyme Activity by Start Codon Exchange

The start codon exchange was implemented in the genetic background of *C. glutamicum* BS87. Via two homologous recombination events, the wild type allele was replaced by the mutant allele. Based on the underlying cloning protocol, the resulting clones from the second recombination event can either again reflect the parent strain or a start codon mutant. Screening for recombinant strains, carrying the point mutation in the start codon, was performed by determination of specific enzyme activity of ICD, PGI, PDH or G6PDH, respectively. As shown in FIG. 9, several clones exhibited a changed activity of the target enzyme when compared to the parent strain BS87.

These clones were investigated in more detail by sequence analysis. The sequences of the selected clones and the parent strain showed 100% identity with exception of the start codon nucleotide. Here, all strains, exhibiting a changed in vitro activity, also revealed the nucleotide exchange in the start codon. After validation of the nucleotide exchange by sequencing, specific activity was determined in minimal medium using glucose as sole carbon source (Table 12).

TABLE 12

Table 12: Specific activity of isocitrate dehydrogenase (ICD), phosphoglucoisomerase (PGI) pyruvate dehydrogenase (PDH) and glucose 6-phosphate dehydrogenase (G6PDH) as a function of the start codon in *C. glutamicum*. Values represent mean values from three biological replicates with coffesponding deviations.

| | ICD [mU $mg^{-1}$] | PGI [mU $mg^{-1}$] | PDH [mU $mg^{-1}$] | G6PDH [mU $mg^{-1}$] |
|---|---|---|---|---|
| ATG variant | 1292 ± 60 | 1073 ± 70 | 30 ± 3 | 170 ± 15 |
| GTG variant | 342 ± 32 | 618 ± 30 | 13 ± 1 | 120 ± 10 |

A prominent effect on enzyme activity was found for the icd gene. In the corresponding mutant, specific ICD activity was reduced by 70%. Exchange of the translational start position of aceE and pgi resulted in a decrease of the specific activity of pyruvate dehydrogenase and phosphoglucoisomerase by 56% and 47%, respectively. In the case of G6PDH, the specific activity was increased by 20% due to the usage of the ATG start codon instead of GTG. A further strategy for translational down-regulation of ICD activity comprised implementation of the rare codons GGG for glycine and AUA for isoleucine. To achieve a maximized effect the natural codons of three adjacent glycines were replaced by the rare GGG variants. These were localized at the positions 570 572. In the case of isoleucine, two codon substitutions were carried out at the positions 78 and 79. Though successfully implemented in the encoding icd gene, as validated by sequencing, an effect on specific enzyme activity was missing. This might be related to the localization of the performed nucleotide exchanges, which was found to play at least a role for codon optimization in myxomycetes (Vervoort, et al., 2000).

Codon exchange as a method for regulation of gene expression is not a novel approach. However, this strategy so far mainly focused on codon-optimization in processes involving heterologous gene expression. Here, adaptation of the codons to their relative appearance in the host strain (Jo, et al., 2007; Wiedemann and Boles, 2008) or, as recently applied, tRNA supplementation (Lee, et al., 2009) has resulted in an improved expression. As compared to these time-consuming and circuitous methods, the start codon exchange carried out in this work is clearly more simple and comfortable as it is solely focused on a single codon. The results from codon-worsening i.e. implementation of GGG for glycine and AUA for isoleucine further suggest that start codon adaptation is a superior method to achieve success. With regard to metabolic engineering, especially the possibility to decrease gene expression by worsening translational initiation is interesting, as down-regulation of undesired pathways is not trivial. So far, carbon flux is often completely blocked by gene deletion which in many cases results in severe growth deficiency or undesired auxotrophy (Blombach, et al., 2007; Marx, et al., 2003) Recently, plasmid-related expression of antisense RNA was successfully applied to reduce activity of the 2-oxoglutarate dehydrogenase complex (ODHC) in glutamate producing *C. glutamicum* (Kim, et al., 2009). This approach, however, required a permanent selection pressure and is therefore not suitable for industrial production processes (Kim, et al., 2009). Start codon exchange offers the opportunity for targeted attenuation of selected enzymes without these disturbing effects. Due to the high frequency of the start codon ATG (72%) in *C. glutamicum* this method has a great potential as general tool for metabolic engineering. Two successful examples of this strategy for optimization of lysine production in *C. glutamicum* will be discussed in more detail below.

Whereas the past two chapters were attributed to key methods as solid basis for strain characterization and genetic engineering, the following paragraphs now deal with different engineering strategies towards improved lysine production by *C. glutamicum*. The key pathways for lysine production in *C. glutamicum*, i.e. NADPH metabolism, lysine biosynthesis, precursor supply and TCA cycle were successively engineered towards improved lysine production.

Engineering of NADPH Metabolism

Due to the high requirement of the biosynthetic pathway of lysine for the co-factor NADPH, the NADPH metabolism in *C. glutamicum* is one of the key targets for rational engineering. It thus appeared promising to enhance the flux through the pentose phosphate pathway, previously identified as major NADPH source (Wittmann and Heinzle, 2002). This was first approached by overexpression and modification of the rate-limiting enzyme glucose 6-phosphate dehydrogenase, complemented by overexpression of the gene fbp, encoding fructose 1,6-bisphosphatase. As alternative approach, up-regulation of glucose 6-phosphate dehydrogenase was achieved concomitantly with overexpression of transaldolase and transketolase by promoter exchange of the tkt-operon comprising, amongst others, the encoding genes zwf, tal and tkt. Moreover, the role of malic enzyme for NADPH supply in lysine producing *C. glutamicum*, so far only poorly understood, was investigated.

Overexpression and Modification of Glucose 6-phosphate Dehydrogenase

Overexpression was realized through genomic replacement of the natural promoter of the zwf gene by the strong promoter of the sod gene, encoding superoxide dismutase. Moreover, an A243T point mutation was introduced into G6PDH. This mutation has been previously identified via comparative sequencing between the wild type and a classically derived production strain and was shown to result in increased lysine production, despite the exact metabolic consequences of this mutation have not been elucidated so far (Zelder, et al., 2005). Subsequently, it was tested, if these targets can be complemented with overexpression of the fructose 1,6-bisphosphatase gene, previously shown to significantly support lysine production by flux redirection towards the PPP (Becker, et al., 2005). All strains were characterized concerning cell growth and lysine production. The studies were complemented by characterization of the wild type and the mutant G6P dehydrogenase to investigate the consequences of the introduced A243T mutation. Additionally, intracellular metabolite levels and metabolic fluxes through the central carbon metabolism were analyzed, in order to unravel the metabolic consequence of the genetic modifications and understand the overall cellular behaviour.

In Vitro Activity

The specific in vitro activity of G6P dehydrogenase was clearly affected by overexpression of the encoding zwf gene (FIG. 10A). Whereas the wild type and the strain BS1 (lysC$^{T311I}$) showed a similar activity, the replacement of the natural promoter of the zwf gene by the promoter of sod, encoding superoxide dismutase, resulted in a fourfold increased activity of the enzyme. This indicates that the use of the sod promoter leads to an increased amount of G6P dehydrogenase in the cell. The point mutation A243T did not significantly influence the specific activity of G6P dehydrogenase as indicated by the similar values observed for BS5 ($P_{sod}$zwf) and BS6 ($P_{sod}$zwf$^{A243T}$).

Kinetic Properties of the Wild Type and the A243T-Variant

To understand the consequence of the point mutation in the zwf gene, the two enzyme variants were compared concerning their kinetic behaviour. In different aspects the mutated enzyme showed superior properties. This included a higher affinity towards NADP, one of its substrates (Table 15). Moreover, a stronger resistance against inhibition by metabolites of the central metabolism could be observed. Upon addition of 5 mM ATP or PEP a much higher activity was retained for the mutant enzyme, whereas a somewhat weaker influence resulted for FBP addition. Combined addition of all three metabolites in a physiological concentration range between 1 and 2 mM also revealed that the A243T point mutation diminishes the regulatory control of G6P dehydrogenase on the metabolic level. No significant difference was observed concerning the affinity of the two enzymes towards the substrate G6P (Table 13) and the inhibition by NADPH (FIG. 10B).

TABLE 13

Table 13: Kinetic characterization of the wild type and the A243T-variant of G6P dehydrogenase from *C. glutamicum*: Michaelis-Menten affinity constants for G6P ($K_{M,\ G6P}$) and NADP ($K_{M,\ NADP}$) and inhibition of enzyme activity through concerted action of ATP, phosphoenolpyravate (PEP) and fructose 1,6-bisphosphate (FBP) added in equimolar amounts. The data represent mean values from three different measurements with cell extracts from cells grown on minimal medium with glucose as carbon source.

| | | | Inhibition by metabolites (Remaining Activity [%])[a] | | | | | |
|---|---|---|---|---|---|---|---|---|
| Enzyme variant | $K_{M,\ G6P}$ [μM] | $K_{M,\ NADP}$ [μM] | 5 mM ATP | 5 mM PEP | 5 mM FBP | 1 mM ATP, PEP, FBP[b] | 2 mM ATP, PEP, FBP[b] | 3 mM ATP, PEP, FBP[b] |
| Wild type | 500 ± 31 | 100 ± 7 | 68.8 ± 0.1 | 62.6 ± 0.1 | 84.4 + 0.2 | 84.8 ± 0.1 | 79.4 ± 0.1 | 71.3 ± 0.2 |
| A243T mutant | 481 ± 31 | 75 ± 4 | 86.0 ± 0.2 | 72.5 ± 0.1 | 87.0 + 0.1 | 89.9 ± 0.1 | 88.8 ± 0.1 | 85.8 ± 0.2 |

[a]given as relative value related to the activity without addition (100%)
[b][ATP] = [FBP] = [PEP]

The benefit of the A243T mutation in the zwf gene is thus due to an improved kinetic behaviour of the encoded G6P dehydrogenase and does not result from an increased specific activity. A significantly weaker inhibition of the mutant enzyme was already observed at a concentration of 1 mM, which is within the physiological range found for the tested metabolites PEP, FBP and ATP in *C. glutamicum* (Moritz, et al., 2002). Hence, it seems likely that the mutant enzyme variant displays a higher activity in vivo. Also the higher affinity towards NADP might contribute to this effect since actual NADP levels are in the range of 100 μm (Moritz, et al., 2002).

Product Formation and Metabolic Fluxes

The different mutants were then compared concerning growth and production characteristics (Tables 14 and 15). To this end, strains were grown in the standard minimal medium containing one of the carbon sources glucose, fructose or sucrose, respectively. For the feedback-resistant parent strain *C. glutamicum* BS1 the lysine yield ranged between 74 c-mmol c-mol$^{-1}$ for fructose-grown cells and 85 c-mmol c-mol$^{-1}$ for glucose-grown cells (Becker, et al., 2005).

TABLE 14

Table 14: Growth and production characteristics of lysine-producing *C. glutamicum* BS1 (lysC$^{T311I}$), *C. glutamicum* BS5 ($P_{sod}$zwf), *C. glutamicum* BS6 ($P_{sod}$zwf$^{A243T}$) and *C. glutamicum* BS7 ($P_{sod}$fbp_zwf$^{A243T}$) on glucose, fructose and sucrose. The data given are lysine yield ($Y_{Lys/S}$) and biomass yield ($Y_{X/S}$) and represent mean values from three parallel cultivation experiments.

| Strain | Carbon source | $Y_{Lys/S}$, [c-mmol c-mol$^{-1}$] | $Y_{X/S}$, [g c-mol$^{-1}$] |
|---|---|---|---|
| *C. glutamicum* BS1[a] | Glucose | 84.7 ± 2.9 | 13.0 ± 0.3 |
| | Fructose | 73.6 ± 1.2 | 8.2 ± 0.1 |
| | Sucrose | 78.8 ± 3.5 | 10.9 ± 0.4 |
| *C. glutamicum* BS5 | Glucose | 112.6 ± 2.1 | 10.4 ± 0.8 |
| | Fructose | 88.4 ± 0.1 | 7.8 ± 0.5 |
| | Sucrose | 101.6 ± 0.2 | 10.4 ± 0.3 |
| *C. glutamicum* BS6 | Glucose | 117.1 ± 2.7 | 11.1 ± 1.0 |
| | Fructose | 97.3 ± 0.3 | 7.6 ± 0.6 |
| | Sucrose | 112.0 ± 3.0 | 10.7 ± 0.3 |
| *C. glutamicum* BS7 | Glucose | 130.0 ± 5.5 | 9.9 ± 0.6 |
| | Fructose | 111.9 ± 7.1 | 8.4 ± 0.2 |
| | Sucrose | 133.5 ± 6.3 | 8.4 ± 0.3 |

[a]data taken from Becker et al. (2005)

Overexpression of the zwf gene via the sod promoter markedly increased the lysine production. A positive effect on lysine production in the corresponding strain *C. glutamicum* BS5 was observed on all tested carbon sources, whereby the highest increase of more than 30% resulted for glucose-grown cells (Table 16). *C. glutamicum* BS6, in which the zwf gene was additionally modified by the A243T amino acid exchange, showed an even higher lysine production. This was most pronounced on fructose and sucrose as carbon source. By the additional overexpression of the fbp gene the lysine production was further enhanced on all carbon sources. The significant impact of the introduced modifications becomes obvious from the comparison of the lysine yield between *C. glutamicum* BS7, carrying all three mutations and the strain *C. glutamicum* BS1. The combined introduction of the modifications led to an overall increase of the lysine yield of about 50% on glucose and on fructose, whereas on sucrose the increase was about 70%. With an increase of the lysine yield, the biomass yield successively decreased on glucose and on sucrose whereas it remained almost constant on fructose (Table 14). Concerning the specific rates, glucose uptake remained almost unaffected by the genetic modifications (Table 15) so that the observed differences between the mutants display a redistribution of carbon flux. In response to that specific growth rate decreased with increasing lysine production.

TABLE 15

Table 15: Specific rates for growth (μ), glucose uptake ($q_{Glc}$) and lysine production ($q_{Lys}$) and respiratory quotient (RQ) of *C. glutamicum* BS1 (lysC$^{T311I}$), *C. glutamicum* BS5 ($P_{sod}$zwf), *C. glutamicum* BS6 ($P_{sod}$zwf$^{A243T}$) and *C. glutamicum* BS7 ($P_{sod}$fbp_zwf$^{A243T}$) grown on glucose.

| Strain | μ [h$^{-1}$] | $q_{Glc}$ [mmol g$^{-1}$ h$^{-1}$] | $q_{Lys}$ [mmol g$^{-1}$ h$^{-1}$] | RQ [mol mol$^{-1}$] |
|---|---|---|---|---|
| *C. glutamicum* BS1[a] | 0.38 ± 0.00 | 4.9 ± 0.1 | 0.42 ± 0.01 | n.d.[b] |
| *C. glutamicum* BS5 | 0.32 ± 0.01 | 5.2 ± 0.2 | 0.59 ± 0.01 | 1.16 ± 0.04 |
| *C. glutamicum* BS6 | 0.33 ± 0.02 | 5.0 ± 0.3 | 0.59 ± 0.01 | 1.15 ± 0.06 |
| *C. glutamicum* BS7 | 0.29 ± 0.01 | 4.9 ± 0.2 | 0.64 ± 0.03 | 1.19 ± 0.08 |

[a]data taken from Becker et al. (2005)
[b]n.d. = not determined

To investigate, how the genetic modifications in detail affected the in vivo flux through the PPP and other metabolic pathways of *C. glutamicum*$^{13}$C metabolic flux analysis was performed for the different strains. For this purpose tracer studies were carried out on [1-$^{13}$C] glucose. The obtained key fluxes of the central metabolic reactions in the different mutants grown on glucose are summarized in FIG. 11 whereby the deviations given for each flux parameter represent the 90% confidence intervals. An excellent fit between simulated and measured labelling patterns was obtained. Twenty fold repetition of the parameter estimation with statistically varied starting values for the free flux parameters led to identical solutions for each of the strains, which ensured the identification of the global minimum.

The strains BS5 and BS6 revealed a strongly enhanced PPP flux in comparison to the parent strain, whereas the glycolytic flux was substantially reduced. Thus the overexpression of the zwf gene caused a clear flux redirection at the G6P node. The additional overexpression of fructose 1,6-bisphosphatase contributed to a further flux increase into the PPP. Beside the PPP, also the flux through the TCA cycle, the other important NADPH-supplying pathway in *C. glutamicum*, was strongly enhanced. The generally high activity of the NADPH-providing pathways PPP and TCA cycle in the different zwf mutants resulted in a strong NADPH supply, which was even higher than the actual demand for anabolism and lysine production, and caused a high apparent NADPH excess in all zwf mutants. A closer inspection of the cofactor metabolism for the PPP engineered mutants was carried out by an extended redox balance. This considered all possible reactions during oxidative phosphorylation leading to oxidation of reduction equivalents (NADH, FADH and NADPH) which are formed in the catabolic and anabolic pathways of carbon metabolism. All mutants revealed a significant surplus of both, NADH/FADH and of NADPH. The overall oxygen consumption was not sufficient to completely account for oxidation of all reduction equivalents formed, i.e. the redox balance did not close as one would expect. This is a clear indication of additional metabolic reactions contributing to oxidation of cofactors, which is discussed in more detail below. Interestingly, the higher demand for oxaloacetate as precursor for lysine in the optimized strains was not reflected by an increased flux through anaplerotic carboxylation (FIG. 11). This is probably related to the reduced oxaloacetate demand for anabolism due to the reduced biomass yield (Table 14).

Via the strategy of overexpression and modification of glucose 6-phosphate dehydrogenase, the lysine production of *C. glutamicum* was significantly improved on different carbon sources, including the industrially relevant carbon sources glucose and sucrose. The 4-fold increase of the in vitro activity of the enzyme was, however, only reflected by a 1.4-fold increase of the corresponding in vivo activity, i.e. the flux, which reveals the strong metabolic regulation of G6P dehydrogenase in vivo (Moritz, et al., 2000). Comparing lysine production of the different strains of the obtained genealogy on glucose, one would guess on a first glance that overexpression via the sod promoter was most beneficial, since this resulted in the largest increase of production, whereas the additional introduction of the point mutation A243T did not give a further improvement (Table 14). Exchanging the order of the introduced mutations, however, revealed a completely different picture. The strain BS3, additionally constructed, only containing the mutated enzyme with its natural promoter, exhibited a high lysine yield of 120 c-mmol c-mol$^{-1-}$, which was not further improved when the zwf gene was additionally over expressed by the sod promoter. This clearly shows that the metabolic response to a genetic perturbation not only depends on the introduced modification, but to a large extent also on the genetic background of the host strain.

By-Product Formation

Additionally to the improvement of lysine production, metabolic engineering also affected the formation of trehalose, the dominating by-product of *C. glutamicum* when grown on glucose. Trehalose excretion is undesired in lysine production since this compound cannot be taken up by the cells due to lack of a corresponding uptake system. The different zwf mutants of *C. glutamicum* all exhibited a significantly reduced trehalose formation which is a positive side effect of metabolic engineering of the PPP flux. As shown in Table 17 overexpression of the zwf gene resulted in a 53% reduced trehalose formation in the strain BS5 compared to the parent strain BS1. In the strain BS6 the trehalose production was even reduced by 67%. In *C. glutamicum*, trehalose can be formed via three different pathways, all of which use G6P as substrate (Tzvetkov, et al., 2003). Intracellular metabolite analysis revealed that the reduced trehalose flux in the strains BS5 and BS6 was linked to a decreased availability of G6P (Table 16).

TABLE 16

Table 16: Trehalose formation and intracellular level of G6P and F6P during cultivation of lysine producing *C. glutamicum* BS1, *C. glutamicum* BS5, *C. glutamicum* BS6, and *C. glutamicum* BS7 on glucose. The trehalose yield was determined from three parallel cultivations. The intracellular G6P and F6P level was measured in two independent cell extracts each analyzed in duplicate.

| *C. glutamicum* | Trehalose Yield [c-mmol c-mol$^{-1}$] | G6P$_{intracellular}$ [μmol g$^{-1}$] | F6P$_{intracellular}$ [μmol g$^{-1}$] |
|---|---|---|---|
| BS1 | 17.6 ± 2.2[a] | 23.5 ± 0.3 | 2.6 ± 0.6 |
| BS5 | 8.1 ± 0.8 | 12.7 ± 0.3 | 2.8 ± 0.4 |
| BS6 | 5.8 ± 0.5 | 12.6 ± 0.7 | 1.8 ± 0.2 |
| BS7 | 12.6 ± 0.3 | 36.0 ± 2.2 | 4.5 ± 1.7 |

[a]value taken from Becker et al. (2005)

An accelerated conversion of G6P by the PPP as a result of the higher G6PDH activity reduces trehalose formation by decreasing the availability of this precursor. The concomitant overexpression of the fbp gene impaired the effect of the zwf modifications so that the reduction of trehalose formation was obvious, but somewhat smaller in the triple-mutant strain (28%). This should be due to the fact that this modification "pushes" carbon into the PPP via the G6P pool, whereas engineering of G6P dehydrogenase "pulls" carbon from the G6P pool into this pathway. Accordingly the G6P pool in this mutant was substantially higher. In response to that also the F6P pool was significantly higher in the BS7 strain (Table 16).

Redox Balancing and NADPH Metabolism

As shown by metabolic flux analysis, the genetic manipulations contributed to extreme changes in the NADPH metabolism of the cell. Increased fluxes through PPP and TCA cycle resulted in a significantly increased NADPH supply. The increased lysine yield associated with these flux changes demonstrates that NADPH supply has definitely a limiting role in lysine production in batch cultures of *C. glutamicum*, although assumptions for chemostat cultures are different (Sahm, et al., 2000). Whereas the parent strain BS1 exhibits a slight apparent NADPH deficiency (Kim, et al., 2006), the NADPH supply in the PPP engineered strains was much higher than their demand (Table 17). The resulting high apparent NADPH excess in these strains indicates that the performed changes could not be fully exploited for lysine production, but leave a remaining potential for further optimization. The extent of this potential is illustrated by the fact that the product yield of the best mutant, *C. glutamicum* BS7, could be even doubled, if one could channel all the excess NADPH into the lysine pathway. This potential might be to some extent lowered by partial oxidation of NADPH by malic enzyme acting in the direction of carboxylation. The unspent or missent NADPH in the zwf mutants points at limitations in other parts of the metabolic network which arise in response to the PPP flux engineering. These limits might be associated with oxaloacetate supply, as it has been shown that especially the increase of the anaplerotic flux in *C. glutamicum* leads to an improved lysine production (Koffas, et al., 2003; Peters-Wendisch, et al., 2001). In fact the anaplerotic net flux remained almost constant in the strains investigated here, so only the reduction of the anabolic oxaloacetate demand enabled the higher flux of this precursor into the lysine pathway.

The high apparent NADPH excess in the PPP mutants points at additional reactions that consume NADPH. Possible candidates comprise superoxide-generating NAD(P)H oxidase in the respiratory chain (Matsushita, et al., 2001) or malic enzyme operation in the carboxylating direction (de Graaf, 2000; Petersen, et al., 2000). Clear experimental evidence supporting the role of either one of these reactions has not been obtained to date. It has however been assumed that the malic enzyme, operating in the decarboxylating direction, can function as additional NADPH source in strains with a seeming NADPH deficiency (Dominguez, et al., 1998). To obtain a closer insight into the cofactor metabolism of the PPP engineered mutants, a complete balance was set up considering all possible redox reactions during the oxidative phosphorylation (Table 17).

TABLE 17

Table 17: Redox balance of PPP engineered C. glutamicum BS5, *C. glutamicum* BS6, and *C. glutamicum* BS7 calculated from the estimated fluxes (FIG. 11), anabolic $CO_2$ and NADH production, anabolic NADPH demand and the respiratory quotient (Table 15).

| Strain | *C. glutamicum* BS5 | *C. glutamicum* BS6 | *C. glutamicum* BS7 |
|---|---|---|---|
| $CO_2$ production | | | |
| glucose 6-P dehydrogenase | 62.1 | 60.9 | 66.1 |
| pyruvate dehydrogenase | 87.4 | 82.4 | 88.3 |
| anaplerotic carboxylation | −30.5 | −32.4 | −31.3 |
| isocitrate dehydrogenase | 67.7 | 61.2 | 69.9 |
| 2-oxoglutarate dehydrogenase | 59.7 | 52.8 | 62.6 |
| lysine secretion | 11.3 | 11.7 | 13.0 |
| anabolism | 6.2 | 7.6 | 6.0 |
| Total | 263.9 | 244.2 | 274.6 |
| $O_2$ consumption | | | |
| Total | 227.5 | 212.3 | 230.8 |
| NADH production | | | |
| glyceraldehyde 3-P dehydrogenase | 159.2 | 158.6 | 160.1 |
| pyruvate dehydrogenase | 87.4 | 82.4 | 88.3 |
| 2-oxoglutarate dehydrogenase | 59.7 | 52.8 | 62.6 |
| fumarase | 59.7 | 52.8 | 62.6 |
| malate dehydrogenase | 59.7 | 52.8 | 62.6 |
| anabolism | 20.0 | 25.0 | 19.0 |
| Total | 445.7 | 424.4 | 455.2 |
| NADPH production | | | |
| glucose 6-P dehydrogenase | 62.1 | 60.9 | 66.1 |
| 6-P gluconate dehydrogenase | 62.1 | 60.9 | 66.1 |
| isocitrate dehydrogenase | 67.7 | 61.2 | 69.9 |
| lysine secretion | −45.0 | −46.8 | −52.1 |
| anabolism | −102.6 | −109.2 | −95.3 |
| Total | 44.3 | 27.0 | 54.8 |
| Redox balance | | | |
| Total | −17.5 | −13.3 | −24.2 |
| [H] oxidation flux | | | |
| Total | 35.0 | 26.8 | 48.4 |

In none of the strains the cofactor balance was closed. This indicates the presence of an additional, so far unassigned flux of [H] oxidation, required to close the balance. In all three strains this [H] oxidation flux was almost as high as the apparent NADPH excess. A significant contribution of NAD(P)H oxidase in the respiratory chain to the NADPH oxidation can be excluded, since the activity of this enzyme as part of the respiratory chain would consume oxygen and thus result in a closed redox balance. This consideration also holds for malic enzyme. NADPH oxidation by the activity of malic enzyme acting in the direction of carboxylation results in the formation of malate which is converted to oxaloacetate thereby forming NADH. Complete NADH oxidation in the respiratory chain would, in turn, be connected to oxygen consumption. Investigation of specific activity of malic enzyme in the wild type and different lysine producers, however, gave some first hint towards a rising physiological importance of malic enzyme in lysine-producing *C. glutamicum* (FIG. 13). Its physiological role was thus examined in more detail.

Overexpression of tkt-Operon

In *C. glutamicum* the zwf gene, encoding glucose 6-phosphate dehydrogenase is located on the tkt-operon together with the genes opcA, encoding a putative subunit of G6PDH, tal, encoding transaldolase, tkt, encoding transketolase and pgl, encoding 6-phosphogluconolactonase. Alternatively to the above described approach, overexpression of G6PDH can thus be realized by amplified expression of the complete operon, thereby up-regulating an enlarged enzymatic set of the pentose phosphate pathway.

Although glucose 6-phosphate dehydrogenase is regarded as rate-controlling enzyme of the PPP (Moritz, et al., 2000), it can not be excluded, that in response to overexpression of zwf, other bottlenecks arise in the non-oxidative part of the PPP due to a limited capacity of transketolase and transaldolase. In this regard, overexpression of tkt has been shown to effectively increase the carbon conversion by the non-oxidative pathway (Ikeda and Katsumata, 1999). A combined overexpression of the enzymes of the oxidative and non-oxidative part of the PPP therefore promises an efficient flux increase through the PPP and thus improved NADPH supply for lysine production.

Strain Construction and Specific Enzyme Activity

Overexpression was achieved by allelic replacement of the wild type promoter of the tkt-operon by the strong sod-promoter. Promoter replacement was validated by PCR analysis. To this end, a site-specific primer, binding within the promoter, was combined with a primer, binding within the tkt-operon. This approach only yielded PCR products from mutants exhibiting the promoter exchange within the genome. To investigate the effect of the implemented promoter exchange on the enzymes of interest, the specific activity was determined. In response to transcriptional up-regulation of the tkt-operon by the sod-promoter, the specific activity of glucose 6-phosphate dehydrogenase, transketolase and transaldolase was significantly increased (FIG. 12).

The basic expression level of the genes of the tkt-operon is obviously controlled by a common promoter, the exchange of which by the stronger sod-promoter raised the basal expression level thereby increasing the specific activity of the encoded enzymes. This clearly simplifies concomitant overexpression of zwf, tkt and tal as it solely requires a single promoter exchange instead of multiple genetic modifications. To achieve an unrestricted carbon flux through the pentose phosphate pathway, overexpression of the whole tkt-operon is thus the most promising and efficient strategy.

Functional Role of Malic Enzyme for NADPH Metabolism

Metabolic flux analysis of the above described strains revealed that none of the investigated strains could achieve a closed NADPH balance only considering PPP and ICD as NADPH-providing and biomass and lysine formation as NADPH-consuming reactions. As NADPH supply is one of the major issues with regard to strain optimization, it was now especially interesting to see how the strain *C. glutamicum* BS1 (lysC$^{T311I}$), which obviously exhibited a NADPH deficiency, could fully satisfy its NADPH demand. A potential candidate is malic enzyme, the role of which is so far poorly understood. Hence, its role for NADPH metabolism was investigated in more detail. To this end, the encoding gene malE, was deleted in the background of *C. glutamicum* BS1 and the PPP-engineered strain *C. glutamicum* BS6 to study the effect on growth and production characteristics.

Strain Construction and Validation

Deletion of malic enzyme was achieved by allelic replacement of the wild type malE gene by a shortened DNA fragment, lacking 400 bp of the malE sequence. Validation was performed by PCR analysis and determination of specific malic enzyme activity. MalE activity in the deletion mutants was below detection limit (<0.01 U mg$^{-1}$).

Malic Enzyme Activity

The specific activity of malic enzyme strongly depended on the genetic background and the nutrient status. In comparison to the wild type, lysine-producing *C. glutamicum* BS1 exhibited a significantly increased malic enzyme activity (FIG. 13). In *C. glutamicum* BS1 the influence of the growth conditions on malic enzyme activity were additionally investigated. Here, MalE activity was increased in fructose-grown cells as compared to cells cultivated on glucose (FIG. 13).

From previous works it is known, that the expression level of malE varies significantly depending on the nutrition status (Dominguez, et al., 1998; Hayashi, et al., 2002; Polen, et al., 2007). The different in vitro activity observed here, indirectly reflecting the enzyme capacity and thus its expression level, suggests an increased expression of malic enzyme due to genetic perturbations.

Physiological Response to malE Deletion

To investigate the physiological role of malic enzyme, the parent strain *C. glutamicum* BS1 and its DmalE derivative were compared considering growth and lysine production in standard minimal medium. As shown in FIG. 14, lysine and biomass yield were decreased in the deletion mutant. Growth, however, was only slightly affected by malE deletion. In the NADPH-engineered strain *C. glutamicum* BS6 with improved NADPH supply via the PPP, the picture was different. Due to overexpression and modification of glucose 6-phosphate dehydrogenase, the NADPH supply in this strain is significantly improved compared to *C. glutamicum* BS1 resulting in changed growth and production characteristics. Deletion of malic enzyme in this strain did not have any effect on lysine and biomass formation (FIG. 14).

To further investigate the resulting consequences for the NADPH-metabolism of *C. glutamicum*, the overall NADPH demand of the strains for biomass formation and lysine production was calculated, considering an anabolic demand of 16.4 mmol NADPH (g cell dry mass)$^{-1}$ and 4 mol NADPH (mol lysine)$^{-1}$. The ratio of the respective NADPH demand of the malE deletion strain *C. glutamicum* BS44 and its parent *C. glutamicum* BS1 was 0.93, showing that the consumption for this cofactor was reduced in the deletion strain. Formation of biomass and lysine in the NADPH-engineered strain *C. glutamicum* BS6 and the corresponding malE deletion strain were identical. Consequently, both strains did not differ concerning their NADPH requirement for product synthesis, resulting in a ratio of their respective NADPH consumption of 1.00. The obtained data set and $^{13}$C metabolic flux analysis with the extended flux model clearly reveals that malic enzyme contributes to NADPH supply in lysine producing *C. glutamicum* BS1. Compared to the wild type, MalE activity was increased in the lysine producer in relation to an increased NADPH demand and deletion of malE resulted in a reduced formation of the NADPH consuming products lysine and biomass. Expressing the NADPH requirement as relative flux [%] normalized to the specific glucose uptake rate, set as 100%, the overall NADPH consumption flux of *C. glutamicum* BS1 was 13% higher than the total NADPH consumption in its malE-deficient derivative. This difference corresponds very well to the in vivo flux of 15% through malic enzyme in *C. glutamicum* BS1, determined by the extended flux model (FIG. 20), and zero flux through malic enzyme in the deletion strain. From the NADPH balance (FIG. 15) it becomes obvious that this in vivo flux through malic enzyme is required in lysine-producing *C. glutamicum* BS1 to achieve a closed NADPH balance.

For the wild type of *C. glutamicum*, however, it was recently demonstrated that, during growth on glucose, PPP and TCA cycle alone supply sufficient NADPH for cell growth (Kr mer, et al., 2008), explaining that deletion of malic enzyme in the wild type background does not influence the growth characteristics on this carbon source (Gourdon, et al., 2000). *C. glutamicum* obviously activates malic enzyme under lysine production conditions to meet the increased NADPH demand, which is reflected in the increased expression level as well as the increased specific MalE activity. The underlying regulatory strategy for control of malE expression has not been clarified so far. Here, several studies revealed an expression control by several regulators. There is, for instance, some evidence that malE belongs to the ramB-regulon (Gerstmeir, et al., 2004), a dependence on the nutrition status has been described (Dominguez, et al., 1998; Hayashi, et al., 2002; Polen, et al., 2007) and recently a connection to the global nitrogen regulation amtR has been discovered (Buchinger, et al., 2009). The intracellular signal, however, still remains unclear. Due to the obvious involvement of malic enzyme in the NADPH metabolism of *C. glutamicum*, the redox state of the cell is conceivable as trigger. Thus, the NADPH/NADP ratio was determined as possible signalling system of the redox state of the cell.

Intracellular NADPH/NADP Ratio as Signal for Expression Control

Determination of the intracellular NADPH/NADP ratio revealed significant differences between the investigated strains. In *C. glutamicum* BS1 the NADPH/NADP ratio was 0.82±0.10. Lack of malic enzyme activity in this genetic background, had no effect, which is reflected by a similar value of 0.76±0.10 in *C. glutamicum* BS44. Improved supply of NADPH by engineering of the PPP, however, clearly influenced the NADPH/NADP ratio. The measured value in *C. glutamicum* BS6 (1.45±0.40) was significantly higher as compared to its parent *C. glutamicum* BS1. *C. glutamicum* BS52 exhibited a NADPH/NADP ratio of 1.76±0.20 and thus, did not differ from its parent strain *C. glutamicum* BS6. As shown in FIG. 16, MalE activity clearly correlates with the NADPH/NADP ratio. *C. glutamicum* ATCC 13032, exhibiting the highest ratio of 2.35 (Kromer, et al., 2008), revealed the lowest MalE activity.

Decrease of the NADPH/NADP ratio, i.e. as intracellular signal for NADPH limitation, seems to trigger malE expression, which is reflected in an increased specific activity in the investigated lysine producers. Previous studies revealed that in *E. coli*, the redox state, reflected by the NADPH availability in the cell is recognized as signal for regulation of superoxide dismutase expression (Gardner and Fridovich, 1993). Due to the improved NADPH supply in the PPP-engineered strain an additional supply of NADPH by malic enzyme is dispensable, explaining the lowered activity of MalE in this strain.

This assumption is confirmed by the response to malE deletion in this strain. Neither lysine production nor biomass formation is effected by the lack of malic enzyme activity, showing that NADPH supply by PPP is sufficient to meet the complete NADPH demand of this strain.

The obtained data clearly show that *C. glutamicum* obviously adapts to different cellular requirements by modulation of MalE-activity. Under conditions with limited NADPH availability, e.g. growth on fructose or lysine production, malE expression is increased and displays an important additional NADPH source in *C. glutamicum*. In this regard MalE supports the metabolic flexibility and robustness to cope with changing cellular requirements. If and how malic enzyme might contribute to redox balancing in the PPP engineered strains with excess NADPH formation, however, remains unclear. What is obvious in this regard: deletion of malic enzyme does not yield in increased production of the NADPH demanding products lysine and biomass, which one would assume, if malE was responsible for oxidation of the apparent NADPH excess. It can, however, not be excluded, that the malE-lacking strain responded by a global rearrangement of the metabolic fluxes including fluxes through PPP and TCA cycle thereby reducing the overall NADPH supply. Disclosure would require further investigations involving metabolic flux analysis using the extended approach and determination of a complete redox and NADPH balance.

Engineering of Lysine Biosynthesis

With regard to strain optimization, the enzymes forming the lysine biosynthetic pathway are key targets in metabolic engineering. The different routes for lysine formation, however, impede strain design as the split pathway confers a high flexibility. In this work, the focus was led on diaminopimelate dehydrogenase compiling the dehydrogenase branch of the lysine pathway in *C. glutamicum*. By implementation of a second copy of the encoding ddh gene, diaminopimelate dehydrogenase was over expressed in the background of the feedback deregulated strain *C. glutamicum* BS1.

Impact of ddh Overexpression on Specific Enzyme Activity

Implementation of a second copy of the ddh gene resulted in a significantly increased specific activity of DDH in crude cell extracts of *C. glutamicum* BS222 as compared to the parent strain BS1. As shown in FIG. 17, the ddh-mutant exhibited a specific activity of 440 mU $mg^{-1}$ while BS1 showed a specific activity of 210 mU $mg^{-1}$. The effect on enzyme activity reflects the additional gene copy of diaminopimelate dehydrogenase.

Influence of the ddh Overexpression on Growth and Production

To see, how the doubled activity of DDH influenced lysine production as well as growth behaviour, cultivation experiments in standard minimal medium on glucose were performed. Both strains exhibited well balanced growth and metabolic stability during the whole cultivation period. The increased DDH activity in the strain *C. glutamicum* BS222 resulted in a 23% improvement of the lysine yield (Table 18).

TABLE 18

Table 18: Growth and production characteristics of *C. glutamicum* BS1 and *C. glutamicum* BS222 in standard minimal medium with glucose as sole carbon source. Yields were determined as slope of the linear best fit between glucose consumption and product formation.

| | $Y_{Lys/S}$ [mmol $mol^{-1}$] | $Y_{X/S}$ [g $mol^{-1}$] | μ [$h^{-1}$] |
|---|---|---|---|
| *C. glutamicum* BS1 | 81.3 ± 4.8 | 90.1 ± 1.1 | 0.38 ± 0.00 |
| *C. glutamicum* BS222 | 100.8 ± 4.8 | 82.0 ± 1.0 | 0.31 ± 0.00 |

The additional gene copy also affected biomass formation as well as growth (Table 19). Both were slightly reduced in *C. glutamicum* BS222 as compared to its parent. This grew with a specific rate of 0.38 $h^{-1}$, whereas in the ddh mutant μ was reduced to 0.31 $h^{-1}$.

Unlike the succinylase branch of the biosynthetic pathway of lysine, diaminopimelate dehydrogenase directly uses ammonium. Due to the low affinity of DDH towards $(NH_4)^+$ (Wehrmann, et al., 1998) its concentration in the medium is likely to influence the in vivo activity of DDH and thus the impact of ddh overexpression on lysine production. In further shake flask cultivations the two strains were hence compared during growth at different ammonium sulphate concentrations.

Growth Acceleration by Increased Ammonium Sulphate Concentrations

Cultivation of the strain *C. glutamicum* BS1 at different ammonium sulphate concentrations revealed a clear correlation between concentration and specific growth rate. As displayed in FIG. 18, the specific growth rate increased with an increased availability of ammonium sulphate.

At the lowest concentration of 2 g $L^{-1}$, *C. glutamicum* BS1 exhibited a specific growth rate of 0.32 $h^{-1}$ and reached a maximum growth rate of 0.43 $h^{-1}$ at a concentration of 15 g $L^{-1}$. In contrast to the growth behaviour, lysine and biomass formation of *C. glutamicum* BS1 were not affected by the varied ammonium sulphate concentration of the medium (Table 19).

TABLE 19

Table 19: Lysine yield and biomass yield of *C. glutamicum* BS1 (lysC$^{T311I}$) grown in minimal medium at varied ammonium sulphate concentrations.

| Ammonium sulphate [g $L^{-1}$] | $Y_{Lys/S}$ [mmol $mol^{-1}$] | $Y_{X/S}$ [g $mol^{-1}$] |
|---|---|---|
| 2 | 80.8 ± 1.8 | 88.9 ± 1.1 |
| 5 | 81.3 ± 4.8 | 90.8 ± 1.3 |
| 10 | 79.8 ± 4.8 | 88.5 ± 1.1 |
| 15 | 82.1 ± 4.2 | 91.2 ± 0.8 |

Improvement of Lysine Production by Increased Ammonium Availability

The picture for the ddh engineered strain *C. glutamicum* B S222 was completely different. Here, lysine production extremely depended on the concentration of ammonium sulphate in the medium. As shown in FIG. 19, lysine yield of BS222 successively increased with a raising availability of ammonium sulphate. At a concentration of 2 g $L^{-1}$ ammonium sulphate the strain exhibited a lysine yield of 89.4 mmol $mol^{-1}$. This was increased up to 125.2 mmol $mol^{-1}$ at 10 g $L^{-1}$ ammonium sulphate. A further supplementation with ammonium sulphate did not yield in a further improved production, suggesting that a concentration of 10 g $L^{-1}$ is sufficient for saturation of the engineered diaminopimelate dehydrogenase, which is in consistence with the $k_m$ value of 34 mM of DDH towards ammonium (Wehrmann, et al., 1998).

In contrast to *C. glutamicum* BS1, the specific growth rate of the ddh mutant was not affected by the ammonium sulphate concentration in the medium. The strain grew with an average growth rate of 0.30 $h^{-1}$±0.01. The only exception here was the cultivation at 2 g $L^{-1}$ ammonium sulphate in which the growth rate was slightly decreased to 0.26 $h^{-1}$. This was the concentration which also resulted in the worst growth of the parent strain BS1. This low amount of ammonium obviously does not support optimal growth but limits biomass formation (Silberbach, et al., 2005b). This is in accordance with the findings that at concentrations below 2.75 g $L^{-1}$ several genes involved in ammonium assimilation are up-regulated to ensure ammonium accommodation. Biomass formation, however, decreased at concentrations above 10 g $L^{-1}$ ammonium sulphate (Table 20), which is probably related to the enormously increasing lysine yield.

TABLE 20

Table 20: Specific growth rate and biomass yield of *C. glutamicum* BS222 grown in minimal medium at varied ammonium sulphate concentrations.

| Ammonium sulphate [g $L^{-1}$] | μ [$h^{-1}$] | $Y_{X/S}$ [g $mol^{-1}$] |
|---|---|---|
| 2 | 0.27 ± 0.00 | 81.4 ± 1.6 |
| 5 | 0.31 ± 0.01 | 82.0 ± 1.0 |
| 10 | 0.29 ± 0.01 | 77.8 ± 1.2 |
| 15 | 0.30 ± 0.01 | 72.0 ± 1.3 |

With its two pathways for lysine biosynthesis *C. glutamicum* is well prepared to adapt to varying ammonium sulphate concentration. The dehydrogenase pathway with a low affinity towards $NH_4^+$ becomes active at high concentrations whereas the succinylase pathway also ensures growth at minor ammonium availability. This is also reflected in the flux partitioning between these two pathways during growth at varied ammonium sulphate concentrations (Eikmanns, et al., 1993; Sonntag, et al., 1993). Down regulation of dapD, encoding the first enzyme of the succinylase branch by the global nitrogen regulator amtR here ensures that this energy consuming pathway has only a minor importance when the ammonium supply is high (Buchinger, et al., 2009; Silberbach, et al., 2005b). This explains the unvaried lysine yield in *C. glutamicum* BS1. Its lysine pathway, comprising succinylase and dehydrogenase branch has a certain capacity and variation of ammonium sulphate here only results in a flux shift between these two branches. Determination of the flux split ratio by NMR analysis revealed, that at 5 g $L^{-1}$ ammonium sulphate, the dehydrogenase branch contributes to about 40% of the overall flux towards lysine. At this ammonium sulphate concentration, DDH does not work at its maximum due to the low affinity towards $NH_4^+$, thereby limiting carbon flux through this branch. Increasing the $NH_4^+$ availability increases DDH activity and thus its contribution to the overall lysine flux (Sonntag, et al., 1993) but in turn decreases expression of enzymes forming the succinylase branch (Buchinger, et al., 2009) so that the total lysine flux is not increased. In *C. glutamicum* BS222, however, the overall capacity of the lysine pathway is increased by overexpression of ddh. Due to the low affinity of diaminopimelate dehydrogenase towards $NH_4^+$, this capacity can only be fully exploited at higher concentrations. Unlike *C. glutamicum* BS1, *C. glutamicum* BS222 uses this increased capacity of the lysine pathway for lysine production and does not respond by accelerated growth. The importance of ddh for lysine production in *C. glutamicum* at high ammonium concentrations is further underlined by deletion experiments previously performed (Schrumpf, et al., 1991). Deletion here resulted in severely reduced lysine productivity.

Plasmid-related overexpression of ddh was, however, not beneficial with regard to lysine production (Cremer, et al., 1991) although sufficient ammonium supply was ensured. Here, two possible explanations should noted: In addition to the dependence on the ammonium availability, the flux split ratio of the lysine biosynthetic pathway also exhibits a significant time dependence (Sonntag, et al., 1993). At high ammonium sulphate concentrations, the dehydrogenase pathway contributes to more than 70% to the overall lysine flux within the first 12 h of the cultivation, corresponding to the cultivation phase investigated in the present study. In the later cultivation phase, however, studied in the previous work, its contribution significantly decreases down to 12% (Sonntag, et al., 1993). Moreover, overexpression was performed in a genetically non-defined producer. This was obtained by chemical mutagenesis and selected with regard to a feedback deregulated aspartate kinase (Menkel, et al., 1989). Accumulation of further mutations that circumvent a positive effect of ddh overexpression can hence not be excluded. From these findings, it becomes obvious, that the benefit of an engineering strategy has to be carefully verified considering both the genetic background of the modified strain as well as the testing conditions as important variables.

Specific activity of diaminopimelate dehydrogenase was not influenced by the concentration of ammonium sulphate in the culture medium. Both strains revealed identical specific activities when grown at 2 g $L^{-1}$ or 15 g $L^{-1}$, respectively, (FIG. 20). This clearly indicates that the observed differences regarding the lysine productivity is correlated to the in vivo activity of DDH which is supported by $NH_4^+$ donation to the medium and not the result of changed expression levels of ddh as response to an altered $NH_4^+$ concentration.

To some extend, the achieved improvement at high ammonium concentration might also be influence by the expression level of lysA, encoding diaminopimelate dehydrogenase. At low ammonium availability lysA expression is repressed by amtR to favour growth instead of lysine formation. This repression, however, is abolished at increasing ammonium sulphate concentrations thereby resulting in an increased lysA (Silberbach, et al., 2005b) expression and thus higher enzyme capacity which might support lysine production in the ddh-engineered strain.

Engineering of Precursor Supply

Due to the excess NADPH supply, the above described PPP engineered strains had a significant remaining potential for lysine production. Here, lysine synthesis is probably limited by the insufficient supply of oxaloacetate which is reflected in the unchanged anaplerotic net flux (FIG. 24). Strain improvement in this regard has been achieved by increasing the OAA supply through overexpression of pyruvate carboxylase or PEP carboxylase (Peters-Wendisch, et al., 2001; Sano, et al., 1987). The strategy applied in this work focussed on novel targets towards improved OAA supply by reducing carbon conversion through metabolic pathways competing for pyruvate and phosphoenolpyruvate as direct carbon precursors of OAA.

Metabolic Response to Pyruvate Kinase Deletion

Pyruvate kinase plays an important role in flux control of the intermediate metabolism. It catalyzes the irreversible conversion of phosphoenolpyruvate into pyruvate and is under allosteric control of ATP and AMP (Jetten, et al., 1994b). In lysine-producing *C. glutamicum*, deletion of pyruvate kinase appears as promising strategy for strain improvement, as in pyruvate kinase deficient strains the required equimolar ratio of the two lysine precursors oxaloacetate and pyruvate could be achieved through concerted action of the phosphotransferase system (PTS) and phosphoenolpyruvate carboxylase (PEPC), whereby a reduced amount of carbon may be lost as $CO_2$ due to reduced flux into the TCA cycle. In previous studies, deletion of pyruvate kinase in lysine-producing *C. glutamicum*, however, did not yield a clear picture so that the exact metabolic consequences are not fully understood (Gubler, et al., 1994; Ozaki and Shiio, 1969; Shiio, et al., 1990). Here, the metabolic response of *C. glutamicum* to pyruvate kinase deletion was investigated in detail on the level of in vivo fluxes using the extended model described above. The pyruvate kinase deficient strain *C. glutamicum* BS13 was constructed by deletion of the encoding pyk gene in the background of the lysine producer *C. glutamicum* BS1 (lysC$^{T311I}$).

Pyruvate Kinase Activity

The pyk deletion mutant *C. glutamicum* BS13 revealed complete absence of in vitro pyruvate kinase activity (<0.6 mU $mg^{-1}$), whereas the parent strain *C. glutamicum* BS1 showed a strong specific activity of 1099 mU $mg^{-1}$ for this enzyme. The lack of PYK activity demonstrated that there is no remaining pyruvate kinase like activity in *C. glutamicum* BS13. In the deletion strain, direct conversion of PEP into pyruvate was thus restricted to glucose uptake by the phosphotransferase system.

Influence of Deletion on Growth and Production Characteristics

To investigate quantitative physiological effects of the pyruvate kinase deletion, lysine producing *C. glutamicum* BS 1 and its pyruvate kinase deficient derivative *C. glutamicum* BS13 were grown in batch culture (FIG. 21A-D).

Both strains exhibited a relatively similar specific growth rate, specific glucose uptake rate or biomass yield. The yield and specific rate of lysine production, however, were slightly lower in *C. glutamicum* BS13 (Table 21). Moreover, lack of pyruvate kinase activity induced the formation of the overflow metabolites dihydroxyacetone (DHA) and glycerol. Trehalose formation was slightly reduced.

TABLE 21

Growth and production characteristics of lysine producing *C. glutamicum* BS1 and BS13 during batch cultivation on glucose. The data given are biomass yield ($Y_{X/S}$), lysine yield ($Y_{Lys/S}$), glycerol yield ($Y_{Gly/S}$), dihydroxyacetone yield ($Y_{DHA/S}$), trehalose yield ($Y_{Tre/S}$) as well as specific growth rate (μ), specific glucose uptake rate ($q_{Glc}$) and specific lysine production rate ($q_{Lys}$). All values represent mean values from three parallel cultivation experiments. The yields were determined as slope of the linear best fit when plotting product formation and substrate consumption as shown in FIG. 21 from three biological replicates.

| | *C. glutamicum* BS1 | *C. glutamicum* BS13 |
|---|---|---|
| | Yields | |
| $Y_{X/S}$ [g $mol^{-1}$] | 82.1 ± 1.5 | 77.1 ± 0.2 |
| $Y_{Lys/S}$ [mmol $mol^{-1}$] | 82.0 ± 2.9 | 73.9 ± 0.9 |
| $Y_{DHA/S}$ [mmol $mol^{-1}$] | 0.0 ± 0.0 | 20.8 ± 1.4 |
| $Y_{Gly/S}$ [mmol $mol^{-1}$] | 0.0 ± 0.0 | 6.2 ± 1.3 |
| $Y_{Tre/S}$ [mmol $mol^{-1}$] | 9.1 ± 0.4 | 2.9 ± 0.1 |
| | Rates | |
| μ [$h^{-1}$] | 0.38 ± 0.00 | 0.35 ± 0.00 |
| $q_{Glc}$ [mmol $mol^{-1}$] | 4.6 ± 0.08 | 4.5 ± 0.01 |
| $q_{Lys}$ [mmol $mol^{-1}$] | 0.38 ± 0.02 | 0.33 ± 0.00 |

Major kinetic and stoichiometric parameters, including specific growth rate and yield for biomass, lysine and byproducts remained constant throughout the cultivation (FIG. 21A-D). This clearly shows that both strains were in metabolic steady-state allowing usage of the above described extended flux model for resolution of the metabolic fluxes.

Metabolic Flux Response to Deletion of Pyruvate Kinase

The response of lysine-producing *C. glutamicum* to pyruvate kinase deletion was now investigated on the level of metabolic carbon fluxes. It was interesting to see in detail, how *C. glutamicum* BS13 could compensate for the loss of this central glycolytic gene and almost maintain growth and production characteristics of the parent strain.

Here, separation of the metabolite pools of PEP and pyruvate and thus, resolution of all fluxes involved in carboxylation and decarboxylation was essential, so that metabolic flux analysis with the enlarged metabolic network and labelling information from tracer experiments with 99% [1-$^{13}$C] glucose and 50% [U-$^{13}$C] glucose was performed. As direct response to the genetic modification, the overall conversion flux from PEP to pyruvate decreased significantly from 138% to 100%, reflecting exclusive conversion of PEP to pyruvate by the phosphotransferase system for glucose uptake. The metabolic flux distribution in FIG. 22 reveals that the deletion of pyruvate kinase further resulted in local rerouting of the flux around the pyruvate node to by-pass the limited direct conversion from PEP into pyruvate. Responses in the pentose phosphate pathway and the TCA cycle were only rather weak. In detail, the two strains differed significantly in the relative contribution of PC and PEPC to anaplerotic supply of the TCA cycle. Whereas PC was the major anaplerotic enzyme in *C. glutamicum* BS1, it was completely inactive in the deletion mutant which rather utilized PEPC for this purpose. The flux through the decarboxylating enzymes PEPCK and malic enzyme showed only slight differences between the two strains. Altogether pyruvate kinase deletion resulted in a strong shift of the anaplerotic net flux from pyruvate to PEP carboxylation and created a metabolic by-pass from PEP via oxaloacetate and malate towards pyruvate involving PEPC, malate dehydrogenase and malic enzyme (FIG. 23). This by-pass enabled a sufficient supply of pyruvate so that a high flux through pyruvate dehydrogenase and TCA cycle was maintained. Overall *C. glutamicum* BS13 could compensate for the gene deletion by local flux rearrangement involving flexible utilization of its anaplerotic enzymes. The narrow confidence intervals underline that all carbon fluxes were estimated with very high precision (FIG. 22). The flux differences discussed here are therefore clearly related to the deletion of pyruvate kinase. Since the specific glucose uptake rate was almost identical for the two strains (Table 22), all conclusions drawn for the relative fluxes also hold for the absolute flux values. For both strains, an excellent fit between experimentally determined and simulated mass isotopomers was achieved.

The conversion of oxaloacetate into malate as part of the metabolic by-pass is in the reverse direction of the net TCA cycle flux, rather forming oxaloacetate from malate, and would require a reversible inter conversion of these two metabolites. As mentioned above, the extended flux model applied here indeed considers malate and oxaloacetate as a single pool, and the excellent fit of the labelling data supports the presence of a reversible inter conversion between malate and oxaloacetate. The activation of this by-pass is the key to compensate for the loss of pyruvate kinase activity and maintain the carbon flux through the TCA cycle as well as through other central pathways including PPP, glycolysis or anabolism. The same metabolic by-pass is also activated in pyruvate kinase deficient *E. coli* during growth on glucose (Al Zaid Siddiquee, et al., 2004; Emmerling, et al., 2002) and obviously displays a general strategy of microorganisms possessing both, PEPC and PC. In contrast, *B. subtilis* lacking PEPC cannot grow on glucose in the absence of pyruvate kinase (Diesterhaft and Freese, 1973; Fry, et al., 2000).

*C. glutamicum* BS1 and the pyk deletion mutant both exhibit a significant flux through malic enzyme demonstrating the important role of this enzyme for the flexibility of the *C. glutamicum* metabolism. In the deletion mutant, malic enzyme is part of the metabolic by-pass created and thus contributes to the robustness of the metabolism against the genetic perturbation. Its flux, i.e. its in vivo activity, in both strains shows that it also plays an important role for the flexibility of the cofactor metabolism in *C. glutamicum* and reveals, as discussed above, the importance of this enzyme as NADPH source in lysine-producing strains of *C. glutamicum*. As shown by the NADPH balance (FIG. 24), malic enzyme is required in both strains to meet the cellular NADPH demand and contributes significantly to the supply of this cofactor. Glucose 6-phosphate dehydrogenase and 6-phosphogluconate dehydrogenase (PPP), isocitrate dehydrogenase (ICD) and malic enzyme (MalE) were considered as NADPH supplying reactions and anabolism with a stoichiometric demand of 16.4 mmol NADPH (g cell dry weight)$^{-1}$ (Wittmann and de Graaf, 2005) and lysine production with a stoichiometric demand of 4 mol NADPH (mol lysine)$^{-1}$ as NADPH consuming reactions. This significantly supports the conclusions drawn from the studies on the physiological role of malic enzyme.

The lower flux through malic enzyme as well as through the PPP in the pyruvate kinase deletion strain might be related to the increased flux through isocitrate dehydrogenase, resulting in enhanced NADPH supply via the TCA cycle. A co-regulation of NADPH supplying pathways, balancing the overall supply has been previously observed in lysine-producing *C. glutamicum* (Wittmann and Heinzle, 2002).

The exact effect of deletion of pyruvate kinase on lysine production in *C. glutamicum* obviously depends on the production strain as well as on cultivation conditions. Whereas, upon deletion of pyruvate kinase, lysine production was enhanced in different strains of *B. flavum* (Ozaki and Shiio, 1969; Shiio, et al., 1990), decreasing production was observed in *C. lactofermentum* (Gubler, et al., 1994) and, to some extent, also in the present work. Since the overall supply of NADPH did not significantly change, a possible explanation might be a limited availability of the lysine precursor oxaloacetate. The physiological characteristics and the intracellular carbon fluxes of *C. glutamicum* BS1 and *C. glutamicum* BS13, studied here, point at possible explanations. In this regard the accumulation of dihydroxyacetone and glycerol, specifically related to deletion of pyruvate kinase, appears interesting. These over-flow metabolites are formed by *C. glutamicum*, when the flux entering into the lower glycolytic chain exceeds the capacity of reactions down-stream of glyceraldehyde 3-phosphate, e.g. during growth on fructose (Dominguez, et al., 1998; Kiefer, et al., 2004). Under these conditions the bottleneck is attributed to glyceraldehyde 3-phosphate dehydrogenase and caused by an unfavourable ratio of NAD/NADH reducing the capacity of this enzyme. The observed metabolic fluxes for *C. glutamicum* BS1 and the pyk deletion mutant, however, do not suggest significant changes of this ratio in the pyruvate kinase deficient strain which could cause a reduced capacity of glyceraldehyde 3-phosphate dehydrogenase. As also the in vivo flux through this enzyme was identical in the two strains studied here, a contribution of glyceraldehyde 3-phosphate dehydrogenase to the observed limitation does not appear very likely. Other candidates are more promising. As shown, the anaplerotic flux is completely shifted to PEPC in the deletion mutant. Compared to the parent strain, the overall flux through this enzyme is increased about 2.5 fold which could display the maximum capacity this enzyme can handle under these conditions. In this regard, strains of *C. glutamicum*, previously showing enhanced lysine production upon pyruvate kinase deletion, additionally contained a feedback-resistant variant of PEPC, insensitive to allosteric control by aspartate (Shiio, et al., 1987), whereas a double mutant, lacking pyruvate kinase and PEPC, exhibited seriously impaired glucose utilization (Park, et al., 1997). It appears also possible that a limited capacity of malic enzyme is involved in the observed limitation. Malic enzyme activity in the pyruvate kinase deficient wild type of *C. glutamicum* is not sufficient to enable growth on acetate or citrate, but growth can be restored by overexpression of this enzyme (Netzer, et al., 2004).

Attenuation of Pyruvate Dehydrogenase

With regard to lysine production in *C. glutamicum*, pyruvate dehydrogenase directly competes with the anaplerotic enzyme pyruvate carboxylase as major source of the lysine precursor oxaloacetate (Peters-Wendisch, et al., 2001). Deletion of aceE, encoding subunit one of this central glycolytic gene was shown to improve lysine production in *C. glutamicum*. This deletion, however, completely blocked carbon flux towards the TCA cycle and resulted in severe growth deficiency and inability of the mutant to grow on typical sugar based production media. Moreover, lack of pyruvate dehydrogenase activity induced extensive by-product formation (Blombach, et al., 2007). In this work, the expression of PDH was gently down-regulated by start codon exchange to reduce carbon flux through PDH and supply of the TCA cycle precursor acetyl-CoA thus aiming at increased lysine production without detrimental side effects.

Strain Construction and Validation

Start codon exchange in the aceE gene was achieved by replacement of the wild type allele through the mutant using homologous recombination. The modification was implemented in the genetic background of *C. glutamicum* BS87. This strain already comprised several modifications within the biosynthetic pathway of lysine as well as an engineered precursor supply by overexpression and modification of pyruvate carboxylase and deletion of PEP carboxykinase (Table 1). Clones from the second recombination were screened with regard to their specific PDH activity as described above (FIG. 21). Further analysis of the mutants by sequencing of the start codon region of aceE comprising a span of about 1000 bp revealed 100% sequence identity to the wild type with exception of the start codon nucleotide. The two mutants with reduced PDH activity carried the nucleotide exchange within the start codon (FIG. 25). As no other mutations have occurred during the strain construction process, the reduced specific PDH activity in the mutants can clearly be attributed to the implemented point mutation. Further experiments were performed with clone 2, which will be referred to as *C. glutamicum* BS238.

Influence of Start Codon Exchange on Specific Enzyme Activity

The specific PDH activity of the recombinant strain BS238 and the parent strain BS87 was determined in minimal medium using glucose as sole carbon source. As shown in FIG. 26, usage of the rare start codon GTG instead of the common ATG resulted in a drastically reduced specific activity of pyruvate dehydrogenase. While the parent strain *C. glutamicum* BS87 exhibited a specific PDH activity of around 30 mU mg$^{-1}$, in *C. glutamicum* BS238 it was only 13 mU mg$^{-1}$.

For successful application of PDH attenuation by start codon exchange in an industrial process, the stability of the implemented point mutation is a major concern. This was validated in a long-time cultivation experiment, comprising subsequent transfer of exponentially growing cells in batch culture. Specific PDH activity in the mutant *C. glutamicum* BS238 was not influenced by this procedure. After 50 generations the mutant strain still exhibited a lowered specific activity of pyruvate dehydrogenase (FIG. 26), showing that the modification was stably implemented into the genome and not subjected to reversion.

Impact on Growth and Production Characteristics

Down-regulation of PDH activity caused an increase of the lysine yield from 142 mmol $mol^{-1}$ in BS87 up to 165 mmol $mol^{-1}$ in *C. glutamicum* BS238, corresponding to an increase of 17%. Biomass formation was hardly affected by the modified enzyme activity (FIG. 27).

The specific growth rate of *C. glutamicum* BS238 ($\mu$=0.25 $h^{-1}$), however, was slightly reduced as compared to *C. glutamicum* BS87 ($\mu$=0.33 $h^{-1}$). The recombinant strain showed neither auxotrophy nor significant differences in by-product formation and only small amounts of trehalose were produced (<10 mmol $mol^{-1}$). The yields for lysine and biomass as well as the specific growth rate were constant throughout the whole cultivation showing that the strains were in metabolic steady-state. The observed differences between the two strains are therefore clearly attributed to the changed start codon sequence and thus reduced specific activity of pyruvate dehydrogenase.

Flux Response to Down-Regulation of Pyruvate Dehydrogenase

The changed physiology of the strain *C. glutamicum* BS238 as response to the reduced specific activity of pyruvate dehydrogenase also suggests changed fluxes around the pyruvate node. To study the impact of the modified enzyme activity on these metabolic pathways in more detail, PDH flux and net flux through pyruvate carboxylase were estimated in *C. glutamicum* BS238 and its parent strain. Here, a stoichiometric correlation between lysine yield, biomass yield and PDH flux obtained from 18 independent $^{13}$C labelling experiments with *C. glutamicum* served as basis of calculation (FIG. 13). This revealed a small but significant flux reduction trough the modified enzyme pyruvate dehydrogenase (Table 23). Together with the concomitant increase of the net flux through pyruvate carboxylase (Table 22) this results in a flux shift from PDH towards anaplerosis. The significance of the observed flux differences was validated by a t-test considering PDH flux and PYC flux (Table 22).

TABLE 22

Table 22: In vivo flux through pyruvate dehydrogenase ($n_{PDH}$) and lumped net flux through anabolic carboxylation ($n_{PYC}$) of glucose-grown *C. glutamicum* BS87 (parent) and *C. glutamicum* BS238 (aceE$^{att}$). The deviation reflects the 90% confidence interval, obtained by Monte-Carlo analysis.

| | *C. glutamicum* BS87 | *C. glutamicum* BS238 | t-value |
|---|---|---|---|
| $v_{PDH}$ [%] | 77.2 ± 1.0 | 76.0 ± 1.2 | 8.0 |
| $v_{PYC}$ [%] | 35.1 ± 0.5 | 36.6 ± 0.5 | −21.8 |

A central goal of rational metabolic engineering approaches, aiming at enhanced lysine production, is the identification and introduction of purely beneficial mutations which do not lead to undesired detrimental side effects (Ohnishi, et al., 2002). This promises superior cell factories without disturbed growth behaviour or impaired stress tolerance (Park and Lee, 2008). One realizes, however, that, in addition to the intended beneficial changes, many of these well-defined targeted modifications still result in disadvantageous side effects since the genetic changes applied are typically strong. A valid example is the recently described deletion of pyruvate dehydrogenase in lysine-producing *C. glutamicum* introducing increased by-product formation and the inability to grow on industrially relevant sugar based production media (Blombach, et al., 2007). This strongly evokes the demand for a more gradual pathway engineering which can balance the positive and negative effects. Beyond the previous work, the 60% attenuation of pyruvate dehydrogenase enhances lysine production, but still allows well balanced growth on industrially relevant sugars. Moreover, extensive by-product formation at the pyruvate node, as found for deletion mutants (Blombach, et al., 2007), can be completely avoided. Estimation of the metabolic fluxes around the pyruvate node revealed that the benefit of the reduced activity can clearly be attributed to a flux shift from pyruvate dehydrogenase towards anaplerotic carboxylation. The modified strain already exhibits an engineered precursor supply comprising an amplified pyruvate carboxylase expression as well as the key mutation P458S in the pyc gene. Both mutations have proven to increase lysine production through an enhanced anaplerotic carboxylation flux (Ohnishi, et al., 2002; Peters-Wendisch, et al., 2001). These modifications and the thus increased capacity of pyruvate carboxylase might contribute to the efficient flux redirection thereby improving lysine production. It is interesting to note, that the 60% decreased pyruvate dehydrogenase activity was achieved by the exchange of only one single nucleotide, i.e. the modification of the translational start codon. This method gives access to enzymes and pathways which are rather sensitive towards genetic perturbations and essential to maintain growth and viability.

Engineering of TCA Cycle

In addition to NADPH metabolism, precursor supply and lysine biosynthesis, the TCA cycle is a promising metabolic pathway for engineering of lysine production in *C. glutamicum* which is reflected in the observed correlation between lysine flux and TCA cycle flux (FIG. 12) (Wittmann and Becker, 2007; Wittmann and Heinzle, 2002). Genetic engineering aiming at a reduced carbon conversion by this pathway is, however, not trivial as the TCA cycle is essential for cell growth prohibiting total block by gene deletion. In this work, the expression of icd, encoding isocitrate dehydrogenase was rationally attenuated. In contrast to other organisms, the expression level of ICD in *C. glutamicum* is independent of either growth phase or growth conditions (Eikmanns, 2005). With a specific activity of around 1 U $mg^{-1}$ (Eikmanns, et al., 1995), ICD is the highest expressed TCA cycle enzyme and thus a promising candidate for down-regulation. This was realized here by start codon exchange of the encoding gene icd. The modification was implemented into the background of the lysine producer *C. glutamicum* BS87. Subsequently, the effect on enzyme activity, production characteristics and TCA cycle flux was investigated.

Strain Construction and Validation

In two homologous recombination events, the wild type allele of isocitrate dehydrogenase containing the ATG start codon was substituted by the mutant GTG-start-codon-allele. Screening was performed as describes above via determination of the specific enzyme activity of the up-growing clones from the second recombination event (FIG. 21). The subsequently performed sequence analysis of the clones with the drastically reduced specific ICD activity clearly identified these clones as carrier of the GTG start codon (FIG. 28).

Resolution of the complete sequence involved in the homologous recombination events ensured that no other mutations have occurred during the strain construction process. Sequence alignment here revealed 100% identity between the selected mutants and the parent strain BS87 over the complete span of 1000 bp with exception of the nucleotide exchange of the start codon. The observed decrease in enzyme activity was thus a direct consequence of the use of the rare start codon GTG.

Impact of Start Codon Exchange on Enzyme Activity

Subsequent to strain validation by sequencing, the specific ICD activity of the parent strain *C. glutamicum* BS87 and the start codon mutant *C. glutamicum* BS205 were compared during growth on fermentation medium. As shown in FIG. 28, usage of the rare start codon GTG instead of the common ATG resulted in a drastically reduced specific activity of isocitrate dehydrogenase. While the parent strain *C. glutamicum* BS87 exhibited a specific ICD activity of around 1.3 U $mg^{-1}$, in *C. glutamicum* BS205 it was only 0.3 U $mg^{-1}$.

The reduced activity of ICD in the strain *C. glutamicum* BS205 can clearly be attributed to the start codon exchange and thus reflects a translational attenuation of gene expression. In comparison to the wild type allele of icd, start codon recognition in the GTG mutant is impaired resulting in a disturbance of the translational initiation process involving mRNA binding to the ribosome (O'Donnell and Janssen, 2001; Vellanoweth and Rabinowitz, 1992). This significantly decreases the frequency of translation as well as mRNA stability, both leading to a reduced completion of a functionally active isocitrate dehydrogenase protein and thus decreased enzyme activity. As validated by long-term cultivation in serial batches, the modification and its effect on enzyme activity was stable (FIG. 29) which is a crucial prerequisite with regard to industrial application.

Effect on Growth and Production Characteristics

To investigate the impact of the changed enzyme activities on production characteristics, cultivation experiments were performed to compare growth, lysine production and biomass formation of the different strains during growth in the modified minimal medium. By down-regulation of ICD, the lysine yield during growth on glucose was increased from 141 mmol $mol^{-1}$ in BS87 up to 200 mmol $mol^{-1}$ in *C. glutamicum* BS205, corresponding to an increase of 42%. Biomass formation was hardly effected (Table 23). Specific growth rate, however, was reduced in the mutant strain. Whereas the parent strain BS87 grew with a specific rate of 0.32 $h^{-1}$, BS205 exhibited a specific growth rate of 0.28 $h^{-1}$.

TABLE 23

Production characteristics of lysine-producing *C. glutamicum* BS87 and *C. glutamicum* BS205 ($icd^{att}$) during growth on glucose. The data given are biomass yield ($Y_{X/S}$) and lysine yield ($Y_{Lys/S}$). Yields were determined from three biological replicates as slope of the linear best fit when plotting product formation against substrate consumption (FIG. 30).

| | $Y_{Lys/S}$ [mmol $mol^{-1}$] | $Y_{X/S}$ [g $mol^{-1}$] |
|---|---|---|
| *C. glutamicum* BS87 | 141.3 ± 3.5 | 72.6 ± 2.0 |
| *C. glutamicum* BS205 | 200.4 ± 4.4 | 68.4 ± 2.5 |

Sufficient oxygen supply avoided formation of by-products induced by oxygen deprivation (Inui, et al., 2004). Only small amounts of trehalose (<10 mmol $mol^{-1}$) were produced in both strains. The yields for lysine and biomass as well as the specific growth rate were constant throughout the whole cultivation showing that the strains were in metabolic steady-state (FIG. 30). The observed differences between the two strains are therefore clearly attributed to the changed start codon sequence and thus reduced specific activity of isocitrate dehydrogenase.

Metabolic Flux Response to Down-Regulation of icd

The data from determination of enzyme activity and the comparative cultivation experiments clearly showed that the use of the rare start codon GTG instead of ATG significantly changed the cellular physiology of the strain. To study the impact of the modified enzyme activity on the metabolic pathways in more detail, the flux through TCA cycle and net flux through pyruvate carboxylase was estimated in *C. glutamicum* BS87 and *C. glutamicum* BS205. To this end, a stoichiometric correlation between lysine yield, biomass yield and TCA cycle flux was established (FIG. 12). The entry flux through citrate synthase was reduced in the icd mutant with a concomitant increase of the net flux through pyruvate carboxylase (FIG. 31). The performed t-test clearly revealed a significant difference between the strains considering the TCA cycle flux (t=−10.1) and PYC flux (t=43.6), respectively. In a sum, these flux changes resulted in a flux redirection from TCA cycle towards anaplerosis.

As already assumed for PDHattenuation, the flux shift towards anaplerotic carboxylation is likely to be supported by the modified pyruvate carboxylase. The here achieved improvement of the lysine yield of 40% is significantly higher than the increase resulting from start codon exchange in the aceE gene. This might reflect the overall achieved decrease in enzyme activity, which was with 70% clearly most pronounced for the icd gene. Despite the benefit of the reduced enzyme activity for lysine production, the modification does not severely impair growth or carbon conversion by the concerned pathways thereby manifesting in by-product formation. The remaining high ICD activity of 300 mU $mg^{-1}$ in the start codon mutant leaves room for continuing optimization by further down-regulation. The lack of any by-product formation as result of the induced bottleneck within the TCA cycles suggests that the metabolic network around the pyruvate node of *C. glutamicum* BS205 had the capacity to meet an even stricter attenuation. One possible strategy could be the implementation of the rarest start codon variant TTG. Beyond the present study, targeted down-regulation of the TCA cycle seems also promising for various other products since the high carbon loss through $CO_2$ formation by the TCA cycle is generally undesired with respect to carbon yield for the desired product. Obvious products in this regard are other amino acids of the aspartate family or the production of diaminopentane which is directly formed from lysine by decarboxylation. The same also holds for attenuation of pyruvate dehydrogenase, described above.

Construction of a Tailor-Made Lysine Hyper-Producer

In the previous chapters, different strategies were successfully employed to rationally optimize lysine production by *C. glutamicum*. Exemplified for the parent strains *C. glutamicum* BS1 and *C. glutamicum* BS87, the benefit of several targets from the key pathways of lysine biosynthesis, NADPH metabolism, precursor supply and $CO_2$ formation were investigated. With the aim to create a wild type based hyper-producer as attractive strain for industrial production, the identified modifications were now combined in a single strain. This work was based on the wild type *C. glutamicum* ATCC 13032 to implement only beneficial modifications and to minimize any detrimental side effect, appearing in industrial production strains.

Strain Construction and Production Performance

The first step towards creation of the hyper-producer was release of aspartate kinase from feedback inhibition by lysine and threonine, introducing the amino acid exchange T311I (Becker, et al., 2005). This was complemented by the above described overexpression of ddh. Sole implementation of these two modifications and additional medium optimization created a lysine producer which already produced 125 mmol lysine (mol glucose)$^{-1}$. To avoid further bottlenecks within the biosynthetic pathway of lysine, dihydrodipicolinate reductase (dapB), aspartate kinase (lysC) and diaminopimelate decarboxylase (lysA) were over expressed in addition to ddh. These enzymes are all part of the common route for lysine biosynthesis. The effect on lysine production should thus be independent of the flux partitioning between the succinylase and the dehydrogenase branch. Further strain optimization was carried out by implementation of several genetic modifications which have already proven valuable in recent years. This comprised replacement of the natural homoserine dehydrogenase by a mutant variant exhibiting the amino acid exchange V59A. This mutation improves lysine production by reducing the carbon flux towards the threonine pathway, which directly competes with lysine biosynthesis (Ohnishi, et al., 2002). To ensure sufficient supply of oxaloacetate for lysine formation, additional modifications focussed on the precursor supply. These implied overexpression and modification of the major anaplerotic enzyme pyruvate carboxylase (Ohnishi, et al., 2002; Peters-Wendisch, et al., 2001) and deletion of the OAA-consuming reaction PEP carboxykinase (Petersen, et al., 2001). The resulting strain *C. glutamicum* BS87 thus comprised 9 modifications within the lysine biosynthesis and the precursor supply (FIG. 32).

From the comparison with its early ancestor strain *C. glutamicum* BS222, only exhibiting the regulatory point mutation in the lysC gene and a second copy of the ddh gene, it becomes obvious, that the additional modifications in *C. glutamicum* BS87 only provide a minor improvement of lysine production (FIG. 18). An engineering strategy that is solely focussed on a specific part of the metabolism is consequently not suitable to create an efficient production strain. The history of strain optimization towards improved lysine production by metabolic engineering, however, is clearly marked by this strategy. The key pathways TCA cycle and NADPH metabolism as major reactions in the concept of an optimized lysine producer were so far almost neglected. In this regard, the present work exposed genetic targets that perfectly complemented with previous strategies to overcome these limitations thereby advancing to the construction of a superior production strain. The next step towards creation of the intended hyper-producer was therefore focussed on the TCA cycle. As described above, attenuation of isocitrate dehydrogenase ($icd^{att}$) in the background of *C. glutamicum* BS87 significantly improved lysine production by efficient flux redirection from TCA cycle towards anaplerotic carboxylation. With regard to lysine production this engineering strategy benefits from an increased supply of oxaloacetate as well as a reduced carbon loss via $CO_2$-formation. Subsequent engineering of the NADPH metabolism was performed via two different strategies. Initially, the gluco-neogenetic enzyme fructose 1,6-bisphosphatase was over expressed, which was previously shown to significantly contribute to an improved NADPH supply (Becker, et al., 2005). As demonstrated above, this approach nicely complements with amplified expression of glucose 6-phosphate dehydrogenase. To circumvent further limitations in the PPP by a limited capacity of transketolase and transaldolase right from the beginning, overexpression of G6PDH was realized concomitantly with overexpression of transketolase and transaldolase by up-regulation of the complete tkt-operon via the sod promoter as described above. In response to the promoter exchange, the specific activity of G6PDH, transketolase and transaldolase was significantly increased. The concept of the engineering strategy is illustrated in FIG. 32. The benefit of the modifications becomes obvious from the comparison of the carbon conversion yield of the obtained genealogy (FIG. 18).

Starting with wild type *C. glutamicum* ATCC 13032, subsequent implementation of the beneficial modifications resulted in a wild type based lysine hyper-producer. The present work is the first report of such a complete rational strain in which all relevant pathways were considered. Of major importance was the initially introduced modification within aspartate kinase to overcome the feedback inhibition of this key regulatory enzyme. The significant benefit of almost 50% improvement resulting from ddh overexpression clearly revealed, that the overall capacity of the lysine biosynthetic pathway in the genetic background of *C. glutamicum* BS1 ($lysC^{T311I}$) strongly limited lysine production. Further modification of the lysine pathway, however, as well as engineering of the precursor supply, which was described as beneficial in previous studies (Ohnishi, et al., 2002; Peters-Wendisch, et al., 2001; Petersen, et al., 2001), was here only of moderate success. This explicitly indicates that other bottlenecks arose within the central metabolism of *C. glutamicum* that impair lysine production. In the present study, the interest towards further engineering of lysine production was thus shifted to other parts of the intermediary metabolism. The success of this concept was immediately reflected by the response to attenuation of isocitrate dehydrogenase ($icd^{att}$). Implementation of a single nucleotide exchange in the start codon of icd increased the lysine yield from 141 mmol $mol^{-1}$ in *C. glutamicum* BS87 up to 200 mmol $mol^{-1}$ in the corresponding icd mutant representing an increase of 40%. Subsequent overexpression of fructose 1,6-bisphosphatase, previously shown to result in efficient flux redirection towards the NADPH providing PPP (Becker, et al., 2005), further enhanced lysine production by 18% (FIG. 18). The finally introduced modification in the here described genealogy comprised promoter exchange of the tkt-operon. This significantly increased the activity of the enzymes G6PDH, TKT and TAL encoded by this operon which in turn resulted in a 13% improved lysine yield. The benefit from overexpression of fbp and the tkt-operon clearly shows that insufficient supply of NADPH strongly limits lysine production in *C. glutamicum* and that engineering strategies aiming at an increased PPP flux are essential with the aim to create an efficient lysine hyper-producing strain. An additional benefit of amplified expression of the pentose phosphate pathway genes was observed concerning the growth behaviour. As compared to its ancestor *C. glutamicum* BS242 ($P_{eftu}$fbp), exhibiting a specific growth rate of 0.23 $h^{-1}$, the tkt-mutant grew with a rate of 0.32 $h^{-1}$. The higher carbon conversion yield $Y_{Lys/S}$ (=26%) in combination with the improved growth behaviour of *C. glutamicum* BS244 increased the overall production performance of this strain, as it allows efficient lysine production in shortened fermentation times. By implementation of the last three modifications, an overall improvement of lysine production of almost 90% was achieved. This is a remarkable and also surprising profit resulting from only three genetic changes. It can thus be assumed, that these engineering strategies partly benefit from previously implemented mutations, e.g. removal of bottlenecks within lysine biosynthesis.

The production characteristics of the investigated strains were so far tested in shake flask cultivations for exponentially growing cells in minimal medium. Under these conditions the best producer *C. glutamicum* BS244 already exhibited a remarkable lysine yield of 26%, although the experimental set-up, comprising shake flask cultivation in minimal medium at low substrate concentrations, certainly limits its productivity. It was thus relevant to investigate the production performance of the lysine hyper-producer in a fed-batch fermentation process on an industrially relevant production medium as this cultivation strategy is most close to industrial production. Moreover, it allows a more realistic evaluation of the potential of the novel hyper-producer, especially in comparison with classically derived production strains. The best producer *C. glutamicum* BS244($P_{sod}$tkt) was investigated under industrial conditions comprising fed-batch fermentation on a molasses based complex medium.

Production Performance under Industrial Fermentation Conditions

The cultivation profile of the fed-batch fermentation of *C. glutamicum* BS244 is displayed in FIG. 19. Lysine production started early on and the lysine concentration in the culture supernatant continuously increased within 30 h up to a surprisingly high final titre of 120 g $L^{-1}$. The major increase was mainly achieved during the feeding phase, which was initiated after the initial sugar supplied in the batch medium (100 g $L^{-1}$) was consumed. As signal for automated feeding, a dissolved oxygen ($pO_2$) based signal was used during the process. The $O_2$ saturation in the fermenter was controlled via the stirrer velocity and kept constant at 20%. Carbon limitation in the medium resulted in an immediate and fast increase of the $pO_2$ which activated the feeding pump when the $pO_2$ increase exceeded 10% $min^{-1}$. The feeding solution, based on molasses and glucose, was additionally enriched with ammonium sulphate to ensure sufficient ammonium supply for lysine production. By this strategy the sugar concentration in the feeding phase was maintained at a concentration below 10 g $L^{-1}$.

The time course of biomass concentration, reflected by the optical density, was clearly different from lysine concentration (FIG. 34). During the batch phase, the optical density increased by a factor of five, whereas in the feeding phase only a threefold enhancement was observed. Moreover, biomass concentration did not increase until the end of the cultivation period but reached a maximum after 24 h.

A closer inspection of the production characteristics of the strain *C. glutamicum* BS244 revealed that the fermentation process can be further divided. As displayed in FIG. 35, the different phases can be distinguished on basis of the achieved lysine yield. In the best production phase, here designated as feed-phase 2, the lysine hyper-producer exhibited a lysine yield of 55%. A further characteristic of this phase is the almost stagnating biomass concentration. The consumed sugar is thus, efficiently channeled towards the lysine biosynthetic pathway. In the beginning of the fermentation process, the lysine yield was lower. This interval comprising batch phase and feed-phase 1 can clearly be described as major growth phase, characterized by extensive biomass formation (FIG. 34). Interestingly, in this phase a lysine yield of 25% was achieved which corresponds very well with the lysine yield achieved in shake flask cultivation experiments during the exponential growth phase.

The lysine hyper-producer created in this work is the best wild type based production strain so far described. Considering the final lysine titre as well as carbon and space-time yield it is clearly superior to previously described rationally created strains (Ikeda, et al., 2006). With a final lysine titre of 120 g $L^{-1}$ and a carbon conversion yield of up to 55% this strain even exhibits production characteristics that lie at the maximum limit of classically derived strains with reported carbon yields of 40-50% (Leuchtenberger, et al., 2005) and lysine titers of 80-120 g $L^{-1}$ (Anastassiadis, 2007). This production performance of the classical producers is, however, typically linked to long fermentation times up to 100 h (Anastassiadis, 2007), which significantly impairs the space-time yield. This is in general related to poor growth caused by numerous detrimental secondary mutations that accumulated during strain development due to the unspecific mutagenesis. By sole implementation of an exclusive set of only 12 beneficial modifications, these undesired side effects could be avoided in the wild type based production strain. The fast growth and thus shortened fermentation time of only 30 h results in a remarkable high space-time yield of 4 g $L^{-1}$ $h^{-1}$ which is considerably higher than the space-time yield of 2.1 g $L^{-1}$ $h^{4}$ achieved during fed-batch fermentation by classical producers (Hirao, et al., 1989).

The wild type based lysine hyper-producer of the present invention demonstrates the potential of systems metabolic engineering as method for strain optimization. The strain *C. glutamicum* BS244 is an excellent proof of concept and proof of value of a complete rational production strain which is highly attractive for industrial application.

Sequence Listing Free Text

| SEQ ID NO: | Description |
|---|---|
| 1 | lysC, DNA sequence encoding *C. glutamicum* aspartate kinase with natural promoter |
| 2 | LysC, amino acid sequence of *C. glutamicum* aspartate kinase |
| 3 | tys$C^{T3111}$ DNA sequence encoding *C. glutamicum* aspartate kinase with T3111-substitution, sod-promoter and start codon exchange GTG → ATG |
| 4 | Lys$C^{T3111}$ amino acid sequence of *C. glutamicum* aspartate kinase with T3111-substitution |
| 5 | ddh, DNA sequence encoding *C. glutamicum* diaminopimelate dehydrogenase with natural promoter |
| 6 | Ddh, amino acid sequence of *C. glutamicum* diaminopimelate dehydrogenase |
| 7 | ddh DNA, two copies encoding *C. glutamicum* diaminopimelate dehydrogenase including flanking regions |
| 8 | pck, DNA sequence encoding wildtype *C. glutamicum* PEP-carboxykinase |
| 9 | Pck, amino acid sequence of *C. glutamicum* PEP-carboxykinase |
| 10 | pck, DNA sequence encoding *C. glutamicum* PEP-carboxykinase with deletion of 927 bp, nucleotides 510 to 1436 of wildtype PEP-carboxykinase and artificially introduced nucleotides at positions 510 to 531 |
| 11 | Pck, amino acid sequence encoded by SEQ ID NO: 10 |

-continued

Sequence Listing Free Text

| SEQ ID NO: | Description |
|---|---|
| 12 | dapB, DNA sequence encoding wildtype *C. glutamicum* dihydrodipicolinate reductase with natural promoter |
| 13 | DapB, amino acid sequence of *C. glutamicum* dihydrodipicolinate reductase dapB, DNA sequence encoding *C. glutamicum* dihydrodipicolinate reductase |
| 14 | dapB-DNA sequence with sod-promoter instead natural promoter of *C. glutamicum* |
| 15 | Gene cluster encoding wildtype argS (arginyl-tRNA-synthetase) and lysA (diaminopimelate decarboxylase) including natural promoter sequence |
| 16 | Two recombinantly joined copies of DNA sequences of argS and lysA including flanking regions |
| 17 | LysA, amino acid sequence of *C. glutamicum* diaminopimelate decarboxylase |
| 18 | hom, DNA sequence encoding wildtype *C. glutamicum* homoserine dehydrogenase |
| 19 | Hom, amino acid sequence of *C. glutamicum* homoserine dehydrogenase |
| 20 | $hom^{V59A}$, DNA sequence sequence encoding *C. glutamicum* homoserine dehydrogenase with V59A substitution |
| 21 | $Hom^{V59A}$, amino acid of *C. glutamicum* homoserine dehydrogenase with V59A substitution |
| 22 | pyc, DNA sequence encoding wildtype *C. glutamicum* pyruvate carboxylase with natural promoter |
| 23 | Pyc, amino acid sequence of *C. glutamicum* pyruvate carboxylase |
| 24 | $pyc^{P458S}$, DNA sequence encoding *C. glutamicum* pyruvate carboxylase with P458S substitution and sod-promoter |
| 25 | $Pyc^{P458S}$ amino acid sequence of *C. glutamicum* pyruvate carboxylase with P458S substitution |
| 26 | icd, DNA sequence encoding wildtype *C. glutamicum* isocitrate dehydrogenase including 150 by of upstream sequence |
| 27 | Icd, amino acid sequence of *C. glutamicum* isocitrate dehydrogenase |
| 28 | $icd^{A1G}$, DNA sequence encoding *C. glutamicum* isocitrate dehydrogenase with substitution ATG → GTG including 150 by of upstream sequence |
| 29 | fbp, DNA sequence encoding wildtype *C. glutamicum* fructose 1,6-bisphosphatase with natural promoter |
| 30 | Fbp, amino acid sequence of *C. glutamicum* fructose 1,6-bisphosphatase |
| 31 | fbp, DNA sequence with eftu (elongation factor Tu)-promoter |
| 32 | tkt-operon, DNA sequence encoding wildtype *C. glutamicum* transketolase operon |
| 33 | Tkt, amino acid sequence of *C. glutamicum* transketolase |
| 34 | tkt-operon with sod-promoter |
| 35 | CCGCTCGAGCCATTGAATCGTGCTGAGAG (P1) |
| 36 | CAGGTGAAGATGATGTCGGTGG (P2) |
| 37 | CCACCGACATCATCTTCACCTG (P3) |
| 38 | CTAGACTAGTGAAACGAACAGTGTCAGCTG (P4) |
| 39 | ATTATTTGAATTCTGAACGGCAACGGATCAAAA (P5) |
| 40 | ATTATTTTCTAGATTCCTCTTGGTCCAGCGAAG (P6) |
| 41 | ATTATTTTCTAGATGAACGGCAACGGATCAAAAA (P7) |
| 42 | ATTATTTGTCGACTTCCTCTTGGTCCAGCGAAG (P8) |
| 43 | GTTCGTTGATGGATCCCAGGC (P9) |

-continued

| Sequence Listing Free Text | |
|---|---|
| SEQ ID NO: | Description |
| 44 | CCCATCCACTAAACTTAAACATTGTCCAGCGCTTCAATACCC (P10) |
| 45 | TGTTTAAGTTTAGTGGATGGGGCAGAACTGGATTGACATGGG (P11) |
| 46 | GGCCGGATCCTTAAGCGTGAGCTGCTGAAAT (P12) |
| 47 | TAGCTGCCAATTATTCCGGG (P13) |
| 48 | GAACGCCAACCTTGATTCCCATGGGTAAAAAATCCTTTCGTA (P14) |
| 49 | TACGAAAGGATTTTTTACCCATGGGAATCAAGGTTGGCGTTC (P15) |
| 50 | CGCGGATCCTCTGACCCTGGGTGCCAAAG (P16) |
| 51 | GCGGCAAAGCAGTGGGGGAAGGGG (P17) |
| 52 | CCCGGAATAATTGGCAGCTATATGCTCCTTCATTTT (P18) |
| 53 | ATTATTTGGATCCGAGGCTGCACTGCAACGAGGT (P19) |
| 54 | CATCGCCGAATTCGGTGGTGGAA (P20) |
| 55 | TCCACCGAATTCGGCGATGA (P21) |
| 56 | CGGAAATCGTCCTCGTCGACTAC (P22) |
| 57 | CACTGTTCGTAGTCGACGAGGAC (P23) |
| 58 | ATTATTTTCTAGAGAAACCCAAAACCGCCCTCC (P24) |
| 59 | ATTATTTTCTAGAGAGGCTGCACTGCAACGAGGT (P25) |
| 60 | ATTATTTAGCTTGAAACCCAAAACCGCCCTCC (P26) |
| 61 | TAGCTGCCAATTATTCCGGG (P27) |
| 62 | TTCTGTACGACCAGGGCCATGGGTAAAAAATCCTTTCGTAGG (P28) |
| 63 | CCTACGAAAGGATTTTTTACCCATGCiCCCTGGTCCiTACAGAA (P29) |
| 64 | TCTACGTCGACACACCCTGGAAACCAGCAAC (P30) |
| 65 | CGCGGATCCTCGAATATCAATATATGGTC (P31) |
| 66 | CCGGAATAATTGGCAGCTAAGTAGGGTTGAAGGGCAT (P32) |
| 67 | AGGGGAACTTGATCAGAGGAATACACCA (P33) |
| 68 | GATATCAGAAGCAGCAATGCC (P34) |
| 69 | GGCATTGCTGCTTCTGATATC (P35) |
| 70 | GTGCATCATCATCGCGCTCTTCCTGTCG (P36) |
| 71 | AATCAACGCGTCAGCATATTGAAGTGCAGATCC (P37) |
| 72 | AGGAGGTGCGGGTGATCGGCAATGAATC (P38) |
| 73 | GATTCATTGCCGATCACCCGCACCTCCT (P39) |
| 74 | ATCTACGTCGACGGTAGTAATCCAGGGTGTAGAG (P40) |
| 75 | TAGCTGCCAATTATTCCGGG (P41) |
| 76 | ATGTGTGAGTCGACACGGGTAAAAAATCCTTTC (P42) |
| 77 | GAAAGGATTTTTTACCCGTGTCGACTCACACAT (P43) |
| 78 | GAGTACACGCGTCAAAGATGGGGTAAGTCTGG (P44) |
| 79 | GAGTACCTCGAGGCTGTGGCAGTGACCAACCG (P45) |
| 80 | GGAATAATTGGCAGCTATAGAGTAATTATTCCTTTCAACAAGAGACC (P46) |

-continued

| Sequence Listing Free Text | |
|---|---|
| SEQ ID NO: | Description |
| 81 | GAGTACCTCGAGCGAAGACCTCGCAGATTCCG (P47) |
| 82 | GAGACTCGTGGCTAAGATCATCTG (P48) |
| 83 | CAGATGATCTTAGCCACGAGTCTC (P49) |
| 84 | CATGAGACGCGTGGAATCTGCAGACCACTCGC (P50) |
| 85 | TGGCCGTTACCCTGCGAATG (P51) |
| 86 | TGTATGTCCTCCTGGACTTC (P52) |
| 87 | GAAGTCCAGGAGGACATACAATGAACCTAAAGAACCCCGA (P53) |
| 88 | ATCTACGTCGACCCAGGATGCCCTGGATTTC (P54) |
| 89 | TATCAACGCGTTCTTCATCGGTAGCAGCACC (P55) |
| 90 | CATTCGCAGGGTAACGGCCACTGAAGGGCCTCCTGGG (P56) |
| 91 | CCGGG (P57) |
| 92 | GGGTAAAAAATCCTTTCGTAG (P58) |
| 93 | TACGAAAGGATTTTTTACCCTTGACCACCTTGACGCTGTC (P59) |
| 94 | ATCTACGTCGACCCATCAGAAGCAATGACTGTAG (P60) |
| 95 | ATCAACGCGTCGGCAAATTAGTCGAATGAAG (P61) |
| 96 | CCCGGAATAATTGGCAGCTATCCTTCCTGGGTTAAAC (P62) |

DEFINITIONS

Abbreviations

2-OXO 2-Oxoglutarate
AA Amino acid
Ac-CoA Acetyl-Coenzyme A
Ace Acetate
aceE Gene, encoding subunit one of pyruvate dehydrogenase complex
ADP Adenosine diphosphate
amtR Gene, encoding the global nitrogen regulator
amyA Gene, encoding α-amylase
ara Gene cluster for arabinose utilization
asd Gene, encoding aspartate semialdehyde dehydrogenase
argS Gene, encoding arginyl-tRNA-synthetase
ATCC American type culture collection
ATP Adenosine triphosphate
BamH1 Restriction enzyme from *Bacillus amyloli*
bp Base pair(s)
BSA Bovine serum albumin
BSTFA N,O-Bis(trimethylsilyl)trifluor-acetamid
CDM Cell dry mass
CIT Citrate
CoA Coenzyme A
CWW Cell wet weight
dapA Gene, encoding dihydrodipicolinate synthase
dapB Gene, encoding dihydrodipicolinate reductase
dapC Gene, encoding Succinyl-amino-ketopimelate transaminase
dapD Gene, encoding tetrahydrodipicolinate succinylase
dapE Gene, encoding succinyl-diaminopimelate desuccinylase
dapF Gene, encoding diaminopimelate epimerase
ddh Gene, encoding diaminopimelate dehydrogenase
DDH Diaminopimelate dehydrogenase
DHA Dihydroxyacetone
DHAP Dihydroxyacetone phosphate
DMSO Dimethyl sulfoxide
DNase Deoxyribonuclease
DTT Dithiothreitol
E4P Erythrose 4-phosphate
eftu Gene, encoding elongation factor tu
F1P Fructose 1-phosphate
F6P Fructose 6-phosphate
FBP Fructose 1,6-bisphosphate
fbp Gene, encoding fructose 1,6-bisphosphatase
FBPase Fructose 1,6-bisphosphatase
fbr Feedback resistant
Fru Fructose
G6P Glucose 6-phosphate
G6PDH Glucose 6-phosphate dehydrogenase
GAP Glyceraldehyde 3-phosphate
GC-MS Gas chromatography/Mass spectrometry
GDH Glycerophosphate dehydrogenase
Glu Glucose
gltA Gene, encoding citrate synthase
Gly Glycerol
GRAS Generally regarded as save
hom Gene, encoding homoserine dehydrogenase
HPLC High performance liquid chromatography
icd Gene, encoding isocitrate dehydrogenase
ICD Isocitrate dehydrogenase
Kan Kanamycin
Lac Lactate
LDH Lactate dehydrogenase Lys Lysine
lysA Gene, encoding diaminopimelate decarboxylase
lysC Gene, encoding aspartate kinase (aspartokinase)
lysE Gene, encoding lysine permease
malE Gene, encoding malic enzyme
MalE Malic enzyme
MHDSTFA N-Methyl-N-tert-butyldimethylsilyl-trifluoracetamide
MCS Multiple cloning site
MDV Mass distribution vector
MDH Cytoplasmatic malate dehydrogenase
MFA Metabolic flux analysis
MQO Membrane-bound malate dehydrogenase
NAD/NADH Nicotinamide adenine dinucleotide ox/red
NADP/NADPH Nicotinamide adenine dinucleotide phosphate ox/red
OAA Oxaloacetate
OD Optical density
ODHC 2-oxoglutarate dehydrogenase complex
OPA ortho-Phthaldialdehyde
opcA Gene, encoding putative subunit of G6PDH
ORF Open reading frame
OR1 Origin of replication
PC Pyruvate carboxylase
pyc Gene, encoding pyruvate carboxylase
pck Gene, encoding PEP carboxykinase
PCR Polymerase chain reaction
PDH Pyruvate dehydrogenase complex
PEP Phosphoenolpyruvate
PEPC Phosphoenolpyruvate carboxylase
PEPCK Phosphoenolpyruvate carboxykinase
pgi Gene, encoding phosphoglucoisomerase
PGI Phosphoglucoisomerase
PPP Pentose phosphate pathway
PTS Phosphotransferase system
Pwo DNA polymerase from *Pyrococcus woesei*
pvk Gene, encoding pyruvate kinase
Pyr Pyruvate
R5P Ribose 5-phosphate
RNase Ribonuclease
RPE Ribulose 5-phosphate epimerase
RPI Ribose 5-phosphate isomerase
RQ Respiratory quotient
S7P Sedoheptulose 7-phosphate
sacB Gene, encoding levansucrase of *Bacillus subtilis*
SAP Shrimp alkaline phosphatase
sod Gene, encoding superoxide dismutase
Suc Sucrose
SUC Succinate
tal Gene, encoding transaldolase
TAL Transaldolase
Taq DNA polymerase from *Thermus aquaticus*
TCA cycle Tricarboxylic acid cycle
Tet Tetracycline
tkt Gene, encoding transketolase/transketolase operon
TKT Transketolase
TP1 Triosephosphate isomerase
TPP Thiamine pyrophosphate
SLS Sum of least squares
Tre Trehalose
rpm Rotations per minute
XhoI Restriction enzyme from *Xanthomonas holcicola*
xyl Gene cluster for xylose utilization Symbols

| | | |
|---|---|---|
| C | Capacity | [F] |
| c | Concentration | [mol $L^{-1}$] or [g $L^{-1}$] |
| m | Mass | [g] |
| μ | Specific growth rate | [$h^{-1}$] |
| n | Amount of substance | [mol] |
| $q_S$ | Specific uptake rate | [mmol $g^{-1}$ $h^{-1}$] |
| $q_P$ | Specific production rate | [mmol $g^{-1}$ $h^{-1}$] |
| R | Resistance | [Ω] |
| T | Temperature | [° C.] |
| t | Time | [h] |
| U | Unit | [μmol $min^{-1}$] |
| ν | Flux | [%] |
| λ | Wave length | [nm] |
| $Y_{P/S}$ | Product yield | [mol $mol^{-1}$] |
| $Y_{X/S}$ | Biomass yield | [g $mol^{-1}$] |

LITERATURE REFERENCES

Al Zaid Siddiquee, K., et al. (2004) *Appl Microbiol Biotechnol* 63, 407-17.
Amidon, T. E. and Liu, S. (2009). *Biotechnol Adv* 27, 542-50.
Anastassiadis, S. (2007). *Recent Pat Biotechnol* 1, 11-24.
Aristidou, A. and Penttila, M. (2000). *Curr Opin Biotechnol* 11, 187-98.
Bailey, J. E. (1991). *Science* 252, 1668-75.
Bathe, B., et al. (1996). *Mol Gen Genet* 252, 255-65.
Becker, J., et al. (2005). *Appl Environ Microbiol* Vol. 71, 8587 8596.
Bellmann, A., et al. (2001). *Microbiology* 147, 1765-74.
Bendt, A. K., et al. (2003). *Proteomics* 3, 1637-46.
Bergmeyer, H. U. and Hohorst, H.-J. (1970). *Methoden der enzymatischen Analyse,* 2 edn. Chemie GmbH Weinheim.
Bernofsky, C. and Swan, M. (1973) *Anal Biochem* 53, 452-8.
Blombach, B., et al. (2007). *Appl Microbiol Biotechnol* 76, 615-23.
Bolten, C. J., et al. (2007). *Anal Chem* 79, 3843-9.
Bonnassie, S., et al., (1990). *Nucleic Acids Res* 18, 6421.
Borner, J., et al. (2007). *Anal Biochem* 367, 143-51.
Bradford, M. M. (1976). *Anal Biochem* 72, 248-54.
Buchinger, S., et al. (2009). *J Biotechnol* 140, 68-74.
Chen, R. and Yang, H. (2000). *Arch Biochem Biophys* 383, 238-45.
Chen, Z., et al. (1998), *Anal Biochem* 259, 203-11.
Christensen, B. and Nielsen, J. (2000) *Adv Biochem Eng Biotechnol* 66, 209-31.
Christensen, B., et al. (2000). *Appl Microbiol Biotechnol* 54, 212-7.
Cocaign-Bousquet, M. and Lindley, N. D. (1995). *Enzyme Microb Technol* 17, 260-267.
Cremer, J., et al. (1991). *Appl Environ Microbiol* 57 (6), 1746-1752.
Cremer, J., et al. (1988). *J Gen Microbiol* 134 (Pt 12), 3221-9.
de Graaf, A. A. (2000). in Schugerl, K. and Bellgard, K. H. (Eds), *Bioreaction Engineering*, Springer Verlag, pp. 506-555.
de Graaf, A. A., et al. (2000). *J Biotechnol* 77, 25-35.
Diesterhaft, M. D. and Freese, E. (1973). *J Biol Chem* 248, 6062-70.
Dominguez, H. and Lindley, N. D. (1996). *Appl Environ Microbiol* 62 (10), 3878-3880.
Dominguez, H., et al. (1998). *Eur J Biochem* 254, 96-102.
Drysch, A., et al. (2003). *Metab Eng* 5, 96-107.
Drysch, A., et al. (2004). *Biotechnol Bioeng* 85, 497-505.
Eggeling, L. and Bott, M. (2005). *Handbook of Corynebacterium glutamicum*. CRC Press.

Eggeling, L., et al. (1998). *Appl Microbiol Biotechnol* 49, 24-30.

Eikmanns, B. J. (2005). in Eggeling, L. and Bott, M. (Eds), *Handbook of Corynebacterium glutamicum*, CRC Press, pp. 241-276.

Eikmanns, B. J., et al. (1993). *Antonie Van Leeuwenhoek* 64, 145-63.

Eikmanns, B. J., et al. (1989). *Mol Gen Genet* 218, 330-9.

Eikmanns, B. J., et al. (1995). *J Bacteriol* 177, 774-82.

El Massaoudi, et al. (2003). *Metab Eng* 5, 86-95.

Emmerling, M., et al. (2002). *J Bacteriol* 184, 152-64.

Fischer, E., et al. (2004). *Anal Biochem* 325, 308-16.

Frick, O. and Wittmann, C. (2005). *Microb Cell Fact* 4, 30.

Fry, B., et al. (2000). *Appl Environ Microbiol* 66, 4045-9.

Gardner, P. R. and Fridovich, I. (1993). *J Biol Chem* 268, 12958-63.

Geen, H. and Freeman, R. (1991). *J. Magn. Reson.* 93, 93-141.

Georgi, T., et al. (2005). *Metab Eng* 7, 291-301.

Gerstmeir, R., et al. (2004). *J Bacteriol* 186, 2798-809.

Glanemann, C., et al. (2003). *Appl Microbiol Biotechnol* 61, 61-8.

Goodfellow, M., et al. (1976). *J Gen Microbiol* 96, 351-8.

Gourdon, P., et al. (2000). *Appl Environ Microbiol* 66, 2981-7.

Gubler, M., et al. (1994). *Appl Environ Microbiol* 60, 2494-500.

Guest, J. R. and Creaghan, I. T. (1974). *J Gen Microbiol* 81, 237-45.

Haberhauer, G., et al. (2001). *Corynebacterium glutamicum* genes encoding proteins involved in membrane synthesis and membrane transport.

Hartmann, M., et al. (2003). *J Biotechnol* 104, 199-211.

Hayashi, M., et al. (2002). *Biosci Biotechnol Biochem* 66, 1337-44.

Hayashi, M., et al. (2006). *Biosci Biotechnol Biochem* 70, 546-50.

Hermann, T., et al. (2000). *TElectrophoresis* 21, 654-9.

Hirao, T., et al. (1989). *Appl Microbiol Biotechnol* 32, 269-273.

Holatko, J., et al. (2009). *J Biotechnol* 139, 203-10.

Hua, Q., et al. (2000). *J Biosci Bioeng* 90, 184-92.

Ihnen, E. D. and Demain, A. L. (1969). *J Bacteriol* 98, 1151-8.

Ikeda, M. (2003). *Adv Biochem Eng Biotechnol* 79, 1-35.

Ikeda, M. and Katsumata, R. (1992). *Appl Environ Microbiol* 58, 781-785.

Ikeda, M. and Katsumata, R. (1999). *Appl Environ Microbiol* 65, 2497-502.

Ikeda, M. and Nakagawa, S. (2003). *Appl Microbiol Biotechnol* 62, 99-109.

Ikeda, M., et al. (1994). *Biosci Biotechnol Biochem* 58, 674-8.

Ikeda, M., et al. (2006). *J Ind Microbiol Biotechnol* 33, 610-5.

Inoue, H., et al. (1990). *Gene* 96, 23-8.

Inui, M., et al. (2004). *J Mol Microbiol Biotechnol* 7, 182-96.

Jager, W., et al. (1995). *FEMS Microbiol Lett* 126, 1-6.

Jager, W., et al. (1992). *J Bacteriol* 174, 5462-5.

Jetten, M., et al. (1994a). *Appl Microbiol Biotechnol* 41, 47-52.

Jetten, M. and Sinskey, A. J. (1993). *FEMS Microbiol Lett* 111, 183-188.

Jetten, M. S., et al. (1995). *Appl Microbiol Biotechnol* 43, 76-82.

Jetten, M. S., et al. (1994b). *Appl Environ Microbiol* 60, 2501-7.

Jetten, M. S, and Sinskey, A. J. (1995). *Antonie Van Leeuwenhoek* 67, 221-7.

Jo, S. J., et al. (2007). *J Biosci Bioeng* 104, 457-63.

Kalinowski, J., et al. (2003). *J Biotechnol* 104, 5-25.

Kalinowski, J., et al. (1991). *Mol Microbiol* 5, 1197-204.

Kawaguchi, H., et al. (2008). *Appl Microbiol Biotechnol* 77, 1053-62.

Kawaguchi, H., et al. (2006). *Appl Environ Microbiol* 72, 3418-28.

Kelle, R., et al. (2005). L-Lysine Production in Eggeling, L. and Bott, M. (Eds), *Handbook of Corynebacterium glutamicum*, CRC Press, pp. 465-488.

Kelleher, J. K. (2001). *Metab Eng* 3, 100-10.

Kiefer, P., et al. (2002). *J Ind Microbiol Biotechnol* 28, 338-43.

Kiefer, P., et al. (2004). *Appl Environ Microbiol* 70, 229-39.

Kim, H. M., et al. (2006). *J Microbiol Biotechnol* 16, 1174-1179.

Kim, J., et al. *Appl Microbiol Biotechnol* 81, 1097-106.

Kinoshita, S., et al. (1961). Method of producing L-lysine by fermentation in Office, U.S. P. (Ed).

Kinoshita, S., et al. (1957) *J. Gen. Appl. Microbiol* 3, 193-205.

Kircher, M. and Pfefferle, W. (2001). *Chemosphere* 43, 27-31.

Kjeldsen, K. R. and Nielsen, J. (2009). *Biotechnol Bioeng* 102, 583-97.

Klapa, M. I., et al. (2003). *Eur J Biochem* 270, 3525-42.

Koffas, M. A., et al. (2003). *Metab Eng* 5, 32-41.

Kohl, T. A. and Tauch, A. (2009). *J. Biotechnol.*

Kromer, J. O., et al. (2008). *Microbiologyl* 54, 3917-30.

Kromer, J. O., et al. (2005). *Anal Biochem* 340, 171-3.

KKromer, J. O., et al. (2004). *J Bacteriol* 186, 1769-84.

Kromer, J. O., et al. (2006). *Metab Eng* 8.

Lange, C., et al. (2003). *Appl Environ Microbiol* 69, 2521-32.

Lee, S. F., et al. (2009). *Microbiology.*

Lee, S. Y., et al. (2005). *Trends Biotechnol* 23, 349-58.

Leuchtenberger, W., et al. (2005). *Appl Microbiol Biotechnol* 69, 1-8.

Liebl, W. (2005). *Corynebacterium* Taxonomy in Eggeling, L. and Bott, M. (Eds), *Handbook of Corynebacterium glutamicum*, CRC Press, pp. 9-34.

Liebl, W., et al. (1989). *FEMS Microbiol Lett* 53, 299-303.

Liebl, W., et al. (1991). *Int J Syst Bacteriol* 41, 255-60.

Malumbres, M. and Martin, J. F. (1996). *FEMS Microbiol Lett* 143, 103-14.

Marx, A., et al., et al. (1996). *Biotechnol Bioeng* 49 (2), 111-129.

Marx, A., E et al., (1999). *Metab Eng* 1, 35-48.

Marx, A., et al., (2003). *J Biotechnol* 104, 185-97.

Marx, A., et al., (1997). *Biotechnol Bioeng* 56 (2), 168-180.

Massou, S., et al., (2007). *Metab Eng* 9, 252-7.

Matsushita, K., et al., (2001). *N FEMS Microbiol Lett* 204, 271-6.

Menkel, E., et al., (1989). *Appl Environ Microbiol* 55, 684-8.

Michal, G. (1999). *Biochemical Pathways.* John Wiley & Sons.

Mimitsuka, T., et al., (2007). *Biosci Biotechnol Biochem* 71, 2130-5.

Mizukami, T., et al., (1994). *Biosci Biotechnol Biochem* 58, 635-8.

Molenaar, D., et al., (2000). *J Bacteriol* 182, 6884-91.

Mollney, M., et al., (1999). *Biotechnol Bioeng* 66, 86-103.

Moon, M. W., et al., (2007). *J Mol Microbiol Biotechnol* 12, 43-50.

Moritz, B., et al., (2000). *Eur J Biochem* 267, 3442-52.

Moritz, B., et al., (2002). *Metab Eng* 4, 295-305.

Muffler, A., et al., (2002). *J Biotechnol* 98, 255-68.

Nakayama, K. and Araki, K. (1973). Process for producing L-lysine.

Nakayama, K., et al., (1978). *Adv Exp Med Biol* 105, 649-61.

Netzer, R., et al., (2004). *Arch Microbiol* 182, 354-63.

Noh, K. and Wiechert, W. (2006). *Biotechnol Bioeng* 94, 234-51.

O'Donnell, S. M. and Janssen, G. R. (2001). *J Bacteriol* 183, 1277-83.

O'Regan, M., et al., (1989). *Gene* 77, 237-51.

Ohnishi, J., et al., (2005). *FEMS Microbiol Lett* 242, 265-74.

Ohnishi, J., et al., (2002). *Appl Microbiol Biotechnol* 58, 217-23.

Ozaki, H. and Shiio, I. (1969). *J Biochem* (*Tokyo*)66, 297-311.

Palsson, B. (2000). *Nat Biotechnol* 18, 1147-50.

Parche, S., et al., (2001). *J Mol Microbiol Biotechnol* 3, 423-8.

Park, J. H. and Lee, S. Y. (2008). *Curr Opin Biotechnol* 19, 454-60.

Park, S. M., (1997). *Biotechnol Bioeng* 55, 864-879.

Peters-Wendisch, et al., (1993). *FEMS Microbiol Lett* 112, 269-274.

Peters-Wendisch, P. G., et al., (1998). *Microbiology* 144 (Pt 4), 915-27.

Peters-Wendisch, P. G., et al., (2001). *J Mol Microbiol Biotechnol* 3, 295-300.

Petersen, S., et al., (2000). *J Biol Chem* 275, 35932-41.

Petersen, S., et al. (2001). *Metab Eng* 3, 344-61.

Pisabarro, A., et al. (1993). *J Bacteriol* 175, 2743-9.

Polen, T., et al. (2007). *FEMS Microbiol Lett* 273, 109-19.

Pompejus, M., et al. (2002). *Corynebacterium glutamicum* genes encoding metabolic pathway proteins, BASF AG (DE).

Riedel, C., et al. (2001). *J Mol Microbiol Biotechnol* 3, 573-83.

Rittmann, D., et al. (2008). *Appl Environ Microbiol* 74, 6216-22.

Roessner, U., et al. (2000). *Plant J* 23, 131-42.

Sahm, H., et al. (2000). *Biol Chem* 381, 899-910.

Sano, K., et al. (1987). *Agric Biol Chem* 51 (2), 597-599.

Sasaki, M., et al. (2009). *Appl Microbiol Biotechnol.*

Sauer, U. (2004). *Curr Opin Biotechnol* 15, 58-63.

Sauer, U. and Eikmanns, B. J. (2005). *FEMS Microbiol Rev* 29, 765-94.

Schaffer, S, and Burkovski, A. (2005). Proteomics in Eggeling, L. and Bott, M. (Eds), *Handbook of Corynebacterium glutamicum*, CRC Press, pp. 99-118.

Schaffer, S., et al. (2001). *Electrophoresis* 22, 4404-22.

Schilling, C. H., et al. (1999). *Biotechnol Prog* 15, 296-303.

Schmid, R., et al. (2000). *FEMS Microbiol Lett* 187, 83-8.

Schmidt, K., et al. (1999). *Metab Eng* 1, 166-79.

Schrumpf, B., et al. (1991). *J Bacteriol* 173, 4510-6.

Seibold, G., et al. (2006). *J Biotechnol* 124, 381-91.

Shiio, I., et al. (1987). *Agric Biol Chem* 51, 2485-2493.

Shiio, I., et al. (1990). *Agric Biol Chem* 54, 3275-3285.

Shinfuku, Y., et al. (2009). *Microb Cell Fact* 8, 43.

Silberbach, M., et al. (2005a). *J. Biotechnol.*

Silberbach, M., et al. (2005b). *Appl Environ Microbiol* 71, 2391-402.

Simic, P., et al. (2002). *Appl Environ Microbiol* 68, 3321-7.

Sonntag, K., et al. (1993). *Eur J Biochem* 213, 1325-31.

Sonntag, K., et al. (1995). *Appl Microbiol Biotechnol* 44, 489-495.

Stephanopoulos, G. (1999). *Metab Eng* 1, 1-11.

Stephanopoulos, G. and Vallino, J. J. (1991). *Science* 252, 1675-81.

Sugimoto, S.-I. and Shiio, I. (1989). *Agric Biol Chem* 53 (5), 1261-1268.

Tauch, A., et al. (2002a). *J Biotechnol* 95, 25-38.

Tauch, A., et al. (2002b). *Curr Microbiol* 45, 362-7.

Tauch, A., et al. (1994). *FEMS Microbiol Lett* 123, 343-7.

Thierbach, G., et al. (1990). *Appl Microbiol Biotechnol* 32, 443-8.

Thrippleton, M. J. and Keeler, J. (2003). *Angew Chem Int Ed Eng* 142, 3938-41.

Tzvetkov, M., et al. (2003). *Microbiology* 149, 1659-73.

Udaka, S. (1960). *J Bacteriol* 79, 754-5.

Van Dien, S. J., et al. (2006). *J Biosci Bioeng* 102, 34-40.

Vasicova, P., et al. (1999). *J Bacteriol* 181, 6188-91.

Vellanoweth, R. L. and Rabinowitz, J. C. (1992). *Mol Microbiol* 6, 1105-14.

Vervoort, E. B., et al. (2000). *Nucleic Acids Res* 28, 2069-74.

Villas-Boas, S. G., et al. (2005). *Mass Spectrom Rev* 24, 613-46.

Vrljic, M., et al. (1996). *Mol Microbiol* 22, 815-26.

Wehrmann, A., et al. (1998). *J Bacteriol* 180, 3159-65.

Wendisch, V. F. (2003). *J Biotechnol* 104, 273-85.

Wendisch, V. F. (2006). *J. Microbiol. Biotechnol.* 16(7), 999-1009.

Wendisch, V. F., et al. (2006). *J Biotechnol* 124, 74-92.

Wendisch, V. F., et al. (2000). *J Bacteriol* 182, 3088-96.

Wiechert, W. (2001). *Metab Eng* 3, 195-206.

Wiechert, W. and Noh, K. (2005). *Adv Biochem Eng Biotechnol* 92, 145-72.

Wiedemann, B. and Boles, E. (2008) *Appl Environ Microbiol* 74, 2043-50.

Wittmann, C. (2002). *Adv Biochem Eng Biotechnol* 74, 39-64.

Wittmann, C. (2007). *Microb Cell Fact* 6, 6.

Wittmann, C. and Becker, J. (2007) in Wendisch, V. F. (Ed), Springer Berlin/Heidelberg pp. 39-70.

Wittmann, C. and de Graaf, A. (2005) in Eggeling, L. and Bott, M. (Eds), *Handbook of Corynebacterium glutamicum*, CRC Press, pp. 277-304.

Wittmann, C., et al. (2002). *Anal Biochem* 307, 379-82.

Wittmann, C. and Heinzle, E. (2001a). *Eur J Biochem* 268, 2441-55.

Wittmann, C. and Heinzle, E. (2001b). *Metab Eng* 3, 173-91.

Wittmann, C. and Heinzle, E. (2002). *Appl Environ Microbiol* 68, 5843-59.

Wittmann, C., et al. (2004a). *Appl Environ Microbiol* 70, 7277-87.

Wittmann, C., et al. (2004b). *Biotechnol Bioeng* 87, 1-6.

Wittmann, et al. (2003). *Biotechnol Lett* 25, 377-80.

Yang, T. H., et al. (2003). *Rapid Commun Mass Spectrom* 17, 2721-31.

Yang, T. H., et al. (2006a). *Metab Eng* 8, 432-46.

Yang, T. H., et al. (2006b). *Metab Eng* 8, 417-31.

Yokota, A. and Lindley, N. D. (2005) in Eggeling, L. and Bott, M. (Eds), *Handbook of Corynebacterium glutamicum*, CRC Press, pp. 215-240.

Zelder, O., et al. Genes coding for glucose 6-phosphate dehydrogenase proteins in Office, U. P. (Ed).

The invention claimed is:

1. A method of producing L-lysine by culturing a *Corynebacterium glutamicum* microorganism in a culture medium suitable for the production of L-lysine by a *Corynebacterium glutamicum* microorganism, wherein the *Corynebacterium glutamicum* microorganism is deposited at the Deutsche Sammlung von Mikroorganismen and Zellkulturen (DSMZ) and has deposit number DSM 23586.

2. The method of producing L-lysine according to claim 1, further comprising the steps of harvesting and purifying the L-lysine.

3. *Corynebacterium glutamicum* deposited at the Deutsche Sammlung von Mikroorganismen and Zellkulturen (DSMZ) and has deposit number DSM 23586.

* * * * *

SEQUENCE LISTING

<160> NUMBER OF SEQ ID NOS: 106

<210> SEQ ID NO 1
<211> LENGTH: 1466
<212> TYPE: DNA
<213> ORGANISM: Corynebacterium glutamicum
<220> FEATURE:
<221> NAME/KEY: CDS
<222> LOCATION: (201)..(1463)
<223> OTHER INFORMATION: lysC, DNA sequence encoding C. glutamicum aspartate kinase with natural promoter

<400> SEQUENCE: 1
gtcacttttg tctcaaatat taaatcgaat atcaatatat ggtctgttta ttggaacgcg 60
tcccagtggc tgagacgcat ccgctaaagc cccaggaacc ctgtgcagaa agaaaacact 120
cctctggcta ggtagacaca gtttataaag gtagagttga gcgggtaact gtcagcacgt 180
agatcgaaag gtgcacaaag gtg gcc ctg gtc gta cag aaa tat ggc ggt tcc 233
Val Ala Leu Val Val Gln Lys Tyr Gly Gly Ser
1 5 10 tcg ctt gag agt gcg gaa cgc att aga aac gtc gct gaa cgg atc gtt 281
Ser Leu Glu Ser Ala Glu Arg Ile Arg Asn Val Ala Glu Arg Ile Val
15 20 25 gcc acc aag aag gct gga aat gat gtc gtg gtt gtc tgc tcc gca atg 329
Ala Thr Lys Lys Ala Gly Asn Asp Val Val Val Val Cys Ser Ala Met
30 35 40 gga gac acc acg gat gaa ctt cta gaa ctt gca gcg gca gtg aat ccc 377
Gly Asp Thr Thr Asp Glu Leu Leu Glu Leu Ala Ala Ala Val Asn Pro
45 50 55 gtt ccg cca gct cgt gaa atg gat atg ctc ctg act gct ggt gag cgt 425
Val Pro Pro Ala Arg Glu Met Asp Met Leu Leu Thr Ala Gly Glu Arg
60 65 70 75 att tct aac gct ctc gtc gcc atg gct att gag tcc ctt ggc gca gaa 473
Ile Ser Asn Ala Leu Val Ala Met Ala Ile Glu Ser Leu Gly Ala Glu
80 85 90 gcc caa tct ttc acg ggc tct cag gct ggt gtg ctc acc acc gag cgc 521
Ala Gln Ser Phe Thr Gly Ser Gln Ala Gly Val Leu Thr Thr Glu Arg
95 100 105 cac gga aac gca cgc att gtt gat gtc act cca ggt cgt gtg cgt gaa 569
His Gly Asn Ala Arg Ile Val Asp Val Thr Pro Gly Arg Val Arg Glu
110 115 120 gca ctc gat gag ggc aag atc tgc att gtt gct ggt ttc cag ggt gtt 617
Ala Leu Asp Glu Gly Lys Ile Cys Ile Val Ala Gly Phe Gln Gly Val
125 130 135 aat aaa gaa acc cgc gat gtc acc acg ttg ggt cgt ggt ggt tct gac 665
Asn Lys Glu Thr Arg Asp Val Thr Thr Leu Gly Arg Gly Gly Ser Asp
140 145 150 155 acc act gca gtt gcg ttg gca gct gct ttg aac gct gat gtg tgt gag 713
Thr Thr Ala Val Ala Leu Ala Ala Ala Leu Asn Ala Asp Val Cys Glu
160 165 170 att tac tcg gac gtt gac ggt gtg tat acc gct gac ccg cgc atc gtt 761
Ile Tyr Ser Asp Val Asp Gly Val Tyr Thr Ala Asp Pro Arg Ile Val
175 180 185 cct aat gca cag aag ctg gaa aag ctc agc ttc gaa gaa atg ctg gaa 809
Pro Asn Ala Gln Lys Leu Glu Lys Leu Ser Phe Glu Glu Met Leu Glu
190 195 200 ctt gct gct gtt ggc tcc aag att ttg gtg ctg cgc agt gtt gaa tac 857
Leu Ala Ala Val Gly Ser Lys Ile Leu Val Leu Arg Ser Val Glu Tyr
205 210 215 gct cgt gca ttc aat gtg cca ctt cgc gta cgc tcg tct tat agt aat 905
Ala Arg Ala Phe Asn Val Pro Leu Arg Val Arg Ser Ser Tyr Ser Asn

```
220                 225                 230                 235

gat ccc ggc act ttg att gcc ggc tct atg gag gat att cct gtg gaa      953
Asp Pro Gly Thr Leu Ile Ala Gly Ser Met Glu Asp Ile Pro Val Glu
                240                 245                 250

gaa gca gtc ctt acc ggt gtc gca acc gac aag tcc gaa gcc aaa gta     1001
Glu Ala Val Leu Thr Gly Val Ala Thr Asp Lys Ser Glu Ala Lys Val
            255                 260                 265

acc gtt ctg ggt att tcc gat aag cca ggc gag gct gcg aag gtt ttc     1049
Thr Val Leu Gly Ile Ser Asp Lys Pro Gly Glu Ala Ala Lys Val Phe
        270                 275                 280

cgt gcg ttg gct gat gca gaa atc aac att gac atg gtt ctg cag aac     1097
Arg Ala Leu Ala Asp Ala Glu Ile Asn Ile Asp Met Val Leu Gln Asn
    285                 290                 295

gtc tct tct gta gaa gac ggc acc acc gac atc acc ttc acc tgc cct     1145
Val Ser Ser Val Glu Asp Gly Thr Thr Asp Ile Thr Phe Thr Cys Pro
300                 305                 310                 315

cgt tcc gac ggc cgc cgc gcg atg gag atc ttg aag aag ctt cag gtt     1193
Arg Ser Asp Gly Arg Arg Ala Met Glu Ile Leu Lys Lys Leu Gln Val
                320                 325                 330

cag ggc aac tgg acc aat gtg ctt tac gac gac cag gtc ggc aaa gtc     1241
Gln Gly Asn Trp Thr Asn Val Leu Tyr Asp Asp Gln Val Gly Lys Val
            335                 340                 345

tcc ctc gtg ggt gct ggc atg aag tct cac cca ggt gtt acc gca gag     1289
Ser Leu Val Gly Ala Gly Met Lys Ser His Pro Gly Val Thr Ala Glu
        350                 355                 360

ttc atg gaa gct ctg cgc gat gtc aac gtg aac atc gaa ttg att tcc     1337
Phe Met Glu Ala Leu Arg Asp Val Asn Val Asn Ile Glu Leu Ile Ser
    365                 370                 375

acc tct gag att cgt att tcc gtg ctg atc cgt gaa gat gat ctg gat     1385
Thr Ser Glu Ile Arg Ile Ser Val Leu Ile Arg Glu Asp Asp Leu Asp
380                 385                 390                 395

gct gct gca cgt gca ttg cat gag cag ttc cag ctg ggc ggc gaa gac     1433
Ala Ala Ala Arg Ala Leu His Glu Gln Phe Gln Leu Gly Gly Glu Asp
                400                 405                 410

gaa gcc gtc gtt tat gca ggc acc gga cgc       taa                   1466
Glu Ala Val Val Tyr Ala Gly Thr Gly Arg
            415                 420


<210> SEQ ID NO 2
<211> LENGTH: 421
<212> TYPE: PRT
<213> ORGANISM: Corynebacterium glutamicum
<220> FEATURE:
<221> NAME/KEY: PEPTIDE
<222> LOCATION: (1)..(421)
<223> OTHER INFORMATION: LysC, amino acid sequence of C. glutamicum
      aspartate kinase

<400> SEQUENCE: 2

Val Ala Leu Val Val Gln Lys Tyr Gly Gly Ser Ser Leu Glu Ser Ala
  1               5                  10                  15

Glu Arg Ile Arg Asn Val Ala Glu Arg Ile Val Ala Thr Lys Lys Ala
             20                  25                  30

Gly Asn Asp Val Val Val Val Cys Ser Ala Met Gly Asp Thr Thr Asp
         35                  40                  45

Glu Leu Leu Glu Leu Ala Ala Ala Val Asn Pro Val Pro Pro Ala Arg
     50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
```

```
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420
```

<210> SEQ ID NO 3
<211> LENGTH: 1458
<212> TYPE: DNA
<213> ORGANISM: Corynebacterium glutamicum
<220> FEATURE:
<221> NAME/KEY: CDS
<222> LOCATION: (193)..(1455)
<223> OTHER INFORMATION: lysCT311I, DNA sequence encoding C. glutamicum
      aspartate kinase with T311I-substitution, sod-promoter and start
      codon exchange GTG -> ATG

<400> SEQUENCE: 3

```
tagctgccaa ttattccggg cttgtgaccc gctacccgat aaataggtcg gctgaaaaat      60

ttcgttgcaa tataaacaaa aaggcctctc attgggaggt gtcgcaccaa gtacttttgc     120

gaagcgccat ctgacggatt ttcaaaagat gtatatgctc ggtgcggaaa cctacgaaag     180

gattttttac cc         atg gcc ctg gtc gta cag aaa tat ggc ggt tcc     225
                      Met Ala Leu Val Val Gln Lys Tyr Gly Gly Ser
                      1               5                   10

tcg ctt gag agt gcg gaa cgc att aga aac gtc gct gaa cgg atc gtt       273
Ser Leu Glu Ser Ala Glu Arg Ile Arg Asn Val Ala Glu Arg Ile Val
            15                  20                  25

gcc acc aag aag gct gga aat gat gtc gtg gtt gtc tgc tcc gca atg       321
Ala Thr Lys Lys Ala Gly Asn Asp Val Val Val Val Cys Ser Ala Met
        30                  35                  40

gga gac acc acg gat gaa ctt cta gaa ctt gca gcg gca gtg aat ccc       369
Gly Asp Thr Thr Asp Glu Leu Leu Glu Leu Ala Ala Ala Val Asn Pro
    45                  50                  55

gtt ccg cca gct cgt gaa atg gat atg ctc ctg act gct ggt gag cgt       417
Val Pro Pro Ala Arg Glu Met Asp Met Leu Leu Thr Ala Gly Glu Arg
60                  65                  70                  75

att tct aac gct ctc gtc gcc atg gct att gag tcc ctt ggc gca gaa       465
Ile Ser Asn Ala Leu Val Ala Met Ala Ile Glu Ser Leu Gly Ala Glu
                80                  85                  90

gcc caa tct ttc acg ggc tct cag gct ggt gtg ctc acc acc gag cgc       513
Ala Gln Ser Phe Thr Gly Ser Gln Ala Gly Val Leu Thr Thr Glu Arg
            95                  100                 105

cac gga aac gca cgc att gtt gat gtc act cca ggt cgt gtg cgt gaa       561
His Gly Asn Ala Arg Ile Val Asp Val Thr Pro Gly Arg Val Arg Glu
        110                 115                 120

gca ctc gat gag ggc aag atc tgc att gtt gct ggt ttc cag ggt gtt       609
Ala Leu Asp Glu Gly Lys Ile Cys Ile Val Ala Gly Phe Gln Gly Val
    125                 130                 135

aat aaa gaa acc cgc gat gtc acc acg ttg ggt cgt ggt ggt tct gac       657
Asn Lys Glu Thr Arg Asp Val Thr Thr Leu Gly Arg Gly Gly Ser Asp
140                 145                 150                 155

acc act gca gtt gcg ttg gca gct gct ttg aac gct gat gtg tgt gag       705
Thr Thr Ala Val Ala Leu Ala Ala Ala Leu Asn Ala Asp Val Cys Glu
                160                 165                 170

att tac tcg gac gtt gac ggt gtg tat acc gct gac ccg cgc atc gtt       753
Ile Tyr Ser Asp Val Asp Gly Val Tyr Thr Ala Asp Pro Arg Ile Val
            175                 180                 185

cct aat gca cag aag ctg gaa aag ctc agc ttc gaa gaa atg ctg gaa       801
Pro Asn Ala Gln Lys Leu Glu Lys Leu Ser Phe Glu Glu Met Leu Glu
        190                 195                 200

ctt gct gct gtt ggc tcc aag att ttg gtg ctg cgc agt gtt gaa tac       849
Leu Ala Ala Val Gly Ser Lys Ile Leu Val Leu Arg Ser Val Glu Tyr
    205                 210                 215

gct cgt gca ttc aat gtg cca ctt cgc gta cgc tcg tct tat agt aat       897
Ala Arg Ala Phe Asn Val Pro Leu Arg Val Arg Ser Ser Tyr Ser Asn
220                 225                 230                 235

gat ccc ggc act ttg att gcc ggc tct atg gag gat att cct gtg gaa       945
Asp Pro Gly Thr Leu Ile Ala Gly Ser Met Glu Asp Ile Pro Val Glu
                240                 245                 250

gaa gca gtc ctt acc ggt gtc gca acc gac aag tcc gaa gcc aaa gta       993
Glu Ala Val Leu Thr Gly Val Ala Thr Asp Lys Ser Glu Ala Lys Val
            255                 260                 265

acc gtt ctg ggt att tcc gat aag cca ggc gag gct gcg aag gtt ttc      1041
Thr Val Leu Gly Ile Ser Asp Lys Pro Gly Glu Ala Ala Lys Val Phe
        270                 275                 280

cgt gcg ttg gct gat gca gaa atc aac att gac atg gtt ctg cag aac      1089
```

```
Arg Ala Leu Ala Asp Ala Glu Ile Asn Ile Asp Met Val Leu Gln Asn
    285                 290                 295

gtc tct tct gta gaa gac ggc acc acc gac atc atc ttc acc tgc cct     1137
Val Ser Ser Val Glu Asp Gly Thr Thr Asp Ile Ile Phe Thr Cys Pro
300                 305                 310                 315

cgt tcc gac ggc cgc cgc gcg atg gag atc ttg aag aag ctt cag gtt     1185
Arg Ser Asp Gly Arg Arg Ala Met Glu Ile Leu Lys Lys Leu Gln Val
                320                 325                 330

cag ggc aac tgg acc aat gtg ctt tac gac gac cag gtc ggc aaa gtc     1233
Gln Gly Asn Trp Thr Asn Val Leu Tyr Asp Asp Gln Val Gly Lys Val
            335                 340                 345

tcc ctc gtg ggt gct ggc atg aag tct cac cca ggt gtt acc gca gag     1281
Ser Leu Val Gly Ala Gly Met Lys Ser His Pro Gly Val Thr Ala Glu
        350                 355                 360

ttc atg gaa gct ctg cgc gat gtc aac gtg aac atc gaa ttg att tcc     1329
Phe Met Glu Ala Leu Arg Asp Val Asn Val Asn Ile Glu Leu Ile Ser
    365                 370                 375

acc tct gag att cgt att tcc gtg ctg atc cgt gaa gat gat ctg gat     1377
Thr Ser Glu Ile Arg Ile Ser Val Leu Ile Arg Glu Asp Asp Leu Asp
380                 385                 390                 395

gct gct gca cgt gca ttg cat gag cag ttc cag ctg ggc ggc gaa gac     1425
Ala Ala Ala Arg Ala Leu His Glu Gln Phe Gln Leu Gly Gly Glu Asp
                400                 405                 410

gaa gcc gtc gtt tat gca ggc acc gga cgc          taa                1458
Glu Ala Val Val Tyr Ala Gly Thr Gly Arg
            415                 420


<210> SEQ ID NO 4
<211> LENGTH: 421
<212> TYPE: PRT
<213> ORGANISM: Corynebacterium glutamicum
<220> FEATURE:
<221> NAME/KEY: PEPTIDE
<222> LOCATION: (1)..(421)
<223> OTHER INFORMATION: LysCT311I amino acid sequence of C. glutamicum
      aspartate kinase with T311I-substitution

<400> SEQUENCE: 4

Met Ala Leu Val Val Gln Lys Tyr Gly Gly Ser Ser Leu Glu Ser Ala
  1               5                  10                  15

Glu Arg Ile Arg Asn Val Ala Glu Arg Ile Val Ala Thr Lys Lys Ala
             20                  25                  30

Gly Asn Asp Val Val Val Val Cys Ser Ala Met Gly Asp Thr Thr Asp
         35                  40                  45

Glu Leu Leu Glu Leu Ala Ala Ala Val Asn Pro Val Pro Pro Ala Arg
     50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
```

```
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420


<210> SEQ ID NO 5
<211> LENGTH: 1193
<212> TYPE: DNA
<213> ORGANISM: Corynebacterium glutamicum
<220> FEATURE:
<221> NAME/KEY: CDS
<222> LOCATION: (231)..(1190)
<223> OTHER INFORMATION: ddh, DNA sequence encoding C. glutamicum
      diaminopimelate dehydrogenase with natural promoter

<400> SEQUENCE: 5

aacggcaacg gatcaaaagt cctgttggtg aagctgcgcc ccacagatcc tgactgctgg      60

gagccatgaa aatagatcag cgcatccgtg gtggaaccaa aaggctcaac aatacgaaac     120

gttcgctttc ggtcctgatg aaagagatgt ccctgaatca tcatctaagt atgcatctcg     180

gtaagctcga ccaggacagt gccaccacaa ttttggagga ttacaagaac atg acc aac    239
                                                       Met Thr Asn
                                                         1

atc cgc gta gct atc gtg ggc tac gga aac ctg gga cgc agc gtc gaa      287
Ile Arg Val Ala Ile Val Gly Tyr Gly Asn Leu Gly Arg Ser Val Glu
      5                  10                  15

aag ctt att gcc aag cag ccc gac atg gac ctt gta gga atc ttc tcg      335
Lys Leu Ile Ala Lys Gln Pro Asp Met Asp Leu Val Gly Ile Phe Ser
```

```
 20                  25                  30                  35

cgc cgg gcc acc ctc gac aca aag acg cca gtc ttt gat gtc gcc gac      383
Arg Arg Ala Thr Leu Asp Thr Lys Thr Pro Val Phe Asp Val Ala Asp
                 40                  45                  50

gtg gac aag cac gcc gac gac gtg gac gtg ctg ttc ctg tgc atg ggc      431
Val Asp Lys His Ala Asp Asp Val Asp Val Leu Phe Leu Cys Met Gly
             55                  60                  65

tcc gcc acc gac atc cct gag cag gca cca aag ttc gcg cag ttc gcc      479
Ser Ala Thr Asp Ile Pro Glu Gln Ala Pro Lys Phe Ala Gln Phe Ala
         70                  75                  80

tgc acc gta gac acc tac gac aac cac cgc gac atc cca cgc cac cgc      527
Cys Thr Val Asp Thr Tyr Asp Asn His Arg Asp Ile Pro Arg His Arg
     85                  90                  95

cag gtc atg aac gaa gcc gcc acc gca gcc ggc aac gtt gca ctg gtc      575
Gln Val Met Asn Glu Ala Ala Thr Ala Ala Gly Asn Val Ala Leu Val
100                 105                 110                 115

tct acc ggc tgg gat cca gga atg ttc tcc atc aac cgc gtc tac gca      623
Ser Thr Gly Trp Asp Pro Gly Met Phe Ser Ile Asn Arg Val Tyr Ala
                120                 125                 130

gcg gca gtc tta gcc gag cac cag cag cac acc ttc tgg ggc cca ggt      671
Ala Ala Val Leu Ala Glu His Gln Gln His Thr Phe Trp Gly Pro Gly
            135                 140                 145

ttg tca cag ggc cac tcc gat gct ttg cga cgc atc cct ggc gtt caa      719
Leu Ser Gln Gly His Ser Asp Ala Leu Arg Arg Ile Pro Gly Val Gln
        150                 155                 160

aag gca gtc cag tac acc ctc cca tcc gaa gac gcc ctg gaa aag gcc      767
Lys Ala Val Gln Tyr Thr Leu Pro Ser Glu Asp Ala Leu Glu Lys Ala
    165                 170                 175

cgc cgc ggc gaa gcc ggc gac ctt acc gga aag caa acc cac aag cgc      815
Arg Arg Gly Glu Ala Gly Asp Leu Thr Gly Lys Gln Thr His Lys Arg
180                 185                 190                 195

caa tgc ttc gtg gtt gcc gac gcg gcc gat cac gag cgc atc gaa aac      863
Gln Cys Phe Val Val Ala Asp Ala Ala Asp His Glu Arg Ile Glu Asn
                200                 205                 210

gac atc cgc acc atg cct gat tac ttc gtt ggc tac gaa gtc gaa gtc      911
Asp Ile Arg Thr Met Pro Asp Tyr Phe Val Gly Tyr Glu Val Glu Val
            215                 220                 225

aac ttc atc gac gaa gca acc ttc gac tcc gag cac acc ggc atg cca      959
Asn Phe Ile Asp Glu Ala Thr Phe Asp Ser Glu His Thr Gly Met Pro
        230                 235                 240

cac ggt ggc cac gtg att acc acc ggc gac acc ggt ggc ttc aac cac     1007
His Gly Gly His Val Ile Thr Thr Gly Asp Thr Gly Gly Phe Asn His
    245                 250                 255

acc gtg gaa tac atc ctc aag ctg gac cga aac cca gat ttc acc gct     1055
Thr Val Glu Tyr Ile Leu Lys Leu Asp Arg Asn Pro Asp Phe Thr Ala
260                 265                 270                 275

tcc tca cag atc gct ttc ggt cgc gca gct cac cgc atg aag cag cag     1103
Ser Ser Gln Ile Ala Phe Gly Arg Ala Ala His Arg Met Lys Gln Gln
                280                 285                 290

ggc caa agc gga gct ttc acc gtc ctc gaa gtt gct cca tac ctg ctc     1151
Gly Gln Ser Gly Ala Phe Thr Val Leu Glu Val Ala Pro Tyr Leu Leu
            295                 300                 305

tcc cca gag aac ttg gac gat ctg atc gca cgc gac gtc    taa          1193
Ser Pro Glu Asn Leu Asp Asp Leu Ile Ala Arg Asp Val
        310                 315                 320
```

<210> SEQ ID NO 6
<211> LENGTH: 320
<212> TYPE: PRT
<213> ORGANISM: Corynebacterium glutamicum

```
<220> FEATURE:
<221> NAME/KEY: PEPTIDE
<222> LOCATION: (1)..(320)
<223> OTHER INFORMATION: Ddh, amino acid sequence of C. glutamicum
      diaminopimelate dehydrogenase

<400> SEQUENCE: 6

Met Thr Asn Ile Arg Val Ala Ile Val Gly Tyr Gly Asn Leu Gly Arg
  1               5                  10                  15

Ser Val Glu Lys Leu Ile Ala Lys Gln Pro Asp Met Asp Leu Val Gly
             20                  25                  30

Ile Phe Ser Arg Arg Ala Thr Leu Asp Thr Lys Thr Pro Val Phe Asp
         35                  40                  45

Val Ala Asp Val Asp Lys His Ala Asp Asp Val Asp Val Leu Phe Leu
     50                  55                  60

Cys Met Gly Ser Ala Thr Asp Ile Pro Glu Gln Ala Pro Lys Phe Ala
 65                  70                  75                  80

Gln Phe Ala Cys Thr Val Asp Thr Tyr Asp Asn His Arg Asp Ile Pro
                 85                  90                  95

Arg His Arg Gln Val Met Asn Glu Ala Ala Thr Ala Ala Gly Asn Val
            100                 105                 110

Ala Leu Val Ser Thr Gly Trp Asp Pro Gly Met Phe Ser Ile Asn Arg
        115                 120                 125

Val Tyr Ala Ala Ala Val Leu Ala Glu His Gln Gln His Thr Phe Trp
    130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
            180                 185                 190

His Lys Arg Gln Cys Phe Val Val Ala Asp Ala Ala Asp His Glu Arg
        195                 200                 205

Ile Glu Asn Asp Ile Arg Thr Met Pro Asp Tyr Phe Val Gly Tyr Glu
    210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
                245                 250                 255

Phe Asn His Thr Val Glu Tyr Ile Leu Lys Leu Asp Arg Asn Pro Asp
            260                 265                 270

Phe Thr Ala Ser Ser Gln Ile Ala Phe Gly Arg Ala Ala His Arg Met
        275                 280                 285

Lys Gln Gln Gly Gln Ser Gly Ala Phe Thr Val Leu Glu Val Ala Pro
    290                 295                 300

Tyr Leu Leu Ser Pro Glu Asn Leu Asp Asp Leu Ile Ala Arg Asp Val
305                 310                 315                 320


<210> SEQ ID NO 7
<211> LENGTH: 2554
<212> TYPE: DNA
<213> ORGANISM: Corynebacterium glutamicum
<220> FEATURE:
<221> NAME/KEY: CDS
<222> LOCATION: (231)..(1190)
<223> OTHER INFORMATION: ddh DNA, two copies encoding C. glutamicum
      diaminopimelate dehydrogenase including flanking regions
```

```
<400> SEQUENCE: 7

aacggcaacg gatcaaaagt cctgttggtg aagctgcgcc ccacagatcc tgactgctgg     60

gagccatgaa aatagatcag cgcatccgtg gtggaaccaa aaggctcaac aatacgaaac    120

gttcgctttc ggtcctgatg aaagagatgt ccctgaatca tcatctaagt atgcatctcg    180

gtaagctcga ccaggacagt gccaccacaa ttttggagga ttacaagaac atg acc aac   239
                                                       Met Thr Asn
                                                         1

atc cgc gta gct atc gtg ggc tac gga aac ctg gga cgc agc gtc gaa      287
Ile Arg Val Ala Ile Val Gly Tyr Gly Asn Leu Gly Arg Ser Val Glu
      5                  10                  15

aag ctt att gcc aag cag ccc gac atg gac ctt gta gga atc ttc tcg      335
Lys Leu Ile Ala Lys Gln Pro Asp Met Asp Leu Val Gly Ile Phe Ser
 20                  25                  30                  35

cgc cgg gcc acc ctc gac aca aag acg cca gtc ttt gat gtc gcc gac      383
Arg Arg Ala Thr Leu Asp Thr Lys Thr Pro Val Phe Asp Val Ala Asp
                 40                  45                  50

gtg gac aag cac gcc gac gac gtg gac gtg ctg ttc ctg tgc atg ggc      431
Val Asp Lys His Ala Asp Asp Val Asp Val Leu Phe Leu Cys Met Gly
             55                  60                  65

tcc gcc acc gac atc cct gag cag gca cca aag ttc gcg cag ttc gcc      479
Ser Ala Thr Asp Ile Pro Glu Gln Ala Pro Lys Phe Ala Gln Phe Ala
         70                  75                  80

tgc acc gta gac acc tac gac aac cac cgc gac atc cca cgc cac cgc      527
Cys Thr Val Asp Thr Tyr Asp Asn His Arg Asp Ile Pro Arg His Arg
     85                  90                  95

cag gtc atg aac gaa gcc gcc acc gca gcc ggc aac gtt gca ctg gtc      575
Gln Val Met Asn Glu Ala Ala Thr Ala Ala Gly Asn Val Ala Leu Val
100                 105                 110                 115

tct acc ggc tgg gat cca gga atg ttc tcc atc aac cgc gtc tac gca      623
Ser Thr Gly Trp Asp Pro Gly Met Phe Ser Ile Asn Arg Val Tyr Ala
                120                 125                 130

gcg gca gtc tta gcc gag cac cag cag cac acc ttc tgg ggc cca ggt      671
Ala Ala Val Leu Ala Glu His Gln Gln His Thr Phe Trp Gly Pro Gly
            135                 140                 145

ttg tca cag ggc cac tcc gat gct ttg cga cgc atc cct ggc gtt caa      719
Leu Ser Gln Gly His Ser Asp Ala Leu Arg Arg Ile Pro Gly Val Gln
        150                 155                 160

aag gca gtc cag tac acc ctc cca tcc gaa gac gcc ctg gaa aag gcc      767
Lys Ala Val Gln Tyr Thr Leu Pro Ser Glu Asp Ala Leu Glu Lys Ala
    165                 170                 175

cgc cgc ggc gaa gcc ggc gac ctt acc gga aag caa acc cac aag cgc      815
Arg Arg Gly Glu Ala Gly Asp Leu Thr Gly Lys Gln Thr His Lys Arg
180                 185                 190                 195

caa tgc ttc gtg gtt gcc gac gcg gcc gat cac gag cgc atc gaa aac      863
Gln Cys Phe Val Val Ala Asp Ala Ala Asp His Glu Arg Ile Glu Asn
                200                 205                 210

gac atc cgc acc atg cct gat tac ttc gtt ggc tac gaa gtc gaa gtc      911
Asp Ile Arg Thr Met Pro Asp Tyr Phe Val Gly Tyr Glu Val Glu Val
            215                 220                 225

aac ttc atc gac gaa gca acc ttc gac tcc gag cac acc ggc atg cca      959
Asn Phe Ile Asp Glu Ala Thr Phe Asp Ser Glu His Thr Gly Met Pro
        230                 235                 240

cac ggt ggc cac gtg att acc acc ggc gac acc ggt ggc ttc aac cac     1007
His Gly Gly His Val Ile Thr Thr Gly Asp Thr Gly Gly Phe Asn His
    245                 250                 255

acc gtg gaa tac atc ctc aag ctg gac cga aac cca gat ttc acc gct     1055
Thr Val Glu Tyr Ile Leu Lys Leu Asp Arg Asn Pro Asp Phe Thr Ala
260                 265                 270                 275
```

```
tcc tca cag atc gct ttc ggt cgc gca gct cac cgc atg aag cag cag     1103
Ser Ser Gln Ile Ala Phe Gly Arg Ala Ala His Arg Met Lys Gln Gln
                280                 285                 290

ggc caa agc gga gct ttc acc gtc ctc gaa gtt gct cca tac ctg ctc     1151
Gly Gln Ser Gly Ala Phe Thr Val Leu Glu Val Ala Pro Tyr Leu Leu
            295                 300                 305

tcc cca gag aac ttg gac gat ctg atc gca cgc gac gtc    taatttagct   1200
Ser Pro Glu Asn Leu Asp Asp Leu Ile Ala Arg Asp Val
        310                 315                 320

cgaggggcaa ggaaacagtg tggtttcctt gcctctttta gccttttcag agggtgtctt   1260

cgctggacca agaggaaaac ggcaacggat caaaagtcct gttggtgaag ctgcgcccca   1320

cagatcctga ctgctgggag ccatgaaaat agatcagcgc atccgtggtg gaaccaaaag   1380

gctcaacaat acgaaacgtt cgctttcggt cctgatgaaa gagatgtccc tgaatcatca   1440

tctaagtatg catctcggta agctcgacca ggacagtgcc accacaattt tggaggatta   1500

caagaacatg accaacatcc gcgtagctat cgtgggctac ggaaacctgg gacgcagcgt   1560

cgaaaagctt attgccaagc agcccgacat ggaccttgta ggaatcttct cgcgccgggc   1620

caccctcgac acaaagacgc cagtctttga tgtcgccgac gtggacaagc acgccgacga   1680

cgtggacgtg ctgttcctgt gcatgggctc cgccaccgac atccctgagc aggcaccaaa   1740

gttcgcgcag ttcgcctgca ccgtagacac ctacgacaac caccgcgaca tcccacgcca   1800

ccgccaggtc atgaacgaag ccgccaccgc agccggcaac gttgcactgg tctctaccgg   1860

ctgggatcca ggaatgttct ccatcaaccg cgtctacgca gcggcagtct tagccgagca   1920

ccagcagcac accttctggg gcccaggttt gtcacagggc cactccgatg ctttgcgacg   1980

catccctggc gttcaaaagg cagtccagta caccctccca tccgaagacg ccctggaaaa   2040

ggcccgccgc ggcgaagccg gcgaccttac cggaaagcaa acccacaagc gccaatgctt   2100

cgtggttgcc gacgcggccg atcacgagcg catcgaaaac gacatccgca ccatgcctga   2160

ttacttcgtt ggctacgaag tcgaagtcaa cttcatcgac gaagcaacct tcgactccga   2220

gcacaccggc atgccacacg gtggccacgt gattaccacc ggcgacaccg gtggcttcaa   2280

ccacaccgtg gaatacatcc tcaagctgga ccgaaaccca gatttcaccg cttcctcaca   2340

gatcgctttc ggtcgcgcag ctcaccgcat gaagcagcag ggccaaagcg gagctttcac   2400

cgtcctcgaa gttgctccat acctgctctc cccagagaac ttggacgatc tgatcgcacg   2460

cgacgtctaa tttagctcga ggggcaagga aacagtgtgg tttccttgcc tcttttagcc   2520

ttttcagagg gtgtcttcgc tggaccaaga ggaa                                2554
```

```
<210> SEQ ID NO 8
<211> LENGTH: 1833
<212> TYPE: DNA
<213> ORGANISM: Corynebacterium glutamicum
<220> FEATURE:
<221> NAME/KEY: CDS
<222> LOCATION: (1)..(1830)
<223> OTHER INFORMATION: pck, DNA sequence encoding wildtype C.
      glutamicum PEP-carboxykinase

<400> SEQUENCE: 8

atg act act gct gca atc agg ggc ctt cag ggc gag gcg ccg acc aag       48
Met Thr Thr Ala Ala Ile Arg Gly Leu Gln Gly Glu Ala Pro Thr Lys
  1               5                  10                  15

aat aag gaa ctg ctg aac tgg atc gca gac gcc gtc gag ctc ttc cag       96
Asn Lys Glu Leu Leu Asn Trp Ile Ala Asp Ala Val Glu Leu Phe Gln
            20                  25                  30
```

```
cct gag gct gtt gtg ttc gtt gat gga tcc cag gct gag tgg gat cgc      144
Pro Glu Ala Val Val Phe Val Asp Gly Ser Gln Ala Glu Trp Asp Arg
        35                  40                  45

atg gcg gag gat ctt gtt gaa gcc ggt acc ctc atc aag ctc aac gag      192
Met Ala Glu Asp Leu Val Glu Ala Gly Thr Leu Ile Lys Leu Asn Glu
    50                  55                  60

gaa aag cgt ccg aac agc tac cta gct cgt tcc aac cca tct gac gtt      240
Glu Lys Arg Pro Asn Ser Tyr Leu Ala Arg Ser Asn Pro Ser Asp Val
65                  70                  75                  80

gcg cgc gtt gag tcc cgc acc ttc atc tgc tcc gag aag gaa gaa gat      288
Ala Arg Val Glu Ser Arg Thr Phe Ile Cys Ser Glu Lys Glu Glu Asp
                85                  90                  95

gct ggc cca acc aac aac tgg gct cca cca cag gca atg aag gac gaa      336
Ala Gly Pro Thr Asn Asn Trp Ala Pro Pro Gln Ala Met Lys Asp Glu
            100                 105                 110

atg tcc aag cat tac gct ggt tcc atg aag ggg cgc acc atg tac gtc      384
Met Ser Lys His Tyr Ala Gly Ser Met Lys Gly Arg Thr Met Tyr Val
        115                 120                 125

gtg cct ttc tgc atg ggt cca atc agc gat ccg gac cct aag ctt ggt      432
Val Pro Phe Cys Met Gly Pro Ile Ser Asp Pro Asp Pro Lys Leu Gly
    130                 135                 140

gtg cag ctc act gac tcc gag tac gtt gtc atg tcc atg cgc atc atg      480
Val Gln Leu Thr Asp Ser Glu Tyr Val Val Met Ser Met Arg Ile Met
145                 150                 155                 160

acc cgc atg ggt att gaa gcg ctg gac aag atc ggc gcg aac ggc agc      528
Thr Arg Met Gly Ile Glu Ala Leu Asp Lys Ile Gly Ala Asn Gly Ser
                165                 170                 175

ttc gtc agg tgc ctc cac tcc gtt ggt gct cct ttg gag cca ggc cag      576
Phe Val Arg Cys Leu His Ser Val Gly Ala Pro Leu Glu Pro Gly Gln
            180                 185                 190

gaa gac gtt gca tgg cct tgc aac gac acc aag tac atc acc cag ttc      624
Glu Asp Val Ala Trp Pro Cys Asn Asp Thr Lys Tyr Ile Thr Gln Phe
        195                 200                 205

cca gag acc aag gaa att tgg tcc tac ggt tcc ggc tac ggc gga aac      672
Pro Glu Thr Lys Glu Ile Trp Ser Tyr Gly Ser Gly Tyr Gly Gly Asn
    210                 215                 220

gca atc ctg gca aag aag tgc tac gca ctg cgt atc gca tct gtc atg      720
Ala Ile Leu Ala Lys Lys Cys Tyr Ala Leu Arg Ile Ala Ser Val Met
225                 230                 235                 240

gct cgc gaa gaa gga tgg atg gct gag cac atg ctc atc ctg aag ctg      768
Ala Arg Glu Glu Gly Trp Met Ala Glu His Met Leu Ile Leu Lys Leu
                245                 250                 255

atc aac cca gag ggc aag gcg tac cac atc gca gca gca ttc cca tct      816
Ile Asn Pro Glu Gly Lys Ala Tyr His Ile Ala Ala Ala Phe Pro Ser
            260                 265                 270

gct tgt ggc aag acc aac ctc gcc atg atc act cca acc atc cca ggc      864
Ala Cys Gly Lys Thr Asn Leu Ala Met Ile Thr Pro Thr Ile Pro Gly
        275                 280                 285

tgg acc gct cag gtt gtt ggc gac gac atc gct tgg ctg aag ctg cgc      912
Trp Thr Ala Gln Val Val Gly Asp Asp Ile Ala Trp Leu Lys Leu Arg
    290                 295                 300

gag gac ggc ctc tac gca gtt aac cca gaa aat ggt ttc ttc ggt gtt      960
Glu Asp Gly Leu Tyr Ala Val Asn Pro Glu Asn Gly Phe Phe Gly Val
305                 310                 315                 320

gct cca ggc acc aac tac gca tcc aac cca atc gcg atg aag acc atg     1008
Ala Pro Gly Thr Asn Tyr Ala Ser Asn Pro Ile Ala Met Lys Thr Met
                325                 330                 335

gaa cca ggc aac acc ctg ttc acc aac gtg gca ctc acc gac gac ggc     1056
Glu Pro Gly Asn Thr Leu Phe Thr Asn Val Ala Leu Thr Asp Asp Gly
```

```
            340                 345                 350

gac atc tgg tgg gaa ggc atg gac ggc gac gcc cca gct cac ctc att     1104
Asp Ile Trp Trp Glu Gly Met Asp Gly Asp Ala Pro Ala His Leu Ile
        355                 360                 365

gac tgg atg ggc aac gac tgg acc cca gag tcc gac gaa aac gct gct     1152
Asp Trp Met Gly Asn Asp Trp Thr Pro Glu Ser Asp Glu Asn Ala Ala
    370                 375                 380

cac cct aac tcc cgt tac tgc gta gca atc gac cag tcc cca gca gca     1200
His Pro Asn Ser Arg Tyr Cys Val Ala Ile Asp Gln Ser Pro Ala Ala
385                 390                 395                 400

gca cct gag ttc aac gac tgg gaa ggc gtc aag atc gac gca atc ctc     1248
Ala Pro Glu Phe Asn Asp Trp Glu Gly Val Lys Ile Asp Ala Ile Leu
                405                 410                 415

ttc ggt gga cgt cgc gca gac acc gtc cca ctg gtt acc cag acc tac     1296
Phe Gly Gly Arg Arg Ala Asp Thr Val Pro Leu Val Thr Gln Thr Tyr
            420                 425                 430

gac tgg gag cac ggc acc atg gtt ggt gca ctg ctc gca tcc ggt cag     1344
Asp Trp Glu His Gly Thr Met Val Gly Ala Leu Leu Ala Ser Gly Gln
        435                 440                 445

acc gca gct tcc gca gaa gca aag gtc ggc aca ctc cgc cac gac cca     1392
Thr Ala Ala Ser Ala Glu Ala Lys Val Gly Thr Leu Arg His Asp Pro
    450                 455                 460

atg gca atg ctc cca ttc att ggc tac aac gct ggt gaa tac ctg cag     1440
Met Ala Met Leu Pro Phe Ile Gly Tyr Asn Ala Gly Glu Tyr Leu Gln
465                 470                 475                 480

aac tgg att gac atg ggt aac aag ggt ggc gac aag atg cca tcc atc     1488
Asn Trp Ile Asp Met Gly Asn Lys Gly Gly Asp Lys Met Pro Ser Ile
                485                 490                 495

ttc ctg gtc aac tgg ttc cgc cgt ggc gaa gat gga cgc ttc ctg tgg     1536
Phe Leu Val Asn Trp Phe Arg Arg Gly Glu Asp Gly Arg Phe Leu Trp
            500                 505                 510

cct ggc ttc ggc gac aac tct cgc gtt ctg aag tgg gtc atc gac cgc     1584
Pro Gly Phe Gly Asp Asn Ser Arg Val Leu Lys Trp Val Ile Asp Arg
        515                 520                 525

atc gaa ggc cac gtt ggc gca gac gag acc gtt gtt gga cac acc gct     1632
Ile Glu Gly His Val Gly Ala Asp Glu Thr Val Val Gly His Thr Ala
    530                 535                 540

aag gcc gaa gac ctc gac ctc gac ggc ctc gac acc cca att gag gat     1680
Lys Ala Glu Asp Leu Asp Leu Asp Gly Leu Asp Thr Pro Ile Glu Asp
545                 550                 555                 560

gtc aag gaa gca ctg acc gct cct gca gag cag tgg gca aac gac gtt     1728
Val Lys Glu Ala Leu Thr Ala Pro Ala Glu Gln Trp Ala Asn Asp Val
                565                 570                 575

gaa gac aac gcc gag tac ctc act ttc ctc gga cca cgt gtt cct gca     1776
Glu Asp Asn Ala Glu Tyr Leu Thr Phe Leu Gly Pro Arg Val Pro Ala
            580                 585                 590

gag gtt cac agc cag ttc gat gct ctg aag gcc cgc att tca gca gct     1824
Glu Val His Ser Gln Phe Asp Ala Leu Lys Ala Arg Ile Ser Ala Ala
        595                 600                 605

cac gct   taa                                                       1833
His Ala
    610
```

```
<210> SEQ ID NO 9
<211> LENGTH: 610
<212> TYPE: PRT
<213> ORGANISM: Corynebacterium glutamicum
<220> FEATURE:
<221> NAME/KEY: PEPTIDE
<222> LOCATION: (1)..(610)
<223> OTHER INFORMATION: Pck, amino acid sequence of C. glutamicum PEP-
```

carboxykinase

<400> SEQUENCE: 9

```
Met Thr Thr Ala Ala Ile Arg Gly Leu Gln Gly Glu Ala Pro Thr Lys
1               5                   10                  15

Asn Lys Glu Leu Leu Asn Trp Ile Ala Asp Ala Val Glu Leu Phe Gln
            20                  25                  30

Pro Glu Ala Val Val Phe Val Asp Gly Ser Gln Ala Glu Trp Asp Arg
        35                  40                  45

Met Ala Glu Asp Leu Val Glu Ala Gly Thr Leu Ile Lys Leu Asn Glu
    50                  55                  60

Glu Lys Arg Pro Asn Ser Tyr Leu Ala Arg Ser Asn Pro Ser Asp Val
65                  70                  75                  80

Ala Arg Val Glu Ser Arg Thr Phe Ile Cys Ser Glu Lys Glu Glu Asp
                85                  90                  95

Ala Gly Pro Thr Asn Asn Trp Ala Pro Pro Gln Ala Met Lys Asp Glu
            100                 105                 110

Met Ser Lys His Tyr Ala Gly Ser Met Lys Gly Arg Thr Met Tyr Val
        115                 120                 125

Val Pro Phe Cys Met Gly Pro Ile Ser Asp Pro Asp Pro Lys Leu Gly
    130                 135                 140

Val Gln Leu Thr Asp Ser Glu Tyr Val Val Met Ser Met Arg Ile Met
145                 150                 155                 160

Thr Arg Met Gly Ile Glu Ala Leu Asp Lys Ile Gly Ala Asn Gly Ser
                165                 170                 175

Phe Val Arg Cys Leu His Ser Val Gly Ala Pro Leu Glu Pro Gly Gln
            180                 185                 190

Glu Asp Val Ala Trp Pro Cys Asn Asp Thr Lys Tyr Ile Thr Gln Phe
        195                 200                 205

Pro Glu Thr Lys Glu Ile Trp Ser Tyr Gly Ser Gly Tyr Gly Gly Asn
    210                 215                 220

Ala Ile Leu Ala Lys Lys Cys Tyr Ala Leu Arg Ile Ala Ser Val Met
225                 230                 235                 240

Ala Arg Glu Glu Gly Trp Met Ala Glu His Met Leu Ile Leu Lys Leu
                245                 250                 255

Ile Asn Pro Glu Gly Lys Ala Tyr His Ile Ala Ala Ala Phe Pro Ser
            260                 265                 270

Ala Cys Gly Lys Thr Asn Leu Ala Met Ile Thr Pro Thr Ile Pro Gly
        275                 280                 285

Trp Thr Ala Gln Val Val Gly Asp Asp Ile Ala Trp Leu Lys Leu Arg
    290                 295                 300

Glu Asp Gly Leu Tyr Ala Val Asn Pro Glu Asn Gly Phe Phe Gly Val
305                 310                 315                 320

Ala Pro Gly Thr Asn Tyr Ala Ser Asn Pro Ile Ala Met Lys Thr Met
                325                 330                 335

Glu Pro Gly Asn Thr Leu Phe Thr Asn Val Ala Leu Thr Asp Asp Gly
            340                 345                 350

Asp Ile Trp Trp Glu Gly Met Asp Gly Asp Ala Pro Ala His Leu Ile
        355                 360                 365

Asp Trp Met Gly Asn Asp Trp Thr Pro Glu Ser Asp Glu Asn Ala Ala
    370                 375                 380

His Pro Asn Ser Arg Tyr Cys Val Ala Ile Asp Gln Ser Pro Ala Ala
385                 390                 395                 400
```

```
Ala Pro Glu Phe Asn Asp Trp Glu Gly Val Lys Ile Asp Ala Ile Leu
                405                 410                 415

Phe Gly Gly Arg Arg Ala Asp Thr Val Pro Leu Val Thr Gln Thr Tyr
            420                 425                 430

Asp Trp Glu His Gly Thr Met Val Gly Ala Leu Leu Ala Ser Gly Gln
        435                 440                 445

Thr Ala Ala Ser Ala Glu Ala Lys Val Gly Thr Leu Arg His Asp Pro
    450                 455                 460

Met Ala Met Leu Pro Phe Ile Gly Tyr Asn Ala Gly Glu Tyr Leu Gln
465                 470                 475                 480

Asn Trp Ile Asp Met Gly Asn Lys Gly Gly Asp Lys Met Pro Ser Ile
                485                 490                 495

Phe Leu Val Asn Trp Phe Arg Arg Gly Glu Asp Gly Arg Phe Leu Trp
            500                 505                 510

Pro Gly Phe Gly Asp Asn Ser Arg Val Leu Lys Trp Val Ile Asp Arg
        515                 520                 525

Ile Glu Gly His Val Gly Ala Asp Glu Thr Val Val Gly His Thr Ala
    530                 535                 540

Lys Ala Glu Asp Leu Asp Leu Asp Gly Leu Asp Thr Pro Ile Glu Asp
545                 550                 555                 560

Val Lys Glu Ala Leu Thr Ala Pro Ala Glu Gln Trp Ala Asn Asp Val
                565                 570                 575

Glu Asp Asn Ala Glu Tyr Leu Thr Phe Leu Gly Pro Arg Val Pro Ala
            580                 585                 590

Glu Val His Ser Gln Phe Asp Ala Leu Lys Ala Arg Ile Ser Ala Ala
        595                 600                 605

His Ala
    610
```

```
<210> SEQ ID NO 10
<211> LENGTH: 927
<212> TYPE: DNA
<213> ORGANISM: Corynebacterium glutamicum
<220> FEATURE:
<221> NAME/KEY: misc_feature
<222> LOCATION: (1)..(927)
<223> OTHER INFORMATION: pck, DNA sequence encoding C. glutamicum PEP-
      carboxykinase with deletion of 927 bp, nucleotides 510 to 1436 of
      wildtype PEP-carboxykinase and artificially introduced nucleotides
      at positions 510 to 531

<400> SEQUENCE: 10

atgactactg ctgcaatcag gggccttcag ggcgaggcgc cgaccaagaa taaggaactg     60

ctgaactgga tcgcagacgc cgtcgagctc ttccagcctg aggctgttgt gttcgttgat    120

ggatcccagg ctgagtggga tcgcatggcg gaggatcttg ttgaagccgg taccctcatc    180

aagctcaacg aggaaaagcg tccgaacagc tacctagctc gttccaaccc atctgacgtt    240

gcgcgcgttg agtcccgcac cttcatctgc tccgagaagg aagaagatgc tggcccaacc    300

aacaactggg ctccaccaca ggcaatgaag gacgaaatgt ccaagcatta cgctggttcc    360

atgaaggggc gcaccatgta cgtcgtgcct ttctgcatgg gtccaatcag cgatccggac    420

cctaagcttg gtgtgcagct cactgactcc gagtacgttg tcatgtccat gcgcatcatg    480

acccgcatgg gtattgaagc gctggacaat gtttaagttt agtggatggg gcagaactgg    540

attgacatgg gtaacaaggg tggcgacaag atgccatcca tcttcctggt caactggttc    600

cgccgtggcg aagatggacg cttcctgtgg cctggcttcg gcgacaactc tcgcgttctg    660
```

```
aagtgggtca tcgaccgcat cgaaggccac gttggcgcag acgagaccgt tgttggacac    720

accgctaagg ccgaagacct cgacctcgac ggcctcgaca ccccaattga ggatgtcaag    780

gaagcactga ccgctcctgc agagcagtgg gcaaacgacg ttgaagacaa cgccgagtac    840

ctcactttcc tcggaccacg tgttcctgca gaggttcaca gccagttcga tgctctgaag    900

gcccgcattt cagcagctca cgcttaa                                        927
```

```
<210> SEQ ID NO 11
<211> LENGTH: 171
<212> TYPE: PRT
<213> ORGANISM: Corynebacterium glutamicum
<220> FEATURE:
<221> NAME/KEY: PEPTIDE
<222> LOCATION: (1)..(171)
<223> OTHER INFORMATION: Pck, amino acid sequence encoded by SEQ ID NO:
      10

<400> SEQUENCE: 11

Met Thr Thr Ala Ala Ile Arg Gly Leu Gln Gly Glu Ala Pro Thr Lys
  1               5                  10                  15

Asn Lys Glu Leu Leu Asn Trp Ile Ala Asp Ala Val Glu Leu Phe Gln
             20                  25                  30

Pro Glu Ala Val Val Phe Val Asp Gly Ser Gln Ala Glu Trp Asp Arg
         35                  40                  45

Met Ala Glu Asp Leu Val Glu Ala Gly Thr Leu Ile Lys Leu Asn Glu
     50                  55                  60

Glu Lys Arg Pro Asn Ser Tyr Leu Ala Arg Ser Asn Pro Ser Asp Val
 65                  70                  75                  80

Ala Arg Val Glu Ser Arg Thr Phe Ile Cys Ser Glu Lys Glu Glu Asp
                 85                  90                  95

Ala Gly Pro Thr Asn Asn Trp Ala Pro Pro Gln Ala Met Lys Asp Glu
            100                 105                 110

Met Ser Lys His Tyr Ala Gly Ser Met Lys Gly Arg Thr Met Tyr Val
        115                 120                 125

Val Pro Phe Cys Met Gly Pro Ile Ser Asp Pro Asp Pro Lys Leu Gly
    130                 135                 140

Val Gln Leu Thr Asp Ser Glu Tyr Val Val Met Ser Met Arg Ile Met
145                 150                 155                 160

Thr Arg Met Gly Ile Glu Ala Leu Asp Asn Val
                165                 170
```

```
<210> SEQ ID NO 12
<211> LENGTH: 947
<212> TYPE: DNA
<213> ORGANISM: Corynebacterium glutamicum
<220> FEATURE:
<221> NAME/KEY: CDS
<222> LOCATION: (201)..(944)
<223> OTHER INFORMATION: dapB, DNA sequence encoding wildtype C.
      glutamicum dihydrodipicolinate reductase with natural promoter

<400> SEQUENCE: 12

aagggcaact taagtctcat atttcaaaca tagttccacc tgtgtgatta atccctagaa     60

cggaacaaac tgatgaacaa tcgttaacaa cacagaccaa aacggtcagt taggtatgga    120

tatcagcacc ttctgaacgg gtacgtctag actggtgggc gtttgaaaaa ctcttcgccc    180

cacgaaaatg aaggagcata atg gga atc aag gtt ggc gtt ctc gga gcc aaa    233
                      Met Gly Ile Lys Val Gly Val Leu Gly Ala Lys
                        1               5                  10
```

```
ggc cgt gtt ggt caa act att gtg gca gca gtc aat gag tcc gac gat      281
Gly Arg Val Gly Gln Thr Ile Val Ala Ala Val Asn Glu Ser Asp Asp
            15                  20                  25

ctg gag ctt gtt gca gag atc ggc gtc gac gat gat ttg agc ctt ctg      329
Leu Glu Leu Val Ala Glu Ile Gly Val Asp Asp Asp Leu Ser Leu Leu
        30                  35                  40

gta gac aac ggc gct gaa gtt gtc gtt gac ttc acc act cct aac gct      377
Val Asp Asn Gly Ala Glu Val Val Val Asp Phe Thr Thr Pro Asn Ala
    45                  50                  55

gtg atg ggc aac ctg gag ttc tgc atc aac aac ggc att tct gcg gtt      425
Val Met Gly Asn Leu Glu Phe Cys Ile Asn Asn Gly Ile Ser Ala Val
 60                 65                  70                  75

gtt gga acc acg ggc ttc gat gat gct cgt ttg gag cag gtt cgc gac      473
Val Gly Thr Thr Gly Phe Asp Asp Ala Arg Leu Glu Gln Val Arg Asp
                80                  85                  90

tgg ctt gaa gga aaa gac aat gtc ggt gtt ctg atc gca cct aac ttt      521
Trp Leu Glu Gly Lys Asp Asn Val Gly Val Leu Ile Ala Pro Asn Phe
            95                  100                 105

gct atc tct gcg gtg ttg acc atg gtc ttt tcc aag cag gct gcc cgc      569
Ala Ile Ser Ala Val Leu Thr Met Val Phe Ser Lys Gln Ala Ala Arg
        110                 115                 120

ttc ttc gaa tca gct gaa gtt att gag ctg cac cac ccc aac aag ctg      617
Phe Phe Glu Ser Ala Glu Val Ile Glu Leu His His Pro Asn Lys Leu
    125                 130                 135

gat gca cct tca ggc acc gcg atc cac act gct cag ggc att gct gcg      665
Asp Ala Pro Ser Gly Thr Ala Ile His Thr Ala Gln Gly Ile Ala Ala
140                 145                 150                 155

gca cgc aaa gaa gca ggc atg gac gca cag cca gat gcg acc gag cag      713
Ala Arg Lys Glu Ala Gly Met Asp Ala Gln Pro Asp Ala Thr Glu Gln
                160                 165                 170

gca ctt gag ggt tcc cgt ggc gca agc gta gat gga atc ccg gtt cat      761
Ala Leu Glu Gly Ser Arg Gly Ala Ser Val Asp Gly Ile Pro Val His
            175                 180                 185

gca gtc cgc atg tcc ggc atg gtt gct cac gag caa gtt atc ttt ggc      809
Ala Val Arg Met Ser Gly Met Val Ala His Glu Gln Val Ile Phe Gly
        190                 195                 200

acc cag ggt cag acc ttg acc atc aag cag gac tcc tat gat cgc aac      857
Thr Gln Gly Gln Thr Leu Thr Ile Lys Gln Asp Ser Tyr Asp Arg Asn
    205                 210                 215

tca ttt gca cca ggt gtc ttg gtg ggt gtg cgc aac att gca cag cac      905
Ser Phe Ala Pro Gly Val Leu Val Gly Val Arg Asn Ile Ala Gln His
220                 225                 230                 235

cca ggc cta gtc gta gga ctt gag cat tac cta ggc ctg        taa       947
Pro Gly Leu Val Val Gly Leu Glu His Tyr Leu Gly Leu
                240                 245
```

<210> SEQ ID NO 13
<211> LENGTH: 248
<212> TYPE: PRT
<213> ORGANISM: Corynebacterium glutamicum
<220> FEATURE:
<221> NAME/KEY: PEPTIDE
<222> LOCATION: (1)..(248)
<223> OTHER INFORMATION: DapB, amino acid sequence of C. glutamicum dihydrodipicolinate reductase dapB, DNA sequence encoding C. glutamicum dihydrodipicolinate reductase

<400> SEQUENCE: 13

```
Met Gly Ile Lys Val Gly Val Leu Gly Ala Lys Gly Arg Val Gly Gln
  1               5                  10                  15

Thr Ile Val Ala Ala Val Asn Glu Ser Asp Asp Leu Glu Leu Val Ala
            20                  25                  30
```

```
Glu Ile Gly Val Asp Asp Asp Leu Ser Leu Leu Val Asp Asn Gly Ala
        35                  40                  45

Glu Val Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
65                  70                  75                  80

Phe Asp Asp Ala Arg Leu Glu Gln Val Arg Asp Trp Leu Glu Gly Lys
                85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245
```

```
<210> SEQ ID NO 14
<211> LENGTH: 939
<212> TYPE: DNA
<213> ORGANISM: Corynebacterium glutamicum
<220> FEATURE:
<221> NAME/KEY: CDS
<222> LOCATION: (193)..(936)
<223> OTHER INFORMATION: dapB-DNA sequence with sod-promoter instead
      natural promoter of C. glutamicum

<400> SEQUENCE: 14

tagctgccaa ttattccggg cttgtgaccc gctacccgat aaataggtcg gctgaaaaat      60

ttcgttgcaa tataaacaaa aaggcctctc attgggaggt gtcgcaccaa gtacttttgc     120

gaagcgccat ctgacggatt ttcaaaagat gtatatgctc ggtgcggaaa cctacgaaag     180

gattttttac cc         atg gga atc aag gtt ggc gtt ctc gga gcc aaa     225
                      Met Gly Ile Lys Val Gly Val Leu Gly Ala Lys
                        1               5                   10

ggc cgt gtt ggt caa act att gtg gca gca gtc aat gag tcc gac gat       273
Gly Arg Val Gly Gln Thr Ile Val Ala Ala Val Asn Glu Ser Asp Asp
            15                  20                  25

ctg gag ctt gtt gca gag atc ggc gtc gac gat gat ttg agc ctt ctg       321
Leu Glu Leu Val Ala Glu Ile Gly Val Asp Asp Asp Leu Ser Leu Leu
        30                  35                  40

gta gac aac ggc gct gaa gtt gtc gtt gac ttc acc act cct aac gct       369
Val Asp Asn Gly Ala Glu Val Val Val Asp Phe Thr Thr Pro Asn Ala
    45                  50                  55

gtg atg ggc aac ctg gag ttc tgc atc aac aac ggc att tct gcg gtt       417
```

```
Val Met Gly Asn Leu Glu Phe Cys Ile Asn Asn Gly Ile Ser Ala Val
 60                  65                  70                  75

gtt gga acc acg ggc ttc gat gat gct cgt ttg gag cag gtt cgc gac      465
Val Gly Thr Thr Gly Phe Asp Asp Ala Arg Leu Glu Gln Val Arg Asp
                 80                  85                  90

tgg ctt gaa gga aaa gac aat gtc ggt gtt ctg atc gca cct aac ttt      513
Trp Leu Glu Gly Lys Asp Asn Val Gly Val Leu Ile Ala Pro Asn Phe
             95                 100                 105

gct atc tct gcg gtg ttg acc atg gtc ttt tcc aag cag gct gcc cgc      561
Ala Ile Ser Ala Val Leu Thr Met Val Phe Ser Lys Gln Ala Ala Arg
        110                 115                 120

ttc ttc gaa tca gct gaa gtt att gag ctg cac cac ccc aac aag ctg      609
Phe Phe Glu Ser Ala Glu Val Ile Glu Leu His His Pro Asn Lys Leu
    125                 130                 135

gat gca cct tca ggc acc gcg atc cac act gct cag ggc att gct gcg      657
Asp Ala Pro Ser Gly Thr Ala Ile His Thr Ala Gln Gly Ile Ala Ala
140                 145                 150                 155

gca cgc aaa gaa gca ggc atg gac gca cag cca gat gcg acc gag cag      705
Ala Arg Lys Glu Ala Gly Met Asp Ala Gln Pro Asp Ala Thr Glu Gln
                160                 165                 170

gca ctt gag ggt tcc cgt ggc gca agc gta gat gga atc ccg gtt cat      753
Ala Leu Glu Gly Ser Arg Gly Ala Ser Val Asp Gly Ile Pro Val His
            175                 180                 185

gca gtc cgc atg tcc ggc atg gtt gct cac gag caa gtt atc ttt ggc      801
Ala Val Arg Met Ser Gly Met Val Ala His Glu Gln Val Ile Phe Gly
        190                 195                 200

acc cag ggt cag acc ttg acc atc aag cag gac tcc tat gat cgc aac      849
Thr Gln Gly Gln Thr Leu Thr Ile Lys Gln Asp Ser Tyr Asp Arg Asn
    205                 210                 215

tca ttt gca cca ggt gtc ttg gtg ggt gtg cgc aac att gca cag cac      897
Ser Phe Ala Pro Gly Val Leu Val Gly Val Arg Asn Ile Ala Gln His
220                 225                 230                 235

cca ggc cta gtc gta gga ctt gag cat tac cta ggc ctg          taa     939
Pro Gly Leu Val Val Gly Leu Glu His Tyr Leu Gly Leu
                240                 245
```

<210> SEQ ID NO 15
<211> LENGTH: 3506
<212> TYPE: DNA
<213> ORGANISM: Corynebacterium glutamicum
<220> FEATURE:
<221> NAME/KEY: CDS
<222> LOCATION: (514)..(2163)
<223> OTHER INFORMATION: Gene cluster encoding wildtype argS (arginyl-tRNA-synthetase) and lysA (diaminopimelate decarboxylase) including natural promoter sequence
<220> FEATURE:
<221> NAME/KEY: CDS
<222> LOCATION: (2169)..(3503)
<223> OTHER INFORMATION: Gene cluster encoding wildtype argS (arginyl-tRNA-synthetase) and lysA (diaminopimelate decarboxylase) including natural promoter sequence

<400> SEQUENCE: 15

```
ggctgcactg caacgaggtc gtagttttgg tacatggctt ctggccagtt catggattgg      60

ctgccgaaga agctataggc atcgccacca gggccaccgg agttaccgaa gatggtgccg     120

tgcttttcgc cttgggcagg gaccttgaca aagcccacgc tgatatcgcc aagtgaggga     180

tcagaatagt gcatgggcac gtcgatgctg ccacattgag cggaggcaat atctacctga     240

ggtgggcatt cttcccagcg gatgttttct tgcgctgctg cagtgggcat tgataccaaa     300

aaggggctaa gcgcagtcga ggcggcaaga actgctacta ccctttttat tgtcgaacgg     360
```

```
ggcattacgg ctccaaggac gtttgttttc tgggtcagtt accccaaaaa gcatatacag    420

agaccaatga tttttcatta aaaaggcagg gatttgttat aagtatgggt cgtattctgt    480

gcgacgggtg tacctcggct agaatttctc ccc atg aca cca gct gat ctc gca     534
                                     Met Thr Pro Ala Asp Leu Ala
                                     1               5

aca ttg att aaa gag acc gcg gta gag gtt ttg acc tcc cgc gag ctc      582
Thr Leu Ile Lys Glu Thr Ala Val Glu Val Leu Thr Ser Arg Glu Leu
        10                  15                  20

gat act tct gtt ctt ccg gag cag gta gtt gtg gag cgt ccg cgt aac      630
Asp Thr Ser Val Leu Pro Glu Gln Val Val Val Glu Arg Pro Arg Asn
    25                  30                  35

cca gag cac ggc gat tac gcc acc aac att gca ttg cag gtg gct aaa      678
Pro Glu His Gly Asp Tyr Ala Thr Asn Ile Ala Leu Gln Val Ala Lys
40                  45                  50                  55

aag gtc ggt cag aac cct cgg gat ttg gct acc tgg ctg gca gag gca      726
Lys Val Gly Gln Asn Pro Arg Asp Leu Ala Thr Trp Leu Ala Glu Ala
                60                  65                  70

ttg gct gca gat gac gcc att gat tct gct gaa att gct ggc cca ggc      774
Leu Ala Ala Asp Asp Ala Ile Asp Ser Ala Glu Ile Ala Gly Pro Gly
            75                  80                  85

ttt ttg aac att cgc ctt gct gca gca gca cag ggt gaa att gtg gcc      822
Phe Leu Asn Ile Arg Leu Ala Ala Ala Ala Gln Gly Glu Ile Val Ala
        90                  95                  100

aag att ctg gca cag ggc gag act ttc gga aac tcc gat cac ctt tcc      870
Lys Ile Leu Ala Gln Gly Glu Thr Phe Gly Asn Ser Asp His Leu Ser
    105                 110                 115

cac ttg gac gtg aac ctc gag ttc gtt tct gca aac cca acc gga cct      918
His Leu Asp Val Asn Leu Glu Phe Val Ser Ala Asn Pro Thr Gly Pro
120                 125                 130                 135

att cac ctt ggc gga acc cgc tgg gct gcc gtg ggt gac tct ttg ggt      966
Ile His Leu Gly Gly Thr Arg Trp Ala Ala Val Gly Asp Ser Leu Gly
                140                 145                 150

cgt gtg ctg gag gct tcc ggc gcg aaa gtg acc cgc gaa tac tac ttc     1014
Arg Val Leu Glu Ala Ser Gly Ala Lys Val Thr Arg Glu Tyr Tyr Phe
            155                 160                 165

aac gat cac ggt cgc cag atc gat cgt ttc gct ttg tcc ctt ctt gca     1062
Asn Asp His Gly Arg Gln Ile Asp Arg Phe Ala Leu Ser Leu Leu Ala
        170                 175                 180

gcg gcg aag ggc gag cca acg cca gaa gac ggt tat ggc ggc gaa tac     1110
Ala Ala Lys Gly Glu Pro Thr Pro Glu Asp Gly Tyr Gly Gly Glu Tyr
    185                 190                 195

att aag gaa att gcg gag gca atc gtc gaa aag cat cct gaa gcg ttg     1158
Ile Lys Glu Ile Ala Glu Ala Ile Val Glu Lys His Pro Glu Ala Leu
200                 205                 210                 215

gct ttg gag cct gcc gca acc cag gag ctt ttc cgc gct gaa ggc gtg     1206
Ala Leu Glu Pro Ala Ala Thr Gln Glu Leu Phe Arg Ala Glu Gly Val
                220                 225                 230

gag atg atg ttc gag cac atc aaa tct tcc ctg cat gag ttc ggc acc     1254
Glu Met Met Phe Glu His Ile Lys Ser Ser Leu His Glu Phe Gly Thr
            235                 240                 245

gat ttc gat gtc tac tac cac gag aac tcc ctg ttc gag tcc ggt gcg     1302
Asp Phe Asp Val Tyr Tyr His Glu Asn Ser Leu Phe Glu Ser Gly Ala
        250                 255                 260

gtg gac aag gcc gtg cag gtg ctg aag gac aac ggc aac ctg tac gaa     1350
Val Asp Lys Ala Val Gln Val Leu Lys Asp Asn Gly Asn Leu Tyr Glu
    265                 270                 275

aac gag ggc gct tgg tgg ctg cgt tcc acc gaa ttc ggc gat gac aaa     1398
Asn Glu Gly Ala Trp Trp Leu Arg Ser Thr Glu Phe Gly Asp Asp Lys
280                 285                 290                 295
```

```
gac cgc gtg gtg atc aag tct gac ggc gac gca gcc tac atc gct ggc      1446
Asp Arg Val Val Ile Lys Ser Asp Gly Asp Ala Ala Tyr Ile Ala Gly
                300                 305                 310

gat atc gcg tac gtg gct gat aag ttc tcc cgc gga cac aac cta aac      1494
Asp Ile Ala Tyr Val Ala Asp Lys Phe Ser Arg Gly His Asn Leu Asn
            315                 320                 325

atc tac atg ttg ggt gct gac cac cat ggt tac atc gcg cgc ctg aag      1542
Ile Tyr Met Leu Gly Ala Asp His His Gly Tyr Ile Ala Arg Leu Lys
        330                 335                 340

gca gcg gcg gcg gca ctt ggc tac aag cca gaa ggc gtt gaa gtc ctg      1590
Ala Ala Ala Ala Ala Leu Gly Tyr Lys Pro Glu Gly Val Glu Val Leu
    345                 350                 355

att ggc cag atg gtg aac ctg ctt cgc gac ggc aag gca gtg cgt atg      1638
Ile Gly Gln Met Val Asn Leu Leu Arg Asp Gly Lys Ala Val Arg Met
360                 365                 370                 375

tcc aag cgt gca ggc acc gtg gtc acc cta gat gac ctc gtt gaa gca      1686
Ser Lys Arg Ala Gly Thr Val Val Thr Leu Asp Asp Leu Val Glu Ala
                380                 385                 390

atc ggc atc gat gcg gcg cgt tac tcc ctg atc cgt tcc tcc gtg gat      1734
Ile Gly Ile Asp Ala Ala Arg Tyr Ser Leu Ile Arg Ser Ser Val Asp
            395                 400                 405

tct tcc ctg gat atc gat ctc ggc ctg tgg gaa tcc cag tcc tcc gac      1782
Ser Ser Leu Asp Ile Asp Leu Gly Leu Trp Glu Ser Gln Ser Ser Asp
        410                 415                 420

aac cct gtg tac tac gtg cag tac gga cac gct cgt ctg tgc tcc atc      1830
Asn Pro Val Tyr Tyr Val Gln Tyr Gly His Ala Arg Leu Cys Ser Ile
    425                 430                 435

gcg cgc aag gca gag acc ttg ggt gtc acc gag gaa ggc gca gac cta      1878
Ala Arg Lys Ala Glu Thr Leu Gly Val Thr Glu Glu Gly Ala Asp Leu
440                 445                 450                 455

tct cta ctg acc cac gac cgc gaa ggc gat ctc atc cgc aca ctc gga      1926
Ser Leu Leu Thr His Asp Arg Glu Gly Asp Leu Ile Arg Thr Leu Gly
                460                 465                 470

gag ttc cca gca gtg gtg aag gct gcc gct gac cta cgt gaa cca cac      1974
Glu Phe Pro Ala Val Val Lys Ala Ala Ala Asp Leu Arg Glu Pro His
            475                 480                 485

cgc att gcc cgc tat gct gag gaa tta gct gga act ttc cac cgc ttc      2022
Arg Ile Ala Arg Tyr Ala Glu Glu Leu Ala Gly Thr Phe His Arg Phe
        490                 495                 500

tac gat tcc tgc cac atc ctt cca aag gtt gat gag gat acg gca cca      2070
Tyr Asp Ser Cys His Ile Leu Pro Lys Val Asp Glu Asp Thr Ala Pro
    505                 510                 515

atc cac aca gca cgt ctg gca ctt gca gca gca acc cgc cag acc ctc      2118
Ile His Thr Ala Arg Leu Ala Leu Ala Ala Ala Thr Arg Gln Thr Leu
520                 525                 530                 535

gct aac gcc ctg cac ctg gtt ggc gtt tcc gca ccg gag aag atg taaca    2168
Ala Asn Ala Leu His Leu Val Gly Val Ser Ala Pro Glu Lys Met
                540                 545                 550

atg gct aca gtt gaa aat ttc aat gaa ctt ccc gca cac gta tgg cca      2216
Met Ala Thr Val Glu Asn Phe Asn Glu Leu Pro Ala His Val Trp Pro
            555                 560                 565

cgc aat gcc gtg cgc caa gaa gac ggc gtt gtc acc gtc gct ggt gtg      2264
Arg Asn Ala Val Arg Gln Glu Asp Gly Val Val Thr Val Ala Gly Val
        570                 575                 580

cct ctg cct gac ctc gct gaa gaa tac gga acc cca ctg ttc gta gtc      2312
Pro Leu Pro Asp Leu Ala Glu Glu Tyr Gly Thr Pro Leu Phe Val Val
    585                 590                 595

gac gag gac gat ttc cgt tcc cgc tgt cgc gac atg gct acc gca ttc      2360
Asp Glu Asp Asp Phe Arg Ser Arg Cys Arg Asp Met Ala Thr Ala Phe
```

```
    600                 605                 610

ggt gga cca ggc aat gtg cac tac gca tct aaa gcg ttc ctg acc aag      2408
Gly Gly Pro Gly Asn Val His Tyr Ala Ser Lys Ala Phe Leu Thr Lys
615                 620                 625                 630

acc att gca cgt tgg gtt gat gaa gag ggg ctg gca ctg gac att gca      2456
Thr Ile Ala Arg Trp Val Asp Glu Glu Gly Leu Ala Leu Asp Ile Ala
                635                 640                 645

tcc atc aac gaa ctg ggc att gcc ctg gcc gct ggt ttc ccc gcc agc      2504
Ser Ile Asn Glu Leu Gly Ile Ala Leu Ala Ala Gly Phe Pro Ala Ser
            650                 655                 660

cgt atc acc gcg cac ggc aac aac aaa ggc gta gag ttc ctg cgc gcg      2552
Arg Ile Thr Ala His Gly Asn Asn Lys Gly Val Glu Phe Leu Arg Ala
        665                 670                 675

ttg gtt caa aac ggt gtg gga cac gtg gtg ctg gac tcc gca cag gaa      2600
Leu Val Gln Asn Gly Val Gly His Val Val Leu Asp Ser Ala Gln Glu
    680                 685                 690

cta gaa ctg ttg gat tac gtt gcc gct ggt gaa ggc aag att cag gac      2648
Leu Glu Leu Leu Asp Tyr Val Ala Ala Gly Glu Gly Lys Ile Gln Asp
695                 700                 705                 710

gtg ttg atc cgc gta aag cca ggc atc gaa gca cac acc cac gag ttc      2696
Val Leu Ile Arg Val Lys Pro Gly Ile Glu Ala His Thr His Glu Phe
                715                 720                 725

atc gcc act agc cac gaa gac cag aag ttc gga ttc tcc ctg gca tcc      2744
Ile Ala Thr Ser His Glu Asp Gln Lys Phe Gly Phe Ser Leu Ala Ser
            730                 735                 740

ggt tcc gca ttc gaa gca gca aaa gcc gcc aac aac gca gaa aac ctg      2792
Gly Ser Ala Phe Glu Ala Ala Lys Ala Ala Asn Asn Ala Glu Asn Leu
        745                 750                 755

aac ctg gtt ggc ctg cac tgc cac gtt ggt tcc cag gtg ttc gac gcc      2840
Asn Leu Val Gly Leu His Cys His Val Gly Ser Gln Val Phe Asp Ala
    760                 765                 770

gaa ggc ttc aag ctg gca gca gaa cgc gtg ttg ggc ctg tac tca cag      2888
Glu Gly Phe Lys Leu Ala Ala Glu Arg Val Leu Gly Leu Tyr Ser Gln
775                 780                 785                 790

atc cac agc gaa ctg ggc gtt gcc ctt cct gaa ctg gat ctc ggt ggc      2936
Ile His Ser Glu Leu Gly Val Ala Leu Pro Glu Leu Asp Leu Gly Gly
                795                 800                 805

gga tac ggc att gcc tat acc gca gct gaa gaa cca ctc aac gtc gca      2984
Gly Tyr Gly Ile Ala Tyr Thr Ala Ala Glu Glu Pro Leu Asn Val Ala
            810                 815                 820

gaa gtt gcc tcc gac ctg ctc acc gca gtc gga aaa atg gca gcg gaa      3032
Glu Val Ala Ser Asp Leu Leu Thr Ala Val Gly Lys Met Ala Ala Glu
        825                 830                 835

cta ggc atc gac gca cca acc gtg ctt gtt gag ccc ggc cgc gct atc      3080
Leu Gly Ile Asp Ala Pro Thr Val Leu Val Glu Pro Gly Arg Ala Ile
    840                 845                 850

gca ggc ccc tcc acc gtg acc atc tac gaa gtc ggc acc acc aaa gac      3128
Ala Gly Pro Ser Thr Val Thr Ile Tyr Glu Val Gly Thr Thr Lys Asp
855                 860                 865                 870

gtc cac gta gac gac gac aaa acc cgc cgt tac atc gcc gtg gac gga      3176
Val His Val Asp Asp Asp Lys Thr Arg Arg Tyr Ile Ala Val Asp Gly
                875                 880                 885

ggc atg tcc gac aac atc cgc cca gca ctc tac ggc tcc gaa tac gac      3224
Gly Met Ser Asp Asn Ile Arg Pro Ala Leu Tyr Gly Ser Glu Tyr Asp
            890                 895                 900

gcc cgc gta gta tcc cgc ttc gcc gaa gga gac cca gta agc acc cgc      3272
Ala Arg Val Val Ser Arg Phe Ala Glu Gly Asp Pro Val Ser Thr Arg
        905                 910                 915

atc gtg ggc tcc cac tgc gaa tcc ggc gat atc ctg atc aac gat gaa      3320
```

```
Ile Val Gly Ser His Cys Glu Ser Gly Asp Ile Leu Ile Asn Asp Glu
    920                 925                 930

atc tac cca tct gac atc acc agc ggc gac ttc ctt gca ctc gca gcc     3368
Ile Tyr Pro Ser Asp Ile Thr Ser Gly Asp Phe Leu Ala Leu Ala Ala
935                 940                 945                 950

acc ggc gca tac tgc tac gcc atg agc tcc cgc tac aac gcc ttc aca     3416
Thr Gly Ala Tyr Cys Tyr Ala Met Ser Ser Arg Tyr Asn Ala Phe Thr
                955                 960                 965

cgg ccc gcc gtc gtg tcc gtc cgc gct ggc agc tcc cgc ctc atg ctg     3464
Arg Pro Ala Val Val Ser Val Arg Ala Gly Ser Ser Arg Leu Met Leu
            970                 975                 980

cgc cgc gaa acg ctc gac gac atc ctc tca cta gag gca taa             3506
Arg Arg Glu Thr Leu Asp Asp Ile Leu Ser Leu Glu Ala
        985                 990                 995


<210> SEQ ID NO 16
<211> LENGTH: 7091
<212> TYPE: DNA
<213> ORGANISM: Corynebacterium glutamicum
<220> FEATURE:
<221> NAME/KEY: misc_feature
<222> LOCATION: (1)..(7091)
<223> OTHER INFORMATION: Two recombinantly joined copies of DNA
      sequences of argS and lysA including flanking regions

<400> SEQUENCE: 16

gaggctgcac tgcaacgagg tcgtagtttt ggtacatggc ttctggccag ttcatggatt     60

ggctgccgaa gaagctatag gcatcgccac cagggccacc ggagttaccg aagatggtgc    120

cgtgcttttc gccttgggca gggaccttga caaagcccac gctgatatcg ccaagtgagg    180

gatcagaata gtgcatgggc acgtcgatgc tgccacattg agcggaggca atatctacct    240

gaggtgggca ttcttcccag cggatgtttt cttgcgctgc tgcagtgggc attgatacca    300

aaaaggggct aagcgcagtc gaggcggcaa gaactgctac taccctttt attgtcgaac    360

ggggcattac ggctccaagg acgtttgttt tctgggtcag ttaccccaaa aagcatatac    420

agagaccaat gatttttcat taaaaaggca gggatttgtt ataagtatgg gtcgtattct    480

gtgcgacggg tgtacctcgg ctagaatttc tccccatgac accagctgat ctcgcaacat    540

tgattaaaga gaccgcggta gaggttttga cctcccgcga gctcgatact tctgttcttc    600

cggagcaggt agttgtggag cgtccgcgta acccagagca cggcgattac gccaccaaca    660

ttgcattgca ggtggctaaa aaggtcggtc agaaccctcg ggatttggct acctggctgg    720

cagaggcatt ggctgcagat gacgccattg attctgctga aattgctggc ccaggctttt    780

tgaacattcg ccttgctgca gcagcacagg gtgaaattgt ggccaagatt ctggcacagg    840

gcgagacttt cggaaactcc gatcaccttt cccacttgga cgtgaacctc gagttcgttt    900

ctgcaaaccc aaccggacct attcaccttg gcggaacccg ctgggctgcc gtgggtgact    960

ctttgggtcg tgtgctggag gcttccggcg cgaaagtgac ccgcgaatac tacttcaacg   1020

atcacggtcg ccagatcgat cgtttcgctt tgtcccttct tgcagcggcg aagggcgagc   1080

caacgccaga agacggttat ggcggcgaat acattaagga aattgcggag gcaatcgtcg   1140

aaaagcatcc tgaagcgttg gctttggagc ctgccgcaac ccaggagctt ttccgcgctg   1200

aaggcgtgga gatgatgttc gagcacatca aatcttccct gcatgagttc ggcaccgatt   1260

tcgatgtcta ctaccacgag aactccctgt tcgagtccgg tgcggtggac aaggccgtgc   1320

aggtgctgaa ggacaacggc aacctgtacg aaaacgaggg cgcttggtgg ctgcgttcca   1380

ccgaattcgg cgatgacaaa gaccgcgtgg tgatcaagtc tgacggcgac gcagcctaca   1440
```

```
tcgctggcga tatcgcgtac gtggctgata agttctcccg cggacacaac ctaaacatct   1500
acatgttggg tgctgaccac catggttaca tcgcgcgcct gaaggcagcg gcggcggcac   1560
ttggctacaa gccagaaggc gttgaagtcc tgattggcca gatggtgaac ctgcttcgcg   1620
acggcaaggc agtgcgtatg tccaagcgtg caggcaccgt ggtcacccta gatgacctcg   1680
ttgaagcaat cggcatcgat gcggcgcgtt actccctgat ccgttcctcc gtggattctt   1740
ccctggatat cgatctcggc ctgtgggaat cccagtcctc cgacaaccct gtgtactacg   1800
tgcagtacgg acacgctcgt ctgtgctcca tcgcgcgcaa ggcagagacc ttgggtgtca   1860
ccgaggaagg cgcagaccta tctctactga cccacgaccg cgaaggcgat ctcatccgca   1920
cactcggaga gttcccagca gtggtgaagg ctgccgctga cctacgtgaa ccacaccgca   1980
ttgcccgcta tgctgaggaa ttagctggaa ctttccaccg cttctacgat tcctgccaca   2040
tccttccaaa ggttgatgag gatacggcac caatccacac agcacgtctg gcacttgcag   2100
cagcaacccg ccagaccctc gctaacgccc tgcacctggt tggcgtttcc gcaccggaga   2160
agatgtaaca atggctacag ttgaaaattt caatgaactt cccgcacacg tatggccacg   2220
caatgccgtg cgccaagaag acggcgttgt caccgtcgct ggtgtgcctc tgcctgacct   2280
cgctgaagaa tacggaaccc cactgttcgt agtcgacgag gacgatttcc gttcccgctg   2340
tcgcgacatg gctaccgcat tcggtggacc aggcaatgtg cactacgcat ctaaagcgtt   2400
cctgaccaag accattgcac gttgggttga tgaagagggg ctggcactgg acattgcatc   2460
catcaacgaa ctgggcattg ccctggccgc tggtttcccc gccagccgta tcaccgcgca   2520
cggcaacaac aaaggcgtag agttcctgcg cgcgttggtt caaaacggtg tgggacacgt   2580
ggtgctggac tccgcacagg aactagaact gttggattac gttgccgctg gtgaaggcaa   2640
gattcaggac gtgttgatcc gcgtaaagcc aggcatcgaa gcacacaccc acgagttcat   2700
cgccactagc cacgaagacc agaagttcgg attctccctg gcatccggtt ccgcattcga   2760
agcagcaaaa gccgccaaca acgcagaaaa cctgaacctg gttggcctgc actgccacgt   2820
tggttcccag gtgttcgacg ccgaaggctt caagctggca gcagaacgcg tgttgggcct   2880
gtactcacag atccacagcg aactgggcgt tgcccttcct gaactggatc tcggtggcgg   2940
atacggcatt gcctataccg cagctgaaga accactcaac gtcgcagaag ttgcctccga   3000
cctgctcacc gcagtcggaa aaatggcagc ggaactaggc atcgacgcac caaccgtgct   3060
tgttgagccc ggccgcgcta tcgcaggccc ctccaccgtg accatctacg aagtcggcac   3120
caccaaagac gtccacgtag acgacgacaa aacccgccgt tacatcgccg tggacggagg   3180
catgtccgac aacatccgcc cagcactcta cggctccgaa tacgacgccc gcgtagtatc   3240
ccgcttcgcc gaaggagacc cagtaagcac ccgcatcgtg ggctcccact gcgaatccgg   3300
cgatatcctg atcaacgatg aaatctaccc atctgacatc accagcggcg acttccttgc   3360
actcgcagcc accggcgcat actgctacgc catgagctcc cgctacaacg ccttcacacg   3420
gcccgccgtc gtgtccgtcc gcgctggcag ctcccgcctc atgctgcgcc gcgaaacgct   3480
cgacgacatc ctctcactag aggcataacg cttttcgacg cctgaccccg ccccttcacct   3540
tcgccgtgga gggcggtttt gggtttctgg gtttctttct agagaggctg cactgcaacg   3600
aggtcgtagt tttggtacat ggcttctggc cagttcatgg attggctgcc gaagaagcta   3660
taggcatcgc caccagggcc accggagtta ccgaagatgg tgccgtgctt ttcgccttgg   3720
gcagggacct tgacaaagcc cacgctgata tcgccaagtg agggatcaga atagtgcatg   3780
```

```
ggcacgtcga tgctgccaca ttgagcggag gcaatatcta cctgaggtgg gcattcttcc   3840
cagcggatgt tttcttgcgc tgctgcagtg ggcattgata ccaaaaaggg gctaagcgca   3900
gtcgaggcgg caagaactgc tactaccctt tttattgtcg aacggggcat tacggctcca   3960
aggacgtttg ttttctgggt cagttacccc aaaaagcata tacagagacc aatgattttt   4020
cattaaaaag gcagggattt gttataagta tgggtcgtat tctgtgcgac gggtgtacct   4080
cggctagaat ttctccccat gacaccagct gatctcgcaa cattgattaa agagaccgcg   4140
gtagaggttt tgacctcccg cgagctcgat acttctgttc ttccggagca ggtagttgtg   4200
gagcgtccgc gtaacccaga gcacggcgat tacgccacca acattgcatt gcaggtggct   4260
aaaaaggtcg gtcagaaccc tcgggatttg gctacctggc tggcagaggc attggctgca   4320
gatgacgcca ttgattctgc tgaaattgct ggcccaggct tttgaacat tcgccttgct   4380
gcagcagcac agggtgaaat tgtggccaag attctggcac agggcgagac tttcggaaac   4440
tccgatcacc tttcccactt ggacgtgaac ctcgagttcg tttctgcaaa cccaaccgga   4500
cctattcacc ttggcggaac ccgctgggct gccgtgggtg actctttggg tcgtgtgctg   4560
gaggcttccg gcgcgaaagt gacccgcgaa tactacttca acgatcacgg tcgccagatc   4620
gatcgtttcg ctttgtccct tcttgcagcg gcgaagggcg agccaacgcc agaagacggt   4680
tatggcggcg aatacattaa ggaaattgcg gaggcaatcg tcgaaaagca tcctgaagcg   4740
ttggctttgg agcctgccgc aacccaggag cttttccgcg ctgaaggcgt ggagatgatg   4800
ttcgagcaca tcaaatcttc cctgcatgag ttcggcaccg atttcgatgt ctactaccac   4860
gagaactccc tgttcgagtc cggtgcggtg gacaaggccg tgcaggtgct gaaggacaac   4920
ggcaacctgt acgaaaacga gggcgcttgg tggctgcgtt ccaccgaatt cggcgatgac   4980
aaagaccgcg tggtgatcaa gtctgacggc gacgcagcct acatcgctgg cgatatcgcg   5040
tacgtggctg ataagttctc ccgcggacac aacctaaaca tctacatgtt gggtgctgac   5100
caccatggtt acatcgcgcg cctgaaggca gcggcggcgg cacttggcta caagccagaa   5160
ggcgttgaag tcctgattgg ccagatggtg aacctgcttc gcgacggcaa ggcagtgcgt   5220
atgtccaagc gtgcaggcac cgtggtcacc ctagatgacc tcgttgaagc aatcggcatc   5280
gatgcggcgc gttactccct gatccgttcc tccgtggatt cttccctgga tatcgatctc   5340
ggcctgtggg aatcccagtc ctccgacaac cctgtgtact acgtgcagta cggacacgct   5400
cgtctgtgct ccatcgcgcg caaggcagag accttgggtg tcaccgagga aggcgcagac   5460
ctatctctac tgacccacga ccgcgaaggc gatctcatcc gcacactcgg agagttccca   5520
gcagtggtga aggctgccgc tgacctacgt gaaccacacc gcattgcccg ctatgctgag   5580
gaattagctg gaactttcca ccgcttctac gattcctgcc acatccttcc aaaggttgat   5640
gaggatacgg caccaatcca cacagcacgt ctggcacttg cagcagcaac ccgccagacc   5700
ctcgctaacg ccctgcacct ggttggcgtt tccgcaccgg agaagatgta acaatggcta   5760
cagttgaaaa tttcaatgaa cttcccgcac acgtatggcc acgcaatgcc gtgcgccaag   5820
aagacggcgt tgtcaccgtc gctggtgtgc ctctgcctga cctcgctgaa gaatacggaa   5880
ccccactgtt cgtagtcgac gaggacgatt tccgttcccg ctgtcgcgac atggctaccg   5940
cattcggtgg accaggcaat gtgcactacg catctaaagc gttcctgacc aagaccattg   6000
cacgttgggt tgatgaagag gggctggcac tggacattgc atccatcaac gaactgggca   6060
ttgccctggc cgctggtttc cccgccagcc gtatcaccgc gcacggcaac aacaaaggcg   6120
tagagttcct gcgcgcgttg gttcaaaacg gtgtgggaca cgtggtgctg gactccgcac   6180
```

-continued

```
aggaactaga actgttggat tacgttgccg ctggtgaagg caagattcag gacgtgttga   6240

tccgcgtaaa gccaggcatc gaagcacaca cccacgagtt catcgccact agccacgaag   6300

accagaagtt cggattctcc ctggcatccg gttccgcatt cgaagcagca aaagccgcca   6360

acaacgcaga aaacctgaac ctggttggcc tgcactgcca cgttggttcc caggtgttcg   6420

acgccgaagg cttcaagctg gcagcagaac gcgtgttggg cctgtactca cagatccaca   6480

gcgaactggg cgttgccctt cctgaactgg atctcggtgg cggatacggc attgcctata   6540

ccgcagctga agaaccactc aacgtcgcag aagttgcctc cgacctgctc accgcagtcg   6600

gaaaaatggc agcggaacta ggcatcgacg caccaaccgt gcttgttgag cccggccgcg   6660

ctatcgcagg cccctccacc gtgaccatct acgaagtcgg caccaccaaa gacgtccacg   6720

tagacgacga caaaacccgc cgttacatcg ccgtggacgg aggcatgtcc gacaacatcc   6780

gcccagcact ctacggctcc gaatacgacg cccgcgtagt atcccgcttc gccgaaggag   6840

acccagtaag cacccgcatc gtgggctccc actgcgaatc cggcgatatc ctgatcaacg   6900

atgaaatcta cccatctgac atcaccagcg gcgacttcct tgcactcgca gccaccggcg   6960

catactgcta cgccatgagc tcccgctaca acgccttcac acggcccgcc gtcgtgtccg   7020

tccgcgctgg cagctcccgc ctcatgctgc gccgcgaaac gctcgacgac atcctctcac   7080

tagaggcata a                                                        7091


<210> SEQ ID NO 17
<211> LENGTH: 445
<212> TYPE: PRT
<213> ORGANISM: Corynebacterium glutamicum
<220> FEATURE:
<221> NAME/KEY: PEPTIDE
<222> LOCATION: (1)..(445)
<223> OTHER INFORMATION: LysA, amino acid sequence of C. glutamicum
      diaminopimelate decarboxylase

<400> SEQUENCE: 17

Met Ala Thr Val Glu Asn Phe Asn Glu Leu Pro Ala His Val Trp Pro
  1               5                  10                  15

Arg Asn Ala Val Arg Gln Glu Asp Gly Val Val Thr Val Ala Gly Val
             20                  25                  30

Pro Leu Pro Asp Leu Ala Glu Glu Tyr Gly Thr Pro Leu Phe Val Val
         35                  40                  45

Asp Glu Asp Asp Phe Arg Ser Arg Cys Arg Asp Met Ala Thr Ala Phe
     50                  55                  60

Gly Gly Pro Gly Asn Val His Tyr Ala Ser Lys Ala Phe Leu Thr Lys
 65                  70                  75                  80

Thr Ile Ala Arg Trp Val Asp Glu Glu Gly Leu Ala Leu Asp Ile Ala
                 85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
        115                 120                 125

Leu Val Gln Asn Gly Val Gly His Val Val Leu Asp Ser Ala Gln Glu
    130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175
```

```
Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
        195                 200                 205

Asn Leu Val Gly Leu His Cys His Val Gly Ser Gln Val Phe Asp Ala
    210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
        275                 280                 285

Leu Gly Ile Asp Ala Pro Thr Val Leu Val Glu Pro Gly Arg Ala Ile
    290                 295                 300

Ala Gly Pro Ser Thr Val Thr Ile Tyr Glu Val Gly Thr Thr Lys Asp
305                 310                 315                 320

Val His Val Asp Asp Asp Lys Thr Arg Arg Tyr Ile Ala Val Asp Gly
                325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
        355                 360                 365

Ile Val Gly Ser His Cys Glu Ser Gly Asp Ile Leu Ile Asn Asp Glu
    370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
        435                 440                 445


<210> SEQ ID NO 18
<211> LENGTH: 1338
<212> TYPE: DNA
<213> ORGANISM: Corynebacterium glutamicum
<220> FEATURE:
<221> NAME/KEY: CDS
<222> LOCATION: (1)..(1335)
<223> OTHER INFORMATION: hom, DNA sequence encoding wildtype C.
      glutamicum homoserine dehydrogenase

<400> SEQUENCE: 18

atg acc tca gca tct gcc cca agc ttt aac ccc ggc aag ggt ccc ggc       48
Met Thr Ser Ala Ser Ala Pro Ser Phe Asn Pro Gly Lys Gly Pro Gly
  1               5                  10                  15

tca gca gtc gga att gcc ctt tta gga ttc gga aca gtc ggc act gag       96
Ser Ala Val Gly Ile Ala Leu Leu Gly Phe Gly Thr Val Gly Thr Glu
             20                  25                  30

gtg atg cgt ctg atg acc gag tac ggt gat gaa ctt gcg cac cgc att      144
Val Met Arg Leu Met Thr Glu Tyr Gly Asp Glu Leu Ala His Arg Ile
         35                  40                  45

ggt ggc cca ctg gag gtt cgt ggc att gct gtt tct gat atc tca aag      192
Gly Gly Pro Leu Glu Val Arg Gly Ile Ala Val Ser Asp Ile Ser Lys
     50                  55                  60
```

```
cca cgt gaa ggc gtt gca cct gag ctg ctc act gag gac gct ttt gca      240
Pro Arg Glu Gly Val Ala Pro Glu Leu Leu Thr Glu Asp Ala Phe Ala
 65                  70                  75                  80

ctc atc gag cgc gag gat gtt gac atc gtc gtt gag gtt atc ggc ggc      288
Leu Ile Glu Arg Glu Asp Val Asp Ile Val Val Glu Val Ile Gly Gly
                 85                  90                  95

att gag tac cca cgt gag gta gtt ctc gca gct ctg aag gcc ggc aag      336
Ile Glu Tyr Pro Arg Glu Val Val Leu Ala Ala Leu Lys Ala Gly Lys
            100                 105                 110

tct gtt gtt acc gcc aat aag gct ctt gtt gca gct cac tct gct gag      384
Ser Val Val Thr Ala Asn Lys Ala Leu Val Ala Ala His Ser Ala Glu
        115                 120                 125

ctt gct gat gca gcg gaa gcc gca aac gtt gac ctg tac ttc gag gct      432
Leu Ala Asp Ala Ala Glu Ala Ala Asn Val Asp Leu Tyr Phe Glu Ala
    130                 135                 140

gct gtt gca ggc gca att cca gtg gtt ggc cca ctg cgt cgc tcc ctg      480
Ala Val Ala Gly Ala Ile Pro Val Val Gly Pro Leu Arg Arg Ser Leu
145                 150                 155                 160

gct ggc gat cag atc cag tct gtg atg ggc atc gtt aac ggc acc acc      528
Ala Gly Asp Gln Ile Gln Ser Val Met Gly Ile Val Asn Gly Thr Thr
                165                 170                 175

aac ttc atc ttg gac gcc atg gat tcc acc ggc gct gac tat gca gat      576
Asn Phe Ile Leu Asp Ala Met Asp Ser Thr Gly Ala Asp Tyr Ala Asp
            180                 185                 190

tct ttg gct gag gca act cgt ttg ggt tac gcc gaa gct gat cca act      624
Ser Leu Ala Glu Ala Thr Arg Leu Gly Tyr Ala Glu Ala Asp Pro Thr
        195                 200                 205

gca gac gtc gaa ggc cat gac gcc gca tcc aag gct gca att ttg gca      672
Ala Asp Val Glu Gly His Asp Ala Ala Ser Lys Ala Ala Ile Leu Ala
    210                 215                 220

tcc atc gct ttc cac acc cgt gtt acc gcg gat gat gtg tac tgc gaa      720
Ser Ile Ala Phe His Thr Arg Val Thr Ala Asp Asp Val Tyr Cys Glu
225                 230                 235                 240

ggt atc agc aac atc agc gct gcc gac att gag gca gca cag cag gca      768
Gly Ile Ser Asn Ile Ser Ala Ala Asp Ile Glu Ala Ala Gln Gln Ala
                245                 250                 255

ggc cac acc atc aag ttg ttg gcc atc tgt gag aag ttc acc aac aag      816
Gly His Thr Ile Lys Leu Leu Ala Ile Cys Glu Lys Phe Thr Asn Lys
            260                 265                 270

gaa gga aag tcg gct att tct gct cgc gtg cac ccg act cta tta cct      864
Glu Gly Lys Ser Ala Ile Ser Ala Arg Val His Pro Thr Leu Leu Pro
        275                 280                 285

gtg tcc cac cca ctg gcg tcg gta aac aag tcc ttt aat gca atc ttt      912
Val Ser His Pro Leu Ala Ser Val Asn Lys Ser Phe Asn Ala Ile Phe
    290                 295                 300

gtt gaa gca gaa gca gct ggt cgc ctg atg ttc tac gga aac ggt gca      960
Val Glu Ala Glu Ala Ala Gly Arg Leu Met Phe Tyr Gly Asn Gly Ala
305                 310                 315                 320

ggt ggc gcg cca acc gcg tct gct gtg ctt ggc gac gtc gtt ggt gcc     1008
Gly Gly Ala Pro Thr Ala Ser Ala Val Leu Gly Asp Val Val Gly Ala
                325                 330                 335

gca cga aac aag gtg cac ggt ggc cgt gct cca ggt gag tcc acc tac     1056
Ala Arg Asn Lys Val His Gly Gly Arg Ala Pro Gly Glu Ser Thr Tyr
            340                 345                 350

gct aac ctg ccg atc gct gat ttc ggt gag acc acc act cgt tac cac     1104
Ala Asn Leu Pro Ile Ala Asp Phe Gly Glu Thr Thr Thr Arg Tyr His
        355                 360                 365

ctc gac atg gat gtg gaa gat cgc gtg ggg gtt ttg gct gaa ttg gct     1152
Leu Asp Met Asp Val Glu Asp Arg Val Gly Val Leu Ala Glu Leu Ala
```

```
    370                 375                 380

agc ctg ttc tct gag caa gga atc tcc ctg cgt aca atc cga cag gaa     1200
Ser Leu Phe Ser Glu Gln Gly Ile Ser Leu Arg Thr Ile Arg Gln Glu
385                 390                 395                 400

gag cgc gat gat gat gca cgt ctg atc gtg gtc acc cac tct gcg ctg     1248
Glu Arg Asp Asp Asp Ala Arg Leu Ile Val Val Thr His Ser Ala Leu
                405                 410                 415

gaa tct gat ctt tcc cgc acc gtt gaa ctg ctg aag gct aag cct gtt     1296
Glu Ser Asp Leu Ser Arg Thr Val Glu Leu Leu Lys Ala Lys Pro Val
            420                 425                 430

gtt aag gca atc aac agt gtg atc cgc ctc gaa agg gac         taa     1338
Val Lys Ala Ile Asn Ser Val Ile Arg Leu Glu Arg Asp
        435                 440                 445


<210> SEQ ID NO 19
<211> LENGTH: 445
<212> TYPE: PRT
<213> ORGANISM: Corynebacterium glutamicum
<220> FEATURE:
<221> NAME/KEY: PEPTIDE
<222> LOCATION: (1)..(445)
<223> OTHER INFORMATION: Hom, amino acid sequence of C. glutamicum
      homoserine dehydrogenase

<400> SEQUENCE: 19

Met Thr Ser Ala Ser Ala Pro Ser Phe Asn Pro Gly Lys Gly Pro Gly
  1               5                  10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
 65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255
```

```
Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445
```

<210> SEQ ID NO 20
<211> LENGTH: 1338
<212> TYPE: DNA
<213> ORGANISM: Corynebacterium glutamicum
<220> FEATURE:
<221> NAME/KEY: CDS
<222> LOCATION: (1)..(1335)
<223> OTHER INFORMATION: homV59A, DNA sequence sequence encoding C. glutamicum homoserine dehydrogenase with V59A substitution

<400> SEQUENCE: 20

```
atg acc tca gca tct gcc cca agc ttt aac ccc ggc aag ggt ccc ggc       48
Met Thr Ser Ala Ser Ala Pro Ser Phe Asn Pro Gly Lys Gly Pro Gly
  1               5                  10                  15

tca gca gtc gga att gcc ctt tta gga ttc gga aca gtc ggc act gag       96
Ser Ala Val Gly Ile Ala Leu Leu Gly Phe Gly Thr Val Gly Thr Glu
             20                  25                  30

gtg atg cgt ctg atg acc gag tac ggt gat gaa ctt gcg cac cgc att      144
Val Met Arg Leu Met Thr Glu Tyr Gly Asp Glu Leu Ala His Arg Ile
         35                  40                  45

ggt ggc cca ctg gag gtt cgt ggc att gct gct tct gat atc tca aag      192
Gly Gly Pro Leu Glu Val Arg Gly Ile Ala Ala Ser Asp Ile Ser Lys
     50                  55                  60

cca cgt gaa ggc gtt gca cct gag ctg ctc act gag gac gct ttt gca      240
Pro Arg Glu Gly Val Ala Pro Glu Leu Leu Thr Glu Asp Ala Phe Ala
 65                  70                  75                  80

ctc atc gag cgc gag gat gtt gac atc gtc gtt gag gtt atc ggc ggc      288
Leu Ile Glu Arg Glu Asp Val Asp Ile Val Val Glu Val Ile Gly Gly
                 85                  90                  95

att gag tac cca cgt gag gta gtt ctc gca gct ctg aag gcc ggc aag      336
Ile Glu Tyr Pro Arg Glu Val Val Leu Ala Ala Leu Lys Ala Gly Lys
            100                 105                 110

tct gtt gtt acc gcc aat aag gct ctt gtt gca gct cac tct gct gag      384
Ser Val Val Thr Ala Asn Lys Ala Leu Val Ala Ala His Ser Ala Glu
```

-continued

```
        115                 120                 125

ctt gct gat gca gcg gaa gcc gca aac gtt gac ctg tac ttc gag gct      432
Leu Ala Asp Ala Ala Glu Ala Ala Asn Val Asp Leu Tyr Phe Glu Ala
    130                 135                 140

gct gtt gca ggc gca att cca gtg gtt ggc cca ctg cgt cgc tcc ctg      480
Ala Val Ala Gly Ala Ile Pro Val Val Gly Pro Leu Arg Arg Ser Leu
145                 150                 155                 160

gct ggc gat cag atc cag tct gtg atg ggc atc gtt aac ggc acc acc      528
Ala Gly Asp Gln Ile Gln Ser Val Met Gly Ile Val Asn Gly Thr Thr
                165                 170                 175

aac ttc atc ttg gac gcc atg gat tcc acc ggc gct gac tat gca gat      576
Asn Phe Ile Leu Asp Ala Met Asp Ser Thr Gly Ala Asp Tyr Ala Asp
            180                 185                 190

tct ttg gct gag gca act cgt ttg ggt tac gcc gaa gct gat cca act      624
Ser Leu Ala Glu Ala Thr Arg Leu Gly Tyr Ala Glu Ala Asp Pro Thr
        195                 200                 205

gca gac gtc gaa ggc cat gac gcc gca tcc aag gct gca att ttg gca      672
Ala Asp Val Glu Gly His Asp Ala Ala Ser Lys Ala Ala Ile Leu Ala
    210                 215                 220

tcc atc gct ttc cac acc cgt gtt acc gcg gat gat gtg tac tgc gaa      720
Ser Ile Ala Phe His Thr Arg Val Thr Ala Asp Asp Val Tyr Cys Glu
225                 230                 235                 240

ggt atc agc aac atc agc gct gcc gac att gag gca gca cag cag gca      768
Gly Ile Ser Asn Ile Ser Ala Ala Asp Ile Glu Ala Ala Gln Gln Ala
                245                 250                 255

ggc cac acc atc aag ttg ttg gcc atc tgt gag aag ttc acc aac aag      816
Gly His Thr Ile Lys Leu Leu Ala Ile Cys Glu Lys Phe Thr Asn Lys
            260                 265                 270

gaa gga aag tcg gct att tct gct cgc gtg cac ccg act cta tta cct      864
Glu Gly Lys Ser Ala Ile Ser Ala Arg Val His Pro Thr Leu Leu Pro
        275                 280                 285

gtg tcc cac cca ctg gcg tcg gta aac aag tcc ttt aat gca atc ttt      912
Val Ser His Pro Leu Ala Ser Val Asn Lys Ser Phe Asn Ala Ile Phe
    290                 295                 300

gtt gaa gca gaa gca gct ggt cgc ctg atg ttc tac gga aac ggt gca      960
Val Glu Ala Glu Ala Ala Gly Arg Leu Met Phe Tyr Gly Asn Gly Ala
305                 310                 315                 320

ggt ggc gcg cca acc gcg tct gct gtg ctt ggc gac gtc gtt ggt gcc     1008
Gly Gly Ala Pro Thr Ala Ser Ala Val Leu Gly Asp Val Val Gly Ala
                325                 330                 335

gca cga aac aag gtg cac ggt ggc cgt gct cca ggt gag tcc acc tac     1056
Ala Arg Asn Lys Val His Gly Gly Arg Ala Pro Gly Glu Ser Thr Tyr
            340                 345                 350

gct aac ctg ccg atc gct gat ttc ggt gag acc acc act cgt tac cac     1104
Ala Asn Leu Pro Ile Ala Asp Phe Gly Glu Thr Thr Thr Arg Tyr His
        355                 360                 365

ctc gac atg gat gtg gaa gat cgc gtg ggg gtt ttg gct gaa ttg gct     1152
Leu Asp Met Asp Val Glu Asp Arg Val Gly Val Leu Ala Glu Leu Ala
    370                 375                 380

agc ctg ttc tct gag caa gga atc tcc ctg cgt aca atc cga cag gaa     1200
Ser Leu Phe Ser Glu Gln Gly Ile Ser Leu Arg Thr Ile Arg Gln Glu
385                 390                 395                 400

gag cgc gat gat gat gca cgt ctg atc gtg gtc acc cac tct gcg ctg     1248
Glu Arg Asp Asp Asp Ala Arg Leu Ile Val Val Thr His Ser Ala Leu
                405                 410                 415

gaa tct gat ctt tcc cgc acc gtt gaa ctg ctg aag gct aag cct gtt     1296
Glu Ser Asp Leu Ser Arg Thr Val Glu Leu Leu Lys Ala Lys Pro Val
            420                 425                 430

gtt aag gca atc aac agt gtg atc cgc ctc gaa agg gac         taa     1338
```

```
Val Lys Ala Ile Asn Ser Val Ile Arg Leu Glu Arg Asp
        435                 440                 445


<210> SEQ ID NO 21
<211> LENGTH: 445
<212> TYPE: PRT
<213> ORGANISM: Corynebacterium glutamicum
<220> FEATURE:
<221> NAME/KEY: PEPTIDE
<222> LOCATION: (1)..(445)
<223> OTHER INFORMATION: HomV59A, amino acid of C. glutamicum homoserine
      dehydrogenase with V59A substitution

<400> SEQUENCE: 21

Met Thr Ser Ala Ser Ala Pro Ser Phe Asn Pro Gly Lys Gly Pro Gly
  1               5                  10                  15

Ser Ala Val Gly Ile Ala Leu Leu Gly Phe Gly Thr Val Gly Thr Glu
             20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Ala Ser Asp Ile Ser Lys
     50                  55                  60

Pro Arg Glu Gly Val Ala Pro Glu Leu Leu Thr Glu Asp Ala Phe Ala
 65                  70                  75                  80

Leu Ile Glu Arg Glu Asp Val Asp Ile Val Val Glu Val Ile Gly Gly
                 85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335
```

```
Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445


<210> SEQ ID NO 22
<211> LENGTH: 3623
<212> TYPE: DNA
<213> ORGANISM: Corynebacterium glutamicum
<220> FEATURE:
<221> NAME/KEY: CDS
<222> LOCATION: (201)..(3620)
<223> OTHER INFORMATION: pyc, DNA sequence encoding wildtype C.
      glutamicum pyruvate carboxylase with natural promoter

<400> SEQUENCE: 22

actggggcgg ggttagatcc tggggggttt atttcattca ctttggcttg aagtcgtgca      60

ggtcagggga gtgttgcccg aaaacattga gaggaaaaca aaaaccgatg tttgattggg     120

ggaatcgggg gttacgatac taggacgcag tgactgctat caccccttggc ggtctcttgt    180

tgaaaggaat aattactcta gtg tcg act cac aca tct tca acg ctt cca gca     233
                      Val Ser Thr His Thr Ser Ser Thr Leu Pro Ala
                      1               5                   10

ttc aaa aag atc ttg gta gca aac cgc ggc gaa atc gcg gtc cgt gct      281
Phe Lys Lys Ile Leu Val Ala Asn Arg Gly Glu Ile Ala Val Arg Ala
            15                  20                  25

ttc cgt gca gca ctc gaa acc ggt gca gcc acg gta gct att tac ccc      329
Phe Arg Ala Ala Leu Glu Thr Gly Ala Ala Thr Val Ala Ile Tyr Pro
        30                  35                  40

cgt gaa gat cgg gga tca ttc cac cgc tct ttt gct tct gaa gct gtc      377
Arg Glu Asp Arg Gly Ser Phe His Arg Ser Phe Ala Ser Glu Ala Val
    45                  50                  55

cgc att ggt acc gaa ggc tca cca gtc aag gcg tac ctg gac atc gat      425
Arg Ile Gly Thr Glu Gly Ser Pro Val Lys Ala Tyr Leu Asp Ile Asp
 60                 65                  70                  75

gaa att atc ggt gca gct aaa aaa gtt aaa gca gat gcc att tac ccg      473
Glu Ile Ile Gly Ala Ala Lys Lys Val Lys Ala Asp Ala Ile Tyr Pro
                80                  85                  90

gga tac ggc ttc ctg tct gaa aat gcc cag ctt gcc cgc gag tgt gcg      521
Gly Tyr Gly Phe Leu Ser Glu Asn Ala Gln Leu Ala Arg Glu Cys Ala
            95                  100                 105

gaa aac ggc att act ttt att ggc cca acc cca gag gtt ctt gat ctc      569
Glu Asn Gly Ile Thr Phe Ile Gly Pro Thr Pro Glu Val Leu Asp Leu
        110                 115                 120

acc ggt gat aag tct cgc gcg gta acc gcc gcg aag aag gct ggt ctg      617
Thr Gly Asp Lys Ser Arg Ala Val Thr Ala Ala Lys Lys Ala Gly Leu
    125                 130                 135

cca gtt ttg gcg gaa tcc acc ccg agc aaa aac atc gat gag atc gtt      665
Pro Val Leu Ala Glu Ser Thr Pro Ser Lys Asn Ile Asp Glu Ile Val
140                 145                 150                 155
```

```
aaa agc gct gaa ggc cag act tac ccc atc ttt gtg aag gca gtt gcc      713
Lys Ser Ala Glu Gly Gln Thr Tyr Pro Ile Phe Val Lys Ala Val Ala
                160                 165                 170

ggt ggt ggc gga cgc ggt atg cgt ttt gtt gct tca cct gat gag ctt      761
Gly Gly Gly Gly Arg Gly Met Arg Phe Val Ala Ser Pro Asp Glu Leu
            175                 180                 185

cgc aaa tta gca aca gaa gca tct cgt gaa gct gaa gcg gct ttc ggc      809
Arg Lys Leu Ala Thr Glu Ala Ser Arg Glu Ala Glu Ala Ala Phe Gly
        190                 195                 200

gat ggc gcg gta tat gtc gaa cgt gct gtg att aac cct cag cat att      857
Asp Gly Ala Val Tyr Val Glu Arg Ala Val Ile Asn Pro Gln His Ile
    205                 210                 215

gaa gtg cag atc ctt ggc gat cac act gga gaa gtt gta cac ctt tat      905
Glu Val Gln Ile Leu Gly Asp His Thr Gly Glu Val Val His Leu Tyr
220                 225                 230                 235

gaa cgt gac tgc tca ctg cag cgt cgt cac caa aaa gtt gtc gaa att      953
Glu Arg Asp Cys Ser Leu Gln Arg Arg His Gln Lys Val Val Glu Ile
                240                 245                 250

gcg cca gca cag cat ttg gat cca gaa ctg cgt gat cgc att tgt gcg     1001
Ala Pro Ala Gln His Leu Asp Pro Glu Leu Arg Asp Arg Ile Cys Ala
            255                 260                 265

gat gca gta aag ttc tgc cgc tcc att ggt tac cag ggc gcg gga acc     1049
Asp Ala Val Lys Phe Cys Arg Ser Ile Gly Tyr Gln Gly Ala Gly Thr
        270                 275                 280

gtg gaa ttc ttg gtc gat gaa aag ggc aac cac gtc ttc atc gaa atg     1097
Val Glu Phe Leu Val Asp Glu Lys Gly Asn His Val Phe Ile Glu Met
    285                 290                 295

aac cca cgt atc cag gtt gag cac acc gtg act gaa gaa gtc acc gag     1145
Asn Pro Arg Ile Gln Val Glu His Thr Val Thr Glu Glu Val Thr Glu
300                 305                 310                 315

gtg gac ctg gtg aag gcg cag atg cgc ttg gct gct ggt gca acc ttg     1193
Val Asp Leu Val Lys Ala Gln Met Arg Leu Ala Ala Gly Ala Thr Leu
                320                 325                 330

aag gaa ttg ggt ctg acc caa gat aag atc aag acc cac ggt gca gca     1241
Lys Glu Leu Gly Leu Thr Gln Asp Lys Ile Lys Thr His Gly Ala Ala
            335                 340                 345

ctg cag tgc cgc atc acc acg gaa gat cca aac aac ggc ttc cgc cca     1289
Leu Gln Cys Arg Ile Thr Thr Glu Asp Pro Asn Asn Gly Phe Arg Pro
        350                 355                 360

gat acc gga act atc acc gcg tac cgc tca cca ggc gga gct ggc gtt     1337
Asp Thr Gly Thr Ile Thr Ala Tyr Arg Ser Pro Gly Gly Ala Gly Val
    365                 370                 375

cgt ctt gac ggt gca gct cag ctc ggt ggc gaa atc acc gca cac ttt     1385
Arg Leu Asp Gly Ala Ala Gln Leu Gly Gly Glu Ile Thr Ala His Phe
380                 385                 390                 395

gac tcc atg ctg gtg aaa atg acc tgc cgt ggt tcc gac ttt gaa act     1433
Asp Ser Met Leu Val Lys Met Thr Cys Arg Gly Ser Asp Phe Glu Thr
                400                 405                 410

gct gtt gct cgt gca cag cgc gcg ttg gct gag ttc acc gtg tct ggt     1481
Ala Val Ala Arg Ala Gln Arg Ala Leu Ala Glu Phe Thr Val Ser Gly
            415                 420                 425

gtt gca acc aac att ggt ttc ttg cgt gcg ttg ctg cgg gaa gag gac     1529
Val Ala Thr Asn Ile Gly Phe Leu Arg Ala Leu Leu Arg Glu Glu Asp
        430                 435                 440

ttc act tcc aag cgc atc gcc acc gga ttc att gcc gat cac ccg cac     1577
Phe Thr Ser Lys Arg Ile Ala Thr Gly Phe Ile Ala Asp His Pro His
    445                 450                 455

ctc ctt cag gct cca cct gct gat gat gag cag gga cgc atc ctg gat     1625
Leu Leu Gln Ala Pro Pro Ala Asp Asp Glu Gln Gly Arg Ile Leu Asp
```

```
460                 465                 470                 475

tac ttg gca gat gtc acc gtg aac aag cct cat ggt gtg cgt cca aag      1673
Tyr Leu Ala Asp Val Thr Val Asn Lys Pro His Gly Val Arg Pro Lys
                480                 485                 490

gat gtt gca gct cct atc gat aag ctg cct aac atc aag gat ctg cca      1721
Asp Val Ala Ala Pro Ile Asp Lys Leu Pro Asn Ile Lys Asp Leu Pro
            495                 500                 505

ctg cca cgc ggt tcc cgt gac cgc ctg aag cag ctt ggc cca gcc gcg      1769
Leu Pro Arg Gly Ser Arg Asp Arg Leu Lys Gln Leu Gly Pro Ala Ala
        510                 515                 520

ttt gct cgt gat ctc cgt gag cag gac gca ctg gca gtt act gat acc      1817
Phe Ala Arg Asp Leu Arg Glu Gln Asp Ala Leu Ala Val Thr Asp Thr
    525                 530                 535

acc ttc cgc gat gca cac cag tct ttg ctt gcg acc cga gtc cgc tca      1865
Thr Phe Arg Asp Ala His Gln Ser Leu Leu Ala Thr Arg Val Arg Ser
540                 545                 550                 555

ttc gca ctg aag cct gcg gca gag gcc gtc gca aag ctg act cct gag      1913
Phe Ala Leu Lys Pro Ala Ala Glu Ala Val Ala Lys Leu Thr Pro Glu
                560                 565                 570

ctt ttg tcc gtg gag gcc tgg ggc ggc gcg acc tac gat gtg gcg atg      1961
Leu Leu Ser Val Glu Ala Trp Gly Gly Ala Thr Tyr Asp Val Ala Met
            575                 580                 585

cgt ttc ctc ttt gag gat ccg tgg gac agg ctc gac gag ctg cgc gag      2009
Arg Phe Leu Phe Glu Asp Pro Trp Asp Arg Leu Asp Glu Leu Arg Glu
        590                 595                 600

gcg atg ccg aat gta aac att cag atg ctg ctt cgc ggc cgc aac acc      2057
Ala Met Pro Asn Val Asn Ile Gln Met Leu Leu Arg Gly Arg Asn Thr
    605                 610                 615

gtg gga tac acc ccg tac cca gac tcc gtc tgc cgc gcg ttt gtt aag      2105
Val Gly Tyr Thr Pro Tyr Pro Asp Ser Val Cys Arg Ala Phe Val Lys
620                 625                 630                 635

gaa gct gcc agc tcc ggc gtg gac atc ttc cgc atc ttc gac gcg ctt      2153
Glu Ala Ala Ser Ser Gly Val Asp Ile Phe Arg Ile Phe Asp Ala Leu
                640                 645                 650

aac gac gtc tcc cag atg cgt cca gca atc gac gca gtc ctg gag acc      2201
Asn Asp Val Ser Gln Met Arg Pro Ala Ile Asp Ala Val Leu Glu Thr
            655                 660                 665

aac acc gcg gta gcc gag gtg gct atg gct tat tct ggt gat ctc tct      2249
Asn Thr Ala Val Ala Glu Val Ala Met Ala Tyr Ser Gly Asp Leu Ser
        670                 675                 680

gat cca aat gaa aag ctc tac acc ctg gat tac tac cta aag atg gca      2297
Asp Pro Asn Glu Lys Leu Tyr Thr Leu Asp Tyr Tyr Leu Lys Met Ala
    685                 690                 695

gag gag atc gtc aag tct ggc gct cac atc ttg gcc att aag gat atg      2345
Glu Glu Ile Val Lys Ser Gly Ala His Ile Leu Ala Ile Lys Asp Met
700                 705                 710                 715

gct ggt ctg ctt cgc cca gct gcg gta acc aag ctg gtc acc gca ctg      2393
Ala Gly Leu Leu Arg Pro Ala Ala Val Thr Lys Leu Val Thr Ala Leu
                720                 725                 730

cgc cgt gaa ttc gat ctg cca gtg cac gtg cac acc cac gac act gcg      2441
Arg Arg Glu Phe Asp Leu Pro Val His Val His Thr His Asp Thr Ala
            735                 740                 745

ggt ggc cag ctg gca acc tac ttt gct gca gct caa gct ggt gca gat      2489
Gly Gly Gln Leu Ala Thr Tyr Phe Ala Ala Ala Gln Ala Gly Ala Asp
        750                 755                 760

gct gtt gac ggt gct tcc gca cca ctg tct ggc acc acc tcc cag cca      2537
Ala Val Asp Gly Ala Ser Ala Pro Leu Ser Gly Thr Thr Ser Gln Pro
    765                 770                 775

tcc ctg tct gcc att gtt gct gca ttc gcg cac acc cgt cgc gat acc      2585
```

```
Ser Leu Ser Ala Ile Val Ala Ala Phe Ala His Thr Arg Arg Asp Thr
780                 785                 790                 795

ggt ttg agc ctc gag gct gtt tct gac ctc gag ccg tac tgg gaa gca      2633
Gly Leu Ser Leu Glu Ala Val Ser Asp Leu Glu Pro Tyr Trp Glu Ala
                800                 805                 810

gtg cgc gga ctg tac ctg cca ttt gag tct gga acc cca ggc cca acc      2681
Val Arg Gly Leu Tyr Leu Pro Phe Glu Ser Gly Thr Pro Gly Pro Thr
            815                 820                 825

ggt cgc gtc tac cgc cac gaa atc cca ggc gga cag ttg tcc aac ctg      2729
Gly Arg Val Tyr Arg His Glu Ile Pro Gly Gly Gln Leu Ser Asn Leu
        830                 835                 840

cgt gca cag gcc acc gca ctg ggc ctt gcg gat cgt ttc gaa ctc atc      2777
Arg Ala Gln Ala Thr Ala Leu Gly Leu Ala Asp Arg Phe Glu Leu Ile
    845                 850                 855

gaa gac aac tac gca gcc gtt aat gag atg ctg gga cgc cca acc aag      2825
Glu Asp Asn Tyr Ala Ala Val Asn Glu Met Leu Gly Arg Pro Thr Lys
860                 865                 870                 875

gtc acc cca tcc tcc aag gtt gtt ggc gac ctc gca ctc cac ctc gtt      2873
Val Thr Pro Ser Ser Lys Val Val Gly Asp Leu Ala Leu His Leu Val
                880                 885                 890

ggt gcg ggt gtg gat cca gca gac ttt gct gcc gat cca caa aag tac      2921
Gly Ala Gly Val Asp Pro Ala Asp Phe Ala Ala Asp Pro Gln Lys Tyr
            895                 900                 905

gac atc cca gac tct gtc atc gcg ttc ctg cgc ggc gag ctt ggt aac      2969
Asp Ile Pro Asp Ser Val Ile Ala Phe Leu Arg Gly Glu Leu Gly Asn
        910                 915                 920

cct cca ggt ggc tgg cca gag cca ctg cgc acc cgc gca ctg gaa ggc      3017
Pro Pro Gly Gly Trp Pro Glu Pro Leu Arg Thr Arg Ala Leu Glu Gly
    925                 930                 935

cgc tcc gaa ggc aag gca cct ctg acg gaa gtt cct gag gaa gag cag      3065
Arg Ser Glu Gly Lys Ala Pro Leu Thr Glu Val Pro Glu Glu Glu Gln
940                 945                 950                 955

gcg cac ctc gac gct gat gat tcc aag gaa cgt cgc aat agc ctc aac      3113
Ala His Leu Asp Ala Asp Asp Ser Lys Glu Arg Arg Asn Ser Leu Asn
                960                 965                 970

cgc ctg ctg ttc ccg aag cca acc gaa gag ttc ctc gag cac cgt cgc      3161
Arg Leu Leu Phe Pro Lys Pro Thr Glu Glu Phe Leu Glu His Arg Arg
            975                 980                 985

cgc ttc ggc aac acc tct gcg ctg gat gat cgt gaa ttc ttc tac ggc      3209
Arg Phe Gly Asn Thr Ser Ala Leu Asp Asp Arg Glu Phe Phe Tyr Gly
        990                 995                1000

ctg gtc gaa ggc cgc gag act ttg atc cgc ctg cca gat gtg cgc acc      3257
Leu Val Glu Gly Arg Glu Thr Leu Ile Arg Leu Pro Asp Val Arg Thr
    1005                1010                1015

cca ctg ctt gtt cgc ctg gat gcg atc tct gag cca gac gat aag ggt      3305
Pro Leu Leu Val Arg Leu Asp Ala Ile Ser Glu Pro Asp Asp Lys Gly
1020                1025                1030                1035

atg cgc aat gtt gtg gcc aac gtc aac ggc cag atc cgc cca atg cgt      3353
Met Arg Asn Val Val Ala Asn Val Asn Gly Gln Ile Arg Pro Met Arg
                1040                1045                1050

gtg cgt gac cgc tcc gtt gag tct gtc acc gca acc gca gaa aag gca      3401
Val Arg Asp Arg Ser Val Glu Ser Val Thr Ala Thr Ala Glu Lys Ala
            1055                1060                1065

gat tcc tcc aac aag ggc cat gtt gct gca cca ttc gct ggt gtt gtc      3449
Asp Ser Ser Asn Lys Gly His Val Ala Ala Pro Phe Ala Gly Val Val
        1070                1075                1080

acc gtg act gtt gct gaa ggt gat gag gtc aag gct gga gat gca gtc      3497
Thr Val Thr Val Ala Glu Gly Asp Glu Val Lys Ala Gly Asp Ala Val
    1085                1090                1095
```

```
gca atc atc gag gct atg aag atg gaa gca aca atc act gct tct gtt     3545
Ala Ile Ile Glu Ala Met Lys Met Glu Ala Thr Ile Thr Ala Ser Val
1100                1105                1110                1115

gac ggc aaa atc gat cgc gtt gtg gtt cct gct gca acg aag gtg gaa     3593
Asp Gly Lys Ile Asp Arg Val Val Val Pro Ala Ala Thr Lys Val Glu
                1120                1125                1130

ggt ggc gac ttg atc gtc gtc gtt tcc         taa                     3623
Gly Gly Asp Leu Ile Val Val Val Ser
            1135                1140


<210> SEQ ID NO 23
<211> LENGTH: 1140
<212> TYPE: PRT
<213> ORGANISM: Corynebacterium glutamicum
<220> FEATURE:
<221> NAME/KEY: PEPTIDE
<222> LOCATION: (1)..(1140)
<223> OTHER INFORMATION: Pyc, amino acid sequence of C. glutamicum
      pyruvate carboxylase

<400> SEQUENCE: 23

Val Ser Thr His Thr Ser Ser Thr Leu Pro Ala Phe Lys Lys Ile Leu
  1               5                  10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285
```

```
Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
```

```
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Val Pro Ala Ala Thr Lys Val Glu Gly Gly Asp Leu Ile
                1125                1130                1135
```

```
Val Val Val Ser
            1140


<210> SEQ ID NO 24
<211> LENGTH: 3615
<212> TYPE: DNA
<213> ORGANISM: Corynebacterium glutamicum
<220> FEATURE:
<221> NAME/KEY: CDS
<222> LOCATION: (193)..(3612)
<223> OTHER INFORMATION: pycP458S, DNA sequence encoding C. glutamicum
      pyruvate carboxylase with P458S substitution and sod-promoter

<400> SEQUENCE: 24

tagctgccaa ttattccggg cttgtgaccc gctacccgat aaataggtcg gctgaaaaat     60

ttcgttgcaa tataaacaaa aaggcctctc attgggaggt gtcgcaccaa gtacttttgc    120

gaagcgccat ctgacggatt ttcaaaagat gtatatgctc ggtgcggaaa cctacgaaag    180

gattttttac cc         gtg tcg act cac aca tct tca acg ctt cca gca    225
                      Val Ser Thr His Thr Ser Ser Thr Leu Pro Ala
                        1               5                   10

ttc aaa aag atc ttg gta gca aac cgc ggc gaa atc gcg gtc cgt gct      273
Phe Lys Lys Ile Leu Val Ala Asn Arg Gly Glu Ile Ala Val Arg Ala
            15                  20                  25

ttc cgt gca gca ctc gaa acc ggt gca gcc acg gta gct att tac ccc      321
Phe Arg Ala Ala Leu Glu Thr Gly Ala Ala Thr Val Ala Ile Tyr Pro
        30                  35                  40

cgt gaa gat cgg gga tca ttc cac cgc tct ttt gct tct gaa gct gtc      369
Arg Glu Asp Arg Gly Ser Phe His Arg Ser Phe Ala Ser Glu Ala Val
    45                  50                  55

cgc att ggt acc gaa ggc tca cca gtc aag gcg tac ctg gac atc gat      417
Arg Ile Gly Thr Glu Gly Ser Pro Val Lys Ala Tyr Leu Asp Ile Asp
 60                  65                  70                  75

gaa att atc ggt gca gct aaa aaa gtt aaa gca gat gcc att tac ccg      465
Glu Ile Ile Gly Ala Ala Lys Lys Val Lys Ala Asp Ala Ile Tyr Pro
                80                  85                  90

gga tac ggc ttc ctg tct gaa aat gcc cag ctt gcc cgc gag tgt gcg      513
Gly Tyr Gly Phe Leu Ser Glu Asn Ala Gln Leu Ala Arg Glu Cys Ala
            95                  100                 105

gaa aac ggc att act ttt att ggc cca acc cca gag gtt ctt gat ctc      561
Glu Asn Gly Ile Thr Phe Ile Gly Pro Thr Pro Glu Val Leu Asp Leu
        110                 115                 120

acc ggt gat aag tct cgc gcg gta acc gcc gcg aag aag gct ggt ctg      609
Thr Gly Asp Lys Ser Arg Ala Val Thr Ala Ala Lys Lys Ala Gly Leu
    125                 130                 135

cca gtt ttg gcg gaa tcc acc ccg agc aaa aac atc gat gag atc gtt      657
Pro Val Leu Ala Glu Ser Thr Pro Ser Lys Asn Ile Asp Glu Ile Val
140                 145                 150                 155

aaa agc gct gaa ggc cag act tac ccc atc ttt gtg aag gca gtt gcc      705
Lys Ser Ala Glu Gly Gln Thr Tyr Pro Ile Phe Val Lys Ala Val Ala
                160                 165                 170

ggt ggt ggc gga cgc ggt atg cgt ttt gtt gct tca cct gat gag ctt      753
Gly Gly Gly Gly Arg Gly Met Arg Phe Val Ala Ser Pro Asp Glu Leu
            175                 180                 185

cgc aaa tta gca aca gaa gca tct cgt gaa gct gaa gcg gct ttc ggc      801
Arg Lys Leu Ala Thr Glu Ala Ser Arg Glu Ala Glu Ala Ala Phe Gly
        190                 195                 200

gat ggc gcg gta tat gtc gaa cgt gct gtg att aac cct cag cat att      849
Asp Gly Ala Val Tyr Val Glu Arg Ala Val Ile Asn Pro Gln His Ile
    205                 210                 215
```

```
gaa gtg cag atc ctt ggc gat cac act gga gaa gtt gta cac ctt tat      897
Glu Val Gln Ile Leu Gly Asp His Thr Gly Glu Val Val His Leu Tyr
220                 225                 230                 235

gaa cgt gac tgc tca ctg cag cgt cgt cac caa aaa gtt gtc gaa att      945
Glu Arg Asp Cys Ser Leu Gln Arg Arg His Gln Lys Val Val Glu Ile
                240                 245                 250

gcg cca gca cag cat ttg gat cca gaa ctg cgt gat cgc att tgt gcg      993
Ala Pro Ala Gln His Leu Asp Pro Glu Leu Arg Asp Arg Ile Cys Ala
            255                 260                 265

gat gca gta aag ttc tgc cgc tcc att ggt tac cag ggc gcg gga acc     1041
Asp Ala Val Lys Phe Cys Arg Ser Ile Gly Tyr Gln Gly Ala Gly Thr
        270                 275                 280

gtg gaa ttc ttg gtc gat gaa aag ggc aac cac gtc ttc atc gaa atg     1089
Val Glu Phe Leu Val Asp Glu Lys Gly Asn His Val Phe Ile Glu Met
    285                 290                 295

aac cca cgt atc cag gtt gag cac acc gtg act gaa gaa gtc acc gag     1137
Asn Pro Arg Ile Gln Val Glu His Thr Val Thr Glu Glu Val Thr Glu
300                 305                 310                 315

gtg gac ctg gtg aag gcg cag atg cgc ttg gct gct ggt gca acc ttg     1185
Val Asp Leu Val Lys Ala Gln Met Arg Leu Ala Ala Gly Ala Thr Leu
                320                 325                 330

aag gaa ttg ggt ctg acc caa gat aag atc aag acc cac ggt gca gca     1233
Lys Glu Leu Gly Leu Thr Gln Asp Lys Ile Lys Thr His Gly Ala Ala
            335                 340                 345

ctg cag tgc cgc atc acc acg gaa gat cca aac aac ggc ttc cgc cca     1281
Leu Gln Cys Arg Ile Thr Thr Glu Asp Pro Asn Asn Gly Phe Arg Pro
        350                 355                 360

gat acc gga act atc acc gcg tac cgc tca cca ggc gga gct ggc gtt     1329
Asp Thr Gly Thr Ile Thr Ala Tyr Arg Ser Pro Gly Gly Ala Gly Val
    365                 370                 375

cgt ctt gac ggt gca gct cag ctc ggt ggc gaa atc acc gca cac ttt     1377
Arg Leu Asp Gly Ala Ala Gln Leu Gly Gly Glu Ile Thr Ala His Phe
380                 385                 390                 395

gac tcc atg ctg gtg aaa atg acc tgc cgt ggt tcc gac ttt gaa act     1425
Asp Ser Met Leu Val Lys Met Thr Cys Arg Gly Ser Asp Phe Glu Thr
                400                 405                 410

gct gtt gct cgt gca cag cgc gcg ttg gct gag ttc acc gtg tct ggt     1473
Ala Val Ala Arg Ala Gln Arg Ala Leu Ala Glu Phe Thr Val Ser Gly
            415                 420                 425

gtt gca acc aac att ggt ttc ttg cgt gcg ttg ctg cgg gaa gag gac     1521
Val Ala Thr Asn Ile Gly Phe Leu Arg Ala Leu Leu Arg Glu Glu Asp
        430                 435                 440

ttc act tcc aag cgc atc gcc acc gga ttc att gcc gat cac tcg cac     1569
Phe Thr Ser Lys Arg Ile Ala Thr Gly Phe Ile Ala Asp His Ser His
    445                 450                 455

ctc ctt cag gct cca cct gct gat gat gag cag gga cgc atc ctg gat     1617
Leu Leu Gln Ala Pro Pro Ala Asp Asp Glu Gln Gly Arg Ile Leu Asp
460                 465                 470                 475

tac ttg gca gat gtc acc gtg aac aag cct cat ggt gtg cgt cca aag     1665
Tyr Leu Ala Asp Val Thr Val Asn Lys Pro His Gly Val Arg Pro Lys
                480                 485                 490

gat gtt gca gct cct atc gat aag ctg cct aac atc aag gat ctg cca     1713
Asp Val Ala Ala Pro Ile Asp Lys Leu Pro Asn Ile Lys Asp Leu Pro
            495                 500                 505

ctg cca cgc ggt tcc cgt gac cgc ctg aag cag ctt ggc cca gcc gcg     1761
Leu Pro Arg Gly Ser Arg Asp Arg Leu Lys Gln Leu Gly Pro Ala Ala
        510                 515                 520

ttt gct cgt gat ctc cgt gag cag gac gca ctg gca gtt act gat acc     1809
Phe Ala Arg Asp Leu Arg Glu Gln Asp Ala Leu Ala Val Thr Asp Thr
    525                 530                 535
```

```
acc ttc cgc gat gca cac cag tct ttg ctt gcg acc cga gtc cgc tca      1857
Thr Phe Arg Asp Ala His Gln Ser Leu Leu Ala Thr Arg Val Arg Ser
540                 545                 550                 555

ttc gca ctg aag cct gcg gca gag gcc gtc gca aag ctg act cct gag      1905
Phe Ala Leu Lys Pro Ala Ala Glu Ala Val Ala Lys Leu Thr Pro Glu
                560                 565                 570

ctt ttg tcc gtg gag gcc tgg ggc ggc gcg acc tac gat gtg gcg atg      1953
Leu Leu Ser Val Glu Ala Trp Gly Gly Ala Thr Tyr Asp Val Ala Met
            575                 580                 585

cgt ttc ctc ttt gag gat ccg tgg gac agg ctc gac gag ctg cgc gag      2001
Arg Phe Leu Phe Glu Asp Pro Trp Asp Arg Leu Asp Glu Leu Arg Glu
        590                 595                 600

gcg atg ccg aat gta aac att cag atg ctg ctt cgc ggc cgc aac acc      2049
Ala Met Pro Asn Val Asn Ile Gln Met Leu Leu Arg Gly Arg Asn Thr
    605                 610                 615

gtg gga tac acc ccg tac cca gac tcc gtc tgc cgc gcg ttt gtt aag      2097
Val Gly Tyr Thr Pro Tyr Pro Asp Ser Val Cys Arg Ala Phe Val Lys
620                 625                 630                 635

gaa gct gcc agc tcc ggc gtg gac atc ttc cgc atc ttc gac gcg ctt      2145
Glu Ala Ala Ser Ser Gly Val Asp Ile Phe Arg Ile Phe Asp Ala Leu
                640                 645                 650

aac gac gtc tcc cag atg cgt cca gca atc gac gca gtc ctg gag acc      2193
Asn Asp Val Ser Gln Met Arg Pro Ala Ile Asp Ala Val Leu Glu Thr
            655                 660                 665

aac acc gcg gta gcc gag gtg gct atg gct tat tct ggt gat ctc tct      2241
Asn Thr Ala Val Ala Glu Val Ala Met Ala Tyr Ser Gly Asp Leu Ser
        670                 675                 680

gat cca aat gaa aag ctc tac acc ctg gat tac tac cta aag atg gca      2289
Asp Pro Asn Glu Lys Leu Tyr Thr Leu Asp Tyr Tyr Leu Lys Met Ala
    685                 690                 695

gag gag atc gtc aag tct ggc gct cac atc ttg gcc att aag gat atg      2337
Glu Glu Ile Val Lys Ser Gly Ala His Ile Leu Ala Ile Lys Asp Met
700                 705                 710                 715

gct ggt ctg ctt cgc cca gct gcg gta acc aag ctg gtc acc gca ctg      2385
Ala Gly Leu Leu Arg Pro Ala Ala Val Thr Lys Leu Val Thr Ala Leu
                720                 725                 730

cgc cgt gaa ttc gat ctg cca gtg cac gtg cac acc cac gac act gcg      2433
Arg Arg Glu Phe Asp Leu Pro Val His Val His Thr His Asp Thr Ala
            735                 740                 745

ggt ggc cag ctg gca acc tac ttt gct gca gct caa gct ggt gca gat      2481
Gly Gly Gln Leu Ala Thr Tyr Phe Ala Ala Ala Gln Ala Gly Ala Asp
        750                 755                 760

gct gtt gac ggt gct tcc gca cca ctg tct ggc acc acc tcc cag cca      2529
Ala Val Asp Gly Ala Ser Ala Pro Leu Ser Gly Thr Thr Ser Gln Pro
    765                 770                 775

tcc ctg tct gcc att gtt gct gca ttc gcg cac acc cgt cgc gat acc      2577
Ser Leu Ser Ala Ile Val Ala Ala Phe Ala His Thr Arg Arg Asp Thr
780                 785                 790                 795

ggt ttg agc ctc gag gct gtt tct gac ctc gag ccg tac tgg gaa gca      2625
Gly Leu Ser Leu Glu Ala Val Ser Asp Leu Glu Pro Tyr Trp Glu Ala
                800                 805                 810

gtg cgc gga ctg tac ctg cca ttt gag tct gga acc cca ggc cca acc      2673
Val Arg Gly Leu Tyr Leu Pro Phe Glu Ser Gly Thr Pro Gly Pro Thr
            815                 820                 825

ggt cgc gtc tac cgc cac gaa atc cca ggc gga cag ttg tcc aac ctg      2721
Gly Arg Val Tyr Arg His Glu Ile Pro Gly Gly Gln Leu Ser Asn Leu
        830                 835                 840

cgt gca cag gcc acc gca ctg ggc ctt gcg gat cgt ttc gaa ctc atc      2769
Arg Ala Gln Ala Thr Ala Leu Gly Leu Ala Asp Arg Phe Glu Leu Ile
```

```
    845                 850                 855

gaa gac aac tac gca gcc gtt aat gag atg ctg gga cgc cca acc aag     2817
Glu Asp Asn Tyr Ala Ala Val Asn Glu Met Leu Gly Arg Pro Thr Lys
860                 865                 870                 875

gtc acc cca tcc tcc aag gtt gtt ggc gac ctc gca ctc cac ctc gtt     2865
Val Thr Pro Ser Ser Lys Val Val Gly Asp Leu Ala Leu His Leu Val
                880                 885                 890

ggt gcg ggt gtg gat cca gca gac ttt gct gcc gat cca caa aag tac     2913
Gly Ala Gly Val Asp Pro Ala Asp Phe Ala Ala Asp Pro Gln Lys Tyr
            895                 900                 905

gac atc cca gac tct gtc atc gcg ttc ctg cgc ggc gag ctt ggt aac     2961
Asp Ile Pro Asp Ser Val Ile Ala Phe Leu Arg Gly Glu Leu Gly Asn
        910                 915                 920

cct cca ggt ggc tgg cca gag cca ctg cgc acc cgc gca ctg gaa ggc     3009
Pro Pro Gly Gly Trp Pro Glu Pro Leu Arg Thr Arg Ala Leu Glu Gly
    925                 930                 935

cgc tcc gaa ggc aag gca cct ctg acg gaa gtt cct gag gaa gag cag     3057
Arg Ser Glu Gly Lys Ala Pro Leu Thr Glu Val Pro Glu Glu Glu Gln
940                 945                 950                 955

gcg cac ctc gac gct gat gat tcc aag gaa cgt cgc aat agc ctc aac     3105
Ala His Leu Asp Ala Asp Asp Ser Lys Glu Arg Arg Asn Ser Leu Asn
                960                 965                 970

cgc ctg ctg ttc ccg aag cca acc gaa gag ttc ctc gag cac cgt cgc     3153
Arg Leu Leu Phe Pro Lys Pro Thr Glu Glu Phe Leu Glu His Arg Arg
            975                 980                 985

cgc ttc ggc aac acc tct gcg ctg gat gat cgt gaa ttc ttc tac ggc     3201
Arg Phe Gly Asn Thr Ser Ala Leu Asp Asp Arg Glu Phe Phe Tyr Gly
        990                 995                1000

ctg gtc gaa ggc cgc gag act ttg atc cgc ctg cca gat gtg cgc acc     3249
Leu Val Glu Gly Arg Glu Thr Leu Ile Arg Leu Pro Asp Val Arg Thr
    1005                1010                1015

cca ctg ctt gtt cgc ctg gat gcg atc tct gag cca gac gat aag ggt     3297
Pro Leu Leu Val Arg Leu Asp Ala Ile Ser Glu Pro Asp Asp Lys Gly
1020                1025                1030                1035

atg cgc aat gtt gtg gcc aac gtc aac ggc cag atc cgc cca atg cgt     3345
Met Arg Asn Val Val Ala Asn Val Asn Gly Gln Ile Arg Pro Met Arg
                1040                1045                1050

gtg cgt gac cgc tcc gtt gag tct gtc acc gca acc gca gaa aag gca     3393
Val Arg Asp Arg Ser Val Glu Ser Val Thr Ala Thr Ala Glu Lys Ala
            1055                1060                1065

gat tcc tcc aac aag ggc cat gtt gct gca cca ttc gct ggt gtt gtc     3441
Asp Ser Ser Asn Lys Gly His Val Ala Ala Pro Phe Ala Gly Val Val
        1070                1075                1080

acc gtg act gtt gct gaa ggt gat gag gtc aag gct gga gat gca gtc     3489
Thr Val Thr Val Ala Glu Gly Asp Glu Val Lys Ala Gly Asp Ala Val
    1085                1090                1095

gca atc atc gag gct atg aag atg gaa gca aca atc act gct tct gtt     3537
Ala Ile Ile Glu Ala Met Lys Met Glu Ala Thr Ile Thr Ala Ser Val
1100                1105                1110                1115

gac ggc aaa atc gat cgc gtt gtg gtt cct gct gca acg aag gtg gaa     3585
Asp Gly Lys Ile Asp Arg Val Val Val Pro Ala Ala Thr Lys Val Glu
                1120                1125                1130

ggt ggc gac ttg atc gtc gtc gtt tcc          taa                    3615
Gly Gly Asp Leu Ile Val Val Val Ser
            1135                1140


<210> SEQ ID NO 25
<211> LENGTH: 1140
<212> TYPE: PRT
<213> ORGANISM: Corynebacterium glutamicum
```

```
<220> FEATURE:
<221> NAME/KEY: PEPTIDE
<222> LOCATION: (1)..(1140)
<223> OTHER INFORMATION: PycP458S amino acid sequence of C. glutamicum
      pyruvate carboxylase with P458S substitution

<400> SEQUENCE: 25

Val Ser Thr His Thr Ser Ser Thr Leu Pro Ala Phe Lys Lys Ile Leu
  1               5                  10                  15

Val Ala Asn Arg Gly Glu Ile Ala Val Arg Ala Phe Arg Ala Ala Leu
             20                  25                  30

Glu Thr Gly Ala Ala Thr Val Ala Ile Tyr Pro Arg Glu Asp Arg Gly
         35                  40                  45

Ser Phe His Arg Ser Phe Ala Ser Glu Ala Val Arg Ile Gly Thr Glu
     50                  55                  60

Gly Ser Pro Val Lys Ala Tyr Leu Asp Ile Asp Glu Ile Ile Gly Ala
 65                  70                  75                  80

Ala Lys Lys Val Lys Ala Asp Ala Ile Tyr Pro Gly Tyr Gly Phe Leu
                 85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380
```

```
Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Ser His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800
```

```
Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Val Pro Ala Ala Thr Lys Val Glu Gly Gly Asp Leu Ile
                1125                1130                1135

Val Val Val Ser
            1140
```

```
<210> SEQ ID NO 26
<211> LENGTH: 2367
<212> TYPE: DNA
<213> ORGANISM: Corynebacterium glutamicum
<220> FEATURE:
<221> NAME/KEY: CDS
<222> LOCATION: (151)..(2364)
<223> OTHER INFORMATION: icd, DNA sequence encoding wildtype C.
      glutamicum isocitrate dehydrogenase including 150 bp of upstream
      sequence

<400> SEQUENCE: 26
```

```
aggcctcgac cgttcccaag tggcattcat ggggtattgg aaacacggcg tttccatgcg     60

gggctgaaac tgccaccata ggcgccagca attagtagaa cactgtattc taggtagctg    120

aacaaaagag cccatcaacc aaggagactc atg gct aag atc atc tgg acc cgc     174
                                 Met Ala Lys Ile Ile Trp Thr Arg
                                   1               5

acc gac gaa gca ccg ctg ctc gcg acc tac tcg ctg aag ccg gtc gtc      222
Thr Asp Glu Ala Pro Leu Leu Ala Thr Tyr Ser Leu Lys Pro Val Val
     10                  15                  20

gag gca ttt gct gct acc gcg ggc att gag gtc gag acc cgg gac att      270
Glu Ala Phe Ala Ala Thr Ala Gly Ile Glu Val Glu Thr Arg Asp Ile
 25                  30                  35                  40

tca ctc gct gga cgc atc ctc gcc cag ttc cca gag cgc ctc acc gaa      318
Ser Leu Ala Gly Arg Ile Leu Ala Gln Phe Pro Glu Arg Leu Thr Glu
                 45                  50                  55

gat cag aag gta ggc aac gca ctc gca gaa ctc ggc gag ctt gct aag      366
Asp Gln Lys Val Gly Asn Ala Leu Ala Glu Leu Gly Glu Leu Ala Lys
             60                  65                  70

act cct gaa gca aac atc att aag ctt cca aac atc tcc gct tct gtt      414
Thr Pro Glu Ala Asn Ile Ile Lys Leu Pro Asn Ile Ser Ala Ser Val
         75                  80                  85

cca cag ctc aag gct gct att aag gaa ctg cag gac cag ggc tac gac      462
Pro Gln Leu Lys Ala Ala Ile Lys Glu Leu Gln Asp Gln Gly Tyr Asp
     90                  95                 100

atc cca gaa ctg cct gat aac gcc acc acc gac gag gaa aaa gac atc      510
Ile Pro Glu Leu Pro Asp Asn Ala Thr Thr Asp Glu Glu Lys Asp Ile
105                 110                 115                 120

ctc gca cgc tac aac gct gtt aag ggt tcc gct gtg aac cca gtg ctg      558
Leu Ala Arg Tyr Asn Ala Val Lys Gly Ser Ala Val Asn Pro Val Leu
                125                 130                 135

cgt gaa ggc aac tct gac cgc cgc gca cca atc gct gtc aag aac ttt      606
Arg Glu Gly Asn Ser Asp Arg Arg Ala Pro Ile Ala Val Lys Asn Phe
            140                 145                 150

gtt aag aag ttc cca cac cgc atg ggc gag tgg tct gca gat tcc aag      654
Val Lys Lys Phe Pro His Arg Met Gly Glu Trp Ser Ala Asp Ser Lys
        155                 160                 165

acc aac gtt gca acc atg gat gca aac gac ttc cgc cac aac gag aag      702
Thr Asn Val Ala Thr Met Asp Ala Asn Asp Phe Arg His Asn Glu Lys
    170                 175                 180

tcc atc atc ctc gac gct gct gat gaa gtt cag atc aag cac atc gca      750
Ser Ile Ile Leu Asp Ala Ala Asp Glu Val Gln Ile Lys His Ile Ala
185                 190                 195                 200

gct gac ggc acc gag acc atc ctc aag gac agc ctc aag ctt ctt gaa      798
Ala Asp Gly Thr Glu Thr Ile Leu Lys Asp Ser Leu Lys Leu Leu Glu
                205                 210                 215

ggc gaa gtt cta gac gga acc gtt ctg tcc gca aag gca ctg gac gca      846
Gly Glu Val Leu Asp Gly Thr Val Leu Ser Ala Lys Ala Leu Asp Ala
            220                 225                 230

ttc ctt ctc gag cag gtc gct cgc gca aag gca gaa ggt atc ctc ttc      894
Phe Leu Leu Glu Gln Val Ala Arg Ala Lys Ala Glu Gly Ile Leu Phe
        235                 240                 245

tcc gca cac ctg aag gcc acc atg atg aag gtc tcc gac cca atc atc      942
Ser Ala His Leu Lys Ala Thr Met Met Lys Val Ser Asp Pro Ile Ile
    250                 255                 260

ttc ggc cac gtt gtg cgc gct tac ttc gca gac gtt ttc gca cag tac      990
Phe Gly His Val Val Arg Ala Tyr Phe Ala Asp Val Phe Ala Gln Tyr
265                 270                 275                 280

ggt gag cag ctg ctc gca gct ggc ctc aac ggc gaa aac ggc ctc gct     1038
Gly Glu Gln Leu Leu Ala Ala Gly Leu Asn Gly Glu Asn Gly Leu Ala
```

-continued

```
                285                 290                 295

gca atc ctc tcc ggc ttg gag tcc ctg gac aac ggc gaa gaa atc aag     1086
Ala Ile Leu Ser Gly Leu Glu Ser Leu Asp Asn Gly Glu Glu Ile Lys
            300                 305                 310

gct gca ttc gag aag ggc ttg gaa gac ggc cca gac ctg gcc atg gtt     1134
Ala Ala Phe Glu Lys Gly Leu Glu Asp Gly Pro Asp Leu Ala Met Val
        315                 320                 325

aac tcc gct cgc ggc atc acc aac ctg cat gtc cct tcc gat gtc atc     1182
Asn Ser Ala Arg Gly Ile Thr Asn Leu His Val Pro Ser Asp Val Ile
    330                 335                 340

gtg gac gct tcc atg cca gca atg att cgt acc tcc ggc cac atg tgg     1230
Val Asp Ala Ser Met Pro Ala Met Ile Arg Thr Ser Gly His Met Trp
345                 350                 355                 360

aac aaa gac gac cag gag cag gac acc ctg gca atc atc cca gac tcc     1278
Asn Lys Asp Asp Gln Glu Gln Asp Thr Leu Ala Ile Ile Pro Asp Ser
                365                 370                 375

tcc tac gct ggc gtc tac cag acc gtt atc gaa gac tgc cgc aag aac     1326
Ser Tyr Ala Gly Val Tyr Gln Thr Val Ile Glu Asp Cys Arg Lys Asn
            380                 385                 390

ggc gca ttc gat cca acc acc atg ggt acc gtc cct aac gtt ggt ctg     1374
Gly Ala Phe Asp Pro Thr Thr Met Gly Thr Val Pro Asn Val Gly Leu
        395                 400                 405

atg gct cag aag gct gaa gag tac ggc tcc cat gac aag acc ttc cgc     1422
Met Ala Gln Lys Ala Glu Glu Tyr Gly Ser His Asp Lys Thr Phe Arg
    410                 415                 420

atc gaa gca gac ggt gtg gtt cag gtt gtt tcc tcc aac ggc gac gtt     1470
Ile Glu Ala Asp Gly Val Val Gln Val Val Ser Ser Asn Gly Asp Val
425                 430                 435                 440

ctc atc gag cac gac gtt gag gca aat gac atc tgg cgt gca tgc cag     1518
Leu Ile Glu His Asp Val Glu Ala Asn Asp Ile Trp Arg Ala Cys Gln
                445                 450                 455

gtc aag gat gcc cca atc cag gat tgg gta aag ctt gct gtc acc cgc     1566
Val Lys Asp Ala Pro Ile Gln Asp Trp Val Lys Leu Ala Val Thr Arg
            460                 465                 470

tcc cgt ctc tcc gga atg cct gca gtg ttc tgg ttg gat cca gag cgc     1614
Ser Arg Leu Ser Gly Met Pro Ala Val Phe Trp Leu Asp Pro Glu Arg
        475                 480                 485

gca cac gac cgc aac ctg gct tcc ctc gtt gag aag tac ctg gct gac     1662
Ala His Asp Arg Asn Leu Ala Ser Leu Val Glu Lys Tyr Leu Ala Asp
    490                 495                 500

cac gac acc gag ggc ctg gac atc cag atc ctc tcc cct gtt gag gca     1710
His Asp Thr Glu Gly Leu Asp Ile Gln Ile Leu Ser Pro Val Glu Ala
505                 510                 515                 520

acc cag ctc tcc atc gac cgc atc cgc cgt ggc gag gac acc atc tct     1758
Thr Gln Leu Ser Ile Asp Arg Ile Arg Arg Gly Glu Asp Thr Ile Ser
                525                 530                 535

gtc acc ggt aac gtt ctg cgt gac tac aac acc gac ctc ttc cca atc     1806
Val Thr Gly Asn Val Leu Arg Asp Tyr Asn Thr Asp Leu Phe Pro Ile
            540                 545                 550

ctg gag ctg ggc acc tct gca aag atg ctg tct gtc gtt cct ttg atg     1854
Leu Glu Leu Gly Thr Ser Ala Lys Met Leu Ser Val Val Pro Leu Met
        555                 560                 565

gct ggc ggc gga ctg ttc gag acc ggt gct ggt gga tct gct cct aag     1902
Ala Gly Gly Gly Leu Phe Glu Thr Gly Ala Gly Gly Ser Ala Pro Lys
    570                 575                 580

cac gtc cag cag gtt cag gaa gaa aac cac ctg cgt tgg gat tcc ctc     1950
His Val Gln Gln Val Gln Glu Glu Asn His Leu Arg Trp Asp Ser Leu
585                 590                 595                 600

ggt gag ttc ctc gca ctg gct gag tcc ttc cgc cac gag ctc aac aac     1998
```

```
Gly Glu Phe Leu Ala Leu Ala Glu Ser Phe Arg His Glu Leu Asn Asn
                605                 610                 615

aac ggc aac acc aag gcc ggc gtt ctg gct gac gct ctg gac aag gca     2046
Asn Gly Asn Thr Lys Ala Gly Val Leu Ala Asp Ala Leu Asp Lys Ala
            620                 625                 630

act gag aag ctg ctg aac gaa gag aag tcc cca tcc cgc aag gtt ggc     2094
Thr Glu Lys Leu Leu Asn Glu Glu Lys Ser Pro Ser Arg Lys Val Gly
        635                 640                 645

gag atc gac aac cgt ggc tcc cac ttc tgg ctg acc aag ttc tgg gct     2142
Glu Ile Asp Asn Arg Gly Ser His Phe Trp Leu Thr Lys Phe Trp Ala
    650                 655                 660

gac gag ctc gct gct cag acc gag gac gca gat ctg gct gct acc ttc     2190
Asp Glu Leu Ala Ala Gln Thr Glu Asp Ala Asp Leu Ala Ala Thr Phe
665                 670                 675                 680

gca cca gtc gca gaa gca ctg aac aca ggc gct gca gac atc gat gct     2238
Ala Pro Val Ala Glu Ala Leu Asn Thr Gly Ala Ala Asp Ile Asp Ala
                685                 690                 695

gca ctg ctc gca gtt cag ggt gga gca act gac ctt ggt ggc tac tac     2286
Ala Leu Leu Ala Val Gln Gly Gly Ala Thr Asp Leu Gly Gly Tyr Tyr
            700                 705                 710

tcc cct aac gag gag aag ctc acc aac atc atg cgc cca gtc gca cag     2334
Ser Pro Asn Glu Glu Lys Leu Thr Asn Ile Met Arg Pro Val Ala Gln
        715                 720                 725

ttc aac gag atc gtt gac gca ctg aag aag         taa                 2367
Phe Asn Glu Ile Val Asp Ala Leu Lys Lys
    730                 735


<210> SEQ ID NO 27
<211> LENGTH: 738
<212> TYPE: PRT
<213> ORGANISM: Corynebacterium glutamicum
<220> FEATURE:
<221> NAME/KEY: PEPTIDE
<222> LOCATION: (1)..(738)
<223> OTHER INFORMATION: Icd, amino acid sequence of C. glutamicum
      isocitrate dehydrogenase

<400> SEQUENCE: 27

Met Ala Lys Ile Ile Trp Thr Arg Thr Asp Glu Ala Pro Leu Leu Ala
  1               5                  10                  15

Thr Tyr Ser Leu Lys Pro Val Val Glu Ala Phe Ala Ala Thr Ala Gly
            20                  25                  30

Ile Glu Val Glu Thr Arg Asp Ile Ser Leu Ala Gly Arg Ile Leu Ala
        35                  40                  45

Gln Phe Pro Glu Arg Leu Thr Glu Asp Gln Lys Val Gly Asn Ala Leu
     50                  55                  60

Ala Glu Leu Gly Glu Leu Ala Lys Thr Pro Glu Ala Asn Ile Ile Lys
 65                  70                  75                  80

Leu Pro Asn Ile Ser Ala Ser Val Pro Gln Leu Lys Ala Ala Ile Lys
                85                  90                  95

Glu Leu Gln Asp Gln Gly Tyr Asp Ile Pro Glu Leu Pro Asp Asn Ala
            100                 105                 110

Thr Thr Asp Glu Glu Lys Asp Ile Leu Ala Arg Tyr Asn Ala Val Lys
        115                 120                 125

Gly Ser Ala Val Asn Pro Val Leu Arg Glu Gly Asn Ser Asp Arg Arg
    130                 135                 140

Ala Pro Ile Ala Val Lys Asn Phe Val Lys Lys Phe Pro His Arg Met
145                 150                 155                 160

Gly Glu Trp Ser Ala Asp Ser Lys Thr Asn Val Ala Thr Met Asp Ala
```

```
                165                 170                 175

Asn Asp Phe Arg His Asn Glu Lys Ser Ile Ile Leu Asp Ala Ala Asp
            180                 185                 190

Glu Val Gln Ile Lys His Ile Ala Ala Asp Gly Thr Glu Thr Ile Leu
        195                 200                 205

Lys Asp Ser Leu Lys Leu Leu Glu Gly Glu Val Leu Asp Gly Thr Val
    210                 215                 220

Leu Ser Ala Lys Ala Leu Asp Ala Phe Leu Leu Glu Gln Val Ala Arg
225                 230                 235                 240

Ala Lys Ala Glu Gly Ile Leu Phe Ser Ala His Leu Lys Ala Thr Met
                245                 250                 255

Met Lys Val Ser Asp Pro Ile Ile Phe Gly His Val Val Arg Ala Tyr
            260                 265                 270

Phe Ala Asp Val Phe Ala Gln Tyr Gly Glu Gln Leu Leu Ala Ala Gly
        275                 280                 285

Leu Asn Gly Glu Asn Gly Leu Ala Ala Ile Leu Ser Gly Leu Glu Ser
    290                 295                 300

Leu Asp Asn Gly Glu Glu Ile Lys Ala Ala Phe Glu Lys Gly Leu Glu
305                 310                 315                 320

Asp Gly Pro Asp Leu Ala Met Val Asn Ser Ala Arg Gly Ile Thr Asn
                325                 330                 335

Leu His Val Pro Ser Asp Val Ile Val Asp Ala Ser Met Pro Ala Met
            340                 345                 350

Ile Arg Thr Ser Gly His Met Trp Asn Lys Asp Asp Gln Glu Gln Asp
        355                 360                 365

Thr Leu Ala Ile Ile Pro Asp Ser Ser Tyr Ala Gly Val Tyr Gln Thr
    370                 375                 380

Val Ile Glu Asp Cys Arg Lys Asn Gly Ala Phe Asp Pro Thr Thr Met
385                 390                 395                 400

Gly Thr Val Pro Asn Val Gly Leu Met Ala Gln Lys Ala Glu Glu Tyr
                405                 410                 415

Gly Ser His Asp Lys Thr Phe Arg Ile Glu Ala Asp Gly Val Val Gln
            420                 425                 430

Val Val Ser Ser Asn Gly Asp Val Leu Ile Glu His Asp Val Glu Ala
        435                 440                 445

Asn Asp Ile Trp Arg Ala Cys Gln Val Lys Asp Ala Pro Ile Gln Asp
    450                 455                 460

Trp Val Lys Leu Ala Val Thr Arg Ser Arg Leu Ser Gly Met Pro Ala
465                 470                 475                 480

Val Phe Trp Leu Asp Pro Glu Arg Ala His Asp Arg Asn Leu Ala Ser
                485                 490                 495

Leu Val Glu Lys Tyr Leu Ala Asp His Asp Thr Glu Gly Leu Asp Ile
            500                 505                 510

Gln Ile Leu Ser Pro Val Glu Ala Thr Gln Leu Ser Ile Asp Arg Ile
        515                 520                 525

Arg Arg Gly Glu Asp Thr Ile Ser Val Thr Gly Asn Val Leu Arg Asp
    530                 535                 540

Tyr Asn Thr Asp Leu Phe Pro Ile Leu Glu Leu Gly Thr Ser Ala Lys
545                 550                 555                 560

Met Leu Ser Val Val Pro Leu Met Ala Gly Gly Gly Leu Phe Glu Thr
                565                 570                 575

Gly Ala Gly Gly Ser Ala Pro Lys His Val Gln Gln Val Gln Glu Glu
            580                 585                 590
```

```
Asn His Leu Arg Trp Asp Ser Leu Gly Glu Phe Leu Ala Leu Ala Glu
        595                 600                 605

Ser Phe Arg His Glu Leu Asn Asn Asn Gly Asn Thr Lys Ala Gly Val
    610                 615                 620

Leu Ala Asp Ala Leu Asp Lys Ala Thr Glu Lys Leu Leu Asn Glu Glu
625                 630                 635                 640

Lys Ser Pro Ser Arg Lys Val Gly Glu Ile Asp Asn Arg Gly Ser His
                645                 650                 655

Phe Trp Leu Thr Lys Phe Trp Ala Asp Glu Leu Ala Ala Gln Thr Glu
            660                 665                 670

Asp Ala Asp Leu Ala Ala Thr Phe Ala Pro Val Ala Glu Ala Leu Asn
        675                 680                 685

Thr Gly Ala Ala Asp Ile Asp Ala Ala Leu Leu Ala Val Gln Gly Gly
    690                 695                 700

Ala Thr Asp Leu Gly Gly Tyr Tyr Ser Pro Asn Glu Glu Lys Leu Thr
705                 710                 715                 720

Asn Ile Met Arg Pro Val Ala Gln Phe Asn Glu Ile Val Asp Ala Leu
                725                 730                 735

Lys Lys


<210> SEQ ID NO 28
<211> LENGTH: 2367
<212> TYPE: DNA
<213> ORGANISM: Corynebacterium glutamicum
<220> FEATURE:
<221> NAME/KEY: CDS
<222> LOCATION: (151)..(2364)
<223> OTHER INFORMATION: icdA1G, DNA sequence encoding C. glutamicum
      isocitrate dehydrogenase with substitution ATG -> GTG including
      150 bp of upstream sequence

<400> SEQUENCE: 28

aggcctcgac cgttcccaag tggcattcat ggggtattgg aaacacggcg tttccatgcg      60

gggctgaaac tgccaccata ggcgccagca attagtagaa cactgtattc taggtagctg     120

aacaaaagag cccatcaacc aaggagactc gtg gct aag atc atc tgg acc cgc      174
                                 Val Ala Lys Ile Ile Trp Thr Arg
                                 1               5

acc gac gaa gca ccg ctg ctc gcg acc tac tcg ctg aag ccg gtc gtc      222
Thr Asp Glu Ala Pro Leu Leu Ala Thr Tyr Ser Leu Lys Pro Val Val
     10                  15                  20

gag gca ttt gct gct acc gcg ggc att gag gtc gag acc cgg gac att      270
Glu Ala Phe Ala Ala Thr Ala Gly Ile Glu Val Glu Thr Arg Asp Ile
 25                  30                  35                  40

tca ctc gct gga cgc atc ctc gcc cag ttc cca gag cgc ctc acc gaa      318
Ser Leu Ala Gly Arg Ile Leu Ala Gln Phe Pro Glu Arg Leu Thr Glu
                 45                  50                  55

gat cag aag gta ggc aac gca ctc gca gaa ctc ggc gag ctt gct aag      366
Asp Gln Lys Val Gly Asn Ala Leu Ala Glu Leu Gly Glu Leu Ala Lys
             60                  65                  70

act cct gaa gca aac atc att aag ctt cca aac atc tcc gct tct gtt      414
Thr Pro Glu Ala Asn Ile Ile Lys Leu Pro Asn Ile Ser Ala Ser Val
         75                  80                  85

cca cag ctc aag gct gct att aag gaa ctg cag gac cag ggc tac gac      462
Pro Gln Leu Lys Ala Ala Ile Lys Glu Leu Gln Asp Gln Gly Tyr Asp
     90                  95                 100

atc cca gaa ctg cct gat aac gcc acc acc gac gag gaa aaa gac atc      510
Ile Pro Glu Leu Pro Asp Asn Ala Thr Thr Asp Glu Glu Lys Asp Ile
105                 110                 115                 120
```

```
ctc gca cgc tac aac gct gtt aag ggt tcc gct gtg aac cca gtg ctg      558
Leu Ala Arg Tyr Asn Ala Val Lys Gly Ser Ala Val Asn Pro Val Leu
                125                 130                 135

cgt gaa ggc aac tct gac cgc cgc gca cca atc gct gtc aag aac ttt      606
Arg Glu Gly Asn Ser Asp Arg Arg Ala Pro Ile Ala Val Lys Asn Phe
            140                 145                 150

gtt aag aag ttc cca cac cgc atg ggc gag tgg tct gca gat tcc aag      654
Val Lys Lys Phe Pro His Arg Met Gly Glu Trp Ser Ala Asp Ser Lys
        155                 160                 165

acc aac gtt gca acc atg gat gca aac gac ttc cgc cac aac gag aag      702
Thr Asn Val Ala Thr Met Asp Ala Asn Asp Phe Arg His Asn Glu Lys
    170                 175                 180

tcc atc atc ctc gac gct gct gat gaa gtt cag atc aag cac atc gca      750
Ser Ile Ile Leu Asp Ala Ala Asp Glu Val Gln Ile Lys His Ile Ala
185                 190                 195                 200

gct gac ggc acc gag acc atc ctc aag gac agc ctc aag ctt ctt gaa      798
Ala Asp Gly Thr Glu Thr Ile Leu Lys Asp Ser Leu Lys Leu Leu Glu
                205                 210                 215

ggc gaa gtt cta gac gga acc gtt ctg tcc gca aag gca ctg gac gca      846
Gly Glu Val Leu Asp Gly Thr Val Leu Ser Ala Lys Ala Leu Asp Ala
            220                 225                 230

ttc ctt ctc gag cag gtc gct cgc gca aag gca gaa ggt atc ctc ttc      894
Phe Leu Leu Glu Gln Val Ala Arg Ala Lys Ala Glu Gly Ile Leu Phe
        235                 240                 245

tcc gca cac ctg aag gcc acc atg atg aag gtc tcc gac cca atc atc      942
Ser Ala His Leu Lys Ala Thr Met Met Lys Val Ser Asp Pro Ile Ile
    250                 255                 260

ttc ggc cac gtt gtg cgc gct tac ttc gca gac gtt ttc gca cag tac      990
Phe Gly His Val Val Arg Ala Tyr Phe Ala Asp Val Phe Ala Gln Tyr
265                 270                 275                 280

ggt gag cag ctg ctc gca gct ggc ctc aac ggc gaa aac ggc ctc gct     1038
Gly Glu Gln Leu Leu Ala Ala Gly Leu Asn Gly Glu Asn Gly Leu Ala
                285                 290                 295

gca atc ctc tcc ggc ttg gag tcc ctg gac aac ggc gaa gaa atc aag     1086
Ala Ile Leu Ser Gly Leu Glu Ser Leu Asp Asn Gly Glu Glu Ile Lys
            300                 305                 310

gct gca ttc gag aag ggc ttg gaa gac ggc cca gac ctg gcc atg gtt     1134
Ala Ala Phe Glu Lys Gly Leu Glu Asp Gly Pro Asp Leu Ala Met Val
        315                 320                 325

aac tcc gct cgc ggc atc acc aac ctg cat gtc cct tcc gat gtc atc     1182
Asn Ser Ala Arg Gly Ile Thr Asn Leu His Val Pro Ser Asp Val Ile
    330                 335                 340

gtg gac gct tcc atg cca gca atg att cgt acc tcc ggc cac atg tgg     1230
Val Asp Ala Ser Met Pro Ala Met Ile Arg Thr Ser Gly His Met Trp
345                 350                 355                 360

aac aaa gac gac cag gag cag gac acc ctg gca atc atc cca gac tcc     1278
Asn Lys Asp Asp Gln Glu Gln Asp Thr Leu Ala Ile Ile Pro Asp Ser
                365                 370                 375

tcc tac gct ggc gtc tac cag acc gtt atc gaa gac tgc cgc aag aac     1326
Ser Tyr Ala Gly Val Tyr Gln Thr Val Ile Glu Asp Cys Arg Lys Asn
            380                 385                 390

ggc gca ttc gat cca acc acc atg ggt acc gtc cct aac gtt ggt ctg     1374
Gly Ala Phe Asp Pro Thr Thr Met Gly Thr Val Pro Asn Val Gly Leu
        395                 400                 405

atg gct cag aag gct gaa gag tac ggc tcc cat gac aag acc ttc cgc     1422
Met Ala Gln Lys Ala Glu Glu Tyr Gly Ser His Asp Lys Thr Phe Arg
    410                 415                 420

atc gaa gca gac ggt gtg gtt cag gtt gtt tcc tcc aac ggc gac gtt     1470
Ile Glu Ala Asp Gly Val Val Gln Val Val Ser Ser Asn Gly Asp Val
```

```
425                 430                 435                 440

ctc atc gag cac gac gtt gag gca aat gac atc tgg cgt gca tgc cag     1518
Leu Ile Glu His Asp Val Glu Ala Asn Asp Ile Trp Arg Ala Cys Gln
                445                 450                 455

gtc aag gat gcc cca atc cag gat tgg gta aag ctt gct gtc acc cgc     1566
Val Lys Asp Ala Pro Ile Gln Asp Trp Val Lys Leu Ala Val Thr Arg
            460                 465                 470

tcc cgt ctc tcc gga atg cct gca gtg ttc tgg ttg gat cca gag cgc     1614
Ser Arg Leu Ser Gly Met Pro Ala Val Phe Trp Leu Asp Pro Glu Arg
        475                 480                 485

gca cac gac cgc aac ctg gct tcc ctc gtt gag aag tac ctg gct gac     1662
Ala His Asp Arg Asn Leu Ala Ser Leu Val Glu Lys Tyr Leu Ala Asp
    490                 495                 500

cac gac acc gag ggc ctg gac atc cag atc ctc tcc cct gtt gag gca     1710
His Asp Thr Glu Gly Leu Asp Ile Gln Ile Leu Ser Pro Val Glu Ala
505                 510                 515                 520

acc cag ctc tcc atc gac cgc atc cgc cgt ggc gag gac acc atc tct     1758
Thr Gln Leu Ser Ile Asp Arg Ile Arg Arg Gly Glu Asp Thr Ile Ser
                525                 530                 535

gtc acc ggt aac gtt ctg cgt gac tac aac acc gac ctc ttc cca atc     1806
Val Thr Gly Asn Val Leu Arg Asp Tyr Asn Thr Asp Leu Phe Pro Ile
            540                 545                 550

ctg gag ctg ggc acc tct gca aag atg ctg tct gtc gtt cct ttg atg     1854
Leu Glu Leu Gly Thr Ser Ala Lys Met Leu Ser Val Val Pro Leu Met
        555                 560                 565

gct ggc ggc gga ctg ttc gag acc ggt gct ggt gga tct gct cct aag     1902
Ala Gly Gly Gly Leu Phe Glu Thr Gly Ala Gly Gly Ser Ala Pro Lys
    570                 575                 580

cac gtc cag cag gtt cag gaa gaa aac cac ctg cgt tgg gat tcc ctc     1950
His Val Gln Gln Val Gln Glu Glu Asn His Leu Arg Trp Asp Ser Leu
585                 590                 595                 600

ggt gag ttc ctc gca ctg gct gag tcc ttc cgc cac gag ctc aac aac     1998
Gly Glu Phe Leu Ala Leu Ala Glu Ser Phe Arg His Glu Leu Asn Asn
                605                 610                 615

aac ggc aac acc aag gcc ggc gtt ctg gct gac gct ctg gac aag gca     2046
Asn Gly Asn Thr Lys Ala Gly Val Leu Ala Asp Ala Leu Asp Lys Ala
            620                 625                 630

act gag aag ctg ctg aac gaa gag aag tcc cca tcc cgc aag gtt ggc     2094
Thr Glu Lys Leu Leu Asn Glu Glu Lys Ser Pro Ser Arg Lys Val Gly
        635                 640                 645

gag atc gac aac cgt ggc tcc cac ttc tgg ctg acc aag ttc tgg gct     2142
Glu Ile Asp Asn Arg Gly Ser His Phe Trp Leu Thr Lys Phe Trp Ala
    650                 655                 660

gac gag ctc gct gct cag acc gag gac gca gat ctg gct gct acc ttc     2190
Asp Glu Leu Ala Ala Gln Thr Glu Asp Ala Asp Leu Ala Ala Thr Phe
665                 670                 675                 680

gca cca gtc gca gaa gca ctg aac aca ggc gct gca gac atc gat gct     2238
Ala Pro Val Ala Glu Ala Leu Asn Thr Gly Ala Ala Asp Ile Asp Ala
                685                 690                 695

gca ctg ctc gca gtt cag ggt gga gca act gac ctt ggt ggc tac tac     2286
Ala Leu Leu Ala Val Gln Gly Gly Ala Thr Asp Leu Gly Gly Tyr Tyr
            700                 705                 710

tcc cct aac gag gag aag ctc acc aac atc atg cgc cca gtc gca cag     2334
Ser Pro Asn Glu Glu Lys Leu Thr Asn Ile Met Arg Pro Val Ala Gln
        715                 720                 725

ttc aac gag atc gtt gac gca ctg aag aag         taa                 2367
Phe Asn Glu Ile Val Asp Ala Leu Lys Lys
    730                 735
```

```
<210> SEQ ID NO 29
<211> LENGTH: 1208
<212> TYPE: DNA
<213> ORGANISM: Corynebacterium glutamicum
<220> FEATURE:
<221> NAME/KEY: CDS
<222> LOCATION: (201)..(1205)
<223> OTHER INFORMATION: fbp, DNA sequence encoding wildtype C.
      glutamicum fructose 1,6-bisphosphatase with natural promoter

<400> SEQUENCE: 29

tcagccaccc gcctagtatg tcacgagttt ggtacgaaac cccctttttgg gtgtccagaa     60

tccaaaattc cgggcacaaa agtgcaacaa tagatgacgt gcgggttgat acagcccaag    120

cgccgataca tttataatgc gcctagatac gtgcaaccca cgtaaccagg tcagatcaag    180

tgccccagga ggcccttcag atg aac cta aag aac ccc gaa acg cca gac cgt    233
                      Met Asn Leu Lys Asn Pro Glu Thr Pro Asp Arg
                        1               5                  10

aac ctt gct atg gag ctg gtg cga gtt acg gaa gca gct gca ctg gct      281
Asn Leu Ala Met Glu Leu Val Arg Val Thr Glu Ala Ala Ala Leu Ala
             15                  20                  25

tct gga cgt tgg gtt gga cgt ggc atg aag aat gaa ggc gac ggt gcc      329
Ser Gly Arg Trp Val Gly Arg Gly Met Lys Asn Glu Gly Asp Gly Ala
         30                  35                  40

gct gtt gac gcc atg cgc cag ctc atc aac tca gtg acc atg aag ggc      377
Ala Val Asp Ala Met Arg Gln Leu Ile Asn Ser Val Thr Met Lys Gly
     45                  50                  55

gtc gtt gtt atc ggc gag ggc gaa aaa gac gaa gct cca atg ctg tac      425
Val Val Val Ile Gly Glu Gly Glu Lys Asp Glu Ala Pro Met Leu Tyr
 60                  65                  70                  75

aac ggc gaa gag gtc gga acc ggc ttt gga cct gag gtt gat atc gca      473
Asn Gly Glu Glu Val Gly Thr Gly Phe Gly Pro Glu Val Asp Ile Ala
                 80                  85                  90

gtt gac cca gtt gac ggc acc acc ctg atg gct gag ggt cgc ccc aac      521
Val Asp Pro Val Asp Gly Thr Thr Leu Met Ala Glu Gly Arg Pro Asn
             95                 100                 105

gca att tcc att ctc gca gct gca gag cgt ggc acc atg tac gat cca      569
Ala Ile Ser Ile Leu Ala Ala Ala Glu Arg Gly Thr Met Tyr Asp Pro
        110                 115                 120

tcc tcc gtc ttc tac atg aag aag atc gcc gtg gga cct gag gcc gca      617
Ser Ser Val Phe Tyr Met Lys Lys Ile Ala Val Gly Pro Glu Ala Ala
    125                 130                 135

ggc aag atc gac atc gaa gct cca gtt gcc cac aac atc aac gcg gtg      665
Gly Lys Ile Asp Ile Glu Ala Pro Val Ala His Asn Ile Asn Ala Val
140                 145                 150                 155

gca aag tcc aag gga atc aac cct tcc gac gtc acc gtt gtc gtg ctt      713
Ala Lys Ser Lys Gly Ile Asn Pro Ser Asp Val Thr Val Val Val Leu
                160                 165                 170

gac cgt cct cgc cac atc gaa ctg atc gca gac att cgt cgt gca ggc      761
Asp Arg Pro Arg His Ile Glu Leu Ile Ala Asp Ile Arg Arg Ala Gly
            175                 180                 185

gca aag gtt cgt ctc atc tcc gac ggc gac gtt gca ggt gca gtt gca      809
Ala Lys Val Arg Leu Ile Ser Asp Gly Asp Val Ala Gly Ala Val Ala
        190                 195                 200

gca gct cag gat tcc aac tcc gtg gac atc atg atg ggc acc ggc gga      857
Ala Ala Gln Asp Ser Asn Ser Val Asp Ile Met Met Gly Thr Gly Gly
    205                 210                 215

acc cca gaa ggc atc atc act gcg tgc gcc atg aag tgc atg ggt ggc      905
Thr Pro Glu Gly Ile Ile Thr Ala Cys Ala Met Lys Cys Met Gly Gly
220                 225                 230                 235

gaa atc cag ggc atc ctg gcc cca atg aac gat ttc gag cgc cag aag      953
```

```
Glu Ile Gln Gly Ile Leu Ala Pro Met Asn Asp Phe Glu Arg Gln Lys
                240                 245                 250

gca cac gac gct ggt ctg gtt ctt gat cag gtt ctg cac acc aac gat     1001
Ala His Asp Ala Gly Leu Val Leu Asp Gln Val Leu His Thr Asn Asp
            255                 260                 265

ctg gtg agc tcc gac aac tgc tac ttc gtg gca acc ggt gtg acc aac     1049
Leu Val Ser Ser Asp Asn Cys Tyr Phe Val Ala Thr Gly Val Thr Asn
        270                 275                 280

ggt gac atg ctc cgt ggc gtt tcc tac cgc gca aac ggc gca acc acc     1097
Gly Asp Met Leu Arg Gly Val Ser Tyr Arg Ala Asn Gly Ala Thr Thr
    285                 290                 295

cgt tcc ctg gtt atg cgc gca aag tca ggc acc atc cgc cac atc gag     1145
Arg Ser Leu Val Met Arg Ala Lys Ser Gly Thr Ile Arg His Ile Glu
300                 305                 310                 315

tct gtc cac cag ctg tcc aag ctg cag gaa tac tcc gtg gtt gac tac     1193
Ser Val His Gln Leu Ser Lys Leu Gln Glu Tyr Ser Val Val Asp Tyr
                320                 325                 330

acc acc gcg acc taa                                                 1208
Thr Thr Ala Thr
            335


<210> SEQ ID NO 30
<211> LENGTH: 335
<212> TYPE: PRT
<213> ORGANISM: Corynebacterium glutamicum
<220> FEATURE:
<221> NAME/KEY: PEPTIDE
<222> LOCATION: (1)..(335)
<223> OTHER INFORMATION: Fbp, amino acid sequence of C. glutamicum
      fructose 1,6-bisphosphatase

<400> SEQUENCE: 30

Met Asn Leu Lys Asn Pro Glu Thr Pro Asp Arg Asn Leu Ala Met Glu
  1               5                  10                  15

Leu Val Arg Val Thr Glu Ala Ala Ala Leu Ala Ser Gly Arg Trp Val
             20                  25                  30

Gly Arg Gly Met Lys Asn Glu Gly Asp Gly Ala Ala Val Asp Ala Met
         35                  40                  45

Arg Gln Leu Ile Asn Ser Val Thr Met Lys Gly Val Val Val Ile Gly
     50                  55                  60

Glu Gly Glu Lys Asp Glu Ala Pro Met Leu Tyr Asn Gly Glu Glu Val
 65                  70                  75                  80

Gly Thr Gly Phe Gly Pro Glu Val Asp Ile Ala Val Asp Pro Val Asp
                 85                  90                  95

Gly Thr Thr Leu Met Ala Glu Gly Arg Pro Asn Ala Ile Ser Ile Leu
            100                 105                 110

Ala Ala Ala Glu Arg Gly Thr Met Tyr Asp Pro Ser Ser Val Phe Tyr
        115                 120                 125

Met Lys Lys Ile Ala Val Gly Pro Glu Ala Ala Gly Lys Ile Asp Ile
    130                 135                 140

Glu Ala Pro Val Ala His Asn Ile Asn Ala Val Ala Lys Ser Lys Gly
145                 150                 155                 160

Ile Asn Pro Ser Asp Val Thr Val Val Val Leu Asp Arg Pro Arg His
                165                 170                 175

Ile Glu Leu Ile Ala Asp Ile Arg Arg Ala Gly Ala Lys Val Arg Leu
            180                 185                 190

Ile Ser Asp Gly Asp Val Ala Gly Ala Val Ala Ala Ala Gln Asp Ser
        195                 200                 205
```

```
Asn Ser Val Asp Ile Met Met Gly Thr Gly Gly Thr Pro Glu Gly Ile
    210                 215                 220

Ile Thr Ala Cys Ala Met Lys Cys Met Gly Gly Glu Ile Gln Gly Ile
225                 230                 235                 240

Leu Ala Pro Met Asn Asp Phe Glu Arg Gln Lys Ala His Asp Ala Gly
                245                 250                 255

Leu Val Leu Asp Gln Val Leu His Thr Asn Asp Leu Val Ser Ser Asp
            260                 265                 270

Asn Cys Tyr Phe Val Ala Thr Gly Val Thr Asn Gly Asp Met Leu Arg
        275                 280                 285

Gly Val Ser Tyr Arg Ala Asn Gly Ala Thr Thr Arg Ser Leu Val Met
    290                 295                 300

Arg Ala Lys Ser Gly Thr Ile Arg His Ile Glu Ser Val His Gln Leu
305                 310                 315                 320

Ser Lys Leu Gln Glu Tyr Ser Val Val Asp Tyr Thr Thr Ala Thr
                325                 330                 335


<210> SEQ ID NO 31
<211> LENGTH: 1208
<212> TYPE: DNA
<213> ORGANISM: Corynebacterium glutamicum
<220> FEATURE:
<221> NAME/KEY: CDS
<222> LOCATION: (201)..(1205)
<223> OTHER INFORMATION: fbp, DNA sequence with eftu (elongation factor
      Tu)-promoter

<400> SEQUENCE: 31

tggccgttac cctgcgaatg tccacagggt agctggtagt ttgaaaatca acgccgttgc     60

ccttaggatt cagtaactgg cacattttgt aatgcgctag atctgtgtgc tcagtcttcc    120

aggctgctta tcacagtgaa agcaaaacca attcgtggct gcgaaagtcg tagccaccac    180

gaagtccagg aggacataca atg aac cta aag aac ccc gaa acg cca gac cgt    233
                      Met Asn Leu Lys Asn Pro Glu Thr Pro Asp Arg
                        1               5                  10

aac ctt gct atg gag ctg gtg cga gtt acg gaa gca gct gca ctg gct      281
Asn Leu Ala Met Glu Leu Val Arg Val Thr Glu Ala Ala Ala Leu Ala
            15                  20                  25

tct gga cgt tgg gtt gga cgt ggc atg aag aat gaa ggc gac ggt gcc      329
Ser Gly Arg Trp Val Gly Arg Gly Met Lys Asn Glu Gly Asp Gly Ala
        30                  35                  40

gct gtt gac gcc atg cgc cag ctc atc aac tca gtg acc atg aag ggc      377
Ala Val Asp Ala Met Arg Gln Leu Ile Asn Ser Val Thr Met Lys Gly
    45                  50                  55

gtc gtt gtt atc ggc gag ggc gaa aaa gac gaa gct cca atg ctg tac      425
Val Val Val Ile Gly Glu Gly Glu Lys Asp Glu Ala Pro Met Leu Tyr
 60                  65                  70                  75

aac ggc gaa gag gtc gga acc ggc ttt gga cct gag gtt gat atc gca      473
Asn Gly Glu Glu Val Gly Thr Gly Phe Gly Pro Glu Val Asp Ile Ala
                80                  85                  90

gtt gac cca gtt gac ggc acc acc ctg atg gct gag ggt cgc ccc aac      521
Val Asp Pro Val Asp Gly Thr Thr Leu Met Ala Glu Gly Arg Pro Asn
            95                 100                 105

gca att tcc att ctc gca gct gca gag cgt ggc acc atg tac gat cca      569
Ala Ile Ser Ile Leu Ala Ala Ala Glu Arg Gly Thr Met Tyr Asp Pro
        110                 115                 120

tcc tcc gtc ttc tac atg aag aag atc gcc gtg gga cct gag gcc gca      617
Ser Ser Val Phe Tyr Met Lys Lys Ile Ala Val Gly Pro Glu Ala Ala
    125                 130                 135
```

```
ggc aag atc gac atc gaa gct cca gtt gcc cac aac atc aac gcg gtg      665
Gly Lys Ile Asp Ile Glu Ala Pro Val Ala His Asn Ile Asn Ala Val
140                 145                 150                 155

gca aag tcc aag gga atc aac cct tcc gac gtc acc gtt gtc gtg ctt      713
Ala Lys Ser Lys Gly Ile Asn Pro Ser Asp Val Thr Val Val Val Leu
                160                 165                 170

gac cgt cct cgc cac atc gaa ctg atc gca gac att cgt cgt gca ggc      761
Asp Arg Pro Arg His Ile Glu Leu Ile Ala Asp Ile Arg Arg Ala Gly
            175                 180                 185

gca aag gtt cgt ctc atc tcc gac ggc gac gtt gca ggt gca gtt gca      809
Ala Lys Val Arg Leu Ile Ser Asp Gly Asp Val Ala Gly Ala Val Ala
        190                 195                 200

gca gct cag gat tcc aac tcc gtg gac atc atg atg ggc acc ggc gga      857
Ala Ala Gln Asp Ser Asn Ser Val Asp Ile Met Met Gly Thr Gly Gly
    205                 210                 215

acc cca gaa ggc atc atc act gcg tgc gcc atg aag tgc atg ggt ggc      905
Thr Pro Glu Gly Ile Ile Thr Ala Cys Ala Met Lys Cys Met Gly Gly
220                 225                 230                 235

gaa atc cag ggc atc ctg gcc cca atg aac gat ttc gag cgc cag aag      953
Glu Ile Gln Gly Ile Leu Ala Pro Met Asn Asp Phe Glu Arg Gln Lys
                240                 245                 250

gca cac gac gct ggt ctg gtt ctt gat cag gtt ctg cac acc aac gat     1001
Ala His Asp Ala Gly Leu Val Leu Asp Gln Val Leu His Thr Asn Asp
            255                 260                 265

ctg gtg agc tcc gac aac tgc tac ttc gtg gca acc ggt gtg acc aac     1049
Leu Val Ser Ser Asp Asn Cys Tyr Phe Val Ala Thr Gly Val Thr Asn
        270                 275                 280

ggt gac atg ctc cgt ggc gtt tcc tac cgc gca aac ggc gca acc acc     1097
Gly Asp Met Leu Arg Gly Val Ser Tyr Arg Ala Asn Gly Ala Thr Thr
    285                 290                 295

cgt tcc ctg gtt atg cgc gca aag tca ggc acc atc cgc cac atc gag     1145
Arg Ser Leu Val Met Arg Ala Lys Ser Gly Thr Ile Arg His Ile Glu
300                 305                 310                 315

tct gtc cac cag ctg tcc aag ctg cag gaa tac tcc gtg gtt gac tac     1193
Ser Val His Gln Leu Ser Lys Leu Gln Glu Tyr Ser Val Val Asp Tyr
                320                 325                 330

acc acc gcg acc taa                                                 1208
Thr Thr Ala Thr
            335


<210> SEQ ID NO 32
<211> LENGTH: 2303
<212> TYPE: DNA
<213> ORGANISM: Corynebacterium glutamicum
<220> FEATURE:
<221> NAME/KEY: CDS
<222> LOCATION: (201)..(2300)
<223> OTHER INFORMATION: tkt-operon, DNA sequence encoding wildtype C.
      glutamicum transketolase operon

<400> SEQUENCE: 32

cacatttgaa ccacagttgg ttataaaatg ggttcaacat cactatggtt agaggtgttg      60

acgggtcaga ttaagcaaag actactttcg ggtagatca cctttgccaa atttgaacca      120

attaacctaa gtcgtagatc tgatcatcgg atctaacgaa aacgaaccaa aactttggtc    180

ccggtttaac ccaggaagga ttg acc acc ttg acg ctg tca cct gaa ctt cag    233
                      Leu Thr Thr Leu Thr Leu Ser Pro Glu Leu Gln
                        1               5                  10

gcg ctc act gta cgc aat tac ccc tct gat tgg tcc gat gtg gac acc      281
Ala Leu Thr Val Arg Asn Tyr Pro Ser Asp Trp Ser Asp Val Asp Thr
            15                  20                  25
```

-continued

```
aag gct gta gac act gtt cgt gtc ctc gct gca gac gct gta gaa aac      329
Lys Ala Val Asp Thr Val Arg Val Leu Ala Ala Asp Ala Val Glu Asn
        30                  35                  40

tgt ggc tcc ggc cac cca ggc acc gca atg agc ctg gct ccc ctt gca      377
Cys Gly Ser Gly His Pro Gly Thr Ala Met Ser Leu Ala Pro Leu Ala
    45                  50                  55

tac acc ttg tac cag cgg gtt atg aac gta gat cca cag gac acc aac      425
Tyr Thr Leu Tyr Gln Arg Val Met Asn Val Asp Pro Gln Asp Thr Asn
 60                 65                  70                  75

tgg gca ggc cgt gac cgc ttc gtt ctt tct tgt ggc cac tcc tct ttg      473
Trp Ala Gly Arg Asp Arg Phe Val Leu Ser Cys Gly His Ser Ser Leu
                80                  85                  90

acc cag tac atc cag ctt tac ttg ggt gga ttc ggc ctt gag atg gat      521
Thr Gln Tyr Ile Gln Leu Tyr Leu Gly Gly Phe Gly Leu Glu Met Asp
            95                  100                 105

gac ctg aag gct ctg cgc acc tgg gat tcc ttg acc cca gga cac cct      569
Asp Leu Lys Ala Leu Arg Thr Trp Asp Ser Leu Thr Pro Gly His Pro
        110                 115                 120

gag tac cgc cac acc aag ggc gtt gag atc acc act ggc cct ctt ggc      617
Glu Tyr Arg His Thr Lys Gly Val Glu Ile Thr Thr Gly Pro Leu Gly
    125                 130                 135

cag ggt ctt gca tct gca gtt ggt atg gcc atg gct gct cgt cgt gag      665
Gln Gly Leu Ala Ser Ala Val Gly Met Ala Met Ala Ala Arg Arg Glu
140                 145                 150                 155

cgt ggc cta ttc gac cca acc gct gct gag ggc gaa tcc cca ttc gac      713
Arg Gly Leu Phe Asp Pro Thr Ala Ala Glu Gly Glu Ser Pro Phe Asp
                160                 165                 170

cac cac atc tac gtc att gct tct gat ggt gac ctg cag gaa ggt gtc      761
His His Ile Tyr Val Ile Ala Ser Asp Gly Asp Leu Gln Glu Gly Val
            175                 180                 185

acc tct gag gca tcc tcc atc gct ggc acc cag cag ctg ggc aac ctc      809
Thr Ser Glu Ala Ser Ser Ile Ala Gly Thr Gln Gln Leu Gly Asn Leu
        190                 195                 200

atc gtg ttc tgg gat gac aac cgc atc tcc atc gaa gac aac act gag      857
Ile Val Phe Trp Asp Asp Asn Arg Ile Ser Ile Glu Asp Asn Thr Glu
    205                 210                 215

atc gct ttc aac gag gac gtt gtt gct cgt tac aag gct tac ggc tgg      905
Ile Ala Phe Asn Glu Asp Val Val Ala Arg Tyr Lys Ala Tyr Gly Trp
220                 225                 230                 235

cag acc att gag gtt gag gct ggc gag gac gtt gca gca atc gaa gct      953
Gln Thr Ile Glu Val Glu Ala Gly Glu Asp Val Ala Ala Ile Glu Ala
                240                 245                 250

gca gtg gct gag gct aag aag gac acc aag cga cct acc ttc atc cgc     1001
Ala Val Ala Glu Ala Lys Lys Asp Thr Lys Arg Pro Thr Phe Ile Arg
            255                 260                 265

gtt cgc acc atc atc ggc ttc cca gct cca act atg atg aac acc ggt     1049
Val Arg Thr Ile Ile Gly Phe Pro Ala Pro Thr Met Met Asn Thr Gly
        270                 275                 280

gct gtg cac ggt gct gct ctt ggc gca gct gag gtt gca gca acc aag     1097
Ala Val His Gly Ala Ala Leu Gly Ala Ala Glu Val Ala Ala Thr Lys
    285                 290                 295

act gag ctt gga ttc gat cct gag gct cac ttc gcg atc gac gat gag     1145
Thr Glu Leu Gly Phe Asp Pro Glu Ala His Phe Ala Ile Asp Asp Glu
300                 305                 310                 315

gtt atc gct cac acc cgc tcc ctc gca gag cgc gct gca cag aag aag     1193
Val Ile Ala His Thr Arg Ser Leu Ala Glu Arg Ala Ala Gln Lys Lys
                320                 325                 330

gct gca tgg cag gtc aag ttc gat gag tgg gca gct gcc aac cct gag     1241
Ala Ala Trp Gln Val Lys Phe Asp Glu Trp Ala Ala Ala Asn Pro Glu
            335                 340                 345
```

```
aac aag gct ctg ttc gat cgc ctg aac tcc cgt gag ctt cca gcg ggc      1289
Asn Lys Ala Leu Phe Asp Arg Leu Asn Ser Arg Glu Leu Pro Ala Gly
        350                 355                 360

tac gct gac gag ctc cca aca tgg gat gca gat gag aag ggc gtc gca      1337
Tyr Ala Asp Glu Leu Pro Thr Trp Asp Ala Asp Glu Lys Gly Val Ala
    365                 370                 375

act cgt aag gct tcc gag gct gca ctt cag gca ctg ggc aag acc ctt      1385
Thr Arg Lys Ala Ser Glu Ala Ala Leu Gln Ala Leu Gly Lys Thr Leu
380                 385                 390                 395

cct gag ctg tgg ggc ggt tcc gct gac ctc gca ggt tcc aac aac acc      1433
Pro Glu Leu Trp Gly Gly Ser Ala Asp Leu Ala Gly Ser Asn Asn Thr
                400                 405                 410

gtg atc aag ggc tcc cct tcc ttc ggc cct gag tcc atc tcc acc gag      1481
Val Ile Lys Gly Ser Pro Ser Phe Gly Pro Glu Ser Ile Ser Thr Glu
            415                 420                 425

acc tgg tct gct gag cct tac ggc cgt aac ctg cac ttc ggt atc cgt      1529
Thr Trp Ser Ala Glu Pro Tyr Gly Arg Asn Leu His Phe Gly Ile Arg
        430                 435                 440

gag cac gct atg gga tcc atc ctc aac ggc att tcc ctc cac ggt ggc      1577
Glu His Ala Met Gly Ser Ile Leu Asn Gly Ile Ser Leu His Gly Gly
    445                 450                 455

acc cgc cca tac ggc gga acc ttc ctc atc ttc tcc gac tac atg cgt      1625
Thr Arg Pro Tyr Gly Gly Thr Phe Leu Ile Phe Ser Asp Tyr Met Arg
460                 465                 470                 475

cct gca gtt cgt ctt gca gct ctc atg gag acc gac gct tac tac gtc      1673
Pro Ala Val Arg Leu Ala Ala Leu Met Glu Thr Asp Ala Tyr Tyr Val
                480                 485                 490

tgg acc cac gac tcc atc ggt ctg ggc gaa gat ggc cca acc cac cag      1721
Trp Thr His Asp Ser Ile Gly Leu Gly Glu Asp Gly Pro Thr His Gln
            495                 500                 505

cct gtt gaa acc ttg gct gca ctg cgc gcc atc cca ggt ctg tcc gtc      1769
Pro Val Glu Thr Leu Ala Ala Leu Arg Ala Ile Pro Gly Leu Ser Val
        510                 515                 520

ctg cgt cct gca gat gcg aac gag acc gcc cag gct tgg gct gca gca      1817
Leu Arg Pro Ala Asp Ala Asn Glu Thr Ala Gln Ala Trp Ala Ala Ala
    525                 530                 535

ctt gag tac aag gaa ggc cct aag ggt ctt gca ctg acc cgc cag aac      1865
Leu Glu Tyr Lys Glu Gly Pro Lys Gly Leu Ala Leu Thr Arg Gln Asn
540                 545                 550                 555

gtt cct gtt ctg gaa ggc acc aag gag aag gct gct gaa ggc gtt cgc      1913
Val Pro Val Leu Glu Gly Thr Lys Glu Lys Ala Ala Glu Gly Val Arg
                560                 565                 570

cgc ggt ggc tac gtc ctg gtt gag ggt tcc aag gaa acc cca gat gtg      1961
Arg Gly Gly Tyr Val Leu Val Glu Gly Ser Lys Glu Thr Pro Asp Val
            575                 580                 585

atc ctc atg ggc tcc ggc tcc gag gtt cag ctt gca gtt aac gct gcg      2009
Ile Leu Met Gly Ser Gly Ser Glu Val Gln Leu Ala Val Asn Ala Ala
        590                 595                 600

aag gct ctg gaa gct gag ggc gtt gca gct cgc gtt gtt tcc gtt cct      2057
Lys Ala Leu Glu Ala Glu Gly Val Ala Ala Arg Val Val Ser Val Pro
    605                 610                 615

tgc atg gat tgg ttc cag gag cag gac gca gag tac atc gag tcc gtt      2105
Cys Met Asp Trp Phe Gln Glu Gln Asp Ala Glu Tyr Ile Glu Ser Val
620                 625                 630                 635

ctg cct gca gct gtg acc gct cgt gtg tct gtt gaa gct ggc atc gca      2153
Leu Pro Ala Ala Val Thr Ala Arg Val Ser Val Glu Ala Gly Ile Ala
                640                 645                 650

atg cct tgg tac cgc ttc ttg ggc acc cag ggc cgt gct gtc tcc ctt      2201
Met Pro Trp Tyr Arg Phe Leu Gly Thr Gln Gly Arg Ala Val Ser Leu
```

```
           655                 660                 665

gag cac ttc ggt gct tct gcg gat tac cag acc ctg ttt gag aag ttc     2249
Glu His Phe Gly Ala Ser Ala Asp Tyr Gln Thr Leu Phe Glu Lys Phe
        670                 675                 680

ggc atc acc acc gat gca gtc gtg gca gcg gcc aag gac tcc att aac     2297
Gly Ile Thr Thr Asp Ala Val Val Ala Ala Ala Lys Asp Ser Ile Asn
    685                 690                 695

ggt        taa                                                      2303
Gly
700


<210> SEQ ID NO 33
<211> LENGTH: 700
<212> TYPE: PRT
<213> ORGANISM: Corynebacterium glutamicum
<220> FEATURE:
<221> NAME/KEY: PEPTIDE
<222> LOCATION: (1)..(700)
<223> OTHER INFORMATION: Tkt, amino acid sequence of C. glutamicum
      transketolase

<400> SEQUENCE: 33

Leu Thr Thr Leu Thr Leu Ser Pro Glu Leu Gln Ala Leu Thr Val Arg
  1               5                  10                  15

Asn Tyr Pro Ser Asp Trp Ser Asp Val Asp Thr Lys Ala Val Asp Thr
             20                  25                  30

Val Arg Val Leu Ala Ala Asp Ala Val Glu Asn Cys Gly Ser Gly His
         35                  40                  45

Pro Gly Thr Ala Met Ser Leu Ala Pro Leu Ala Tyr Thr Leu Tyr Gln
     50                  55                  60

Arg Val Met Asn Val Asp Pro Gln Asp Thr Asn Trp Ala Gly Arg Asp
 65                  70                  75                  80

Arg Phe Val Leu Ser Cys Gly His Ser Ser Leu Thr Gln Tyr Ile Gln
                 85                  90                  95

Leu Tyr Leu Gly Gly Phe Gly Leu Glu Met Asp Asp Leu Lys Ala Leu
            100                 105                 110

Arg Thr Trp Asp Ser Leu Thr Pro Gly His Pro Glu Tyr Arg His Thr
        115                 120                 125

Lys Gly Val Glu Ile Thr Thr Gly Pro Leu Gly Gln Gly Leu Ala Ser
    130                 135                 140

Ala Val Gly Met Ala Met Ala Ala Arg Arg Glu Arg Gly Leu Phe Asp
145                 150                 155                 160

Pro Thr Ala Ala Glu Gly Glu Ser Pro Phe Asp His His Ile Tyr Val
                165                 170                 175

Ile Ala Ser Asp Gly Asp Leu Gln Glu Gly Val Thr Ser Glu Ala Ser
            180                 185                 190

Ser Ile Ala Gly Thr Gln Gln Leu Gly Asn Leu Ile Val Phe Trp Asp
        195                 200                 205

Asp Asn Arg Ile Ser Ile Glu Asp Asn Thr Glu Ile Ala Phe Asn Glu
    210                 215                 220

Asp Val Val Ala Arg Tyr Lys Ala Tyr Gly Trp Gln Thr Ile Glu Val
225                 230                 235                 240

Glu Ala Gly Glu Asp Val Ala Ala Ile Glu Ala Ala Val Ala Glu Ala
                245                 250                 255

Lys Lys Asp Thr Lys Arg Pro Thr Phe Ile Arg Val Arg Thr Ile Ile
            260                 265                 270

Gly Phe Pro Ala Pro Thr Met Met Asn Thr Gly Ala Val His Gly Ala
```

```
        275                 280                 285

Ala Leu Gly Ala Ala Glu Val Ala Ala Thr Lys Thr Glu Leu Gly Phe
    290                 295                 300

Asp Pro Glu Ala His Phe Ala Ile Asp Asp Glu Val Ile Ala His Thr
305                 310                 315                 320

Arg Ser Leu Ala Glu Arg Ala Ala Gln Lys Lys Ala Ala Trp Gln Val
                325                 330                 335

Lys Phe Asp Glu Trp Ala Ala Ala Asn Pro Glu Asn Lys Ala Leu Phe
            340                 345                 350

Asp Arg Leu Asn Ser Arg Glu Leu Pro Ala Gly Tyr Ala Asp Glu Leu
        355                 360                 365

Pro Thr Trp Asp Ala Asp Glu Lys Gly Val Ala Thr Arg Lys Ala Ser
    370                 375                 380

Glu Ala Ala Leu Gln Ala Leu Gly Lys Thr Leu Pro Glu Leu Trp Gly
385                 390                 395                 400

Gly Ser Ala Asp Leu Ala Gly Ser Asn Asn Thr Val Ile Lys Gly Ser
                405                 410                 415

Pro Ser Phe Gly Pro Glu Ser Ile Ser Thr Glu Thr Trp Ser Ala Glu
            420                 425                 430

Pro Tyr Gly Arg Asn Leu His Phe Gly Ile Arg Glu His Ala Met Gly
        435                 440                 445

Ser Ile Leu Asn Gly Ile Ser Leu His Gly Gly Thr Arg Pro Tyr Gly
    450                 455                 460

Gly Thr Phe Leu Ile Phe Ser Asp Tyr Met Arg Pro Ala Val Arg Leu
465                 470                 475                 480

Ala Ala Leu Met Glu Thr Asp Ala Tyr Tyr Val Trp Thr His Asp Ser
                485                 490                 495

Ile Gly Leu Gly Glu Asp Gly Pro Thr His Gln Pro Val Glu Thr Leu
            500                 505                 510

Ala Ala Leu Arg Ala Ile Pro Gly Leu Ser Val Leu Arg Pro Ala Asp
        515                 520                 525

Ala Asn Glu Thr Ala Gln Ala Trp Ala Ala Ala Leu Glu Tyr Lys Glu
    530                 535                 540

Gly Pro Lys Gly Leu Ala Leu Thr Arg Gln Asn Val Pro Val Leu Glu
545                 550                 555                 560

Gly Thr Lys Glu Lys Ala Ala Glu Gly Val Arg Arg Gly Gly Tyr Val
                565                 570                 575

Leu Val Glu Gly Ser Lys Glu Thr Pro Asp Val Ile Leu Met Gly Ser
            580                 585                 590

Gly Ser Glu Val Gln Leu Ala Val Asn Ala Ala Lys Ala Leu Glu Ala
        595                 600                 605

Glu Gly Val Ala Ala Arg Val Val Ser Val Pro Cys Met Asp Trp Phe
    610                 615                 620

Gln Glu Gln Asp Ala Glu Tyr Ile Glu Ser Val Leu Pro Ala Ala Val
625                 630                 635                 640

Thr Ala Arg Val Ser Val Glu Ala Gly Ile Ala Met Pro Trp Tyr Arg
                645                 650                 655

Phe Leu Gly Thr Gln Gly Arg Ala Val Ser Leu Glu His Phe Gly Ala
            660                 665                 670

Ser Ala Asp Tyr Gln Thr Leu Phe Glu Lys Phe Gly Ile Thr Thr Asp
        675                 680                 685

Ala Val Val Ala Ala Ala Lys Asp Ser Ile Asn Gly
    690                 695                 700
```

```
<210> SEQ ID NO 34
<211> LENGTH: 2295
<212> TYPE: DNA
<213> ORGANISM: Corynebacterium glutamicum
<220> FEATURE:
<221> NAME/KEY: CDS
<222> LOCATION: (193)..(2292)
<223> OTHER INFORMATION: tkt-operon with sod-promoter

<400> SEQUENCE: 34

tagctgccaa ttattccggg cttgtgaccc gctacccgat aaataggtcg gctgaaaaat      60

ttcgttgcaa tataaacaaa aaggcctctc attgggaggt gtcgcaccaa gtacttttgc     120

gaagcgccat ctgacggatt ttcaaaagat gtatatgctc ggtgcggaaa cctacgaaag     180

gattttttac cc         ttg acc acc ttg acg ctg tca cct gaa ctt cag     225
                      Leu Thr Thr Leu Thr Leu Ser Pro Glu Leu Gln
                        1               5                  10

gcg ctc act gta cgc aat tac ccc tct gat tgg tcc gat gtg gac acc       273
Ala Leu Thr Val Arg Asn Tyr Pro Ser Asp Trp Ser Asp Val Asp Thr
            15                  20                  25

aag gct gta gac act gtt cgt gtc ctc gct gca gac gct gta gaa aac       321
Lys Ala Val Asp Thr Val Arg Val Leu Ala Ala Asp Ala Val Glu Asn
        30                  35                  40

tgt ggc tcc ggc cac cca ggc acc gca atg agc ctg gct ccc ctt gca       369
Cys Gly Ser Gly His Pro Gly Thr Ala Met Ser Leu Ala Pro Leu Ala
    45                  50                  55

tac acc ttg tac cag cgg gtt atg aac gta gat cca cag gac acc aac       417
Tyr Thr Leu Tyr Gln Arg Val Met Asn Val Asp Pro Gln Asp Thr Asn
 60                  65                  70                  75

tgg gca ggc cgt gac cgc ttc gtt ctt tct tgt ggc cac tcc tct ttg       465
Trp Ala Gly Arg Asp Arg Phe Val Leu Ser Cys Gly His Ser Ser Leu
                 80                  85                  90

acc cag tac atc cag ctt tac ttg ggt gga ttc ggc ctt gag atg gat       513
Thr Gln Tyr Ile Gln Leu Tyr Leu Gly Gly Phe Gly Leu Glu Met Asp
             95                 100                 105

gac ctg aag gct ctg cgc acc tgg gat tcc ttg acc cca gga cac cct       561
Asp Leu Lys Ala Leu Arg Thr Trp Asp Ser Leu Thr Pro Gly His Pro
        110                 115                 120

gag tac cgc cac acc aag ggc gtt gag atc acc act ggc cct ctt ggc       609
Glu Tyr Arg His Thr Lys Gly Val Glu Ile Thr Thr Gly Pro Leu Gly
    125                 130                 135

cag ggt ctt gca tct gca gtt ggt atg gcc atg gct gct cgt cgt gag       657
Gln Gly Leu Ala Ser Ala Val Gly Met Ala Met Ala Ala Arg Arg Glu
140                 145                 150                 155

cgt ggc cta ttc gac cca acc gct gct gag ggc gaa tcc cca ttc gac       705
Arg Gly Leu Phe Asp Pro Thr Ala Ala Glu Gly Glu Ser Pro Phe Asp
                160                 165                 170

cac cac atc tac gtc att gct tct gat ggt gac ctg cag gaa ggt gtc       753
His His Ile Tyr Val Ile Ala Ser Asp Gly Asp Leu Gln Glu Gly Val
            175                 180                 185

acc tct gag gca tcc tcc atc gct ggc acc cag cag ctg ggc aac ctc       801
Thr Ser Glu Ala Ser Ser Ile Ala Gly Thr Gln Gln Leu Gly Asn Leu
        190                 195                 200

atc gtg ttc tgg gat gac aac cgc atc tcc atc gaa gac aac act gag       849
Ile Val Phe Trp Asp Asp Asn Arg Ile Ser Ile Glu Asp Asn Thr Glu
    205                 210                 215

atc gct ttc aac gag gac gtt gtt gct cgt tac aag gct tac ggc tgg       897
Ile Ala Phe Asn Glu Asp Val Val Ala Arg Tyr Lys Ala Tyr Gly Trp
220                 225                 230                 235
```

```
cag acc att gag gtt gag gct ggc gag gac gtt gca gca atc gaa gct      945
Gln Thr Ile Glu Val Glu Ala Gly Glu Asp Val Ala Ala Ile Glu Ala
                240                 245                 250

gca gtg gct gag gct aag aag gac acc aag cga cct acc ttc atc cgc      993
Ala Val Ala Glu Ala Lys Lys Asp Thr Lys Arg Pro Thr Phe Ile Arg
            255                 260                 265

gtt cgc acc atc atc ggc ttc cca gct cca act atg atg aac acc ggt     1041
Val Arg Thr Ile Ile Gly Phe Pro Ala Pro Thr Met Met Asn Thr Gly
        270                 275                 280

gct gtg cac ggt gct gct ctt ggc gca gct gag gtt gca gca acc aag     1089
Ala Val His Gly Ala Ala Leu Gly Ala Ala Glu Val Ala Ala Thr Lys
    285                 290                 295

act gag ctt gga ttc gat cct gag gct cac ttc gcg atc gac gat gag     1137
Thr Glu Leu Gly Phe Asp Pro Glu Ala His Phe Ala Ile Asp Asp Glu
300                 305                 310                 315

gtt atc gct cac acc cgc tcc ctc gca gag cgc gct gca cag aag aag     1185
Val Ile Ala His Thr Arg Ser Leu Ala Glu Arg Ala Ala Gln Lys Lys
                320                 325                 330

gct gca tgg cag gtc aag ttc gat gag tgg gca gct gcc aac cct gag     1233
Ala Ala Trp Gln Val Lys Phe Asp Glu Trp Ala Ala Ala Asn Pro Glu
            335                 340                 345

aac aag gct ctg ttc gat cgc ctg aac tcc cgt gag ctt cca gcg ggc     1281
Asn Lys Ala Leu Phe Asp Arg Leu Asn Ser Arg Glu Leu Pro Ala Gly
        350                 355                 360

tac gct gac gag ctc cca aca tgg gat gca gat gag aag ggc gtc gca     1329
Tyr Ala Asp Glu Leu Pro Thr Trp Asp Ala Asp Glu Lys Gly Val Ala
    365                 370                 375

act cgt aag gct tcc gag gct gca ctt cag gca ctg ggc aag acc ctt     1377
Thr Arg Lys Ala Ser Glu Ala Ala Leu Gln Ala Leu Gly Lys Thr Leu
380                 385                 390                 395

cct gag ctg tgg ggc ggt tcc gct gac ctc gca ggt tcc aac aac acc     1425
Pro Glu Leu Trp Gly Gly Ser Ala Asp Leu Ala Gly Ser Asn Asn Thr
                400                 405                 410

gtg atc aag ggc tcc cct tcc ttc ggc cct gag tcc atc tcc acc gag     1473
Val Ile Lys Gly Ser Pro Ser Phe Gly Pro Glu Ser Ile Ser Thr Glu
            415                 420                 425

acc tgg tct gct gag cct tac ggc cgt aac ctg cac ttc ggt atc cgt     1521
Thr Trp Ser Ala Glu Pro Tyr Gly Arg Asn Leu His Phe Gly Ile Arg
        430                 435                 440

gag cac gct atg gga tcc atc ctc aac ggc att tcc ctc cac ggt ggc     1569
Glu His Ala Met Gly Ser Ile Leu Asn Gly Ile Ser Leu His Gly Gly
    445                 450                 455

acc cgc cca tac ggc gga acc ttc ctc atc ttc tcc gac tac atg cgt     1617
Thr Arg Pro Tyr Gly Gly Thr Phe Leu Ile Phe Ser Asp Tyr Met Arg
460                 465                 470                 475

cct gca gtt cgt ctt gca gct ctc atg gag acc gac gct tac tac gtc     1665
Pro Ala Val Arg Leu Ala Ala Leu Met Glu Thr Asp Ala Tyr Tyr Val
                480                 485                 490

tgg acc cac gac tcc atc ggt ctg ggc gaa gat ggc cca acc cac cag     1713
Trp Thr His Asp Ser Ile Gly Leu Gly Glu Asp Gly Pro Thr His Gln
            495                 500                 505

cct gtt gaa acc ttg gct gca ctg cgc gcc atc cca ggt ctg tcc gtc     1761
Pro Val Glu Thr Leu Ala Ala Leu Arg Ala Ile Pro Gly Leu Ser Val
        510                 515                 520

ctg cgt cct gca gat gcg aac gag acc gcc cag gct tgg gct gca gca     1809
Leu Arg Pro Ala Asp Ala Asn Glu Thr Ala Gln Ala Trp Ala Ala Ala
    525                 530                 535

ctt gag tac aag gaa ggc cct aag ggt ctt gca ctg acc cgc cag aac     1857
Leu Glu Tyr Lys Glu Gly Pro Lys Gly Leu Ala Leu Thr Arg Gln Asn
540                 545                 550                 555
```

```
gtt cct gtt ctg gaa ggc acc aag gag aag gct gct gaa ggc gtt cgc     1905
Val Pro Val Leu Glu Gly Thr Lys Glu Lys Ala Ala Glu Gly Val Arg
                560                 565                 570

cgc ggt ggc tac gtc ctg gtt gag ggt tcc aag gaa acc cca gat gtg     1953
Arg Gly Gly Tyr Val Leu Val Glu Gly Ser Lys Glu Thr Pro Asp Val
            575                 580                 585

atc ctc atg ggc tcc ggc tcc gag gtt cag ctt gca gtt aac gct gcg     2001
Ile Leu Met Gly Ser Gly Ser Glu Val Gln Leu Ala Val Asn Ala Ala
        590                 595                 600

aag gct ctg gaa gct gag ggc gtt gca gct cgc gtt gtt tcc gtt cct     2049
Lys Ala Leu Glu Ala Glu Gly Val Ala Ala Arg Val Val Ser Val Pro
    605                 610                 615

tgc atg gat tgg ttc cag gag cag gac gca gag tac atc gag tcc gtt     2097
Cys Met Asp Trp Phe Gln Glu Gln Asp Ala Glu Tyr Ile Glu Ser Val
620                 625                 630                 635

ctg cct gca gct gtg acc gct cgt gtg tct gtt gaa gct ggc atc gca     2145
Leu Pro Ala Ala Val Thr Ala Arg Val Ser Val Glu Ala Gly Ile Ala
                640                 645                 650

atg cct tgg tac cgc ttc ttg ggc acc cag ggc cgt gct gtc tcc ctt     2193
Met Pro Trp Tyr Arg Phe Leu Gly Thr Gln Gly Arg Ala Val Ser Leu
            655                 660                 665

gag cac ttc ggt gct tct gcg gat tac cag acc ctg ttt gag aag ttc     2241
Glu His Phe Gly Ala Ser Ala Asp Tyr Gln Thr Leu Phe Glu Lys Phe
        670                 675                 680

ggc atc acc acc gat gca gtc gtg gca gcg gcc aag gac tcc att aac     2289
Gly Ile Thr Thr Asp Ala Val Val Ala Ala Ala Lys Asp Ser Ile Asn
    685                 690                 695

ggt         taa                                                     2295
Gly
700


<210> SEQ ID NO 35
<211> LENGTH: 29
<212> TYPE: DNA
<213> ORGANISM: Artificial Sequence
<220> FEATURE:
<223> OTHER INFORMATION: Primer (P1)

<400> SEQUENCE: 35

ccgctcgagc cattgaatcg tgctgagag                                       29


<210> SEQ ID NO 36
<211> LENGTH: 22
<212> TYPE: DNA
<213> ORGANISM: Artificial Sequence
<220> FEATURE:
<223> OTHER INFORMATION: Primer (P2)

<400> SEQUENCE: 36

caggtgaaga tgatgtcggt gg                                              22


<210> SEQ ID NO 37
<211> LENGTH: 22
<212> TYPE: DNA
<213> ORGANISM: Artificial Sequence
<220> FEATURE:
<223> OTHER INFORMATION: Primer (P3)

<400> SEQUENCE: 37

ccaccgacat catcttcacc tg                                              22


<210> SEQ ID NO 38
```

<211> LENGTH: 30
<212> TYPE: DNA
<213> ORGANISM: Artificial Sequence
<220> FEATURE:
<223> OTHER INFORMATION: Primer (P4)

<400> SEQUENCE: 38
ctagactagt gaaacgaaca gtgtcagctg 30

<210> SEQ ID NO 39
<211> LENGTH: 33
<212> TYPE: DNA
<213> ORGANISM: Artificial Sequence
<220> FEATURE:
<223> OTHER INFORMATION: Primer (P5)

<400> SEQUENCE: 39
attatttgaa ttctgaacgg caacggatca aaa 33

<210> SEQ ID NO 40
<211> LENGTH: 33
<212> TYPE: DNA
<213> ORGANISM: Artificial Sequence
<220> FEATURE:
<223> OTHER INFORMATION: Primer (P6)

<400> SEQUENCE: 40
attattttct agattcctct tggtccagcg aag 33

<210> SEQ ID NO 41
<211> LENGTH: 34
<212> TYPE: DNA
<213> ORGANISM: Artificial Sequence
<220> FEATURE:
<223> OTHER INFORMATION: Primer (P7)

<400> SEQUENCE: 41
attattttct agatgaacgg caacggatca aaaa 34

<210> SEQ ID NO 42
<211> LENGTH: 33
<212> TYPE: DNA
<213> ORGANISM: Artificial Sequence
<220> FEATURE:
<223> OTHER INFORMATION: Primer (P8)

<400> SEQUENCE: 42
attatttgtc gacttcctct tggtccagcg aag 33

<210> SEQ ID NO 43
<211> LENGTH: 21
<212> TYPE: DNA
<213> ORGANISM: Artificial Sequence
<220> FEATURE:
<223> OTHER INFORMATION: Primer (P9)

<400> SEQUENCE: 43
gttcgttgat ggatcccagg c 21

<210> SEQ ID NO 44
<211> LENGTH: 42
<212> TYPE: DNA
<213> ORGANISM: Artificial Sequence
<220> FEATURE:
<223> OTHER INFORMATION: Primer (P10)

<400> SEQUENCE: 44
cccatccact aaacttaaac attgtccagc gcttcaatac cc 42

<210> SEQ ID NO 45
<211> LENGTH: 42
<212> TYPE: DNA
<213> ORGANISM: Artificial Sequence
<220> FEATURE:
<223> OTHER INFORMATION: Primer (P11)

<400> SEQUENCE: 45
tgtttaagtt tagtggatgg ggcagaactg gattgacatg gg 42

<210> SEQ ID NO 46
<211> LENGTH: 31
<212> TYPE: DNA
<213> ORGANISM: Artificial Sequence
<220> FEATURE:
<223> OTHER INFORMATION: Primer (P12)

<400> SEQUENCE: 46
ggccggatcc ttaagcgtga gctgctgaaa t 31

<210> SEQ ID NO 47
<211> LENGTH: 20
<212> TYPE: DNA
<213> ORGANISM: Artificial Sequence
<220> FEATURE:
<223> OTHER INFORMATION: Primer (P13)

<400> SEQUENCE: 47
tagctgccaa ttattccggg 20

<210> SEQ ID NO 48
<211> LENGTH: 42
<212> TYPE: DNA
<213> ORGANISM: Artificial Sequence
<220> FEATURE:
<223> OTHER INFORMATION: Primer (P14)

<400> SEQUENCE: 48
gaacgccaac cttgattccc atgggtaaaa aatcctttcg ta 42

<210> SEQ ID NO 49
<211> LENGTH: 42
<212> TYPE: DNA
<213> ORGANISM: Artificial Sequence
<220> FEATURE:
<223> OTHER INFORMATION: Primer (P15)

<400> SEQUENCE: 49
tacgaaagga ttttttaccc atgggaatca aggttggcgt tc 42

<210> SEQ ID NO 50
<211> LENGTH: 29
<212> TYPE: DNA
<213> ORGANISM: Artificial Sequence
<220> FEATURE:
<223> OTHER INFORMATION: Primer (P16)

<400> SEQUENCE: 50
cgcggatcct ctgaccctgg gtgccaaag 29

<210> SEQ ID NO 51
<211> LENGTH: 24
<212> TYPE: DNA

<213> ORGANISM: Artificial Sequence
<220> FEATURE:
<223> OTHER INFORMATION: Primer (P17)

<400> SEQUENCE: 51
gcggcaaagc agtgggggaa gggg 24

<210> SEQ ID NO 52
<211> LENGTH: 36
<212> TYPE: DNA
<213> ORGANISM: Artificial Sequence
<220> FEATURE:
<223> OTHER INFORMATION: Primer (P18)

<400> SEQUENCE: 52
cccggaataa ttggcagcta tatgctcctt catttt 36

<210> SEQ ID NO 53
<211> LENGTH: 34
<212> TYPE: DNA
<213> ORGANISM: Artificial Sequence
<220> FEATURE:
<223> OTHER INFORMATION: Primer (P19)

<400> SEQUENCE: 53
attatttgga tccgaggctg cactgcaacg aggt 34

<210> SEQ ID NO 54
<211> LENGTH: 23
<212> TYPE: DNA
<213> ORGANISM: Artificial Sequence
<220> FEATURE:
<223> OTHER INFORMATION: Primer (P20)

<400> SEQUENCE: 54
catcgccgaa ttcggtggtg gaa 23

<210> SEQ ID NO 55
<211> LENGTH: 20
<212> TYPE: DNA
<213> ORGANISM: Artificial Sequence
<220> FEATURE:
<223> OTHER INFORMATION: Primer (P21)

<400> SEQUENCE: 55
tccaccgaat tcggcgatga 20

<210> SEQ ID NO 56
<211> LENGTH: 23
<212> TYPE: DNA
<213> ORGANISM: Artificial Sequence
<220> FEATURE:
<223> OTHER INFORMATION: Primer (P22)

<400> SEQUENCE: 56
cggaaatcgt cctcgtcgac tac 23

<210> SEQ ID NO 57
<211> LENGTH: 23
<212> TYPE: DNA
<213> ORGANISM: Artificial Sequence
<220> FEATURE:
<223> OTHER INFORMATION: Primer (P23)

<400> SEQUENCE: 57
cactgttcgt agtcgacgag gac 23

<210> SEQ ID NO 58
<211> LENGTH: 33
<212> TYPE: DNA
<213> ORGANISM: Artificial Sequence
<220> FEATURE:
<223> OTHER INFORMATION: Primer (P24)

<400> SEQUENCE: 58
attattttct agagaaaccc aaaaccgccc tcc 33

<210> SEQ ID NO 59
<211> LENGTH: 34
<212> TYPE: DNA
<213> ORGANISM: Artificial Sequence
<220> FEATURE:
<223> OTHER INFORMATION: Primer (P25)

<400> SEQUENCE: 59
attattttct agagaggctg cactgcaacg aggt 34

<210> SEQ ID NO 60
<211> LENGTH: 32
<212> TYPE: DNA
<213> ORGANISM: Artificial Sequence
<220> FEATURE:
<223> OTHER INFORMATION: Primer (P26)

<400> SEQUENCE: 60
attatttagc ttgaaaccca aaaccgccct cc 32

<210> SEQ ID NO 61
<211> LENGTH: 20
<212> TYPE: DNA
<213> ORGANISM: Artificial Sequence
<220> FEATURE:
<223> OTHER INFORMATION: Primer (P27)

<400> SEQUENCE: 61
tagctgccaa ttattccggg 20

<210> SEQ ID NO 62
<211> LENGTH: 42
<212> TYPE: DNA
<213> ORGANISM: Artificial Sequence
<220> FEATURE:
<223> OTHER INFORMATION: Primer (P28)

<400> SEQUENCE: 62
ttctgtacga ccagggccat gggtaaaaaa tcctttcgta gg 42

<210> SEQ ID NO 63
<211> LENGTH: 42
<212> TYPE: DNA
<213> ORGANISM: Artificial Sequence
<220> FEATURE:
<223> OTHER INFORMATION: Primer (P29)

<400> SEQUENCE: 63
cctacgaaag gattttttac ccatggccct ggtcgtacag aa 42

<210> SEQ ID NO 64
<211> LENGTH: 32
<212> TYPE: DNA
<213> ORGANISM: Artificial Sequence
<220> FEATURE:

<223> OTHER INFORMATION: Primer (P30)

<400> SEQUENCE: 64
atctacgtcg acacaccctg gaaaccagca ac 32

<210> SEQ ID NO 65
<211> LENGTH: 29
<212> TYPE: DNA
<213> ORGANISM: Artificial Sequence
<220> FEATURE:
<223> OTHER INFORMATION: Primer (P31)

<400> SEQUENCE: 65
cgcggatcct cgaatatcaa tatatggtc 29

<210> SEQ ID NO 66
<211> LENGTH: 37
<212> TYPE: DNA
<213> ORGANISM: Artificial Sequence
<220> FEATURE:
<223> OTHER INFORMATION: Primer (P32)

<400> SEQUENCE: 66
ccggaataat tggcagctaa gtagggttga agggcat 37

<210> SEQ ID NO 67
<211> LENGTH: 28
<212> TYPE: DNA
<213> ORGANISM: Artificial Sequence
<220> FEATURE:
<223> OTHER INFORMATION: Primer (P33)

<400> SEQUENCE: 67
aggggaactt gatcagagga atacacca 28

<210> SEQ ID NO 68
<211> LENGTH: 21
<212> TYPE: DNA
<213> ORGANISM: Artificial Sequence
<220> FEATURE:
<223> OTHER INFORMATION: Primer (P34)

<400> SEQUENCE: 68
gatatcagaa gcagcaatgc c 21

<210> SEQ ID NO 69
<211> LENGTH: 21
<212> TYPE: DNA
<213> ORGANISM: Artificial Sequence
<220> FEATURE:
<223> OTHER INFORMATION: Primer (P35)

<400> SEQUENCE: 69
ggcattgctg cttctgatat c 21

<210> SEQ ID NO 70
<211> LENGTH: 28
<212> TYPE: DNA
<213> ORGANISM: Artificial Sequence
<220> FEATURE:
<223> OTHER INFORMATION: Primer (P36)

<400> SEQUENCE: 70
gtgcatcatc atcgcgctct tcctgtcg 28

<210> SEQ ID NO 71
<211> LENGTH: 33
<212> TYPE: DNA
<213> ORGANISM: Artificial Sequence
<220> FEATURE:
<223> OTHER INFORMATION: Primer (P37)

<400> SEQUENCE: 71
aatcaacgcg tcagcatatt gaagtgcaga tcc 33

<210> SEQ ID NO 72
<211> LENGTH: 28
<212> TYPE: DNA
<213> ORGANISM: Artificial Sequence
<220> FEATURE:
<223> OTHER INFORMATION: Primer (P38)

<400> SEQUENCE: 72
aggaggtgcg ggtgatcggc aatgaatc 28

<210> SEQ ID NO 73
<211> LENGTH: 28
<212> TYPE: DNA
<213> ORGANISM: Artificial Sequence
<220> FEATURE:
<223> OTHER INFORMATION: Primer (P39)

<400> SEQUENCE: 73
gattcattgc cgatcacccg cacctcct 28

<210> SEQ ID NO 74
<211> LENGTH: 34
<212> TYPE: DNA
<213> ORGANISM: Artificial Sequence
<220> FEATURE:
<223> OTHER INFORMATION: Primer (P40)

<400> SEQUENCE: 74
atctacgtcg acggtagtaa tccagggtgt agag 34

<210> SEQ ID NO 75
<211> LENGTH: 20
<212> TYPE: DNA
<213> ORGANISM: Artificial Sequence
<220> FEATURE:
<223> OTHER INFORMATION: Primer (P41)

<400> SEQUENCE: 75
tagctgccaa ttattccggg 20

<210> SEQ ID NO 76
<211> LENGTH: 33
<212> TYPE: DNA
<213> ORGANISM: Artificial Sequence
<220> FEATURE:
<223> OTHER INFORMATION: Primer (P42)

<400> SEQUENCE: 76
atgtgtgagt cgacacgggt aaaaaatcct ttc 33

<210> SEQ ID NO 77
<211> LENGTH: 33
<212> TYPE: DNA
<213> ORGANISM: Artificial Sequence
<220> FEATURE:
<223> OTHER INFORMATION: Primer (P43)

<400> SEQUENCE: 77
gaaaggattt tttacccgtg tcgactcaca cat 33

<210> SEQ ID NO 78
<211> LENGTH: 32
<212> TYPE: DNA
<213> ORGANISM: Artificial Sequence
<220> FEATURE:
<223> OTHER INFORMATION: Primer (P44)

<400> SEQUENCE: 78
gagtacacgc gtcaaagatg gggtaagtct gg 32

<210> SEQ ID NO 79
<211> LENGTH: 32
<212> TYPE: DNA
<213> ORGANISM: Artificial Sequence
<220> FEATURE:
<223> OTHER INFORMATION: Primer (P45)

<400> SEQUENCE: 79
gagtacctcg aggctgtggc agtgaccaac cg 32

<210> SEQ ID NO 80
<211> LENGTH: 47
<212> TYPE: DNA
<213> ORGANISM: Artificial Sequence
<220> FEATURE:
<223> OTHER INFORMATION: Primer (P46)

<400> SEQUENCE: 80
ggaataattg gcagctatag agtaattatt cctttcaaca agagacc 47

<210> SEQ ID NO 81
<211> LENGTH: 32
<212> TYPE: DNA
<213> ORGANISM: Artificial Sequence
<220> FEATURE:
<223> OTHER INFORMATION: Primer (P47)

<400> SEQUENCE: 81
gagtacctcg agcgaagacc tcgcagattc cg 32

<210> SEQ ID NO 82
<211> LENGTH: 24
<212> TYPE: DNA
<213> ORGANISM: Artificial Sequence
<220> FEATURE:
<223> OTHER INFORMATION: Primer (P48)

<400> SEQUENCE: 82
gagactcgtg gctaagatca tctg 24

<210> SEQ ID NO 83
<211> LENGTH: 24
<212> TYPE: DNA
<213> ORGANISM: Artificial Sequence
<220> FEATURE:
<223> OTHER INFORMATION: Primer (P49)

<400> SEQUENCE: 83
cagatgatct tagccacgag tctc 24

<210> SEQ ID NO 84
<211> LENGTH: 32

<212> TYPE: DNA
<213> ORGANISM: Artificial Sequence
<220> FEATURE:
<223> OTHER INFORMATION: Primer (P50)

<400> SEQUENCE: 84
catgagacgc gtggaatctg cagaccactc gc 32

<210> SEQ ID NO 85
<211> LENGTH: 20
<212> TYPE: DNA
<213> ORGANISM: Artificial Sequence
<220> FEATURE:
<223> OTHER INFORMATION: Primer (P51)

<400> SEQUENCE: 85
tggccgttac cctgcgaatg 20

<210> SEQ ID NO 86
<211> LENGTH: 20
<212> TYPE: DNA
<213> ORGANISM: Artificial Sequence
<220> FEATURE:
<223> OTHER INFORMATION: Primer (P52)

<400> SEQUENCE: 86
tgtatgtcct cctggacttc 20

<210> SEQ ID NO 87
<211> LENGTH: 40
<212> TYPE: DNA
<213> ORGANISM: Artificial Sequence
<220> FEATURE:
<223> OTHER INFORMATION: Primer (P53)

<400> SEQUENCE: 87
gaagtccagg aggacataca atgaacctaa agaaccccga 40

<210> SEQ ID NO 88
<211> LENGTH: 31
<212> TYPE: DNA
<213> ORGANISM: Artificial Sequence
<220> FEATURE:
<223> OTHER INFORMATION: Primer (P54)

<400> SEQUENCE: 88
atctacgtcg acccaggatg ccctggattt c 31

<210> SEQ ID NO 89
<211> LENGTH: 31
<212> TYPE: DNA
<213> ORGANISM: Artificial Sequence
<220> FEATURE:
<223> OTHER INFORMATION: Primer (P55)

<400> SEQUENCE: 89
tatcaacgcg ttcttcatcg gtagcagcac c 31

<210> SEQ ID NO 90
<211> LENGTH: 37
<212> TYPE: DNA
<213> ORGANISM: Artificial Sequence
<220> FEATURE:
<223> OTHER INFORMATION: Primer (P56)

<400> SEQUENCE: 90
cattcgcagg gtaacggcca ctgaagggcc tcctggg 37

<210> SEQ ID NO 91
<211> LENGTH: 20
<212> TYPE: DNA
<213> ORGANISM: Artificial Sequence
<220> FEATURE:
<223> OTHER INFORMATION: Primer (P57)

<400> SEQUENCE: 91
tagctgccaa ttattccggg 20

<210> SEQ ID NO 92
<211> LENGTH: 21
<212> TYPE: DNA
<213> ORGANISM: Artificial Sequence
<220> FEATURE:
<223> OTHER INFORMATION: Primer (P58)

<400> SEQUENCE: 92
gggtaaaaaa tcctttcgta g 21

<210> SEQ ID NO 93
<211> LENGTH: 40
<212> TYPE: DNA
<213> ORGANISM: Artificial Sequence
<220> FEATURE:
<223> OTHER INFORMATION: Primer (P59)

<400> SEQUENCE: 93
tacgaaagga tttttaccc ttgaccacct tgacgctgtc 40

<210> SEQ ID NO 94
<211> LENGTH: 33
<212> TYPE: DNA
<213> ORGANISM: Artificial Sequence
<220> FEATURE:
<223> OTHER INFORMATION: Primer (P60)

<400> SEQUENCE: 94
atctacgtcg acccatcaga agcaatgacg tag 33

<210> SEQ ID NO 95
<211> LENGTH: 31
<212> TYPE: DNA
<213> ORGANISM: Artificial Sequence
<220> FEATURE:
<223> OTHER INFORMATION: Primer (P61)

<400> SEQUENCE: 95
atcaacgcgt cggcaaatta gtcgaatgaa g 31

<210> SEQ ID NO 96
<211> LENGTH: 37
<212> TYPE: DNA
<213> ORGANISM: Artificial Sequence
<220> FEATURE:
<223> OTHER INFORMATION: Primer (P62)

<400> SEQUENCE: 96
cccggaataa ttggcagcta tccttcctgg gttaaac 37

<210> SEQ ID NO 97
<211> LENGTH: 28
<212> TYPE: DNA
<213> ORGANISM: Corynebacterium glutamicum

<400> SEQUENCE: 97
ggaggtgtgg aagtggccga tcaagcaa 28

<210> SEQ ID NO 98
<211> LENGTH: 28
<212> TYPE: DNA
<213> ORGANISM: Corynebacterium glutamicum

<400> SEQUENCE: 98
ggaggtgtgg aagtggccga tcaagcaa 28

<210> SEQ ID NO 99
<211> LENGTH: 28
<212> TYPE: DNA
<213> ORGANISM: Corynebacterium glutamicum

<400> SEQUENCE: 99
ggaggtgtgg aagtggccga tcaagcaa 28

<210> SEQ ID NO 100
<211> LENGTH: 28
<212> TYPE: DNA
<213> ORGANISM: Corynebacterium glutamicum

<400> SEQUENCE: 100
ggaggtgtgg aaatggccga tcaagcaa 28

<210> SEQ ID NO 101
<211> LENGTH: 33
<212> TYPE: DNA
<213> ORGANISM: Corynebacterium glutamicum

<400> SEQUENCE: 101
atcaaccaag gagactcgtg gctaagatca tct 33

<210> SEQ ID NO 102
<211> LENGTH: 33
<212> TYPE: DNA
<213> ORGANISM: Corynebacterium glutamicum

<400> SEQUENCE: 102
atcaaccaag gagactcgtg gctaagatca tct 33

<210> SEQ ID NO 103
<211> LENGTH: 33
<212> TYPE: DNA
<213> ORGANISM: Corynebacterium glutamicum

<400> SEQUENCE: 103
atcaaccaag gagactcgtg gctaagatca tct 33

<210> SEQ ID NO 104
<211> LENGTH: 33
<212> TYPE: DNA
<213> ORGANISM: Corynebacterium glutamicum

<400> SEQUENCE: 104
atcaaccaag gagactcgtg gctaagatca tct 33

<210> SEQ ID NO 105
<211> LENGTH: 33
<212> TYPE: DNA
<213> ORGANISM: Corynebacterium glutamicum

```
<400> SEQUENCE: 105

atcaaccaag gagactcgtg gctaagatca tct                              33


<210> SEQ ID NO 106
<211> LENGTH: 33
<212> TYPE: DNA
<213> ORGANISM: Corynebacterium glutamicum

<400> SEQUENCE: 106

atcaaccaag gagactcatg gctaagatca tct                              33
```